(12) United States Patent
Bowen et al.

(10) Patent No.: US 10,512,282 B2
(45) Date of Patent: Dec. 24, 2019

(54) CALIBRATED DOSE CONTROL

(71) Applicant: JUUL Labs, Inc., San Francisco, CA (US)

(72) Inventors: Adam Bowen, San Mateo, CA (US); James Monsees, San Francisco, CA (US); Ariel Atkins, San Francisco, CA (US); Bradley Ingebrethsen, Saugerties, NY (US); Esteban Leon Duque, San Francisco, CA (US)

(73) Assignee: Juul Labs, Inc., San Francisco, CA (US)

( * ) Notice: Subject to any disclaimer, the term of this patent is extended or adjusted under 35 U.S.C. 154(b) by 0 days.

(21) Appl. No.: 14/960,259

(22) Filed: Dec. 4, 2015

(65) Prior Publication Data
US 2016/0157524 A1 Jun. 9, 2016

Related U.S. Application Data

(60) Provisional application No. 62/088,464, filed on Dec. 5, 2014, provisional application No. 62/199,828, filed on Jul. 31, 2015.

(51) Int. Cl.
A24F 47/00 (2006.01)
A61M 15/00 (2006.01)
(Continued)

(52) U.S. Cl.
CPC ......... *A24F 47/008* (2013.01); *A61M 11/042* (2014.02); *A61M 15/0065* (2013.01);
(Continued)

(58) Field of Classification Search
CPC . A24F 47/008; A61M 15/0065; A61M 15/06; A61M 2205/33;
(Continued)

(56) References Cited

U.S. PATENT DOCUMENTS 374,584 A 12/1887 Cook
576,653 A 2/1897 Bowlby
(Continued)

FOREIGN PATENT DOCUMENTS

AU 2014206215 A1 8/2014
AU 2014208287 A1 8/2014
(Continued)

OTHER PUBLICATIONS

Monsees, J.; U.S. Appl. No. 12/115,400 entitled "Method and System for Vaporization of a Substance", filed May 5, 2008.
(Continued)

*Primary Examiner* — Joseph D. Boecker
(74) *Attorney, Agent, or Firm* — Mintz, Levin, Cohn, Ferris, Glovsky and Popeo, P.C.

(57) ABSTRACT

Methods and vaporizer apparatuses that estimate, measure and/or predict the amount of vapor and/or material (including active ingredients) released by the vaporizer apparatus. In particular, described herein are electronic vaporizers and methods of using them that determine a dose/amount of vapor and/or a material in the vapor based primarily or exclusively on the electrical and thermal properties, e.g., power or energy applied to the vaporizing element (e.g., heating coil) and the temperature of the material immediately before and as it is vaporized. Dose information may be used to control operation of the device and/or reported to the user.

25 Claims, 11 Drawing Sheets

(51) Int. Cl.
*A61M 15/06* (2006.01)
*G01K 7/22* (2006.01)
*G01N 33/00* (2006.01)
*H05B 1/02* (2006.01)
*A61M 11/04* (2006.01)
*A61M 16/00* (2006.01)

(52) U.S. Cl.
CPC ............... *A61M 15/06* (2013.01); *G01K 7/22* (2013.01); *G01N 33/0027* (2013.01); *H05B 1/0244* (2013.01); *A61M 2016/0027* (2013.01); *A61M 2016/0039* (2013.01); *A61M 2205/14* (2013.01); *A61M 2205/33* (2013.01); *A61M 2205/3368* (2013.01); *A61M 2205/581* (2013.01); *A61M 2205/582* (2013.01); *A61M 2205/583* (2013.01); *A61M 2205/8206* (2013.01); *A61M 2205/8237* (2013.01)

(58) Field of Classification Search
CPC .......................... A61M 11/041–11/044; A61M 16/108–16/109; A61M 16/14–16/147; A61M 16/16–16/168; A61M 11/042; A61M 2016/0027; A61M 2016/0039; A61M 2205/14; A61M 2205/3368; A61M 2205/581; A61M 2205/582; A61M 2205/583; A61M 2205/8206; A61M 2205/8237; G01K 7/22; G01N 33/0027; H05B 1/0244
See application file for complete search history.

(56) References Cited

U.S. PATENT DOCUMENTS

| | | |
|---|---|---|
| 595,070 A | 12/1897 | Oldenbusch |
| 720,007 A | 2/1903 | Dexter |
| 799,844 A | 9/1905 | Fuller |
| 968,160 A | 8/1910 | Johnson |
| 969,076 A | 8/1910 | Pender |
| 1,067,531 A | 7/1913 | MacGregor |
| 1,163,183 A | 12/1915 | Stoll |
| 1,299,162 A | 4/1919 | Fisher |
| 1,505,748 A | 8/1924 | Louis |
| 1,552,877 A | 9/1925 | Phillipps et al. |
| 1,632,335 A | 6/1927 | Hiering |
| 1,706,244 A | 3/1929 | Louis |
| 1,845,340 A | 2/1932 | Ritz |
| 1,972,118 A | 9/1934 | McDill |
| 1,998,683 A | 4/1935 | Montgomery |
| 2,031,363 A | 2/1936 | Elof |
| 2,039,559 A | 5/1936 | Segal |
| 2,104,266 A | 1/1938 | McCormick |
| 2,159,698 A | 5/1939 | Harris et al. |
| 2,177,636 A | 10/1939 | Coffelt et al. |
| 2,195,260 A | 3/1940 | Rasener |
| 2,231,909 A | 2/1941 | Hempal |
| 2,327,120 A | 8/1943 | McCoon |
| D142,178 S | 8/1945 | Becwar |
| 2,460,427 A | 2/1949 | Musselman et al. |
| 2,483,304 A | 9/1949 | Rudolf |
| 2,502,561 A | 4/1950 | Ludwig |
| 2,765,949 A | 10/1956 | Swan |
| 2,830,597 A | 4/1958 | Kummli |
| 2,860,638 A | 11/1958 | Bartolomeo |
| 2,897,958 A | 8/1959 | Tarleton et al. |
| 2,935,987 A | 5/1960 | Ackerbauer |
| 3,085,145 A | 4/1963 | Wray |
| 3,146,937 A | 9/1964 | Joseph |
| 3,258,015 A | 6/1966 | Ellis et al. |
| 3,271,719 A | 9/1966 | Ovshinsky |
| 3,292,634 A | 12/1966 | Beucler |
| D207,887 S | 6/1967 | Parsisson |
| 3,373,915 A | 3/1968 | Anderson et al. |
| 3,420,360 A | 1/1969 | Young |
| 3,443,827 A | 5/1969 | Acker et al. |
| 3,456,645 A | 7/1969 | Brock |
| 3,479,561 A | 11/1969 | Janning |
| 3,565,071 A | 2/1971 | Sanford Cobb et al. |
| 3,567,014 A | 3/1971 | Feigelman |
| 3,675,661 A | 7/1972 | Weaver |
| 3,707,017 A | 12/1972 | Paquette |
| 3,792,704 A | 2/1974 | Parker |
| 3,815,597 A | 6/1974 | Goettelman |
| 3,861,523 A | 1/1975 | Fountain et al. |
| 3,941,300 A | 3/1976 | Troth |
| 4,020,853 A | 5/1977 | Nuttall |
| 4,049,005 A | 9/1977 | Hernandez et al. |
| 4,066,088 A | 1/1978 | Ensor |
| D250,485 S | 12/1978 | Cuthbertson |
| D255,548 S | 6/1980 | Grodin |
| 4,207,976 A | 6/1980 | Herman |
| 4,215,708 A | 8/1980 | Bron |
| 4,219,032 A | 8/1980 | Tabatznik et al. |
| D260,690 S | 9/1981 | Stutzer |
| 4,303,083 A | 12/1981 | Burruss, Jr. |
| 4,312,367 A | 1/1982 | Seeman |
| 4,347,855 A | 9/1982 | Lanzillotti et al. |
| 4,391,285 A | 7/1983 | Burnett et al. |
| D271,255 S | 11/1983 | Rousseau |
| 4,492,480 A | 1/1985 | Wadso et al. |
| 4,506,683 A | 3/1985 | Cantrell et al. |
| 4,519,319 A | 5/1985 | Howlett |
| 4,520,938 A | 6/1985 | Finke |
| D280,494 S | 9/1985 | Abel |
| 4,595,024 A | 6/1986 | Greene et al. |
| 4,625,737 A | 12/1986 | Keritsis et al. |
| 4,648,393 A | 3/1987 | Landis et al. |
| 4,676,237 A | 6/1987 | Wood et al. |
| 4,708,151 A | 11/1987 | Shelar |
| 4,735,217 A | 4/1988 | Gerth et al. |
| 4,771,796 A | 9/1988 | Myer |
| 4,793,365 A | 12/1988 | Sensabaugh, Jr. et al. |
| 4,794,323 A | 12/1988 | Zhou et al. |
| 4,798,310 A | 1/1989 | Kasai et al. |
| 4,813,536 A | 3/1989 | Willis |
| 4,819,665 A | 4/1989 | Roberts et al. |
| 4,830,028 A | 5/1989 | Lawson et al. |
| D301,837 S | 6/1989 | Peterson et al. |
| 4,836,224 A | 6/1989 | Lawson et al. |
| 4,846,199 A | 7/1989 | Rose |
| 4,848,374 A | 7/1989 | Chard et al. |
| 4,848,563 A | 7/1989 | Robbins |
| D302,659 S | 8/1989 | Peterson et al. |
| D303,722 S | 9/1989 | Marlow et al. |
| 4,870,748 A | 10/1989 | Hensgen et al. |
| D304,771 S | 11/1989 | Katayama |
| 4,893,639 A | 1/1990 | White |
| 4,896,683 A | 1/1990 | Cohen et al. |
| 4,907,606 A | 3/1990 | Lilja et al. |
| 4,924,883 A | 5/1990 | Perfetti et al. |
| 4,938,236 A | 7/1990 | Banerjee et al. |
| 4,941,483 A | 7/1990 | Ridings et al. |
| 4,944,317 A | 7/1990 | Thal |
| D310,171 S | 8/1990 | Cusenza |
| 4,945,929 A | 8/1990 | Egilmex |
| 4,947,874 A | 8/1990 | Brooks et al. |
| 4,947,875 A | 8/1990 | Brooks et al. |
| D310,349 S | 9/1990 | Rowen |
| 4,955,397 A | 9/1990 | Johnson et al. |
| 4,974,609 A | 12/1990 | Southwick et al. |
| 4,984,588 A | 1/1991 | Stewart, Jr. |
| D315,032 S | 2/1991 | Hayes |
| 5,005,759 A | 4/1991 | Bouche |
| 5,019,122 A | 5/1991 | Clearman et al. |
| 5,020,548 A | 6/1991 | Farrier et al. |
| 5,027,836 A | 7/1991 | Shannon et al. |
| 5,031,646 A | 7/1991 | Lippiello et al. |
| 5,040,551 A | 8/1991 | Schlatter et al. |
| 5,042,509 A | 8/1991 | Banerjee et al. |
| 5,050,621 A | 9/1991 | Creighton et al. |
| 5,060,671 A | 10/1991 | Counts et al. |
| 5,065,776 A | 11/1991 | Lawson et al. |
| 5,076,297 A | 12/1991 | Farrier et al. |

(56) References Cited

U.S. PATENT DOCUMENTS

| | | | |
|---|---|---|---|
| 5,101,838 A | 4/1992 | Schwartz et al. | |
| 5,105,831 A | 4/1992 | Banerjee et al. | |
| 5,105,836 A | 4/1992 | Gentry et al. | |
| 5,105,838 A | 4/1992 | White et al. | |
| 5,123,530 A | 6/1992 | Lee | |
| 5,127,511 A | 7/1992 | Keen, Jr. et al. | |
| 5,133,368 A | 7/1992 | Neumann et al. | |
| 5,141,004 A | 8/1992 | Porenski | |
| 5,144,962 A | 9/1992 | Counts et al. | |
| 5,148,817 A | 9/1992 | Houminer et al. | |
| 5,152,456 A | 10/1992 | Ross et al. | |
| 5,175,791 A * | 12/1992 | Muderlak | A61L 9/03 219/492 |
| 5,183,062 A | 2/1993 | Clearman et al. | |
| D336,346 S | 6/1993 | Miller et al. | |
| 5,224,498 A | 7/1993 | Deevi et al. | |
| 5,228,460 A | 7/1993 | Sprinkel et al. | |
| 5,240,012 A | 8/1993 | Ehrman et al. | |
| 5,249,586 A | 10/1993 | Morgan et al. | |
| 5,261,424 A | 11/1993 | Sprinkel, Jr. | |
| 5,269,237 A | 12/1993 | Baker et al. | |
| 5,269,327 A | 12/1993 | Counts et al. | |
| 5,296,685 A | 3/1994 | Burstein et al. | |
| 5,303,720 A | 4/1994 | Banerjee et al. | |
| 5,322,075 A | 6/1994 | Deevi et al. | |
| 5,324,498 A | 6/1994 | Streusand et al. | |
| 5,345,951 A | 9/1994 | Serrano et al. | |
| 5,369,723 A | 11/1994 | Counts et al. | |
| 5,372,148 A | 12/1994 | McCafferty et al. | |
| 5,388,574 A | 2/1995 | Ingebrethsen | |
| 5,449,078 A | 9/1995 | Akers | |
| 5,456,269 A | 10/1995 | Kollasch | |
| 5,472,001 A | 12/1995 | Nicholson | |
| D367,605 S | 3/1996 | Moore | |
| 5,497,791 A | 3/1996 | Bowen et al. | |
| D368,552 S | 4/1996 | Adams | |
| 5,529,078 A | 6/1996 | Rehder et al. | |
| D371,633 S | 7/1996 | Chenard | |
| 5,545,904 A | 8/1996 | Orbach | |
| 5,564,442 A | 10/1996 | MacDonald et al. | |
| 5,579,934 A | 12/1996 | Buono | |
| 5,591,368 A | 1/1997 | Fleischhauer et al. | |
| 5,605,226 A | 2/1997 | Hernlein | |
| D379,810 S | 6/1997 | Giordano, Jr. et al. | |
| 5,641,064 A | 6/1997 | Goserud | |
| D380,293 S | 7/1997 | Cudmore | |
| 5,649,552 A | 7/1997 | Cho et al. | |
| D382,146 S | 8/1997 | Sandy | |
| 5,666,977 A | 9/1997 | Higgins et al. | |
| 5,666,978 A | 9/1997 | Counts et al. | |
| 5,708,258 A | 1/1998 | Counts et al. | |
| 5,730,118 A | 3/1998 | Hermanson | |
| 5,730,158 A | 3/1998 | Collins et al. | |
| 5,743,251 A | 4/1998 | Howell et al. | |
| 5,746,587 A | 5/1998 | Racine et al. | |
| D397,504 S | 8/1998 | Zelenik | |
| D398,150 S | 9/1998 | Vonarburg | |
| 5,810,164 A | 9/1998 | Rennecamp | |
| 5,819,756 A | 10/1998 | Mielordt | |
| 5,845,649 A | 12/1998 | Saito et al. | |
| D405,007 S | 2/1999 | Naas, Sr. | |
| 5,865,185 A | 2/1999 | Collins et al. | |
| 5,865,186 A | 2/1999 | Volsey, II | |
| 5,878,752 A | 3/1999 | Adams et al. | |
| 5,881,884 A | 3/1999 | Podosek | |
| 5,894,841 A | 4/1999 | Voges | |
| D411,332 S | 6/1999 | Zelenik | |
| D412,279 S | 7/1999 | Brice | |
| 5,931,828 A | 8/1999 | Durkee | |
| 5,934,289 A | 8/1999 | Watkins et al. | |
| 5,938,018 A | 8/1999 | Keaveney et al. | |
| 5,944,025 A | 8/1999 | Cook et al. | |
| 5,954,979 A | 9/1999 | Counts et al. | |
| D414,893 S | 10/1999 | Moore | |
| 5,967,310 A | 10/1999 | Hill | |
| 5,975,415 A | 11/1999 | Zehnal | |
| 5,979,460 A | 11/1999 | Matsumura | |
| 5,994,025 A | 11/1999 | Iwasa et al. | |
| 5,996,589 A | 12/1999 | St. Charles | |
| 6,024,097 A | 2/2000 | Von Wielligh | |
| 6,026,820 A | 2/2000 | Baggett, Jr. et al. | |
| 6,040,560 A | 3/2000 | Fleischhauer et al. | |
| D422,884 S | 4/2000 | Lafond | |
| 6,053,176 A | 4/2000 | Adams et al. | |
| D424,236 S | 5/2000 | Reed | |
| 6,089,857 A | 7/2000 | Matsuura et al. | |
| 6,095,153 A | 8/2000 | Kessler et al. | |
| 6,102,036 A | 8/2000 | Slutsky et al. | |
| 6,119,684 A | 9/2000 | Nohl et al. | |
| 6,125,853 A | 10/2000 | Susa et al. | |
| D433,532 S | 11/2000 | Higgins et al. | |
| 6,155,268 A | 12/2000 | Takeuchi | |
| 6,164,287 A | 12/2000 | White | |
| D436,686 S | 1/2001 | Fujisawa | |
| 6,196,232 B1 | 3/2001 | Chkadua | |
| 6,216,705 B1 | 4/2001 | Ossepian | |
| D442,328 S | 5/2001 | Barmes | |
| 6,234,167 B1 | 5/2001 | Cox et al. | |
| 6,234,169 B1 | 5/2001 | Bulbrook et al. | |
| 6,265,789 B1 | 7/2001 | Honda et al. | |
| D447,276 S | 8/2001 | Gustafson | |
| 6,269,966 B1 | 8/2001 | Pallo et al. | |
| D450,313 S | 11/2001 | Koinuma | |
| D450,662 S | 11/2001 | Kwok | |
| 6,324,261 B1 | 11/2001 | Merte | |
| 6,349,728 B1 | 2/2002 | Pham | |
| D454,079 S | 3/2002 | Fong | |
| 6,381,739 B1 | 4/2002 | Breternitz, Jr. et al. | |
| 6,386,371 B1 | 5/2002 | Parsons | |
| 6,407,371 B1 | 6/2002 | Toya et al. | |
| 6,418,938 B1 | 7/2002 | Fleischhauer et al. | |
| 6,431,363 B1 | 8/2002 | Hacker | |
| 6,443,146 B1 | 9/2002 | Voges | |
| 6,446,793 B1 | 9/2002 | Layshock | |
| D465,660 S | 11/2002 | Doeing | |
| 6,501,052 B2 | 12/2002 | Cox et al. | |
| 6,510,982 B2 | 1/2003 | White et al. | |
| D471,104 S | 3/2003 | Hunt | |
| 6,532,965 B1 | 3/2003 | Abhulimen et al. | |
| 6,536,442 B2 | 3/2003 | St. Charles et al. | |
| 6,557,708 B2 | 5/2003 | Polacco | |
| 6,598,607 B2 | 7/2003 | Adiga et al. | |
| D477,920 S | 8/2003 | McCarty et al. | |
| D478,569 S | 8/2003 | Hussaini et al. | |
| D478,897 S | 8/2003 | Tsuge | |
| 6,603,924 B2 | 8/2003 | Brown et al. | |
| 6,606,998 B1 | 8/2003 | Gold | |
| 6,612,404 B2 | 9/2003 | Sweet et al. | |
| 6,615,840 B1 | 9/2003 | Fournier et al. | |
| 6,622,867 B2 | 9/2003 | Menceles | |
| 6,637,430 B1 | 10/2003 | Voges et al. | |
| 6,655,379 B2 | 12/2003 | Clark et al. | |
| D485,639 S | 1/2004 | Stronski | |
| 6,672,762 B1 | 1/2004 | Faircloth et al. | |
| 6,688,313 B2 | 2/2004 | Wrenn et al. | |
| 6,701,921 B2 | 3/2004 | Sprinkel, Jr. et al. | |
| 6,701,922 B2 | 3/2004 | Hindle et al. | |
| 6,707,274 B1 | 3/2004 | Karr | |
| 6,708,846 B1 | 3/2004 | Fuchs et al. | |
| 6,726,006 B1 | 4/2004 | Funderburk et al. | |
| 6,743,030 B2 | 6/2004 | Lin et al. | |
| 6,747,573 B1 | 6/2004 | Gerlach et al. | |
| 6,752,649 B2 | 6/2004 | Arkin et al. | |
| 6,766,220 B2 | 7/2004 | McRae et al. | |
| D494,315 S | 8/2004 | Cartier | |
| 6,769,436 B2 | 8/2004 | Horian | |
| 6,772,756 B2 | 8/2004 | Shayan | |
| D495,599 S | 9/2004 | Biesecker | |
| 6,799,576 B2 | 10/2004 | Farr | |
| 6,803,545 B2 | 10/2004 | Blake et al. | |
| 6,803,744 B1 | 10/2004 | Sabo | |
| 6,805,545 B2 | 10/2004 | Slaboden | |
| 6,810,883 B2 | 11/2004 | Felter et al. | |
| D500,301 S | 12/2004 | Deguchi | |

(56) References Cited

U.S. PATENT DOCUMENTS

| | | |
|---|---|---|
| D500,302 S | 12/2004 | Deguchi |
| 6,827,573 B2 | 12/2004 | St. Charles et al. |
| 6,854,470 B1 | 2/2005 | Pu |
| 6,874,507 B2 | 4/2005 | Farr |
| 6,889,687 B1 | 5/2005 | Olsson |
| D505,922 S | 6/2005 | Mayo et al. |
| D506,447 S | 6/2005 | Mayo et al. |
| D506,731 S | 6/2005 | Mayo et al. |
| 6,909,840 B2 | 6/2005 | Harwig et al. |
| D507,244 S | 7/2005 | Mayo et al. |
| 6,923,890 B2 | 8/2005 | Ricatto et al. |
| 6,954,979 B2 | 10/2005 | Logan |
| 6,994,096 B2 | 2/2006 | Rostami et al. |
| 7,000,775 B2 | 2/2006 | Gelardi et al. |
| 7,015,796 B2 | 3/2006 | Snyder |
| 7,025,066 B2 | 4/2006 | Lawson et al. |
| D523,171 S | 6/2006 | Mitten et al. |
| D525,948 S | 8/2006 | Blair et al. |
| 7,082,825 B2 | 8/2006 | Aoshima et al. |
| D528,992 S | 9/2006 | Hobart et al. |
| D529,044 S | 9/2006 | Andre et al. |
| 7,109,876 B2 | 9/2006 | Smith et al. |
| D530,340 S | 10/2006 | Andre et al. |
| D531,190 S | 10/2006 | Lee et al. |
| 7,117,707 B2 | 10/2006 | Adams et al. |
| D532,927 S | 11/2006 | Sann |
| 7,143,766 B2 | 12/2006 | Schuster et al. |
| D534,921 S | 1/2007 | Andre et al. |
| D535,261 S | 1/2007 | Daniels |
| D535,308 S | 1/2007 | Andre et al. |
| 7,167,776 B2 | 1/2007 | Maharajh et al. |
| 7,173,222 B2 * | 2/2007 | Cox .................. A61M 11/041 128/200.14 |
| 7,185,651 B2 | 3/2007 | Alston et al. |
| 7,185,659 B2 | 3/2007 | Sharpe |
| D539,813 S | 4/2007 | Chen |
| D540,687 S | 4/2007 | Egawa |
| D540,749 S | 4/2007 | Kaule |
| 7,214,075 B2 | 5/2007 | He et al. |
| D544,643 S | 6/2007 | Lin |
| D545,303 S | 6/2007 | Chang |
| 7,234,593 B2 | 6/2007 | Fath et al. |
| D545,904 S | 7/2007 | Chen et al. |
| D546,782 S | 7/2007 | Poulet et al. |
| D547,002 S | 7/2007 | Lin |
| D551,548 S | 9/2007 | Didier |
| D551,970 S | 10/2007 | Didier |
| 7,275,941 B1 | 10/2007 | Bushby |
| D556,154 S | 11/2007 | Poulet et al. |
| 7,290,549 B2 | 11/2007 | Banerjee et al. |
| D557,209 S | 12/2007 | Ahlgren et al. |
| D558,060 S | 12/2007 | Milan Sir |
| D562,151 S | 2/2008 | Larocca et al. |
| D565,496 S | 4/2008 | Disla |
| D568,298 S | 5/2008 | Lundgren et al. |
| D569,727 S | 5/2008 | Moretti |
| 7,367,334 B2 | 5/2008 | Faison, Jr. et al. |
| 7,374,048 B2 | 5/2008 | Mazurek |
| D571,202 S | 6/2008 | Vogt |
| D571,556 S | 6/2008 | Raile |
| D573,474 S | 7/2008 | Beam et al. |
| 7,415,982 B1 | 8/2008 | Sheridan |
| D576,619 S | 9/2008 | Udagawa et al. |
| D577,019 S | 9/2008 | Udagawa et al. |
| D577,150 S | 9/2008 | Bryman et al. |
| D577,591 S | 9/2008 | Bouroullec et al. |
| 7,428,905 B2 | 9/2008 | Mua |
| 7,434,584 B2 | 10/2008 | Steinberg |
| D580,756 S | 11/2008 | Seebold |
| D585,077 S | 1/2009 | Sheba et al. |
| 7,488,171 B2 | 2/2009 | St. Charles et al. |
| D589,941 S | 4/2009 | Maier et al. |
| D590,988 S | 4/2009 | Hon |
| D590,989 S | 4/2009 | Hon |
| D590,990 S | 4/2009 | Hon |
| D590,991 S | 4/2009 | Hon |
| D591,758 S | 5/2009 | Lee |
| 7,530,352 B2 | 5/2009 | Childers et al. |
| 7,546,703 B2 | 6/2009 | Johnske et al. |
| D599,670 S | 9/2009 | Qin |
| 7,581,540 B2 | 9/2009 | Hale et al. |
| 7,621,403 B2 | 11/2009 | Althoff et al. |
| D605,509 S | 12/2009 | Leonardis |
| D606,505 S | 12/2009 | Seflic et al. |
| 7,633,270 B2 | 12/2009 | Wong et al. |
| 7,644,823 B2 | 1/2010 | Gelardi et al. |
| D610,588 S | 2/2010 | Chen |
| D611,409 S | 3/2010 | Green et al. |
| D616,753 S | 6/2010 | Beam et al. |
| 7,726,320 B2 | 6/2010 | Robinson et al. |
| 7,753,055 B2 | 7/2010 | Bryman |
| D621,357 S | 8/2010 | Dong |
| 7,767,698 B2 | 8/2010 | Warchol et al. |
| D624,238 S | 9/2010 | Turner |
| 7,793,860 B2 | 9/2010 | Bankers et al. |
| 7,793,861 B2 | 9/2010 | Bankers et al. |
| 7,801,573 B2 | 9/2010 | Yazdi et al. |
| D624,880 S | 10/2010 | Felegy, Jr. et al. |
| 7,813,832 B2 | 10/2010 | Sundar |
| 7,815,332 B1 | 10/2010 | Smith |
| D627,962 S | 11/2010 | Mudrick |
| 7,832,397 B2 | 11/2010 | Lipowicz |
| 7,832,410 B2 | 11/2010 | Hon |
| 7,845,359 B2 | 12/2010 | Montaser |
| D631,055 S | 1/2011 | Gilbert et al. |
| D631,458 S | 1/2011 | Liao et al. |
| 7,886,507 B2 | 2/2011 | McGuinness, Jr. |
| 7,891,666 B2 | 2/2011 | Kuenzler et al. |
| D634,735 S | 3/2011 | Maier |
| 7,905,230 B2 | 3/2011 | Schuler et al. |
| 7,905,236 B2 | 3/2011 | Bryman et al. |
| 7,913,686 B2 | 3/2011 | Hughes et al. |
| D639,303 S | 6/2011 | Ni et al. |
| D639,782 S | 6/2011 | Kim |
| D641,718 S | 7/2011 | Sakai |
| D642,330 S | 7/2011 | Turner |
| D644,375 S | 8/2011 | Zhou |
| 7,987,846 B2 | 8/2011 | Hale et al. |
| 7,988,034 B2 | 8/2011 | Pezzoli |
| 8,003,080 B2 | 8/2011 | Rabinowitz et al. |
| D645,817 S | 9/2011 | Sasada et al. |
| D647,247 S | 10/2011 | Jones |
| 8,042,550 B2 | 10/2011 | Urtsev et al. |
| D649,708 S | 11/2011 | Oneil |
| D649,932 S | 12/2011 | Symons |
| 8,079,361 B2 | 12/2011 | Schuler et al. |
| 8,079,371 B2 | 12/2011 | Robinson et al. |
| 8,080,975 B2 | 12/2011 | Bessa et al. |
| 8,091,558 B2 | 1/2012 | Martzel |
| D653,803 S | 2/2012 | Timmermans |
| D656,496 S | 3/2012 | Andre et al. |
| 8,141,701 B2 | 3/2012 | Hodges |
| 8,156,944 B2 | 4/2012 | Han |
| 8,157,918 B2 | 4/2012 | Becker et al. |
| 8,170,623 B2 | 5/2012 | Dorogusker et al. |
| D661,889 S | 6/2012 | Wu |
| D661,991 S | 6/2012 | Brummelhuis et al. |
| 8,205,622 B2 | 6/2012 | Pan |
| D664,146 S | 7/2012 | Hoehn et al. |
| D664,636 S | 7/2012 | Robinson et al. |
| 8,251,060 B2 | 8/2012 | White et al. |
| 8,282,995 B2 | 10/2012 | Calzia et al. |
| D670,272 S | 11/2012 | Suzuki |
| D670,659 S | 11/2012 | Ishikawa et al. |
| 8,308,624 B2 | 11/2012 | Travers et al. |
| 8,314,235 B2 | 11/2012 | Dixit et al. |
| D672,715 S | 12/2012 | Brunner et al. |
| 8,322,350 B2 | 12/2012 | Lipowicz |
| D674,182 S | 1/2013 | Copeland et al. |
| D674,748 S | 1/2013 | Ferber et al. |
| 8,344,693 B2 | 1/2013 | Budziszek et al. |
| D676,741 S | 2/2013 | van Landsveld et al. |
| 8,365,742 B2 | 2/2013 | Hon |
| 8,371,310 B2 | 2/2013 | Brenneise |

(56) References Cited

U.S. PATENT DOCUMENTS

| | | |
|---|---|---|
| 8,375,957 B2 | 2/2013 | Hon |
| 8,381,739 B2 | 2/2013 | Gonda |
| 8,387,612 B2 | 3/2013 | Damani et al. |
| 8,393,331 B2 | 3/2013 | Hon |
| 8,402,978 B2 | 3/2013 | Karles et al. |
| 8,424,539 B2 | 4/2013 | Braunshteyn et al. |
| D681,445 S | 5/2013 | van Landsveld et al. |
| D682,090 S | 5/2013 | Scatterday |
| D682,698 S | 5/2013 | Young |
| D682,841 S | 5/2013 | Suetake et al. |
| 8,443,534 B2 | 5/2013 | Goodfellow et al. |
| D684,683 S | 6/2013 | Curti et al. |
| 8,464,867 B2 | 6/2013 | Holloway et al. |
| D686,336 S | 7/2013 | Horian |
| D686,987 S | 7/2013 | Vanstone et al. |
| D687,042 S | 7/2013 | Yoneta et al. |
| 8,479,747 B2 | 7/2013 | O'Connell |
| 8,485,180 B2 | 7/2013 | Smutney et al. |
| 8,490,628 B2 | 7/2013 | Hon |
| 8,490,629 B1 | 7/2013 | Shenassa et al. |
| 8,495,998 B2 | 7/2013 | Schennum |
| 8,499,766 B1 | 8/2013 | Newton |
| 8,511,318 B2 | 8/2013 | Hon |
| D690,461 S | 9/2013 | Chen |
| 8,528,568 B2 | 9/2013 | Onishi et al. |
| 8,539,959 B1 | 9/2013 | Scatterday |
| 8,541,401 B2 | 9/2013 | Mishra et al. |
| D691,324 S | 10/2013 | Saliman |
| D692,615 S | 10/2013 | Verleur |
| 8,550,069 B2 | 10/2013 | Alelov |
| 8,552,691 B2 | 10/2013 | Wu |
| D693,054 S | 11/2013 | Verleur |
| 8,578,942 B2 | 11/2013 | Schennum |
| 8,578,943 B2 | 11/2013 | Luan et al. |
| D695,450 S | 12/2013 | Benassayag et al. |
| D696,051 S | 12/2013 | Scatterday |
| 8,596,460 B2 | 12/2013 | Scatterday |
| 8,646,462 B2 | 2/2014 | Yamada et al. |
| D700,572 S | 3/2014 | Esses |
| 8,671,952 B2 | 3/2014 | Winterson et al. |
| 8,678,012 B2 | 3/2014 | Li et al. |
| 8,689,789 B2 | 4/2014 | Andrus et al. |
| 8,689,805 B2 | 4/2014 | Hon |
| 8,695,794 B2 | 4/2014 | Scatterday |
| 8,707,965 B2 | 4/2014 | Newton |
| D704,629 S | 5/2014 | Liu |
| D704,634 S | 5/2014 | Eidelman et al. |
| D705,918 S | 5/2014 | Robinson et al. |
| 8,714,150 B2 | 5/2014 | Alelov |
| 8,714,161 B2 | 5/2014 | Liu |
| 8,733,345 B2 | 5/2014 | Siller |
| 8,733,346 B2 | 5/2014 | Rinker |
| D707,389 S | 6/2014 | Liu |
| D707,627 S | 6/2014 | Brunner et al. |
| 8,739,788 B2 | 6/2014 | Yomtov |
| 8,741,348 B2 | 6/2014 | Hansson et al. |
| 8,752,545 B2 | 6/2014 | Buchberger |
| 8,752,557 B2 | 6/2014 | Lipowicz |
| 8,757,169 B2 | 6/2014 | Gysland |
| D708,727 S | 7/2014 | Postma |
| 8,770,187 B2 | 7/2014 | Murphy |
| 8,781,307 B2 | 7/2014 | Buzzetti |
| 8,790,556 B2 | 7/2014 | Bundren et al. |
| 8,794,231 B2 | 8/2014 | Thorens et al. |
| 8,794,244 B2 | 8/2014 | Hammel et al. |
| 8,794,245 B1 | 8/2014 | Scatterday |
| 8,794,434 B2 | 8/2014 | Scatterday et al. |
| 8,807,140 B1 | 8/2014 | Scatterday |
| 8,809,261 B2 | 8/2014 | Elsohly et al. |
| 8,813,747 B2 | 8/2014 | Gibson et al. |
| 8,813,759 B1 | 8/2014 | Horian |
| 8,820,330 B2 | 9/2014 | Bellinger et al. |
| 8,829,395 B2 | 9/2014 | Bao |
| D752,284 S | 10/2014 | Doster |
| 8,851,068 B2 | 10/2014 | Cohen et al. |
| 8,851,081 B2 | 10/2014 | Fernando et al. |
| 8,851,083 B2 | 10/2014 | Oglesby et al. |
| 8,857,446 B2 | 10/2014 | Wu |
| 8,863,752 B2 | 10/2014 | Hon |
| 8,869,792 B1 | 10/2014 | Lee |
| 8,881,737 B2 | 11/2014 | Collett et al. |
| 8,881,738 B2 | 11/2014 | Bryman |
| 8,893,726 B2 | 11/2014 | Hon |
| 8,897,628 B2 | 11/2014 | Conley et al. |
| D718,621 S | 12/2014 | Mitchell et al. |
| D718,723 S | 12/2014 | Clymer et al. |
| D718,933 S | 12/2014 | Brown, Jr. |
| D719,701 S | 12/2014 | Scatterday |
| D720,095 S | 12/2014 | Alima |
| D720,496 S | 12/2014 | Alima |
| D720,497 S | 12/2014 | Alima |
| 8,899,238 B2 | 12/2014 | Robinson et al. |
| 8,899,239 B2 | 12/2014 | Hon |
| 8,899,240 B2 | 12/2014 | Mass |
| 8,905,040 B2 | 12/2014 | Scatterday et al. |
| 8,910,630 B2 | 12/2014 | Todd |
| 8,910,639 B2 | 12/2014 | Chang et al. |
| 8,910,640 B2 | 12/2014 | Sears et al. |
| 8,910,641 B2 | 12/2014 | Hon |
| 8,910,783 B2 | 12/2014 | Liu |
| 8,915,254 B2 | 12/2014 | Monsees et al. |
| 8,919,561 B2 | 12/2014 | Boisseau |
| D721,202 S | 1/2015 | Liu |
| D721,577 S | 1/2015 | Scatterday |
| 8,925,555 B2 | 1/2015 | Monsees et al. |
| 8,928,277 B2 | 1/2015 | Xiang et al. |
| 8,931,492 B2 | 1/2015 | Scatterday |
| D721,972 S | 2/2015 | Brewer et al. |
| D722,023 S | 2/2015 | Brunner et al. |
| 8,948,578 B2 | 2/2015 | Buchberger |
| 8,950,395 B2 | 2/2015 | Schennum |
| 8,955,522 B1 | 2/2015 | Bowen et al. |
| 8,960,199 B2 | 2/2015 | Zhuang et al. |
| 8,961,492 B2 | 2/2015 | Imran et al. |
| 8,963,725 B2 | 2/2015 | Xiang |
| D723,735 S | 3/2015 | Liu |
| D723,736 S | 3/2015 | Liu |
| D724,037 S | 3/2015 | Yoshioka |
| D725,310 S | 3/2015 | Eksouzian |
| D725,823 S | 3/2015 | Scatterday et al. |
| 8,967,382 B2 | 3/2015 | Liu |
| 8,973,587 B2 | 3/2015 | Liu |
| 8,975,764 B1 | 3/2015 | Abehasera |
| 8,978,663 B2 | 3/2015 | Newton |
| 8,991,402 B2 | 3/2015 | Bowen et al. |
| 8,993,836 B2 | 3/2015 | Tissier et al. |
| D726,727 S | 4/2015 | Holz et al. |
| 9,004,073 B2 | 4/2015 | Tucker et al. |
| 9,010,335 B1 | 4/2015 | Scatterday |
| 9,016,274 B1 | 4/2015 | White |
| 9,018,899 B2 | 4/2015 | Xiang |
| D728,855 S | 5/2015 | Liu |
| D729,030 S | 5/2015 | Novick et al. |
| D729,277 S | 5/2015 | Uchida |
| D729,366 S | 5/2015 | Kauss et al. |
| D729,439 S | 5/2015 | Scatterday |
| D729,444 S | 5/2015 | Leidel |
| D729,445 S | 5/2015 | Leidel |
| D730,571 S | 5/2015 | Chen |
| D730,572 S | 5/2015 | Leidel |
| 9,022,026 B2 | 5/2015 | Fang |
| 9,022,039 B2 | 5/2015 | Hearn |
| 9,025,291 B2 | 5/2015 | Xiang |
| 9,028,808 B2 | 5/2015 | Huland |
| 9,032,968 B2 | 5/2015 | Glasberg et al. |
| 9,038,626 B2 | 5/2015 | Yamada et al. |
| 9,038,642 B2 | 5/2015 | Liu |
| D731,114 S | 6/2015 | Leidel |
| D733,142 S | 6/2015 | Solomon et al. |
| D733,356 S | 6/2015 | Leidel |
| 9,046,278 B2 | 6/2015 | Koller |
| 9,050,431 B2 | 6/2015 | Turner et al. |
| 9,055,617 B2 | 6/2015 | Thorens et al. |
| 9,055,770 B2 | 6/2015 | Liu |

(56) References Cited

U.S. PATENT DOCUMENTS

| | | |
|---|---|---|
| 9,060,388 B2 | 6/2015 | Liu |
| 9,060,548 B2 | 6/2015 | Zheng et al. |
| 9,066,543 B2 | 6/2015 | Cameron |
| 9,072,321 B2 | 7/2015 | Liu |
| 9,072,322 B2 | 7/2015 | Liu |
| 9,078,472 B2 | 7/2015 | Liu |
| 9,078,473 B2 | 7/2015 | Worm et al. |
| 9,078,474 B2 | 7/2015 | Thompson |
| 9,078,475 B2 | 7/2015 | Li et al. |
| 9,089,166 B1 | 7/2015 | Scatterday |
| 9,089,168 B2 | 7/2015 | Liu |
| 9,090,173 B2 | 7/2015 | Oishi |
| D736,706 S | 8/2015 | Huang et al. |
| D736,995 S | 8/2015 | Recio |
| D737,508 S | 8/2015 | Liu |
| 9,095,174 B2 | 8/2015 | Capuano |
| 9,095,175 B2 | 8/2015 | Terry et al. |
| 9,099,873 B2 | 8/2015 | Xiang |
| 9,101,729 B2 | 8/2015 | Liu |
| 9,113,659 B2 | 8/2015 | Liu |
| D737,566 S | 9/2015 | Gaddis |
| D738,038 S | 9/2015 | Smith |
| D739,973 S | 9/2015 | Chao |
| 9,131,733 B2 | 9/2015 | Liu |
| D741,001 S | 10/2015 | Alarcon et al. |
| D741,002 S | 10/2015 | Liu |
| D741,541 S | 10/2015 | Liu |
| D742,063 S | 10/2015 | Recio |
| D742,064 S | 10/2015 | Leidel |
| 9,155,336 B2 | 10/2015 | Liu |
| 9,166,424 B2 | 10/2015 | Oakley, Jr. |
| 9,167,849 B2 | 10/2015 | Adamic |
| 9,167,850 B2 | 10/2015 | Liu |
| 9,167,852 B2 | 10/2015 | Xiu |
| 9,167,853 B2 | 10/2015 | Xiang |
| D742,492 S | 11/2015 | Robinson et al. |
| D742,624 S | 11/2015 | Meyers |
| D743,099 S | 11/2015 | Oglesby |
| D744,159 S | 11/2015 | Lukas |
| 9,185,937 B2 | 11/2015 | Liu |
| 9,197,726 B2 | 11/2015 | Stanimirovic et al. |
| D744,342 S | 12/2015 | Blasko et al. |
| D744,419 S | 12/2015 | Bowen et al. |
| D744,696 S | 12/2015 | Malhi |
| D745,004 S | 12/2015 | Kim |
| D745,388 S | 12/2015 | Taylor |
| D746,291 S | 12/2015 | Solomon et al. |
| 9,198,463 B2 | 12/2015 | Liu |
| 9,198,464 B2 | 12/2015 | Liu |
| 9,198,466 B2 | 12/2015 | Liu |
| 9,204,670 B2 | 12/2015 | Liu |
| 9,215,895 B2 | 12/2015 | Bowen et al. |
| 9,220,302 B2 | 12/2015 | DePiano et al. |
| 9,220,303 B2 | 12/2015 | Li et al. |
| D747,035 S | 1/2016 | Moradian |
| D747,265 S | 1/2016 | Marini |
| D747,546 S | 1/2016 | Liu |
| D747,603 S | 1/2016 | Gaddis |
| D747,722 S | 1/2016 | Webb |
| D747,852 S | 1/2016 | Meyers |
| D748,329 S | 1/2016 | Bagai et al. |
| 9,226,525 B2 | 1/2016 | Liu |
| 9,226,526 B2 | 1/2016 | Liu |
| 9,233,217 B2 | 1/2016 | Jones |
| 9,240,695 B2 | 1/2016 | Xiang |
| 9,240,697 B2 | 1/2016 | Xiang |
| D748,852 S | 2/2016 | Wu |
| D748,853 S | 2/2016 | Seibel et al. |
| D749,260 S | 2/2016 | Wu |
| D749,261 S | 2/2016 | Chen |
| D749,505 S | 2/2016 | Verleur et al. |
| D749,510 S | 2/2016 | Liu |
| D749,781 S | 2/2016 | Lane |
| D750,320 S | 2/2016 | Verleur et al. |
| D750,321 S | 2/2016 | Chen |
| 9,247,773 B2 | 2/2016 | Memari et al. |
| 9,254,002 B2 | 2/2016 | Chong et al. |
| 9,254,005 B2 | 2/2016 | Liu |
| 9,255,277 B2 | 2/2016 | Bakker et al. |
| D750,835 S | 3/2016 | Wei |
| D751,250 S | 3/2016 | Vuong |
| D751,527 S | 3/2016 | Hinokio et al. |
| D751,755 S | 3/2016 | Van Riper |
| D751,757 S | 3/2016 | Stern |
| D752,277 S | 3/2016 | Liu |
| D752,278 S | 3/2016 | Verleur et al. |
| D752,279 S | 3/2016 | Liu |
| D752,280 S | 3/2016 | Verleur et al. |
| D752,282 S | 3/2016 | Doster |
| D752,283 S | 3/2016 | Doster |
| D752,285 S | 3/2016 | Doster |
| D752,286 S | 3/2016 | Doster |
| D752,808 S | 3/2016 | Hearn |
| 9,271,525 B2 | 3/2016 | Liu |
| 9,271,526 B2 | 3/2016 | Liu |
| 9,271,529 B2 | 3/2016 | Alima |
| 9,272,103 B2 | 3/2016 | Storz |
| 9,277,768 B2 | 3/2016 | Xiu |
| 9,277,769 B2 | 3/2016 | Liu |
| 9,281,705 B2 | 3/2016 | Xiang |
| 9,282,772 B2 | 3/2016 | Tucker et al. |
| 9,282,773 B2 | 3/2016 | Greim et al. |
| 9,289,014 B2 | 3/2016 | Tucker et al. |
| 9,295,286 B2 | 3/2016 | Shin |
| D753,090 S | 4/2016 | Langhammer et al. |
| D753,338 S | 4/2016 | Chen |
| D753,873 S | 4/2016 | Schuessler |
| D753,874 S | 4/2016 | Moreno Medina et al. |
| D754,919 S | 4/2016 | Alarcon et al. |
| 9,301,545 B2 | 4/2016 | Li et al. |
| 9,301,549 B2 | 4/2016 | Liu |
| 9,302,800 B2 | 4/2016 | Holmes et al. |
| 9,302,825 B2 | 4/2016 | Liu |
| 9,308,336 B2 | 4/2016 | Newton |
| 9,312,687 B2 | 4/2016 | Xiang |
| 9,315,890 B1 | 4/2016 | Frick et al. |
| 9,320,300 B2 | 4/2016 | Hon |
| D755,057 S | 5/2016 | Mutter |
| D755,506 S | 5/2016 | Neely, III et al. |
| D755,733 S | 5/2016 | Ikegaya et al. |
| D755,735 S | 5/2016 | Kashimoto |
| D756,030 S | 5/2016 | Chen |
| D756,031 S | 5/2016 | Wu |
| D756,559 S | 5/2016 | Li |
| D757,352 S | 5/2016 | Bagai |
| D757,353 S | 5/2016 | Nunnelly et al. |
| D757,690 S | 5/2016 | Lee et al. |
| D757,994 S | 5/2016 | Moradian |
| D757,995 S | 5/2016 | Liu |
| 9,326,547 B2 | 5/2016 | Tucker et al. |
| 9,326,549 B2 | 5/2016 | Hon |
| 9,332,787 B2 | 5/2016 | Liu |
| 9,345,269 B2 | 5/2016 | Liu |
| 9,350,102 B2 | 5/2016 | Wu |
| 9,350,178 B2 | 5/2016 | Xiang |
| 9,350,181 B2 | 5/2016 | Xiang |
| 9,351,522 B2 | 5/2016 | Safari |
| D758,647 S | 6/2016 | Liu |
| D758,649 S | 6/2016 | Liu |
| D758,650 S | 6/2016 | Wu |
| D759,031 S | 6/2016 | Ozolins et al. |
| D759,297 S | 6/2016 | Liu |
| D759,303 S | 6/2016 | Afridi |
| D760,431 S | 6/2016 | Liu |
| 9,357,802 B2 | 6/2016 | Liu |
| 9,360,379 B2 | 6/2016 | Liu |
| 9,364,025 B2 | 6/2016 | Liu |
| 9,364,026 B2 | 6/2016 | Liu |
| 9,364,027 B2 | 6/2016 | Hon |
| 9,364,800 B2 | 6/2016 | Dubief |
| 9,379,364 B2 | 6/2016 | Alima |
| D760,952 S | 7/2016 | Mayor |
| D761,488 S | 7/2016 | Alarcon et al. |
| D761,999 S | 7/2016 | Liu |

(56) References Cited

U.S. PATENT DOCUMENTS

| | | |
|---|---|---|
| D762,000 S | 7/2016 | Liu |
| D762,001 S | 7/2016 | Liu |
| D762,003 S | 7/2016 | Lomeli |
| D762,326 S | 7/2016 | Liu |
| 9,380,810 B2 | 7/2016 | Rose et al. |
| 9,380,812 B2 | 7/2016 | Chung |
| 9,383,053 B2 | 7/2016 | Liu |
| 9,385,554 B2 | 7/2016 | Xiang |
| 9,386,803 B2 | 7/2016 | Burke et al. |
| D763,203 S | 8/2016 | Ikegaya et al. |
| D763,204 S | 8/2016 | Ikegaya et al. |
| D763,502 S | 8/2016 | Verleur et al. |
| D764,098 S | 8/2016 | Liu |
| D764,703 S | 8/2016 | Liu |
| D765,307 S | 8/2016 | Liu |
| D765,308 S | 8/2016 | Liu |
| D765,309 S | 8/2016 | Liu |
| 9,408,416 B2 | 8/2016 | Monsees et al. |
| 9,413,180 B2 | 8/2016 | Liu |
| 9,414,627 B2 | 8/2016 | Liu |
| 9,414,628 B2 | 8/2016 | Liu |
| 9,415,929 B2 | 8/2016 | Liu |
| 9,417,107 B2 | 8/2016 | Xiang |
| 9,420,831 B2 | 8/2016 | Liu |
| 9,427,022 B2 | 8/2016 | Levin et al. |
| 9,427,023 B2 | 8/2016 | Liu |
| 9,427,024 B2 | 8/2016 | Liu |
| 9,427,025 B2 | 8/2016 | Liu |
| 9,427,026 B2 | 8/2016 | Wu |
| D765,907 S | 9/2016 | Liu |
| D766,503 S | 9/2016 | Liu |
| D766,873 S | 9/2016 | Washio |
| D767,200 S | 9/2016 | Liu |
| D767,201 S | 9/2016 | Starr |
| D767,820 S | 9/2016 | Jordan et al. |
| D767,822 S | 9/2016 | Jordan et al. |
| 9,433,242 B1 | 9/2016 | Buffone |
| 9,438,049 B2 | 9/2016 | Xiang |
| 9,438,051 B2 | 9/2016 | Firman, II et al. |
| 9,439,455 B2 | 9/2016 | Alarcon et al. |
| 9,439,456 B2 | 9/2016 | Liu |
| 9,440,035 B2 | 9/2016 | Chung |
| 9,451,790 B2 | 9/2016 | Liu |
| 9,451,793 B2 | 9/2016 | Zhou |
| 9,455,579 B2 | 9/2016 | Xiang |
| D768,331 S | 10/2016 | Chen |
| D768,920 S | 10/2016 | Jones et al. |
| D768,980 S | 10/2016 | Alexander |
| D769,518 S | 10/2016 | Liu |
| D769,519 S | 10/2016 | Chen |
| D769,520 S | 10/2016 | Hua |
| D769,830 S | 10/2016 | Clymer et al. |
| D770,088 S | 10/2016 | Abadi et al. |
| 9,456,632 B2 | 10/2016 | Hon |
| 9,456,633 B2 | 10/2016 | Liu |
| 9,456,634 B2 | 10/2016 | Wang et al. |
| 9,459,021 B2 | 10/2016 | Greim et al. |
| 9,462,832 B2 | 10/2016 | Lord |
| 9,465,081 B2 | 10/2016 | Xiang |
| 9,474,305 B2 | 10/2016 | Liu |
| D770,395 S | 11/2016 | Clymer et al. |
| D770,676 S | 11/2016 | Bennett et al. |
| D770,678 S | 11/2016 | Shin |
| D770,679 S | 11/2016 | Weigensberg |
| D771,219 S | 11/2016 | Gilbarte |
| D771,307 S | 11/2016 | Wu |
| D771,308 S | 11/2016 | Saydar et al. |
| D772,477 S | 11/2016 | Shin |
| D772,478 S | 11/2016 | Liu |
| D772,479 S | 11/2016 | Stowers et al. |
| D772,480 S | 11/2016 | Hua |
| D772,879 S | 11/2016 | Eliyahu |
| D773,114 S | 11/2016 | Leidel et al. |
| D773,115 S | 11/2016 | Liu |
| D773,116 S | 11/2016 | Liu et al. |
| 9,480,285 B2 | 11/2016 | Liu |
| 9,480,286 B2 | 11/2016 | Liu |
| 9,497,993 B2 | 11/2016 | Vallar |
| 9,497,994 B2 | 11/2016 | Liu |
| 9,497,995 B2 | 11/2016 | Liu |
| 9,497,997 B2 | 11/2016 | Wu |
| 9,497,998 B2 | 11/2016 | Chen |
| 9,497,999 B2 | 11/2016 | Lord |
| 9,498,001 B2 | 11/2016 | Wu |
| 9,498,002 B1 | 11/2016 | Soreide |
| 9,498,588 B2 | 11/2016 | Benassayag et al. |
| 9,502,917 B2 | 11/2016 | Xiang |
| 9,504,278 B2 | 11/2016 | Liu |
| 9,504,279 B2 | 11/2016 | Chen |
| D773,391 S | 12/2016 | Haarburger et al. |
| D773,727 S | 12/2016 | Eksouzian |
| D773,729 S | 12/2016 | Jordan et al. |
| D774,247 S | 12/2016 | Chen |
| D774,248 S | 12/2016 | Jordan et al. |
| D774,514 S | 12/2016 | Turksu et al. |
| D774,693 S | 12/2016 | Liu |
| D774,892 S | 12/2016 | Liu |
| D775,412 S | 12/2016 | Di Bari |
| D775,413 S | 12/2016 | Liu |
| 9,510,624 B2 | 12/2016 | Li et al. |
| 9,516,898 B2 | 12/2016 | Liu |
| 9,521,867 B2 | 12/2016 | Xiang |
| 9,526,272 B2 | 12/2016 | Liu |
| 9,526,273 B2 | 12/2016 | Liu |
| 9,531,183 B2 | 12/2016 | Xiang |
| D776,051 S | 1/2017 | Wang |
| D776,162 S | 1/2017 | Beck et al. |
| D776,270 S | 1/2017 | Wilcox et al. |
| D776,338 S | 1/2017 | Lomeli |
| D776,340 S | 1/2017 | Seibel et al. |
| D776,659 S | 1/2017 | Hou |
| D777,372 S | 1/2017 | Liu |
| D777,976 S | 1/2017 | Mahlmeister |
| 9,532,598 B2 | 1/2017 | Liu |
| 9,532,599 B2 | 1/2017 | Liu |
| 9,532,601 B2 | 1/2017 | Liu |
| 9,532,602 B2 | 1/2017 | Liu |
| 9,532,604 B2 | 1/2017 | Conley et al. |
| 9,532,605 B2 | 1/2017 | Yamada et al. |
| 9,538,781 B2 | 1/2017 | Zheng |
| 9,538,783 B2 | 1/2017 | Xiang |
| 9,538,787 B2 | 1/2017 | Liu |
| 9,538,789 B2 | 1/2017 | Liu |
| 9,545,489 B2 | 1/2017 | Turner et al. |
| 9,549,572 B2 | 1/2017 | Dincer et al. |
| 9,549,573 B2 | 1/2017 | Monsees et al. |
| 9,554,596 B2 | 1/2017 | Liu |
| 9,554,597 B2 | 1/2017 | Liu |
| 9,555,203 B2 | 1/2017 | Terry et al. |
| D778,493 S | 2/2017 | Scott |
| D778,831 S | 2/2017 | Chen |
| D779,677 S | 2/2017 | Chen |
| D779,719 S | 2/2017 | Qiu |
| D780,179 S | 2/2017 | Bae et al. |
| D780,372 S | 2/2017 | Liu |
| 9,560,882 B2 | 2/2017 | Xiang |
| 9,565,873 B2 | 2/2017 | Zheng |
| 9,565,876 B2 | 2/2017 | Tsai |
| 9,572,372 B2 | 2/2017 | Liu |
| 9,572,373 B2 | 2/2017 | Chen |
| 9,572,374 B2 | 2/2017 | Gabbay |
| 9,573,751 B2 | 2/2017 | Liu |
| 9,578,002 B2 | 2/2017 | Wu |
| 9,578,898 B2 | 2/2017 | Liu |
| D780,990 S | 3/2017 | Liu |
| D780,991 S | 3/2017 | Liu |
| D782,108 S | 3/2017 | Jordan et al. |
| D782,728 S | 3/2017 | Pinder |
| D782,729 S | 3/2017 | Wright et al. |
| 9,591,876 B2 | 3/2017 | Alima |
| 9,596,881 B2 | 3/2017 | Chiolini et al. |
| 9,596,884 B2 | 3/2017 | Liu |
| 9,596,885 B2 | 3/2017 | Liu |
| 9,596,886 B2 | 3/2017 | Liu |

(56) References Cited

U.S. PATENT DOCUMENTS

| | | |
|---|---|---|
| 9,596,887 B2 | 3/2017 | Newton |
| 9,602,646 B2 | 3/2017 | Stanimirovic et al. |
| 9,603,198 B2 | 3/2017 | Liu |
| 9,603,386 B2 | 3/2017 | Xiang |
| 9,603,387 B2 | 3/2017 | Liu |
| 9,603,389 B2 | 3/2017 | Chen |
| 9,603,390 B2 | 3/2017 | Li et al. |
| D784,609 S | 4/2017 | Liu |
| D785,234 S | 4/2017 | Liu |
| D785,237 S | 4/2017 | Wu |
| 9,609,893 B2 | 4/2017 | Novak, III et al. |
| 9,615,605 B2 | 4/2017 | Liu |
| 9,615,606 B2 | 4/2017 | Liu |
| 9,615,607 B2 | 4/2017 | Liu |
| 9,620,958 B2 | 4/2017 | Liu |
| 9,622,511 B2 | 4/2017 | Zhu |
| 9,623,592 B2 | 4/2017 | Liu |
| 9,627,661 B2 | 4/2017 | Liu |
| 9,629,391 B2 | 4/2017 | Dube et al. |
| 9,629,394 B2 | 4/2017 | Aronie et al. |
| D785,859 S | 5/2017 | Pang |
| D785,862 S | 5/2017 | Wu |
| D786,789 S | 5/2017 | Jordan et al. |
| D787,114 S | 5/2017 | Scott |
| D788,362 S | 5/2017 | Qiu |
| 9,635,886 B2 | 5/2017 | Tu |
| 9,641,208 B2 | 5/2017 | Sela et al. |
| 9,642,396 B2 | 5/2017 | Liu |
| 9,642,397 B2 | 5/2017 | Dai et al. |
| 9,645,134 B1 | 5/2017 | Farmen et al. |
| 9,648,905 B2 | 5/2017 | Levitz et al. |
| 9,648,908 B1 | 5/2017 | Rinehart et al. |
| 9,648,909 B2 | 5/2017 | Zhou et al. |
| 9,655,383 B2 | 5/2017 | Holzherr et al. |
| 9,655,890 B2 | 5/2017 | Hearn et al. |
| 9,661,878 B2 | 5/2017 | Liu |
| 9,663,266 B2 | 5/2017 | Schwester |
| D788,697 S | 6/2017 | Verleur et al. |
| D790,122 S | 6/2017 | Hawes et al. |
| D790,126 S | 6/2017 | Bennett et al. |
| D790,129 S | 6/2017 | Bennett et al. |
| D790,766 S | 6/2017 | Li |
| 9,668,517 B2 | 6/2017 | Liu |
| 9,668,518 B2 | 6/2017 | Esses |
| 9,668,519 B2 | 6/2017 | Mishra et al. |
| 9,668,520 B2 | 6/2017 | Boldrini |
| 9,668,521 B2 | 6/2017 | Kuczaj |
| 9,668,522 B2 | 6/2017 | Memari et al. |
| 9,668,523 B2 | 6/2017 | Tucker et al. |
| 9,675,108 B2 | 6/2017 | Liu |
| 9,675,113 B2 | 6/2017 | Liu |
| 9,675,114 B2 | 6/2017 | Timmermans |
| 9,675,115 B2 | 6/2017 | Liu |
| 9,675,116 B2 | 6/2017 | Liu |
| 9,675,117 B2 | 6/2017 | Li et al. |
| 9,675,118 B2 | 6/2017 | Chen |
| 9,681,687 B2 | 6/2017 | Liu |
| 9,681,688 B1 | 6/2017 | Rinehart et al. |
| 9,682,203 B2 | 6/2017 | Dahne et al. |
| 9,682,204 B2 | 6/2017 | Matsumoto et al. |
| 9,682,800 B2 | 6/2017 | Xiang |
| 9,687,025 B2 | 6/2017 | Cyphert et al. |
| 9,687,027 B2 | 6/2017 | Poston et al. |
| 9,687,028 B2 | 6/2017 | Park |
| 9,687,029 B2 | 6/2017 | Liu |
| D792,021 S | 7/2017 | Beer et al. |
| D792,022 S | 7/2017 | Li |
| D792,644 S | 7/2017 | Jordan et al. |
| D793,004 S | 7/2017 | Liu |
| 9,693,584 B2 | 7/2017 | Hearn et al. |
| 9,693,586 B2 | 7/2017 | Liu |
| 9,693,587 B2 | 7/2017 | Plojoux et al. |
| 9,693,588 B2 | 7/2017 | Zhu |
| 9,695,033 B1 | 7/2017 | Alshouse et al. |
| 9,700,074 B2 | 7/2017 | Liu |
| 9,700,075 B2 | 7/2017 | Liu |
| 9,700,076 B2 | 7/2017 | Xiang |
| 9,713,345 B2 | 7/2017 | Farine et al. |
| 9,713,346 B2 | 7/2017 | Hon |
| 9,714,878 B2 | 7/2017 | Powers et al. |
| D793,620 S | 8/2017 | Bennett et al. |
| 9,717,274 B2 | 8/2017 | Daehne et al. |
| 9,717,275 B2 | 8/2017 | Liu |
| 9,717,276 B2 | 8/2017 | Brammer et al. |
| 9,717,277 B2 | 8/2017 | Mironov |
| 9,717,278 B2 | 8/2017 | Hon |
| 9,717,279 B2 | 8/2017 | Hon |
| 9,723,872 B2 | 8/2017 | Liu |
| 9,723,873 B2 | 8/2017 | Liu |
| 9,723,874 B2 | 8/2017 | Liu |
| 9,723,875 B2 | 8/2017 | Liu |
| 9,723,876 B2 | 8/2017 | Cadieux et al. |
| 9,723,877 B2 | 8/2017 | Wong et al. |
| 9,730,471 B2 | 8/2017 | Li et al. |
| 9,738,622 B2 | 8/2017 | Dull et al. |
| 9,763,478 B2 | 9/2017 | Cameron et al. |
| 9,770,055 B2 | 9/2017 | Cameron et al. |
| D799,746 S | 10/2017 | Leidel et al. |
| 9,775,380 B2 | 10/2017 | Fernando et al. |
| 9,802,011 B2 | 10/2017 | Davidson et al. |
| 9,806,549 B2 | 10/2017 | Liberti et al. |
| D802,206 S | 11/2017 | Huang et al. |
| 9,809,567 B2 | 11/2017 | Willis et al. |
| 9,814,263 B2 | 11/2017 | Cochand et al. |
| 9,814,272 B2 | 11/2017 | Li et al. |
| 9,820,508 B2 | 11/2017 | Arnel et al. |
| D806,311 S | 12/2017 | Smith |
| 9,999,250 B2 | 6/2018 | Minskoff et al. |
| 2001/0015209 A1 | 8/2001 | Zielke |
| 2001/0032643 A1 | 10/2001 | Hochrainer et al. |
| 2001/0032795 A1 | 10/2001 | Weinstein et al. |
| 2001/0052480 A1 | 12/2001 | Kawaguchi et al. |
| 2002/0029779 A1 | 3/2002 | Schmidt et al. |
| 2002/0043554 A1 | 4/2002 | White et al. |
| 2002/0078951 A1 | 6/2002 | Nichols et al. |
| 2002/0088469 A1 | 7/2002 | Rennecamp |
| 2002/0142291 A1 | 10/2002 | Bauer et al. |
| 2002/0175164 A1 | 11/2002 | Dees et al. |
| 2003/0004426 A1 | 1/2003 | Melker et al. |
| 2003/0005926 A1 | 1/2003 | Jones et al. |
| 2003/0089377 A1 | 5/2003 | Hajaligol et al. |
| 2003/0132219 A1 | 7/2003 | Cox et al. |
| 2003/0149372 A1 | 8/2003 | Smith et al. |
| 2003/0150451 A1 | 8/2003 | Shayan |
| 2003/0154991 A1 | 8/2003 | Fournier et al. |
| 2004/0031495 A1 | 2/2004 | Steinberg |
| 2004/0050382 A1 | 3/2004 | Goodchild |
| 2004/0099266 A1 | 5/2004 | Cross et al. |
| 2004/0129280 A1 | 7/2004 | Woodson et al. |
| 2004/0149296 A1 | 8/2004 | Rostami et al. |
| 2004/0149624 A1 | 8/2004 | Wischusen et al. |
| 2004/0173224 A1 | 9/2004 | Burgard et al. |
| 2004/0173229 A1 | 9/2004 | Crooks et al. |
| 2004/0182403 A1 | 9/2004 | Andersson et al. |
| 2004/0191322 A1 | 9/2004 | Hansson |
| 2004/0221857 A1 | 11/2004 | Dominguez |
| 2004/0226569 A1 | 11/2004 | Yang et al. |
| 2004/0237974 A1 | 12/2004 | Min |
| 2005/0016549 A1 | 1/2005 | Banerjee et al. |
| 2005/0016550 A1 | 1/2005 | Katase |
| 2005/0022806 A1 | 2/2005 | Beaumont et al. |
| 2005/0029137 A1 | 2/2005 | Wang |
| 2005/0034723 A1 | 2/2005 | Bennett et al. |
| 2005/0061759 A1 | 3/2005 | Doucette |
| 2005/0069831 A1 | 3/2005 | St. Charles et al. |
| 2005/0081601 A1 | 4/2005 | Lawson |
| 2005/0090798 A1 | 4/2005 | Clark et al. |
| 2005/0118545 A1 | 6/2005 | Wong |
| 2005/0145533 A1 | 7/2005 | Seligson |
| 2005/0172976 A1 | 8/2005 | Newman et al. |
| 2005/0229918 A1 | 10/2005 | Shim |
| 2005/0236006 A1 | 10/2005 | Cowan |
| 2005/0244521 A1 | 11/2005 | Strickland et al. |
| 2005/0251289 A1 | 11/2005 | Bonney et al. |

(56) References Cited

U.S. PATENT DOCUMENTS

| | | |
|---|---|---|
| 2005/0268911 A1 | 12/2005 | Cross et al. |
| 2006/0016453 A1 | 1/2006 | Kim |
| 2006/0018840 A1 | 1/2006 | Lechuga-Ballesteros et al. |
| 2006/0054676 A1 | 3/2006 | Wischusen |
| 2006/0102175 A1 | 5/2006 | Nelson |
| 2006/0150991 A1 | 7/2006 | Lee |
| 2006/0185687 A1 | 8/2006 | Hearn et al. |
| 2006/0191546 A1 | 8/2006 | Takano et al. |
| 2006/0191548 A1 | 8/2006 | Strickland et al. |
| 2006/0196518 A1 | 9/2006 | Hon |
| 2006/0254948 A1 | 11/2006 | Herbert et al. |
| 2006/0255105 A1 | 11/2006 | Sweet |
| 2007/0006889 A1 | 1/2007 | Kobal et al. |
| 2007/0045288 A1 | 3/2007 | Nelson |
| 2007/0062523 A1 | 3/2007 | Sexton et al. |
| 2007/0062548 A1 | 3/2007 | Horstmann et al. |
| 2007/0074734 A1 | 4/2007 | Braunshteyn et al. |
| 2007/0089757 A1 | 4/2007 | Bryman |
| 2007/0098148 A1 | 5/2007 | Sherman |
| 2007/0102013 A1 | 5/2007 | Adams et al. |
| 2007/0125765 A1 | 6/2007 | Nelson |
| 2007/0144514 A1 | 6/2007 | Yeates et al. |
| 2007/0163610 A1 | 7/2007 | Lindell et al. |
| 2007/0191756 A1 | 8/2007 | Tapper |
| 2007/0215164 A1 | 9/2007 | Mehio |
| 2007/0215168 A1 | 9/2007 | Banerjee et al. |
| 2007/0235046 A1 | 10/2007 | Gedevanishvili |
| 2007/0267033 A1 | 11/2007 | Mishra et al. |
| 2007/0277816 A1 | 12/2007 | Morrison et al. |
| 2007/0280652 A1 | 12/2007 | Williams |
| 2007/0283972 A1 | 12/2007 | Monsees et al. |
| 2007/0295347 A1 | 12/2007 | Paine et al. |
| 2008/0000763 A1 | 1/2008 | Cove |
| 2008/0023003 A1 | 1/2008 | Rosenthal |
| 2008/0029095 A1 | 2/2008 | Esser |
| 2008/0092912 A1 | 4/2008 | Robinson et al. |
| 2008/0138423 A1 | 6/2008 | Gonda |
| 2008/0149118 A1 | 6/2008 | Oglesby et al. |
| 2008/0207276 A1 | 8/2008 | Burrell |
| 2008/0216828 A1 | 9/2008 | Wensley et al. |
| 2008/0241255 A1 | 10/2008 | Rose et al. |
| 2008/0257367 A1 | 10/2008 | Paterno et al. |
| 2008/0276947 A1 | 11/2008 | Martzel |
| 2008/0286340 A1 | 11/2008 | Andersson et al. |
| 2008/0302375 A1 | 12/2008 | Andersson et al. |
| 2009/0004249 A1 | 1/2009 | Gonda |
| 2009/0095287 A1 | 4/2009 | Emarlou |
| 2009/0095311 A1 | 4/2009 | Han |
| 2009/0111287 A1 | 4/2009 | Lindberg et al. |
| 2009/0126745 A1 | 5/2009 | Hon |
| 2009/0133691 A1 | 5/2009 | Yamada et al. |
| 2009/0133703 A1 | 5/2009 | Strickland et al. |
| 2009/0133704 A1 | 5/2009 | Strickland et al. |
| 2009/0151717 A1 | 6/2009 | Bowen et al. |
| 2009/0188490 A1 | 7/2009 | Han |
| 2009/0192443 A1 | 7/2009 | Collins, Jr. |
| 2009/0230117 A1 | 9/2009 | Fernando et al. |
| 2009/0255534 A1 | 10/2009 | Paterno |
| 2009/0260641 A1 | 10/2009 | Monsees et al. |
| 2009/0260642 A1 | 10/2009 | Monsees et al. |
| 2009/0267252 A1 | 10/2009 | Ikeyama |
| 2009/0272379 A1 | 11/2009 | Thorens et al. |
| 2009/0283103 A1 | 11/2009 | Nielsen et al. |
| 2009/0288668 A1 | 11/2009 | Inagaki |
| 2009/0288669 A1 | 11/2009 | Hutchens |
| 2009/0293892 A1 | 12/2009 | Williams et al. |
| 2009/0293895 A1 | 12/2009 | Axelsson et al. |
| 2009/0308387 A1 | 12/2009 | Andersen et al. |
| 2010/0000672 A1 | 1/2010 | Fogle |
| 2010/0006092 A1 | 1/2010 | Hale et al. |
| 2010/0024834 A1 | 2/2010 | Oglesby et al. |
| 2010/0031968 A1 | 2/2010 | Sheikh et al. |
| 2010/0059073 A1 | 3/2010 | Hoffmann et al. |
| 2010/0156193 A1 | 6/2010 | Rhodes et al. |
| 2010/0163063 A1 | 7/2010 | Fernando et al. |
| 2010/0163065 A1 | 7/2010 | Chang |
| 2010/0186757 A1 | 7/2010 | Crooks et al. |
| 2010/0200006 A1 | 8/2010 | Robinson et al. |
| 2010/0200008 A1 | 8/2010 | Taieb |
| 2010/0236562 A1 | 9/2010 | Hearn et al. |
| 2010/0242974 A1 | 9/2010 | Pan |
| 2010/0242976 A1 | 9/2010 | Katayama et al. |
| 2010/0275938 A1 | 11/2010 | Roth et al. |
| 2010/0276333 A1 | 11/2010 | Couture |
| 2010/0307116 A1 | 12/2010 | Fisher |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0030706 A1 | 2/2011 | Gibson et al. |
| 2011/0036346 A1 | 2/2011 | Cohen et al. |
| 2011/0036363 A1 | 2/2011 | Urtsev et al. |
| 2011/0041861 A1 | 2/2011 | Sebastian et al. |
| 2011/0049226 A1 | 3/2011 | Moreau et al. |
| 2011/0083684 A1 | 4/2011 | Luan et al. |
| 2011/0094523 A1 | 4/2011 | Thorens et al. |
| 2011/0097060 A1 | 4/2011 | Michael Buzzetti |
| 2011/0108023 A1 | 5/2011 | McKinney et al. |
| 2011/0120482 A1 | 5/2011 | Brenneise |
| 2011/0126831 A1 | 6/2011 | Fernandez Pernia |
| 2011/0155151 A1 | 6/2011 | Newman et al. |
| 2011/0155153 A1 | 6/2011 | Thorens et al. |
| 2011/0162667 A1 | 7/2011 | Burke et al. |
| 2011/0168194 A1 | 7/2011 | Hon |
| 2011/0180433 A1 | 7/2011 | Rennecamp |
| 2011/0192397 A1 | 8/2011 | Saskar et al. |
| 2011/0226236 A1 | 9/2011 | Buchberger |
| 2011/0226266 A1 | 9/2011 | Tao |
| 2011/0232654 A1 | 9/2011 | Mass |
| 2011/0232655 A1 | 9/2011 | Chan et al. |
| 2011/0236002 A1 | 9/2011 | Oglesby et al. |
| 2011/0240047 A1 | 10/2011 | Adamic |
| 2011/0263947 A1 | 10/2011 | Utley et al. |
| 2011/0265788 A1 | 11/2011 | Wu |
| 2011/0265806 A1* | 11/2011 | Alarcon ............... A24F 47/00 131/273 |
| 2011/0268809 A1 | 11/2011 | Brinkley et al. |
| 2011/0277780 A1 | 11/2011 | Terry et al. |
| 2011/0278189 A1 | 11/2011 | Terry et al. |
| 2011/0284520 A1* | 11/2011 | Fong ............... H05B 1/0272 219/494 |
| 2011/0290248 A1 | 12/2011 | Schennum |
| 2011/0290269 A1 | 12/2011 | Shimizu |
| 2011/0293535 A1 | 12/2011 | Kosik et al. |
| 2011/0308521 A1 | 12/2011 | Kofford |
| 2011/0315152 A1 | 12/2011 | Hearn et al. |
| 2011/0315701 A1 | 12/2011 | Everson |
| 2012/0006342 A1 | 1/2012 | Rose et al. |
| 2012/0060853 A1 | 3/2012 | Robinson et al. |
| 2012/0077849 A1 | 3/2012 | Howson et al. |
| 2012/0086391 A1 | 4/2012 | Smith |
| 2012/0111346 A1 | 5/2012 | Rinker et al. |
| 2012/0111347 A1 | 5/2012 | Hon |
| 2012/0118301 A1 | 5/2012 | Montaser |
| 2012/0118307 A1 | 5/2012 | Tu |
| 2012/0125353 A1 | 5/2012 | Wollin |
| 2012/0138052 A1 | 6/2012 | Hearn et al. |
| 2012/0174914 A1 | 7/2012 | Pirshafiey et al. |
| 2012/0199146 A1 | 8/2012 | Marangos |
| 2012/0199572 A1 | 8/2012 | Shen et al. |
| 2012/0199663 A1 | 8/2012 | Qiu |
| 2012/0204889 A1 | 8/2012 | Xiu |
| 2012/0211015 A1 | 8/2012 | Li et al. |
| 2012/0227753 A1 | 9/2012 | Newton |
| 2012/0234315 A1 | 9/2012 | Li et al. |
| 2012/0234821 A1 | 9/2012 | Shimizu |
| 2012/0247494 A1 | 10/2012 | Oglesby et al. |
| 2012/0255567 A1 | 10/2012 | Rose et al. |
| 2012/0260926 A1 | 10/2012 | Tu et al. |
| 2012/0260927 A1 | 10/2012 | Liu |
| 2012/0261286 A1 | 10/2012 | Holloway et al. |
| 2012/0267383 A1 | 10/2012 | Van Rooyen |
| 2012/0279512 A1 | 11/2012 | Hon |
| 2012/0285475 A1 | 11/2012 | Liu |

(56) References Cited

U.S. PATENT DOCUMENTS

| | | |
|---|---|---|
| 2012/0291791 A1 | 11/2012 | Pradeep |
| 2012/0298676 A1 | 11/2012 | Cooks |
| 2012/0312313 A1 | 12/2012 | Frija |
| 2012/0318882 A1 | 12/2012 | Abehasera |
| 2012/0325227 A1 | 12/2012 | Robinson et al. |
| 2012/0325228 A1 | 12/2012 | Williams |
| 2013/0008457 A1 | 1/2013 | Zheng et al. |
| 2013/0014755 A1 | 1/2013 | Kumar et al. |
| 2013/0014772 A1 | 1/2013 | Liu |
| 2013/0019887 A1 | 1/2013 | Liu |
| 2013/0023850 A1 | 1/2013 | Imran et al. |
| 2013/0025609 A1 | 1/2013 | Liu |
| 2013/0037041 A1 | 2/2013 | Worm et al. |
| 2013/0042865 A1 | 2/2013 | Monsees et al. |
| 2013/0047984 A1 | 2/2013 | Dahne et al. |
| 2013/0056012 A1 | 3/2013 | Hearn et al. |
| 2013/0056013 A1 | 3/2013 | Terry et al. |
| 2013/0068239 A1 | 3/2013 | Youn |
| 2013/0074857 A1 | 3/2013 | Buchberger |
| 2013/0081642 A1 | 4/2013 | Safari |
| 2013/0087160 A1 | 4/2013 | Gherghe |
| 2013/0125906 A1 | 5/2013 | Hon |
| 2013/0133675 A1 | 5/2013 | Shinozaki et al. |
| 2013/0139833 A1 | 6/2013 | Hon |
| 2013/0140200 A1 | 6/2013 | Scatterday |
| 2013/0146489 A1 | 6/2013 | Scatterday |
| 2013/0152922 A1 | 6/2013 | Benassayag et al. |
| 2013/0152954 A1 | 6/2013 | Youn |
| 2013/0167854 A1 | 7/2013 | Shin |
| 2013/0168880 A1 | 7/2013 | Duke |
| 2013/0174842 A1 | 7/2013 | Young et al. |
| 2013/0186416 A1 | 7/2013 | Gao et al. |
| 2013/0192615 A1 | 8/2013 | Tucker et al. |
| 2013/0192618 A1 | 8/2013 | Li et al. |
| 2013/0192619 A1 | 8/2013 | Tucker et al. |
| 2013/0199528 A1* | 8/2013 | Goodman ............ A24F 47/008 131/329 |
| 2013/0213417 A1 | 8/2013 | Chong et al. |
| 2013/0213418 A1 | 8/2013 | Tucker et al. |
| 2013/0213419 A1 | 8/2013 | Tucker et al. |
| 2013/0220315 A1 | 8/2013 | Conley et al. |
| 2013/0220847 A1 | 8/2013 | Fisher et al. |
| 2013/0228190 A1 | 9/2013 | Weiss et al. |
| 2013/0228191 A1 | 9/2013 | Newton |
| 2013/0233086 A1 | 9/2013 | Besling et al. |
| 2013/0247924 A1 | 9/2013 | Scatterday et al. |
| 2013/0248385 A1 | 9/2013 | Scatterday et al. |
| 2013/0255702 A1 | 10/2013 | Griffith, Jr. et al. |
| 2013/0263869 A1 | 10/2013 | Zhu |
| 2013/0276802 A1 | 10/2013 | Scatterday |
| 2013/0284190 A1 | 10/2013 | Scatterday et al. |
| 2013/0284191 A1 | 10/2013 | Scatterday et al. |
| 2013/0284192 A1 | 10/2013 | Peleg et al. |
| 2013/0298905 A1 | 11/2013 | Levin et al. |
| 2013/0306065 A1 | 11/2013 | Thorens et al. |
| 2013/0306084 A1 | 11/2013 | Flick |
| 2013/0312742 A1 | 11/2013 | Monsees et al. |
| 2013/0319431 A1 | 12/2013 | Cyphert et al. |
| 2013/0319435 A1 | 12/2013 | Flick |
| 2013/0319436 A1 | 12/2013 | Liu |
| 2013/0319437 A1 | 12/2013 | Liu |
| 2013/0319438 A1 | 12/2013 | Liu |
| 2013/0319439 A1 | 12/2013 | Gorelick et al. |
| 2013/0319440 A1 | 12/2013 | Capuano |
| 2013/0333700 A1 | 12/2013 | Buchberger |
| 2013/0333711 A1 | 12/2013 | Liu |
| 2013/0336358 A1 | 12/2013 | Liu |
| 2013/0340775 A1 | 12/2013 | Juster et al. |
| 2013/0342157 A1 | 12/2013 | Liu |
| 2014/0000638 A1 | 1/2014 | Sebastian et al. |
| 2014/0007891 A1 | 1/2014 | Liu |
| 2014/0007892 A1 | 1/2014 | Liu |
| 2014/0014124 A1 | 1/2014 | Glasberg et al. |
| 2014/0014126 A1 | 1/2014 | Peleg et al. |
| 2014/0020697 A1 | 1/2014 | Liu |
| 2014/0034071 A1 | 2/2014 | Levitz et al. |
| 2014/0035391 A1 | 2/2014 | Kitani |
| 2014/0041655 A1 | 2/2014 | Barron et al. |
| 2014/0041658 A1 | 2/2014 | Goodman et al. |
| 2014/0048086 A1 | 2/2014 | Zhanghua |
| 2014/0053856 A1 | 2/2014 | Liu |
| 2014/0053858 A1 | 2/2014 | Liu |
| 2014/0060528 A1 | 3/2014 | Liu |
| 2014/0060529 A1 | 3/2014 | Zhang |
| 2014/0060552 A1 | 3/2014 | Cohen |
| 2014/0060556 A1 | 3/2014 | Liu |
| 2014/0062417 A1 | 3/2014 | Li et al. |
| 2014/0069424 A1 | 3/2014 | Poston et al. |
| 2014/0069425 A1 | 3/2014 | Zhang |
| 2014/0083442 A1 | 3/2014 | Scatterday |
| 2014/0096781 A1 | 4/2014 | Sears et al. |
| 2014/0096782 A1 | 4/2014 | Ampolini et al. |
| 2014/0107815 A1 | 4/2014 | LaMothe |
| 2014/0109898 A1 | 4/2014 | Li et al. |
| 2014/0109921 A1 | 4/2014 | Chen |
| 2014/0116455 A1 | 5/2014 | Youn |
| 2014/0123989 A1 | 5/2014 | LaMothe |
| 2014/0123990 A1 | 5/2014 | Timmermans |
| 2014/0130796 A1 | 5/2014 | Liu |
| 2014/0130797 A1 | 5/2014 | Liu |
| 2014/0130816 A1 | 5/2014 | Liu |
| 2014/0130817 A1 | 5/2014 | Li et al. |
| 2014/0144429 A1* | 5/2014 | Wensley ............... A61M 15/06 128/200.14 |
| 2014/0144453 A1 | 5/2014 | Capuano et al. |
| 2014/0150784 A1 | 6/2014 | Liu |
| 2014/0150785 A1 | 6/2014 | Malik et al. |
| 2014/0150810 A1 | 6/2014 | Hon |
| 2014/0158129 A1 | 6/2014 | Pratt, Jr. et al. |
| 2014/0161301 A1 | 6/2014 | Merenda |
| 2014/0166028 A1 | 6/2014 | Fuisz et al. |
| 2014/0166029 A1 | 6/2014 | Weigensberg et al. |
| 2014/0166030 A1 | 6/2014 | Li et al. |
| 2014/0166032 A1 | 6/2014 | Gindrat |
| 2014/0174458 A1 | 6/2014 | Katz |
| 2014/0174459 A1 | 6/2014 | Burstyn |
| 2014/0175081 A1 | 6/2014 | Hwa |
| 2014/0178461 A1 | 6/2014 | Rigas |
| 2014/0182609 A1 | 7/2014 | Liu |
| 2014/0182610 A1 | 7/2014 | Liu |
| 2014/0182611 A1 | 7/2014 | Liu |
| 2014/0182612 A1 | 7/2014 | Chen |
| 2014/0190477 A1 | 7/2014 | Qiu |
| 2014/0190478 A1 | 7/2014 | Liu |
| 2014/0190496 A1 | 7/2014 | Wensley et al. |
| 2014/0190501 A1 | 7/2014 | Liu |
| 2014/0190502 A1 | 7/2014 | Liu |
| 2014/0190503 A1 | 7/2014 | Li et al. |
| 2014/0196716 A1 | 7/2014 | Liu |
| 2014/0196718 A1 | 7/2014 | Li et al. |
| 2014/0196731 A1 | 7/2014 | Scatterday |
| 2014/0196733 A1 | 7/2014 | Liu |
| 2014/0196734 A1 | 7/2014 | Liu |
| 2014/0196735 A1 | 7/2014 | Liu |
| 2014/0202474 A1 | 7/2014 | Peleg et al. |
| 2014/0202475 A1 | 7/2014 | Liu |
| 2014/0202477 A1 | 7/2014 | Qi et al. |
| 2014/0209096 A1 | 7/2014 | Cheyene |
| 2014/0209106 A1 | 7/2014 | Liu |
| 2014/0209107 A1 | 7/2014 | Liu |
| 2014/0209108 A1 | 7/2014 | Li et al. |
| 2014/0209109 A1 | 7/2014 | Larson |
| 2014/0209110 A1 | 7/2014 | Hon |
| 2014/0216450 A1 | 8/2014 | Liu |
| 2014/0216483 A1 | 8/2014 | Alima |
| 2014/0216484 A1 | 8/2014 | Liu |
| 2014/0224244 A1 | 8/2014 | Liu |
| 2014/0224267 A1 | 8/2014 | Levitz et al. |
| 2014/0230835 A1 | 8/2014 | Saliman |
| 2014/0238421 A1 | 8/2014 | Shapiro |
| 2014/0238422 A1 | 8/2014 | Plunkett et al. |
| 2014/0238423 A1 | 8/2014 | Tucker et al. |
| 2014/0238424 A1 | 8/2014 | Macko et al. |
| 2014/0246031 A1 | 9/2014 | Liu |

(56) References Cited

U.S. PATENT DOCUMENTS

| | | |
|---|---|---|
| 2014/0246033 A1 | 9/2014 | Daehne et al. |
| 2014/0251324 A1 | 9/2014 | Xiang |
| 2014/0251325 A1 | 9/2014 | Liu |
| 2014/0251356 A1 | 9/2014 | Xiang |
| 2014/0253144 A1 | 9/2014 | Novak, III et al. |
| 2014/0254055 A1 | 9/2014 | Xiang |
| 2014/0259026 A1 | 9/2014 | Xiang |
| 2014/0261408 A1 | 9/2014 | DePiano et al. |
| 2014/0261474 A1 | 9/2014 | Gonda |
| 2014/0261479 A1 | 9/2014 | Xu et al. |
| 2014/0261483 A1 | 9/2014 | Hopps |
| 2014/0261486 A1 | 9/2014 | Potter et al. |
| 2014/0261487 A1 | 9/2014 | Chapman et al. |
| 2014/0261488 A1 | 9/2014 | Tucker |
| 2014/0261489 A1 | 9/2014 | Cadieux et al. |
| 2014/0261490 A1 | 9/2014 | Kane |
| 2014/0261491 A1 | 9/2014 | Hawes |
| 2014/0261492 A1 | 9/2014 | Kane et al. |
| 2014/0261493 A1 | 9/2014 | Smith et al. |
| 2014/0261494 A1 | 9/2014 | Scatterday |
| 2014/0261495 A1 | 9/2014 | Novak, III et al. |
| 2014/0261497 A1 | 9/2014 | Liu |
| 2014/0261498 A1 | 9/2014 | Liu |
| 2014/0261500 A1 | 9/2014 | Park |
| 2014/0270727 A1* | 9/2014 | Ampolini ............ A24F 47/008 392/387 |
| 2014/0270729 A1 | 9/2014 | DePiano et al. |
| 2014/0270730 A1 | 9/2014 | DePiano et al. |
| 2014/0271946 A1 | 9/2014 | Kobal et al. |
| 2014/0274940 A1 | 9/2014 | Mishra et al. |
| 2014/0276536 A1 | 9/2014 | Estes |
| 2014/0278250 A1 | 9/2014 | Smith et al. |
| 2014/0278258 A1 | 9/2014 | Shafer |
| 2014/0283823 A1 | 9/2014 | Liu |
| 2014/0283855 A1 | 9/2014 | Hawes et al. |
| 2014/0283856 A1 | 9/2014 | Xiang |
| 2014/0283857 A1 | 9/2014 | Liu |
| 2014/0283858 A1 | 9/2014 | Liu |
| 2014/0290673 A1 | 10/2014 | Liu |
| 2014/0290676 A1 | 10/2014 | Liu |
| 2014/0290677 A1 | 10/2014 | Liu |
| 2014/0299137 A1 | 10/2014 | Kieckbusch et al. |
| 2014/0299138 A1 | 10/2014 | Xiang |
| 2014/0299139 A1 | 10/2014 | Liu |
| 2014/0299140 A1 | 10/2014 | Liu |
| 2014/0299141 A1 | 10/2014 | Flick |
| 2014/0301721 A1 | 10/2014 | Ruscio et al. |
| 2014/0305450 A1 | 10/2014 | Xiang |
| 2014/0305451 A1 | 10/2014 | Liu |
| 2014/0305452 A1 | 10/2014 | Liu |
| 2014/0305454 A1 | 10/2014 | Rinker et al. |
| 2014/0311503 A1 | 10/2014 | Liu |
| 2014/0311504 A1 | 10/2014 | Liu |
| 2014/0311505 A1 | 10/2014 | Liu |
| 2014/0318560 A1 | 10/2014 | Hon |
| 2014/0321837 A1 | 10/2014 | Flick |
| 2014/0332016 A1 | 11/2014 | Bellinger et al. |
| 2014/0332017 A1 | 11/2014 | Liu |
| 2014/0332018 A1 | 11/2014 | Liu |
| 2014/0332019 A1 | 11/2014 | Liu |
| 2014/0332020 A1 | 11/2014 | Li et al. |
| 2014/0332022 A1 | 11/2014 | Li et al. |
| 2014/0334803 A1 | 11/2014 | Li et al. |
| 2014/0334804 A1 | 11/2014 | Choi |
| 2014/0338680 A1 | 11/2014 | Abramov et al. |
| 2014/0338681 A1 | 11/2014 | Liu |
| 2014/0338682 A1 | 11/2014 | Liu |
| 2014/0338683 A1 | 11/2014 | Liu |
| 2014/0338684 A1 | 11/2014 | Liu |
| 2014/0338685 A1 | 11/2014 | Amir |
| 2014/0345606 A1 | 11/2014 | Talon |
| 2014/0345630 A1 | 11/2014 | Lipowicz |
| 2014/0345631 A1 | 11/2014 | Bowen et al. |
| 2014/0345632 A1 | 11/2014 | Scatterday |
| 2014/0345633 A1 | 11/2014 | Talon et al. |
| 2014/0345635 A1 | 11/2014 | Rabinowitz et al. |
| 2014/0352177 A1 | 12/2014 | Rehkemper |
| 2014/0352705 A1 | 12/2014 | Liu |
| 2014/0352707 A1 | 12/2014 | Liu |
| 2014/0353856 A1 | 12/2014 | Dubief |
| 2014/0353867 A1 | 12/2014 | Liu |
| 2014/0354215 A1 | 12/2014 | Xiang |
| 2014/0355969 A1 | 12/2014 | Stern |
| 2014/0356607 A1 | 12/2014 | Woodcock |
| 2014/0360512 A1 | 12/2014 | Xiang |
| 2014/0360516 A1 | 12/2014 | Liu |
| 2014/0366894 A1 | 12/2014 | Liu |
| 2014/0366895 A1 | 12/2014 | Li et al. |
| 2014/0366896 A1 | 12/2014 | Li et al. |
| 2014/0366897 A1 | 12/2014 | Liu |
| 2014/0366898 A1 | 12/2014 | Monsees et al. |
| 2014/0366902 A1 | 12/2014 | Chiolini et al. |
| 2014/0373833 A1 | 12/2014 | Liu |
| 2014/0373855 A1 | 12/2014 | Zheng |
| 2014/0373858 A1 | 12/2014 | Liu |
| 2014/0376895 A1 | 12/2014 | Han |
| 2014/0378790 A1 | 12/2014 | Cohen |
| 2015/0000682 A1 | 1/2015 | Liu |
| 2015/0000683 A1 | 1/2015 | Liu |
| 2015/0007834 A1 | 1/2015 | Liu |
| 2015/0007835 A1 | 1/2015 | Liu |
| 2015/0007836 A1 | 1/2015 | Li et al. |
| 2015/0013692 A1 | 1/2015 | Liu |
| 2015/0013693 A1 | 1/2015 | Fuisz et al. |
| 2015/0013696 A1 | 1/2015 | Plojoux et al. |
| 2015/0013700 A1 | 1/2015 | Liu |
| 2015/0013701 A1 | 1/2015 | Liu |
| 2015/0013702 A1 | 1/2015 | Liu |
| 2015/0015187 A1 | 1/2015 | Xiang |
| 2015/0020822 A1 | 1/2015 | Janardhan et al. |
| 2015/0020823 A1 | 1/2015 | Lipowicz et al. |
| 2015/0020824 A1 | 1/2015 | Bowen et al. |
| 2015/0020825 A1 | 1/2015 | Galloway et al. |
| 2015/0020826 A1 | 1/2015 | Liu |
| 2015/0020827 A1 | 1/2015 | Liu |
| 2015/0020828 A1 | 1/2015 | Liu |
| 2015/0020829 A1 | 1/2015 | Li |
| 2015/0020830 A1 | 1/2015 | Koller |
| 2015/0020831 A1 | 1/2015 | Weigensberg et al. |
| 2015/0020833 A1 | 1/2015 | Conley et al. |
| 2015/0020961 A1 | 1/2015 | Grisle et al. |
| 2015/0027454 A1 | 1/2015 | Li et al. |
| 2015/0027455 A1 | 1/2015 | Peleg et al. |
| 2015/0027456 A1 | 1/2015 | Janardhan et al. |
| 2015/0027457 A1 | 1/2015 | Janardhan et al. |
| 2015/0027460 A1 | 1/2015 | Liu |
| 2015/0027461 A1 | 1/2015 | Liu |
| 2015/0027462 A1 | 1/2015 | Liu |
| 2015/0027463 A1 | 1/2015 | Liu |
| 2015/0027464 A1 | 1/2015 | Liu |
| 2015/0027465 A1 | 1/2015 | Liu |
| 2015/0027466 A1 | 1/2015 | Xiang |
| 2015/0027467 A1 | 1/2015 | Liu |
| 2015/0027468 A1 | 1/2015 | Li et al. |
| 2015/0027469 A1 | 1/2015 | Tucker et al. |
| 2015/0027470 A1 | 1/2015 | Kane et al. |
| 2015/0027471 A1 | 1/2015 | Feldman et al. |
| 2015/0027472 A1 | 1/2015 | Amir |
| 2015/0027473 A1 | 1/2015 | Graf |
| 2015/0034102 A1 | 2/2015 | Faramarzian |
| 2015/0034103 A1 | 2/2015 | Hon |
| 2015/0034104 A1 | 2/2015 | Zhou |
| 2015/0034105 A1 | 2/2015 | Liu |
| 2015/0034106 A1 | 2/2015 | Liu |
| 2015/0034107 A1 | 2/2015 | Liu |
| 2015/0034507 A1 | 2/2015 | Liu |
| 2015/0035540 A1 | 2/2015 | Xiang |
| 2015/0038567 A1 | 2/2015 | Herkenroth et al. |
| 2015/0040927 A1 | 2/2015 | Li et al. |
| 2015/0040928 A1 | 2/2015 | Saydar et al. |
| 2015/0040929 A1 | 2/2015 | Hon |
| 2015/0041482 A1 | 2/2015 | Liu |
| 2015/0047658 A1 | 2/2015 | Cyphert et al. |
| 2015/0047659 A1 | 2/2015 | Liu |

(56) References Cited

U.S. PATENT DOCUMENTS

| | | |
|---|---|---|
| 2015/0047660 A1 | 2/2015 | Liu |
| 2015/0047661 A1 | 2/2015 | Blackley et al. |
| 2015/0047662 A1 | 2/2015 | Hopps |
| 2015/0047663 A1 | 2/2015 | Liu |
| 2015/0053215 A1 | 2/2015 | Liu |
| 2015/0053216 A1 | 2/2015 | Liu |
| 2015/0053217 A1 | 2/2015 | Steingraber et al. |
| 2015/0053220 A1 | 2/2015 | Levy et al. |
| 2015/0057341 A1 | 2/2015 | Perry |
| 2015/0059779 A1 | 3/2015 | Alarcon et al. |
| 2015/0059780 A1 | 3/2015 | Davis et al. |
| 2015/0059782 A1 | 3/2015 | Liu |
| 2015/0059783 A1 | 3/2015 | Liu |
| 2015/0059784 A1 | 3/2015 | Liu |
| 2015/0059785 A1 | 3/2015 | Liu |
| 2015/0068523 A1 | 3/2015 | Powers et al. |
| 2015/0068543 A1 | 3/2015 | Liu |
| 2015/0068545 A1 | 3/2015 | Moldoveanu et al. |
| 2015/0075545 A1 | 3/2015 | Xiang |
| 2015/0075546 A1 | 3/2015 | Kueny, Sr. et al. |
| 2015/0078735 A1 | 3/2015 | Cormack |
| 2015/0080265 A1 | 3/2015 | Elzinga et al. |
| 2015/0082859 A1 | 3/2015 | Xiang |
| 2015/0083144 A1 | 3/2015 | Xiang |
| 2015/0083145 A1 | 3/2015 | Li et al. |
| 2015/0083146 A1 | 3/2015 | Goldman et al. |
| 2015/0083147 A1 | 3/2015 | Schiff et al. |
| 2015/0090256 A1 | 4/2015 | Chung |
| 2015/0090277 A1 | 4/2015 | Xiang |
| 2015/0090278 A1 | 4/2015 | Schiff et al. |
| 2015/0090279 A1 | 4/2015 | Chen |
| 2015/0090280 A1 | 4/2015 | Chen |
| 2015/0090281 A1 | 4/2015 | Chen |
| 2015/0100441 A1 | 4/2015 | Alarcon et al. |
| 2015/0101606 A1 | 4/2015 | White |
| 2015/0101622 A1 | 4/2015 | Liu |
| 2015/0101623 A1 | 4/2015 | Liu |
| 2015/0101625 A1 | 4/2015 | Newton et al. |
| 2015/0101626 A1 | 4/2015 | Li et al. |
| 2015/0101945 A1 | 4/2015 | Scatterday |
| 2015/0102777 A1 | 4/2015 | Cooper |
| 2015/0105455 A1 | 4/2015 | Bjorncrantz |
| 2015/0107609 A1 | 4/2015 | Liu |
| 2015/0107610 A1 | 4/2015 | Metrangolo et al. |
| 2015/0107611 A1 | 4/2015 | Metrangolo et al. |
| 2015/0107612 A1 | 4/2015 | Liu |
| 2015/0108019 A1 | 4/2015 | Liu |
| 2015/0114407 A1 | 4/2015 | Duncan et al. |
| 2015/0114410 A1 | 4/2015 | Doster |
| 2015/0117842 A1 | 4/2015 | Brammer et al. |
| 2015/0122252 A1 | 5/2015 | Frija |
| 2015/0122274 A1 | 5/2015 | Cohen et al. |
| 2015/0122278 A1 | 5/2015 | Hardgrove et al. |
| 2015/0128965 A1 | 5/2015 | Lord |
| 2015/0128966 A1 | 5/2015 | Lord |
| 2015/0128967 A1 | 5/2015 | Robinson et al. |
| 2015/0128969 A1 | 5/2015 | Chapman et al. |
| 2015/0128970 A1 | 5/2015 | Liu |
| 2015/0128971 A1 | 5/2015 | Verleur et al. |
| 2015/0128972 A1 | 5/2015 | Verleur et al. |
| 2015/0128973 A1 | 5/2015 | Li et al. |
| 2015/0128974 A1 | 5/2015 | Hon |
| 2015/0128976 A1 | 5/2015 | Verleur et al. |
| 2015/0128977 A1 | 5/2015 | Li et al. |
| 2015/0136153 A1 | 5/2015 | Lord |
| 2015/0136154 A1 | 5/2015 | Mitrev et al. |
| 2015/0136155 A1 | 5/2015 | Verleur et al. |
| 2015/0136156 A1 | 5/2015 | Liu |
| 2015/0136157 A1 | 5/2015 | Liu |
| 2015/0136158 A1 | 5/2015 | Stevens et al. |
| 2015/0142387 A1 | 5/2015 | Alarcon et al. |
| 2015/0144145 A1 | 5/2015 | Chang et al. |
| 2015/0144147 A1 | 5/2015 | Li et al. |
| 2015/0144148 A1 | 5/2015 | Chen |
| 2015/0150302 A1 | 6/2015 | Metrangolo et al. |
| 2015/0150303 A1 | 6/2015 | Jensen |
| 2015/0150305 A1 | 6/2015 | Shenkal |
| 2015/0150306 A1 | 6/2015 | Chen |
| 2015/0150307 A1 | 6/2015 | Liu |
| 2015/0150308 A1 | 6/2015 | Monsees et al. |
| 2015/0157053 A1 | 6/2015 | Mayor |
| 2015/0157054 A1 | 6/2015 | Liu |
| 2015/0157055 A1 | 6/2015 | Lord |
| 2015/0157056 A1 | 6/2015 | Bowen et al. |
| 2015/0163859 A1 | 6/2015 | Schneider et al. |
| 2015/0164138 A1 | 6/2015 | Liu |
| 2015/0164141 A1 | 6/2015 | Newton |
| 2015/0164142 A1 | 6/2015 | Li et al. |
| 2015/0164143 A1 | 6/2015 | Maas |
| 2015/0164144 A1 | 6/2015 | Liu |
| 2015/0164145 A1 | 6/2015 | Zhou |
| 2015/0164146 A1 | 6/2015 | Li et al. |
| 2015/0164147 A1 | 6/2015 | Verleur et al. |
| 2015/0167976 A1 | 6/2015 | Recio |
| 2015/0173124 A1 | 6/2015 | Qiu |
| 2015/0173417 A1 | 6/2015 | Gennrich et al. |
| 2015/0173419 A1 | 6/2015 | Tu |
| 2015/0173421 A1 | 6/2015 | Hsieh |
| 2015/0173422 A1 | 6/2015 | Liu |
| 2015/0181928 A1 | 7/2015 | Liu |
| 2015/0181937 A1 | 7/2015 | Dubief et al. |
| 2015/0181939 A1 | 7/2015 | Liu |
| 2015/0181940 A1 | 7/2015 | Liu |
| 2015/0181941 A1 | 7/2015 | Liu |
| 2015/0181943 A1 | 7/2015 | Li et al. |
| 2015/0181944 A1 | 7/2015 | Li et al. |
| 2015/0184846 A1 | 7/2015 | Liu |
| 2015/0186837 A1 | 7/2015 | Bianco et al. |
| 2015/0189695 A1 | 7/2015 | Xiang |
| 2015/0189915 A1 | 7/2015 | Liu |
| 2015/0189918 A1 | 7/2015 | Liu |
| 2015/0189919 A1 | 7/2015 | Liu |
| 2015/0189920 A1 | 7/2015 | Liu |
| 2015/0196055 A1 | 7/2015 | Liu |
| 2015/0196056 A1 | 7/2015 | Liu |
| 2015/0196057 A1 | 7/2015 | Wu |
| 2015/0196058 A1 | 7/2015 | Lord |
| 2015/0196059 A1 | 7/2015 | Liu |
| 2015/0196060 A1 | 7/2015 | Wensley et al. |
| 2015/0196062 A1 | 7/2015 | Li et al. |
| 2015/0200385 A1 | 7/2015 | Liu |
| 2015/0201674 A1 | 7/2015 | Dooly et al. |
| 2015/0201675 A1 | 7/2015 | Lord |
| 2015/0201676 A1 | 7/2015 | Shin |
| 2015/0208724 A1 | 7/2015 | Wu |
| 2015/0208725 A1 | 7/2015 | Tsai |
| 2015/0208726 A1 | 7/2015 | Liu |
| 2015/0208728 A1 | 7/2015 | Lord |
| 2015/0208729 A1 | 7/2015 | Monsees et al. |
| 2015/0208730 A1 | 7/2015 | Li et al. |
| 2015/0208731 A1 | 7/2015 | Malamud et al. |
| 2015/0216232 A1 | 8/2015 | Bless et al. |
| 2015/0216233 A1 | 8/2015 | Sears et al. |
| 2015/0216234 A1 | 8/2015 | Chung |
| 2015/0216235 A1 | 8/2015 | Liu |
| 2015/0216237 A1 | 8/2015 | Wensley et al. |
| 2015/0217067 A1 | 8/2015 | Hearn et al. |
| 2015/0217068 A1 | 8/2015 | Wakalopulos |
| 2015/0223520 A1 | 8/2015 | Phillips et al. |
| 2015/0223521 A1 | 8/2015 | Menting et al. |
| 2015/0223522 A1 | 8/2015 | Ampolini et al. |
| 2015/0223523 A1 | 8/2015 | McCullough |
| 2015/0224268 A1 | 8/2015 | Henry et al. |
| 2015/0227471 A1 | 8/2015 | Stafford et al. |
| 2015/0230521 A1 | 8/2015 | Talon |
| 2015/0237914 A1 | 8/2015 | Han |
| 2015/0237916 A1 | 8/2015 | Farine et al. |
| 2015/0237917 A1 | 8/2015 | Lord |
| 2015/0237918 A1 | 8/2015 | Liu |
| 2015/0238723 A1 | 8/2015 | Knudsen |
| 2015/0245654 A1 | 9/2015 | Memari et al. |
| 2015/0245655 A1 | 9/2015 | Memari et al. |
| 2015/0245657 A1 | 9/2015 | Memari et al. |
| 2015/0245658 A1 | 9/2015 | Worm et al. |

(56) References Cited

U.S. PATENT DOCUMENTS

| | | |
|---|---|---|
| 2015/0245659 A1 | 9/2015 | DePiano et al. |
| 2015/0245660 A1 | 9/2015 | Lord |
| 2015/0245661 A1 | 9/2015 | Milin |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0245669 A1 | 9/2015 | Cadieux et al. |
| 2015/0250229 A1 | 9/2015 | Hon |
| 2015/0257441 A1 | 9/2015 | Gerkin |
| 2015/0257444 A1 | 9/2015 | Chung |
| 2015/0257445 A1 | 9/2015 | Henry, Jr. et al. |
| 2015/0257446 A1 | 9/2015 | Chung |
| 2015/0257447 A1 | 9/2015 | Sullivan |
| 2015/0257449 A1 | 9/2015 | Gabbay |
| 2015/0257451 A1 | 9/2015 | Brannon et al. |
| 2015/0258289 A1 | 9/2015 | Henry, Jr. et al. |
| 2015/0272211 A1 | 10/2015 | Chung |
| 2015/0272215 A1 | 10/2015 | Esses |
| 2015/0272217 A1 | 10/2015 | Chen |
| 2015/0272218 A1 | 10/2015 | Chen |
| 2015/0272220 A1* | 10/2015 | Spinka .................. A24F 47/008 131/329 |
| 2015/0272221 A1 | 10/2015 | Liu |
| 2015/0272222 A1 | 10/2015 | Spinka et al. |
| 2015/0272223 A1 | 10/2015 | Weigensberg et al. |
| 2015/0272224 A1 | 10/2015 | Hon |
| 2015/0276262 A1 | 10/2015 | Dai et al. |
| 2015/0280273 A1 | 10/2015 | Liu |
| 2015/0282524 A1 | 10/2015 | Elhalwani |
| 2015/0282525 A1 | 10/2015 | Plojoux et al. |
| 2015/0282526 A1 | 10/2015 | Wu |
| 2015/0282527 A1 | 10/2015 | Henry, Jr. |
| 2015/0282529 A1 | 10/2015 | Li et al. |
| 2015/0282530 A1 | 10/2015 | Johnson et al. |
| 2015/0288468 A1 | 10/2015 | Xiang |
| 2015/0289565 A1 | 10/2015 | Cadieux et al. |
| 2015/0289567 A1 | 10/2015 | Liu |
| 2015/0295921 A1 | 10/2015 | Cao |
| 2015/0296883 A1 | 10/2015 | Wu |
| 2015/0296885 A1 | 10/2015 | Liu |
| 2015/0296886 A1 | 10/2015 | Li et al. |
| 2015/0296887 A1 | 10/2015 | Zhu |
| 2015/0296888 A1 | 10/2015 | Liu |
| 2015/0296889 A1 | 10/2015 | Liu |
| 2015/0304401 A1 | 10/2015 | Liu |
| 2015/0304402 A1 | 10/2015 | Liu |
| 2015/0305403 A1 | 10/2015 | Coelho Belo Fernandes De Carvalho |
| 2015/0305404 A1 | 10/2015 | Rosales |
| 2015/0305406 A1 | 10/2015 | Li et al. |
| 2015/0305407 A1 | 10/2015 | Li et al. |
| 2015/0305408 A1 | 10/2015 | Liu |
| 2015/0305409 A1 | 10/2015 | Verleur et al. |
| 2015/0305464 A1 | 10/2015 | Nelson, Jr. et al. |
| 2015/0313275 A1 | 11/2015 | Anderson et al. |
| 2015/0313282 A1 | 11/2015 | Ademe et al. |
| 2015/0313283 A1 | 11/2015 | Collett et al. |
| 2015/0313284 A1 | 11/2015 | Liu |
| 2015/0313285 A1 | 11/2015 | Waller et al. |
| 2015/0313287 A1 | 11/2015 | Verleur et al. |
| 2015/0313288 A1 | 11/2015 | Liu |
| 2015/0313868 A1 | 11/2015 | Morgan |
| 2015/0320114 A1 | 11/2015 | Wu |
| 2015/0320116 A1 | 11/2015 | Bleloch et al. |
| 2015/0322451 A1 | 11/2015 | Kudithipudi et al. |
| 2015/0327595 A1 | 11/2015 | Scatterday |
| 2015/0327596 A1 | 11/2015 | Alarcon et al. |
| 2015/0327597 A1 | 11/2015 | Li et al. |
| 2015/0327598 A1 | 11/2015 | Xiang |
| 2015/0328415 A1 | 11/2015 | Minskoff et al. |
| 2015/0332379 A1 | 11/2015 | Alarcon |
| 2015/0333542 A1 | 11/2015 | Alarcon et al. |
| 2015/0333552 A1 | 11/2015 | Alarcon |
| 2015/0333561 A1 | 11/2015 | Alarcon |
| 2015/0335071 A1 | 11/2015 | Brinkley et al. |
| 2015/0335072 A1 | 11/2015 | Giller |
| 2015/0335074 A1 | 11/2015 | Leung |
| 2015/0335075 A1 | 11/2015 | Minskoff et al. |
| 2015/0342254 A1 | 12/2015 | Mironov et al. |
| 2015/0342255 A1 | 12/2015 | Wu |
| 2015/0342256 A1 | 12/2015 | Chen |
| 2015/0342257 A1 | 12/2015 | Chen |
| 2015/0342258 A1 | 12/2015 | Chen |
| 2015/0342259 A1 | 12/2015 | Baker et al. |
| 2015/0351449 A1 | 12/2015 | Righetti |
| 2015/0351454 A1 | 12/2015 | Huang |
| 2015/0351455 A1 | 12/2015 | Liu |
| 2015/0351456 A1 | 12/2015 | Johnson et al. |
| 2015/0351457 A1 | 12/2015 | Liu |
| 2015/0357608 A1 | 12/2015 | Huang |
| 2015/0357839 A1 | 12/2015 | Cai et al. |
| 2015/0359258 A1 | 12/2015 | Mishra et al. |
| 2015/0359261 A1 | 12/2015 | Li et al. |
| 2015/0359262 A1 | 12/2015 | Liu et al. |
| 2015/0359263 A1 | 12/2015 | Bellinger |
| 2015/0359264 A1 | 12/2015 | Fernando et al. |
| 2015/0359265 A1 | 12/2015 | Liu |
| 2015/0366250 A1 | 12/2015 | Landau |
| 2015/0366265 A1 | 12/2015 | Lansing |
| 2015/0366266 A1 | 12/2015 | Chen |
| 2015/0366267 A1 | 12/2015 | Liu |
| 2015/0366268 A1 | 12/2015 | Shabat |
| 2015/0374035 A1 | 12/2015 | Sanchez et al. |
| 2015/0374039 A1 | 12/2015 | Zhu |
| 2015/0374040 A1 | 12/2015 | Chen |
| 2016/0000147 A1 | 1/2016 | Li et al. |
| 2016/0000148 A1 | 1/2016 | Liu |
| 2016/0000149 A1 | 1/2016 | Scatterday |
| 2016/0002649 A1 | 1/2016 | Kudithipudi et al. |
| 2016/0007650 A1 | 1/2016 | Duncan et al. |
| 2016/0007651 A1 | 1/2016 | Ampolini et al. |
| 2016/0007653 A1 | 1/2016 | Tu |
| 2016/0007654 A1 | 1/2016 | Zhu |
| 2016/0007655 A1 | 1/2016 | Li et al. |
| 2016/0010103 A1 | 1/2016 | Kudithipudi et al. |
| 2016/0015082 A1 | 1/2016 | Liu |
| 2016/0020048 A1 | 1/2016 | Ware |
| 2016/0021771 A1 | 1/2016 | Zhang et al. |
| 2016/0021930 A1 | 1/2016 | Minskoff et al. |
| 2016/0021931 A1 | 1/2016 | Hawes et al. |
| 2016/0021932 A1 | 1/2016 | Silvestrini et al. |
| 2016/0021933 A1 | 1/2016 | Thorens et al. |
| 2016/0021934 A1 | 1/2016 | Cadieux et al. |
| 2016/0029225 A1 | 1/2016 | Hu |
| 2016/0029694 A1 | 2/2016 | Clements et al. |
| 2016/0029697 A1 | 2/2016 | Shafer |
| 2016/0029698 A1 | 2/2016 | Xiang |
| 2016/0029699 A1 | 2/2016 | Li et al. |
| 2016/0029700 A1 | 2/2016 | Li et al. |
| 2016/0037826 A1 | 2/2016 | Hearn et al. |
| 2016/0044961 A1 | 2/2016 | Liu |
| 2016/0044963 A1 | 2/2016 | Saleem |
| 2016/0044964 A1 | 2/2016 | Liu |
| 2016/0044965 A1 | 2/2016 | Liu |
| 2016/0044966 A1 | 2/2016 | Li et al. |
| 2016/0044967 A1 | 2/2016 | Bowen et al. |
| 2016/0044968 A1 | 2/2016 | Bowen et al. |
| 2016/0049682 A1 | 2/2016 | Won et al. |
| 2016/0051716 A1 | 2/2016 | Wheelock |
| 2016/0053988 A1 | 2/2016 | Quintana |
| 2016/0057811 A1 | 2/2016 | Alarcon et al. |
| 2016/0058066 A1 | 3/2016 | Banks et al. |
| 2016/0058071 A1 | 3/2016 | Hearn |
| 2016/0058072 A1 | 3/2016 | Liu |
| 2016/0058073 A1 | 3/2016 | Chen |
| 2016/0058074 A1 | 3/2016 | Liu |
| 2016/0066617 A1 | 3/2016 | Yilmaz et al. |
| 2016/0073677 A1 | 3/2016 | Kappel et al. |
| 2016/0073678 A1 | 3/2016 | Fujisawa et al. |
| 2016/0073690 A1 | 3/2016 | Liu |
| 2016/0073691 A1 | 3/2016 | Liu |
| 2016/0073692 A1 | 3/2016 | Alarcon et al. |
| 2016/0073693 A1 | 3/2016 | Reevell |

(56) References Cited

U.S. PATENT DOCUMENTS

| | | |
|---|---|---|
| 2016/0073694 A1 | 3/2016 | Liu |
| 2016/0080469 A1 | 3/2016 | Liu |
| 2016/0081393 A1 | 3/2016 | Black |
| 2016/0081394 A1 | 3/2016 | Alarcon et al. |
| 2016/0081395 A1 | 3/2016 | Thorens et al. |
| 2016/0088874 A1 | 3/2016 | Lipowicz |
| 2016/0089508 A1 | 3/2016 | Smith et al. |
| 2016/0091194 A1 | 3/2016 | Liu |
| 2016/0095352 A1 | 4/2016 | Liu |
| 2016/0095353 A1 | 4/2016 | Liu |
| 2016/0095354 A1 | 4/2016 | Wu |
| 2016/0095355 A1 | 4/2016 | Hearn |
| 2016/0095356 A1 | 4/2016 | Chan |
| 2016/0095357 A1 | 4/2016 | Burton |
| 2016/0099592 A1 | 4/2016 | Gatta et al. |
| 2016/0100456 A1 | 4/2016 | Tsai |
| 2016/0100632 A1 | 4/2016 | Debono et al. |
| 2016/0101909 A1 | 4/2016 | Schennum et al. |
| 2016/0106144 A1 | 4/2016 | Muehlbauer et al. |
| 2016/0106151 A1 | 4/2016 | Swepston et al. |
| 2016/0106152 A1 | 4/2016 | Liu |
| 2016/0106154 A1 | 4/2016 | Lord |
| 2016/0106155 A1 | 4/2016 | Reevell |
| 2016/0106156 A1 | 4/2016 | Qiu |
| 2016/0106936 A1 | 4/2016 | Kimmel |
| 2016/0109115 A1 | 4/2016 | Lipowicz |
| 2016/0113323 A1 | 4/2016 | Liu |
| 2016/0113325 A1 | 4/2016 | Liu |
| 2016/0113326 A1 | 4/2016 | Li et al. |
| 2016/0113327 A1 | 4/2016 | Wu |
| 2016/0120218 A1 | 5/2016 | Schennum et al. |
| 2016/0120220 A1 | 5/2016 | Malgat et al. |
| 2016/0120222 A1 | 5/2016 | Bagai et al. |
| 2016/0120223 A1 | 5/2016 | Keen et al. |
| 2016/0120224 A1 | 5/2016 | Mishra et al. |
| 2016/0120225 A1 | 5/2016 | Mishra et al. |
| 2016/0120226 A1 | 5/2016 | Rado |
| 2016/0120227 A1 | 5/2016 | Levitz et al. |
| 2016/0120228 A1 | 5/2016 | Rostami et al. |
| 2016/0121058 A1 | 5/2016 | Chen |
| 2016/0128384 A1 | 5/2016 | Luciani et al. |
| 2016/0128385 A1 | 5/2016 | Lin |
| 2016/0128387 A1 | 5/2016 | Chen |
| 2016/0128388 A1 | 5/2016 | Liu |
| 2016/0128389 A1 | 5/2016 | Lamb et al. |
| 2016/0128390 A1 | 5/2016 | Liu |
| 2016/0129205 A1 | 5/2016 | Shahaf et al. |
| 2016/0131629 A1 | 5/2016 | Cadieux, Jr. et al. |
| 2016/0132898 A1 | 5/2016 | Cadieux et al. |
| 2016/0134143 A1 | 5/2016 | Liu |
| 2016/0135494 A1 | 5/2016 | Liu et al. |
| 2016/0135500 A1 | 5/2016 | Hearn et al. |
| 2016/0135501 A1 | 5/2016 | Liu |
| 2016/0135503 A1 | 5/2016 | Liu |
| 2016/0135504 A1 | 5/2016 | Li et al. |
| 2016/0135505 A1 | 5/2016 | Li et al. |
| 2016/0135506 A1 | 5/2016 | Sanchez et al. |
| 2016/0135507 A1 | 5/2016 | Thorens et al. |
| 2016/0136153 A1 | 5/2016 | Jenkins |
| 2016/0136213 A1 | 5/2016 | Paul |
| 2016/0138795 A1 | 5/2016 | Meinhart et al. |
| 2016/0143354 A1 | 5/2016 | Liu |
| 2016/0143357 A1 | 5/2016 | Liu |
| 2016/0143358 A1 | 5/2016 | Zhu |
| 2016/0143359 A1 | 5/2016 | Xiang |
| 2016/0143360 A1 | 5/2016 | Sanchez et al. |
| 2016/0143361 A1 | 5/2016 | Juster et al. |
| 2016/0143362 A1 | 5/2016 | Boldrini |
| 2016/0143363 A1 | 5/2016 | Boldrini |
| 2016/0143365 A1 | 5/2016 | Liu |
| 2016/0144458 A1 | 5/2016 | Boldrini |
| 2016/0150820 A1 | 6/2016 | Liu |
| 2016/0150821 A1 | 6/2016 | Liu |
| 2016/0150823 A1 | 6/2016 | Liu |
| 2016/0150824 A1 | 6/2016 | Memari et al. |
| 2016/0150826 A1 | 6/2016 | Liu |
| 2016/0150827 A1 | 6/2016 | Liu |
| 2016/0150828 A1 | 6/2016 | Goldstein et al. |
| 2016/0150872 A1 | 6/2016 | Zayat |
| 2016/0157523 A1 | 6/2016 | Liu |
| 2016/0157524 A1 | 6/2016 | Bowen et al. |
| 2016/0157525 A1 | 6/2016 | Tucker et al. |
| 2016/0158782 A1 | 6/2016 | Henry, Jr. et al. |
| 2016/0165952 A1 | 6/2016 | Liu |
| 2016/0165955 A1 | 6/2016 | Home |
| 2016/0166564 A1 | 6/2016 | Myers et al. |
| 2016/0167846 A1 | 6/2016 | Zahr et al. |
| 2016/0174076 A1 | 6/2016 | Wu |
| 2016/0174609 A1 | 6/2016 | Mironov |
| 2016/0174611 A1 | 6/2016 | Monsees et al. |
| 2016/0174613 A1 | 6/2016 | Zuber et al. |
| 2016/0176564 A1 | 6/2016 | Garthaffner |
| 2016/0177285 A1 | 6/2016 | Voerman et al. |
| 2016/0183592 A1 | 6/2016 | Liu |
| 2016/0183593 A1 | 6/2016 | Liu |
| 2016/0183594 A1 | 6/2016 | Liu |
| 2016/0183595 A1 | 6/2016 | Grimandi et al. |
| 2016/0183597 A1 | 6/2016 | Li et al. |
| 2016/0189216 A1 | 6/2016 | Liu |
| 2016/0192705 A1 | 7/2016 | Borkovec et al. |
| 2016/0192706 A1 | 7/2016 | Kananen |
| 2016/0192707 A1 | 7/2016 | Li et al. |
| 2016/0192708 A1 | 7/2016 | Dermitt et al. |
| 2016/0192709 A1 | 7/2016 | Liu |
| 2016/0192710 A1 | 7/2016 | Liu |
| 2016/0198759 A1 | 7/2016 | Kuntawala et al. |
| 2016/0198763 A1 | 7/2016 | Adkins et al. |
| 2016/0198765 A1 | 7/2016 | Liu |
| 2016/0198766 A1 | 7/2016 | Liu |
| 2016/0198767 A1 | 7/2016 | Verleur |
| 2016/0198768 A1 | 7/2016 | Liu |
| 2016/0198769 A1 | 7/2016 | Liu |
| 2016/0198770 A1 | 7/2016 | Alarcon |
| 2016/0200463 A1 | 7/2016 | Hodges et al. |
| 2016/0201224 A1 | 7/2016 | Xiang |
| 2016/0204637 A1 | 7/2016 | Alarcon et al. |
| 2016/0205998 A1 | 7/2016 | Matsumoto et al. |
| 2016/0205999 A1 | 7/2016 | Liu |
| 2016/0206000 A1 | 7/2016 | Lord et al. |
| 2016/0206002 A1 | 7/2016 | Borkovec et al. |
| 2016/0206005 A1 | 7/2016 | Yamada et al. |
| 2016/0206006 A1 | 7/2016 | Li et al. |
| 2016/0211693 A1 | 7/2016 | Stevens et al. |
| 2016/0212520 A1 | 7/2016 | Merenda |
| 2016/0213060 A1 | 7/2016 | Thaler |
| 2016/0213061 A1 | 7/2016 | Liu |
| 2016/0213062 A1 | 7/2016 | Doyle |
| 2016/0213065 A1 | 7/2016 | Wensley et al. |
| 2016/0213066 A1 | 7/2016 | Zitzke et al. |
| 2016/0213067 A1 | 7/2016 | Hon |
| 2016/0213866 A1 | 7/2016 | Tan |
| 2016/0219932 A1 | 8/2016 | Glaser |
| 2016/0219933 A1 | 8/2016 | Henry, Jr. et al. |
| 2016/0219934 A1 | 8/2016 | Li et al. |
| 2016/0219936 A1 | 8/2016 | Alarcon |
| 2016/0219937 A1 | 8/2016 | Rado |
| 2016/0219938 A1* | 8/2016 | Mamoun ............... G05B 15/02 |
| 2016/0221707 A1 | 8/2016 | Xu et al. |
| 2016/0226286 A1 | 8/2016 | Xiang |
| 2016/0227837 A1 | 8/2016 | Hammel et al. |
| 2016/0227838 A1 | 8/2016 | Johnson et al. |
| 2016/0227839 A1 | 8/2016 | Zuber et al. |
| 2016/0227840 A1 | 8/2016 | Xiang |
| 2016/0227841 A1 | 8/2016 | Li et al. |
| 2016/0227842 A1 | 8/2016 | Xiang |
| 2016/0233705 A1 | 8/2016 | Liu |
| 2016/0233708 A1 | 8/2016 | Liu |
| 2016/0235119 A1 | 8/2016 | Liu |
| 2016/0235120 A1 | 8/2016 | Liu |
| 2016/0235121 A1 | 8/2016 | Rogan et al. |
| 2016/0235124 A1 | 8/2016 | Krietzman |
| 2016/0235125 A1 | 8/2016 | Safari |
| 2016/0242463 A1 | 8/2016 | Liu |
| 2016/0242464 A1 | 8/2016 | Liu |

(56) References Cited

U.S. PATENT DOCUMENTS

| | | |
|---|---|---|
| 2016/0242465 A1 | 8/2016 | Zheng et al. |
| 2016/0242466 A1 | 8/2016 | Lord et al. |
| 2016/0242467 A1 | 8/2016 | Vaughn |
| 2016/0242468 A1 | 8/2016 | Liu |
| 2016/0249680 A1 | 9/2016 | Liu |
| 2016/0249682 A1 | 9/2016 | Leadley et al. |
| 2016/0249683 A1 | 9/2016 | Li et al. |
| 2016/0249684 A1 | 9/2016 | Liu |
| 2016/0255876 A1 | 9/2016 | Rostami |
| 2016/0255878 A1 | 9/2016 | Huang et al. |
| 2016/0260156 A1 | 9/2016 | Liu |
| 2016/0261021 A1 | 9/2016 | Marion et al. |
| 2016/0262443 A1 | 9/2016 | Piccirilli et al. |
| 2016/0262445 A1 | 9/2016 | Benjak et al. |
| 2016/0262449 A1 | 9/2016 | Liu |
| 2016/0262450 A1 | 9/2016 | Liu |
| 2016/0262451 A1 | 9/2016 | Liu |
| 2016/0262452 A1 | 9/2016 | Zhu |
| 2016/0262453 A1 | 9/2016 | Ampolini et al. |
| 2016/0262454 A1 | 9/2016 | Sears et al. |
| 2016/0262455 A1 | 9/2016 | Chen |
| 2016/0262456 A1 | 9/2016 | Borkovec et al. |
| 2016/0262457 A1 | 9/2016 | Borkovec et al. |
| 2016/0262459 A1 | 9/2016 | Monsees et al. |
| 2016/0262526 A1 | 9/2016 | Gonzalez |
| 2016/0268824 A1 | 9/2016 | Liu |
| 2016/0270441 A1 | 9/2016 | Lewis et al. |
| 2016/0270442 A1 | 9/2016 | Liu |
| 2016/0270443 A1 | 9/2016 | Liu |
| 2016/0270444 A1 | 9/2016 | Lin |
| 2016/0270445 A1 | 9/2016 | Liu |
| 2016/0270446 A1 | 9/2016 | Shenkal et al. |
| 2016/0270447 A1 | 9/2016 | Borkovec |
| 2016/0271347 A1 | 9/2016 | Raichman |
| 2016/0278163 A1 | 9/2016 | Chen |
| 2016/0278431 A1 | 9/2016 | Liu |
| 2016/0278432 A1 | 9/2016 | Liu |
| 2016/0278433 A1 | 9/2016 | Xiang |
| 2016/0278434 A1 | 9/2016 | Liu |
| 2016/0278435 A1 | 9/2016 | Choukroun et al. |
| 2016/0278436 A1 | 9/2016 | Verleur et al. |
| 2016/0280450 A1 | 9/2016 | Hearn et al. |
| 2016/0284197 A1 | 9/2016 | Liu |
| 2016/0285983 A1 | 9/2016 | Liu |
| 2016/0286856 A1 | 10/2016 | Liu |
| 2016/0286858 A1 | 10/2016 | Liu |
| 2016/0286859 A1 | 10/2016 | Liu |
| 2016/0286860 A1 | 10/2016 | Flayler |
| 2016/0286862 A1 | 10/2016 | Silvetrini |
| 2016/0286863 A1 | 10/2016 | Lin |
| 2016/0286864 A1 | 10/2016 | Lin |
| 2016/0286865 A1 | 10/2016 | King et al. |
| 2016/0295913 A1 | 10/2016 | Guo et al. |
| 2016/0295915 A1 | 10/2016 | Jochnowitz et al. |
| 2016/0295916 A1 | 10/2016 | Malgat et al. |
| 2016/0295917 A1 | 10/2016 | Malgat et al. |
| 2016/0295918 A1 | 10/2016 | Liu |
| 2016/0295920 A1 | 10/2016 | Liu |
| 2016/0295922 A1 | 10/2016 | John et al. |
| 2016/0295923 A1 | 10/2016 | Lin |
| 2016/0295924 A1 | 10/2016 | Liu |
| 2016/0295925 A1 | 10/2016 | Chen |
| 2016/0295926 A1 | 10/2016 | Zuber |
| 2016/0297341 A1 | 10/2016 | Wallace et al. |
| 2016/0302471 A1 | 10/2016 | Bowen et al. |
| 2016/0302483 A1 | 10/2016 | Liu |
| 2016/0302484 A1 | 10/2016 | Gupta et al. |
| 2016/0302485 A1 | 10/2016 | Alima |
| 2016/0302486 A1 | 10/2016 | Eroch |
| 2016/0302487 A1 | 10/2016 | Chen |
| 2016/0302488 A1 | 10/2016 | Fernando et al. |
| 2016/0309775 A1 | 10/2016 | Parker |
| 2016/0309779 A1 | 10/2016 | Liu |
| 2016/0309780 A1 | 10/2016 | Chen et al. |
| 2016/0309781 A1 | 10/2016 | Malgat et al. |
| 2016/0309783 A1 | 10/2016 | Hopps et al. |
| 2016/0309784 A1 | 10/2016 | Silvestrini et al. |
| 2016/0309785 A1 | 10/2016 | Holtz |
| 2016/0309786 A1 | 10/2016 | Holtz et al. |
| 2016/0309789 A1 | 10/2016 | Thomas, Jr. |
| 2016/0315488 A1 | 10/2016 | Moon |
| 2016/0316818 A1 | 11/2016 | Liu |
| 2016/0316820 A1 | 11/2016 | Liu |
| 2016/0316821 A1 | 11/2016 | Liu |
| 2016/0316822 A1 | 11/2016 | Liu |
| 2016/0321879 A1 | 11/2016 | Oh et al. |
| 2016/0323404 A1 | 11/2016 | Liu |
| 2016/0324211 A1 | 11/2016 | Yankelevich |
| 2016/0324213 A1 | 11/2016 | Liu |
| 2016/0324215 A1 | 11/2016 | Mironov et al. |
| 2016/0324217 A1 | 11/2016 | Cameron |
| 2016/0324218 A1 | 11/2016 | Wang et al. |
| 2016/0324219 A1 | 11/2016 | Li et al. |
| 2016/0324845 A1 | 11/2016 | Myers et al. |
| 2016/0325055 A1 | 11/2016 | Cameron |
| 2016/0325858 A1 | 11/2016 | Ampolini et al. |
| 2016/0331022 A1 | 11/2016 | Cameron |
| 2016/0331023 A1 | 11/2016 | Cameron |
| 2016/0331024 A1 | 11/2016 | Cameron |
| 2016/0331025 A1 | 11/2016 | Cameron |
| 2016/0331026 A1 | 11/2016 | Cameron |
| 2016/0331027 A1 | 11/2016 | Cameron |
| 2016/0331028 A1 | 11/2016 | Xu |
| 2016/0331029 A1 | 11/2016 | Contreras |
| 2016/0331030 A1 | 11/2016 | Ampolini et al. |
| 2016/0331032 A1 | 11/2016 | Malgat et al. |
| 2016/0331033 A1 | 11/2016 | Hopps et al. |
| 2016/0331034 A1 | 11/2016 | Cameron |
| 2016/0331035 A1 | 11/2016 | Cameron |
| 2016/0331037 A1 | 11/2016 | Cameron |
| 2016/0331038 A1 | 11/2016 | Farine et al. |
| 2016/0331039 A1 | 11/2016 | Thorens et al. |
| 2016/0331040 A1 | 11/2016 | Nakano et al. |
| 2016/0331912 A1 | 11/2016 | Trzecieski |
| 2016/0332754 A1 | 11/2016 | Brown et al. |
| 2016/0334847 A1 | 11/2016 | Cameron |
| 2016/0337141 A1 | 11/2016 | Cameron |
| 2016/0337362 A1 | 11/2016 | Cameron |
| 2016/0337444 A1 | 11/2016 | Cameron |
| 2016/0338402 A1 | 11/2016 | Buehler et al. |
| 2016/0338405 A1 | 11/2016 | Liu |
| 2016/0338406 A1 | 11/2016 | Liu |
| 2016/0338407 A1 | 11/2016 | Kerdemelidis |
| 2016/0338408 A1 | 11/2016 | Guenther, Jr. et al. |
| 2016/0338409 A1 | 11/2016 | Varone |
| 2016/0338410 A1 | 11/2016 | Batista et al. |
| 2016/0338411 A1 | 11/2016 | Liu |
| 2016/0338412 A1 | 11/2016 | Monsees et al. |
| 2016/0338413 A1 | 11/2016 | Li et al. |
| 2016/0338945 A1 | 11/2016 | Knight |
| 2016/0345621 A1 | 12/2016 | Li et al. |
| 2016/0345625 A1 | 12/2016 | Liu |
| 2016/0345626 A1 | 12/2016 | Wong et al. |
| 2016/0345627 A1 | 12/2016 | Liu |
| 2016/0345628 A1 | 12/2016 | Sabet |
| 2016/0345630 A1 | 12/2016 | Mironov et al. |
| 2016/0345631 A1 | 12/2016 | Monsees et al. |
| 2016/0345632 A1 | 12/2016 | Lipowicz |
| 2016/0345633 A1 | 12/2016 | DePiano et al. |
| 2016/0345634 A1 | 12/2016 | Fernando et al. |
| 2016/0345636 A1 | 12/2016 | Liu |
| 2016/0351044 A1 | 12/2016 | Liu |
| 2016/0353798 A1 | 12/2016 | Liu |
| 2016/0353800 A1 | 12/2016 | Di Carlo |
| 2016/0353805 A1 | 12/2016 | Hawes et al. |
| 2016/0356751 A1 | 12/2016 | Blackley |
| 2016/0360784 A1 | 12/2016 | Liu |
| 2016/0360785 A1 | 12/2016 | Bless et al. |
| 2016/0360786 A1 | 12/2016 | Bellinger et al. |
| 2016/0360787 A1 | 12/2016 | Bailey |
| 2016/0360788 A1 | 12/2016 | Wang |
| 2016/0360789 A1 | 12/2016 | Hawes et al. |
| 2016/0360790 A1 | 12/2016 | Calfee et al. |
| 2016/0360792 A1 | 12/2016 | Liu |

(56) References Cited

U.S. PATENT DOCUMENTS

| | | |
|---|---|---|
| 2016/0360793 A1 | 12/2016 | Liu |
| 2016/0363570 A1 | 12/2016 | Blackley |
| 2016/0363917 A1 | 12/2016 | Blackley |
| 2016/0366725 A1 | 12/2016 | Tucker et al. |
| 2016/0366927 A1 | 12/2016 | Liu |
| 2016/0366928 A1 | 12/2016 | Liu |
| 2016/0366933 A1 | 12/2016 | Liu |
| 2016/0366935 A1 | 12/2016 | Liu |
| 2016/0366936 A1 | 12/2016 | Liu |
| 2016/0366937 A1 | 12/2016 | Liu |
| 2016/0366938 A1 | 12/2016 | Wu |
| 2016/0366939 A1 | 12/2016 | Alarcon et al. |
| 2016/0366940 A1 | 12/2016 | Liu |
| 2016/0366941 A1 | 12/2016 | Lin |
| 2016/0366942 A1 | 12/2016 | Liu |
| 2016/0366943 A1 | 12/2016 | Li et al. |
| 2016/0366945 A1 | 12/2016 | Rado |
| 2016/0366947 A1 | 12/2016 | Monsees et al. |
| 2016/0367925 A1 | 12/2016 | Blackley |
| 2016/0368670 A1 | 12/2016 | Beardsall |
| 2016/0368677 A1 | 12/2016 | Parsons et al. |
| 2016/0370335 A1 | 12/2016 | Blackley |
| 2016/0371437 A1 | 12/2016 | Alarcon et al. |
| 2016/0371464 A1 | 12/2016 | Bricker |
| 2016/0374390 A1 | 12/2016 | Liu |
| 2016/0374391 A1 | 12/2016 | Liu |
| 2016/0374392 A1 | 12/2016 | Liu |
| 2016/0374393 A1 | 12/2016 | Chen |
| 2016/0374394 A1 | 12/2016 | Hawes et al. |
| 2016/0374395 A1 | 12/2016 | Jordan et al. |
| 2016/0374396 A1 | 12/2016 | Jordan et al. |
| 2016/0374397 A1 | 12/2016 | Jordan et al. |
| 2016/0374398 A1 | 12/2016 | Amir |
| 2016/0374399 A1 | 12/2016 | Monsees et al. |
| 2016/0374400 A1 | 12/2016 | Monsees et al. |
| 2016/0374401 A1 | 12/2016 | Liu |
| 2017/0000190 A1 | 1/2017 | Wu |
| 2017/0000192 A1 | 1/2017 | Li |
| 2017/0006915 A1 | 1/2017 | Li et al. |
| 2017/0006916 A1 | 1/2017 | Liu |
| 2017/0006917 A1 | 1/2017 | Alvarez |
| 2017/0006918 A1 | 1/2017 | Chen et al. |
| 2017/0006919 A1 | 1/2017 | Liu |
| 2017/0006920 A1 | 1/2017 | Liu |
| 2017/0006921 A1 | 1/2017 | Lemay et al. |
| 2017/0006922 A1 | 1/2017 | Wang et al. |
| 2017/0013875 A1 | 1/2017 | Schennum et al. |
| 2017/0013876 A1 | 1/2017 | Schennum et al. |
| 2017/0013878 A1 | 1/2017 | Schuler et al. |
| 2017/0013880 A1 | 1/2017 | O'Brien et al. |
| 2017/0013881 A1 | 1/2017 | Liu |
| 2017/0013882 A1 | 1/2017 | Liu |
| 2017/0013883 A1 | 1/2017 | Han et al. |
| 2017/0013885 A1 | 1/2017 | Qiu |
| 2017/0014582 A1 | 1/2017 | Skoda |
| 2017/0018000 A1 | 1/2017 | Cameron |
| 2017/0019951 A1 | 1/2017 | Louveau et al. |
| 2017/0020188 A1 | 1/2017 | Cameron |
| 2017/0020191 A1 | 1/2017 | Lamb et al. |
| 2017/0020193 A1 | 1/2017 | Davis et al. |
| 2017/0020194 A1 | 1/2017 | Rehders |
| 2017/0020195 A1 | 1/2017 | Cameron |
| 2017/0020196 A1 | 1/2017 | Cameron |
| 2017/0020197 A1 | 1/2017 | Cameron |
| 2017/0020198 A1 | 1/2017 | Naqwi et al. |
| 2017/0020201 A1 | 1/2017 | Xiang |
| 2017/0020791 A1 | 1/2017 | Moszner et al. |
| 2017/0021969 A1 | 1/2017 | Smith et al. |
| 2017/0023952 A1 | 1/2017 | Henry, Jr. et al. |
| 2017/0027221 A1 | 2/2017 | Liu |
| 2017/0027223 A1 | 2/2017 | Eksouzian |
| 2017/0027224 A1 | 2/2017 | Volodarsky |
| 2017/0027227 A1 | 2/2017 | Lipowicz |
| 2017/0027228 A1 | 2/2017 | Rastogi |
| 2017/0027229 A1 | 2/2017 | Cameron |
| 2017/0027230 A1 | 2/2017 | Fornarelli |
| 2017/0027231 A1 | 2/2017 | Xiang |
| 2017/0027232 A1 | 2/2017 | Scheck et al. |
| 2017/0027233 A1 | 2/2017 | Mironov |
| 2017/0027234 A1 | 2/2017 | Farine et al. |
| 2017/0033568 A1 | 2/2017 | Holzherr |
| 2017/0033836 A1 | 2/2017 | Bernauer et al. |
| 2017/0035101 A1 | 2/2017 | Balder |
| 2017/0035109 A1 | 2/2017 | Liu |
| 2017/0035110 A1 | 2/2017 | Keen |
| 2017/0035111 A1 | 2/2017 | Slurink et al. |
| 2017/0035112 A1 | 2/2017 | Thorens |
| 2017/0035113 A1 | 2/2017 | Thorens |
| 2017/0035114 A1 | 2/2017 | Lord |
| 2017/0035115 A1 | 2/2017 | Monsees et al. |
| 2017/0035117 A1 | 2/2017 | Lin |
| 2017/0035118 A1 | 2/2017 | Liu |
| 2017/0035119 A1 | 2/2017 | Otto |
| 2017/0041646 A1 | 2/2017 | Pizzurro et al. |
| 2017/0042225 A1 | 2/2017 | Liu |
| 2017/0042227 A1 | 2/2017 | Gavrielov et al. |
| 2017/0042228 A1 | 2/2017 | Liu |
| 2017/0042229 A1 | 2/2017 | Liu |
| 2017/0042230 A1 | 2/2017 | Cameron |
| 2017/0042231 A1 | 2/2017 | Cameron |
| 2017/0042242 A1 | 2/2017 | Hon |
| 2017/0042243 A1 | 2/2017 | Plojoux et al. |
| 2017/0042245 A1 | 2/2017 | Buchberger et al. |
| 2017/0042246 A1 | 2/2017 | Lau et al. |
| 2017/0042247 A1 | 2/2017 | Xiang |
| 2017/0042248 A1 | 2/2017 | Xiang |
| 2017/0042250 A1 | 2/2017 | Takeuchi et al. |
| 2017/0046357 A1 | 2/2017 | Cameron |
| 2017/0046722 A1 | 2/2017 | Ertugrul |
| 2017/0046738 A1 | 2/2017 | Cameron |
| 2017/0047756 A1 | 2/2017 | Xiang |
| 2017/0048691 A1 | 2/2017 | Liu |
| 2017/0049149 A1 | 2/2017 | Carty |
| 2017/0049150 A1 | 2/2017 | Xue et al. |
| 2017/0049151 A1 | 2/2017 | Xue et al. |
| 2017/0049152 A1 | 2/2017 | Liu |
| 2017/0049153 A1 | 2/2017 | Guo et al. |
| 2017/0049154 A1 | 2/2017 | Batista |
| 2017/0049155 A1 | 2/2017 | Liu |
| 2017/0049156 A1 | 2/2017 | Wang et al. |
| 2017/0050798 A1 | 2/2017 | Ludewig et al. |
| 2017/0055577 A1 | 3/2017 | Batista |
| 2017/0055579 A1 | 3/2017 | Kuna et al. |
| 2017/0055586 A1 | 3/2017 | Liu |
| 2017/0055588 A1 | 3/2017 | Cameron |
| 2017/0055589 A1 | 3/2017 | Fernando et al. |
| 2017/0064994 A1 | 3/2017 | Xu et al. |
| 2017/0064999 A1 | 3/2017 | Perez et al. |
| 2017/0065000 A1 | 3/2017 | Sears et al. |
| 2017/0065001 A1 | 3/2017 | Li et al. |
| 2017/0066556 A1 | 3/2017 | Liu |
| 2017/0071249 A1 | 3/2017 | Ampolini et al. |
| 2017/0071251 A1 | 3/2017 | Goch |
| 2017/0071252 A1 | 3/2017 | Liu |
| 2017/0071256 A1 | 3/2017 | Verleur et al. |
| 2017/0071257 A1 | 3/2017 | Lin |
| 2017/0071258 A1 | 3/2017 | Li et al. |
| 2017/0071260 A1 | 3/2017 | Li et al. |
| 2017/0071262 A1 | 3/2017 | Liu |
| 2017/0079110 A1 | 3/2017 | Plattner |
| 2017/0079319 A1 | 3/2017 | Muhammed et al. |
| 2017/0079321 A1 | 3/2017 | Golz |
| 2017/0079322 A1 | 3/2017 | Li et al. |
| 2017/0079323 A1 | 3/2017 | Wang |
| 2017/0079324 A1 | 3/2017 | Eksouzian |
| 2017/0079327 A1 | 3/2017 | Wu et al. |
| 2017/0079328 A1 | 3/2017 | Wu |
| 2017/0079329 A1 | 3/2017 | Zitzke |
| 2017/0079330 A1 | 3/2017 | Mironov et al. |
| 2017/0079331 A1 | 3/2017 | Monsees et al. |
| 2017/0079332 A1 | 3/2017 | Li et al. |
| 2017/0086496 A1 | 3/2017 | Cameron |
| 2017/0086497 A1 | 3/2017 | Cameron |
| 2017/0086498 A1 | 3/2017 | Daryani |

(56) References Cited

U.S. PATENT DOCUMENTS

| | | |
|---|---|---|
| 2017/0086499 A1 | 3/2017 | Mize |
| 2017/0086500 A1 | 3/2017 | Li et al. |
| 2017/0086501 A1 | 3/2017 | Buehler et al. |
| 2017/0086502 A1 | 3/2017 | Hearn et al. |
| 2017/0086503 A1 | 3/2017 | Cameron |
| 2017/0086504 A1 | 3/2017 | Cameron |
| 2017/0086505 A1 | 3/2017 | Cameron |
| 2017/0086506 A1 | 3/2017 | Rado |
| 2017/0086507 A1 | 3/2017 | Rado |
| 2017/0086508 A1 | 3/2017 | Mironov et al. |
| 2017/0091490 A1 | 3/2017 | Cameron |
| 2017/0091853 A1 | 3/2017 | Cameron |
| 2017/0092106 A1 | 3/2017 | Cameron |
| 2017/0092900 A1 | 3/2017 | Yang |
| 2017/0093960 A1 | 3/2017 | Cameron |
| 2017/0093981 A1 | 3/2017 | Cameron |
| 2017/0094998 A1 | 4/2017 | Bernauer et al. |
| 2017/0094999 A1 | 4/2017 | Hearn et al. |
| 2017/0095000 A1 | 4/2017 | Spirito et al. |
| 2017/0095001 A1 | 4/2017 | Liu |
| 2017/0095002 A1 | 4/2017 | Silvestrini |
| 2017/0095003 A1 | 4/2017 | Mironov |
| 2017/0095004 A1 | 4/2017 | Liu |
| 2017/0095005 A1 | 4/2017 | Monsees et al. |
| 2017/0095518 A1 | 4/2017 | Bjorncrantz |
| 2017/0095623 A1 | 4/2017 | Trzecieski |
| 2017/0099877 A1 | 4/2017 | Worm et al. |
| 2017/0099879 A1 | 4/2017 | Heidl |
| 2017/0099880 A1 | 4/2017 | Hawes |
| 2017/0101256 A1 | 4/2017 | Zeitlin et al. |
| 2017/0102013 A1 | 4/2017 | Wallman et al. |
| 2017/0105448 A1 | 4/2017 | Scarpulla |
| 2017/0105449 A1 | 4/2017 | Hearn et al. |
| 2017/0105450 A1 | 4/2017 | Reed et al. |
| 2017/0105451 A1 | 4/2017 | Fornarelli |
| 2017/0105452 A1 | 4/2017 | Mironov et al. |
| 2017/0105453 A1 | 4/2017 | Li et al. |
| 2017/0105454 A1 | 4/2017 | Li et al. |
| 2017/0105455 A1 | 4/2017 | Qiu |
| 2017/0108210 A1 | 4/2017 | Meinhart et al. |
| 2017/0108840 A1 | 4/2017 | Hawes et al. |
| 2017/0109877 A1 | 4/2017 | Peleg et al. |
| 2017/0112182 A1 | 4/2017 | Arnold |
| 2017/0112190 A1 | 4/2017 | Buchberger |
| 2017/0112192 A1 | 4/2017 | Shan |
| 2017/0112193 A1 | 4/2017 | Chen |
| 2017/0112196 A1 | 4/2017 | Sur et al. |
| 2017/0112197 A1 | 4/2017 | Li et al. |
| 2017/0113819 A1 | 4/2017 | Marz |
| 2017/0117654 A1 | 4/2017 | Cruz |
| 2017/0118292 A1 | 4/2017 | Xiang |
| 2017/0118584 A1 | 4/2017 | Xiang |
| 2017/0119040 A1 | 5/2017 | Cameron |
| 2017/0119044 A1 | 5/2017 | Oligschlaeger et al. |
| 2017/0119050 A1 | 5/2017 | Blandino et al. |
| 2017/0119052 A1 | 5/2017 | Williams et al. |
| 2017/0119053 A1 | 5/2017 | Henry, Jr. et al. |
| 2017/0119054 A1 | 5/2017 | Zinovik et al. |
| 2017/0119055 A1 | 5/2017 | Liu |
| 2017/0119057 A1 | 5/2017 | Liu |
| 2017/0119058 A1 | 5/2017 | Cameron |
| 2017/0119060 A1 | 5/2017 | Li et al. |
| 2017/0119061 A1 | 5/2017 | Li et al. |
| 2017/0127722 A1 | 5/2017 | Davis et al. |
| 2017/0127723 A1 | 5/2017 | Wu |
| 2017/0127724 A1 | 5/2017 | Liu |
| 2017/0127725 A1 | 5/2017 | Buchberger et al. |
| 2017/0127726 A1 | 5/2017 | Xiang |
| 2017/0127728 A1 | 5/2017 | Li et al. |
| 2017/0129661 A1 | 5/2017 | Van Tassell, III et al. |
| 2017/0135397 A1 | 5/2017 | Buehler et al. |
| 2017/0135398 A1 | 5/2017 | Scott et al. |
| 2017/0135399 A1 | 5/2017 | Gavrielov et al. |
| 2017/0135400 A1 | 5/2017 | Liu |
| 2017/0135401 A1 | 5/2017 | Dickens |
| 2017/0135402 A1 | 5/2017 | Zitzke |
| 2017/0135403 A1 | 5/2017 | Liu |
| 2017/0135407 A1 | 5/2017 | Cameron |
| 2017/0135408 A1 | 5/2017 | Cameron |
| 2017/0135409 A1 | 5/2017 | Cameron |
| 2017/0135410 A1 | 5/2017 | Cameron |
| 2017/0135411 A1 | 5/2017 | Cameron |
| 2017/0135412 A1 | 5/2017 | Cameron |
| 2017/0136193 A1 | 5/2017 | Cameron |
| 2017/0136194 A1 | 5/2017 | Cameron |
| 2017/0136301 A1 | 5/2017 | Cameron |
| 2017/0143035 A1 | 5/2017 | Pucci |
| 2017/0143037 A9 | 5/2017 | Larson |
| 2017/0143038 A1 | 5/2017 | Dickens |
| 2017/0143040 A1 | 5/2017 | Liu |
| 2017/0143043 A1 | 5/2017 | Liu |
| 2017/0143917 A1 | 5/2017 | Cohen et al. |
| 2017/0144827 A1 | 5/2017 | Batista |
| 2017/0146005 A1 | 5/2017 | Edelen |
| 2017/0150753 A1 | 6/2017 | Macko |
| 2017/0150754 A1 | 6/2017 | Lin |
| 2017/0150755 A1 | 6/2017 | Batista |
| 2017/0150756 A1 | 6/2017 | Rexroad et al. |
| 2017/0150758 A1 | 6/2017 | Fernando et al. |
| 2017/0156397 A1 | 6/2017 | Sur et al. |
| 2017/0156398 A1 | 6/2017 | Sur et al. |
| 2017/0156400 A1 | 6/2017 | Liu |
| 2017/0156401 A1 | 6/2017 | Liu |
| 2017/0156402 A1 | 6/2017 | Liu |
| 2017/0156403 A1 | 6/2017 | Gill et al. |
| 2017/0156404 A1 | 6/2017 | Novak, III et al. |
| 2017/0156408 A1 | 6/2017 | Li et al. |
| 2017/0158436 A1 | 6/2017 | Slurink |
| 2017/0162523 A1 | 6/2017 | Hu |
| 2017/0162979 A1 | 6/2017 | Liu |
| 2017/0164655 A1 | 6/2017 | Chen |
| 2017/0164656 A1 | 6/2017 | Eusepi et al. |
| 2017/0164657 A1 | 6/2017 | Batista |
| 2017/0164658 A1 | 6/2017 | Lin et al. |
| 2017/0170439 A1 | 6/2017 | Jarvis et al. |
| 2017/0172204 A1 | 6/2017 | Kane et al. |
| 2017/0172205 A1 | 6/2017 | Chang et al. |
| 2017/0172207 A1 | 6/2017 | Liu |
| 2017/0172208 A1 | 6/2017 | Mironov |
| 2017/0172209 A1 | 6/2017 | Saydar et al. |
| 2017/0172213 A1 | 6/2017 | Hon |
| 2017/0172214 A1 | 6/2017 | Li et al. |
| 2017/0172215 A1 | 6/2017 | Li et al. |
| 2017/0181223 A1 | 6/2017 | Sur et al. |
| 2017/0181467 A1 | 6/2017 | Cameron |
| 2017/0181468 A1 | 6/2017 | Bowen et al. |
| 2017/0181470 A1 | 6/2017 | Li |
| 2017/0181471 A1 | 6/2017 | Phillips et al. |
| 2017/0181473 A1 | 6/2017 | Batista et al. |
| 2017/0181474 A1 | 6/2017 | Cameron |
| 2017/0181475 A1 | 6/2017 | Cameron |
| 2017/0181476 A1 | 6/2017 | Li et al. |
| 2017/0181928 A1 | 6/2017 | Collins et al. |
| 2017/0185364 A1 | 6/2017 | Cameron |
| 2017/0186122 A1 | 6/2017 | Levings et al. |
| 2017/0188626 A1 | 7/2017 | Davis et al. |
| 2017/0188627 A1 | 7/2017 | Sur |
| 2017/0188628 A1 | 7/2017 | Montgomery |
| 2017/0188629 A1 | 7/2017 | Dickens et al. |
| 2017/0188631 A1 | 7/2017 | Lin |
| 2017/0188632 A1 | 7/2017 | Hon |
| 2017/0188634 A1 | 7/2017 | Plojoux et al. |
| 2017/0188635 A1 | 7/2017 | Force et al. |
| 2017/0188636 A1 | 7/2017 | Li et al. |
| 2017/0196263 A1 | 7/2017 | Sur |
| 2017/0196264 A1 | 7/2017 | Liu |
| 2017/0196265 A1 | 7/2017 | Liu |
| 2017/0196267 A1 | 7/2017 | Zou et al. |
| 2017/0196268 A1 | 7/2017 | Reevell |
| 2017/0196269 A1 | 7/2017 | Bernauer et al. |
| 2017/0196270 A1 | 7/2017 | Vick et al. |
| 2017/0196271 A1 | 7/2017 | Levitz et al. |
| 2017/0196272 A1 | 7/2017 | Li et al. |
| 2017/0196273 A1 | 7/2017 | Qiu |

(56) References Cited

U.S. PATENT DOCUMENTS

| | | |
|---|---|---|
| 2017/0202265 A1 | 7/2017 | Hawes et al. |
| 2017/0202266 A1 | 7/2017 | Sur |
| 2017/0202267 A1 | 7/2017 | Liu |
| 2017/0202268 A1 | 7/2017 | Li et al. |
| 2017/0207499 A1 | 7/2017 | Leadley |
| 2017/0208857 A1 | 7/2017 | Branton et al. |
| 2017/0208858 A1 | 7/2017 | Li |
| 2017/0208862 A1 | 7/2017 | Li et al. |
| 2017/0208863 A1 | 7/2017 | Davis et al. |
| 2017/0208864 A1 | 7/2017 | Anderson, Jr. et al. |
| 2017/0208865 A1 | 7/2017 | Nettenstrom et al. |
| 2017/0208866 A1 | 7/2017 | Liu |
| 2017/0208867 A1 | 7/2017 | Li et al. |
| 2017/0208868 A1 | 7/2017 | Li et al. |
| 2017/0208869 A1 | 7/2017 | Li et al. |
| 2017/0208870 A1 | 7/2017 | Liu |
| 2017/0208882 A1 | 7/2017 | Lambertz |
| 2017/0214261 A1 | 7/2017 | Gratton |
| 2017/0215470 A1 | 8/2017 | Piccirilli et al. |
| 2017/0215473 A1 | 8/2017 | Nakano et al. |
| 2017/0215474 A1 | 8/2017 | Li |
| 2017/0215476 A1 | 8/2017 | Dickens et al. |
| 2017/0215477 A1 | 8/2017 | Reevell |
| 2017/0215478 A1 | 8/2017 | Harrison et al. |
| 2017/0215479 A1 | 8/2017 | Kies |
| 2017/0215480 A1 | 8/2017 | Qiu |
| 2017/0215481 A1 | 8/2017 | Li et al. |
| 2017/0215482 A1 | 8/2017 | Levitz et al. |
| 2017/0215483 A1 | 8/2017 | Li et al. |
| 2017/0215484 A1 | 8/2017 | Xiang |
| 2017/0215485 A1 | 8/2017 | Zitzke |
| 2017/0217607 A1 | 8/2017 | Slurink |
| 2017/0219199 A1 | 8/2017 | Lou et al. |
| 2017/0219391 A1 | 8/2017 | Lin et al. |
| 2017/0222468 A1 | 8/2017 | Schennum et al. |
| 2017/0224013 A1 | 8/2017 | Huang |
| 2017/0224014 A1 | 8/2017 | Fraser |
| 2017/0224016 A1 | 8/2017 | Reevell |
| 2017/0224017 A1 | 8/2017 | Li et al. |
| 2017/0224018 A1 | 8/2017 | Li et al. |
| 2017/0224022 A1 | 8/2017 | Liu |
| 2017/0224023 A1 | 8/2017 | Lin et al. |
| 2017/0224024 A1 | 8/2017 | Jochnowitz et al. |
| 2017/0229885 A1 | 8/2017 | Bernauer |
| 2017/0229888 A1 | 8/2017 | Liu |
| 2017/0231266 A1 | 8/2017 | Mishra et al. |
| 2017/0231267 A1 | 8/2017 | Shi et al. |
| 2017/0231269 A1 | 8/2017 | Besso et al. |
| 2017/0231273 A1 | 8/2017 | Xiang |
| 2017/0231275 A1 | 8/2017 | Guenther |
| 2017/0231276 A1 | 8/2017 | Mironov et al. |
| 2017/0231277 A1 | 8/2017 | Mironov et al. |
| 2017/0231278 A1 | 8/2017 | Mironov et al. |
| 2017/0231279 A1 | 8/2017 | Watson |
| 2017/0231280 A1 | 8/2017 | Anton |
| 2017/0231281 A1 | 8/2017 | Hatton et al. |
| 2017/0231282 A1 | 8/2017 | Bowen et al. |
| 2017/0231283 A1 | 8/2017 | Gadas |
| 2017/0231284 A1 | 8/2017 | Newns |
| 2017/0231285 A1 | 8/2017 | Holzherr et al. |
| 2017/0231286 A1 | 8/2017 | Borkovec et al. |
| 2017/0233114 A1 | 8/2017 | Christensen et al. |
| 2017/0238596 A1 | 8/2017 | Matsumoto et al. |
| 2017/0238605 A1 | 8/2017 | Matsumoto et al. |
| 2017/0238606 A1 | 8/2017 | Matsumoto et al. |
| 2017/0238608 A1 | 8/2017 | Matsumoto et al. |
| 2017/0238609 A1 | 8/2017 | Schlipf |
| 2017/0238611 A1 | 8/2017 | Buchberger |
| 2017/0238612 A1 | 8/2017 | Daryani et al. |
| 2017/0238613 A1 | 8/2017 | Suess et al. |
| 2017/0238614 A1 | 8/2017 | Li et al. |
| 2017/0238617 A1 | 8/2017 | Scatterday |
| 2017/0241857 A1 | 8/2017 | Hearn et al. |
| 2017/0245543 A1 | 8/2017 | Karles et al. |
| 2017/0245546 A1 | 8/2017 | Huang |
| 2017/0245547 A1 | 8/2017 | Lipowicz |
| 2017/0245550 A1 | 8/2017 | Freelander |
| 2017/0245551 A1 | 8/2017 | Reevell |
| 2017/0245554 A1 | 8/2017 | Perez et al. |
| 2017/0246399 A1 | 8/2017 | Forlani et al. |
| 2017/0246405 A1 | 8/2017 | Wensley et al. |
| 2017/0246407 A1 | 8/2017 | Matsumoto et al. |
| 2017/0250552 A1 | 8/2017 | Liu |
| 2017/0251714 A1 | 9/2017 | Mishra et al. |
| 2017/0251718 A1 | 9/2017 | Armoush et al. |
| 2017/0251719 A1 | 9/2017 | Cyphert et al. |
| 2017/0251721 A1 | 9/2017 | Rostami et al. |
| 2017/0251722 A1 | 9/2017 | Kobal et al. |
| 2017/0251723 A1 | 9/2017 | Kobal et al. |
| 2017/0251724 A1 | 9/2017 | Lamb et al. |
| 2017/0251725 A1 | 9/2017 | Buchberger et al. |
| 2017/0251726 A1 | 9/2017 | Nielsen |
| 2017/0251727 A1 | 9/2017 | Nielsen |
| 2017/0251728 A1 | 9/2017 | Peleg et al. |
| 2017/0251729 A1 | 9/2017 | Li et al. |
| 2017/0258129 A1 | 9/2017 | Haun |
| 2017/0258132 A1 | 9/2017 | Rostami et al. |
| 2017/0258134 A1 | 9/2017 | Kane |
| 2017/0258137 A1 | 9/2017 | Smith et al. |
| 2017/0258138 A1 | 9/2017 | Rostami et al. |
| 2017/0258139 A1 | 9/2017 | Rostami et al. |
| 2017/0258140 A1 | 9/2017 | Rostami et al. |
| 2017/0258142 A1 | 9/2017 | Hatton et al. |
| 2017/0258143 A1 | 9/2017 | Lederer |
| 2017/0259170 A1 | 9/2017 | Bowen et al. |
| 2017/0259954 A1 | 9/2017 | Schwester |
| 2017/0261200 A1 | 9/2017 | Stultz |
| 2017/0265517 A1 | 9/2017 | Swede et al. |
| 2017/0265522 A1 | 9/2017 | Li et al. |
| 2017/0265524 A1 | 9/2017 | Cadieux et al. |
| 2017/0265525 A1 | 9/2017 | Li et al. |
| 2017/0266397 A1 | 9/2017 | Mayle et al. |
| 2017/0273353 A1 | 9/2017 | Gindrat |
| 2017/0273354 A1 | 9/2017 | Tucker et al. |
| 2017/0273355 A1 | 9/2017 | Rogers et al. |
| 2017/0273357 A1 | 9/2017 | Barbuck |
| 2017/0273358 A1 | 9/2017 | Batista et al. |
| 2017/0273359 A1 | 9/2017 | Liu |
| 2017/0273360 A1 | 9/2017 | Brinkley et al. |
| 2017/0273361 A1 | 9/2017 | Li et al. |
| 2017/0273914 A1 | 9/2017 | Knudsen |
| 2017/0280767 A1 | 10/2017 | Li et al. |
| 2017/0280768 A1 | 10/2017 | Lipowicz |
| 2017/0280769 A1 | 10/2017 | Li et al. |
| 2017/0280770 A1 | 10/2017 | Wang et al. |
| 2017/0280771 A1 | 10/2017 | Courbat et al. |
| 2017/0280775 A1 | 10/2017 | Manca et al. |
| 2017/0280776 A1 | 10/2017 | Manca et al. |
| 2017/0280778 A1 | 10/2017 | Force |
| 2017/0281883 A1 | 10/2017 | Li et al. |
| 2017/0283154 A1 | 10/2017 | Karles et al. |
| 2017/0285810 A1 | 10/2017 | Krah |
| 2017/0290368 A1 | 10/2017 | Hearn |
| 2017/0290369 A1 | 10/2017 | Norasak |
| 2017/0290370 A1 | 10/2017 | Garthaffner et al. |
| 2017/0290371 A1 | 10/2017 | Davis et al. |
| 2017/0290373 A1 | 10/2017 | Hon |
| 2017/0290998 A1 | 10/2017 | Poston et al. |
| 2017/0295840 A1 | 10/2017 | Rath et al. |
| 2017/0295843 A1 | 10/2017 | Storch |
| 2017/0295844 A1 | 10/2017 | Thevenaz et al. |
| 2017/0295845 A1 | 10/2017 | Bajpai et al. |
| 2017/0295846 A1 | 10/2017 | Liu |
| 2017/0295847 A1 | 10/2017 | Liu |
| 2017/0295848 A1 | 10/2017 | LaMothe |
| 2017/0295849 A1 | 10/2017 | Cadieux et al. |
| 2017/0297892 A1 | 10/2017 | Li et al. |
| 2017/0301898 A1 | 10/2017 | Lin et al. |
| 2017/0302089 A1 | 10/2017 | Bernauer et al. |
| 2017/0302324 A1 | 10/2017 | Stanimirovic et al. |
| 2017/0303597 A1 | 10/2017 | Tsui |
| 2017/0311648 A1 | 11/2017 | Gill et al. |
| 2017/0318860 A1 | 11/2017 | Adair |
| 2017/0318861 A1 | 11/2017 | Thorens |

(56) References Cited

U.S. PATENT DOCUMENTS

| | | | |
|---|---|---|---|
| 2017/0325503 A1 | 11/2017 | Liu | |
| 2017/0325504 A1 | 11/2017 | Liu | |
| 2017/0325506 A1 | 11/2017 | Batista | |
| 2017/0332695 A1 | 11/2017 | Zappoli et al. | |
| 2017/0333415 A1 | 11/2017 | Williams | |
| 2017/0333650 A1 | 11/2017 | Buchberger et al. | |
| 2017/0333651 A1 | 11/2017 | Qiu | |
| 2017/0334605 A1 | 11/2017 | Murphy et al. | |
| 2017/0367406 A1 | 12/2017 | Schuler et al. | |
| 2018/0093050 A1 | 4/2018 | Stenzler et al. | |
| 2018/0153218 A1 | 6/2018 | Verleur et al. | |
| 2018/0153219 A1 | 6/2018 | Verleur et al. | |
| 2018/0153220 A1 | 6/2018 | Verleur et al. | |
| 2018/0153221 A1 | 6/2018 | Verleur et al. | |

FOREIGN PATENT DOCUMENTS

| | | |
|---|---|---|
| AU | 2017202891 A1 | 5/2017 |
| CA | 2641869 A1 | 5/2010 |
| CA | 2641869 A1 | 5/2010 |
| CN | 85106876 A | 9/1986 |
| CN | 1122213 A | 5/1996 |
| CN | 1122213 A | 5/1996 |
| CN | 201018481 Y | 2/2008 |
| CN | 201430916 Y | 3/2010 |
| CN | 101869356 A | 10/2010 |
| CN | 101869356 A | 10/2010 |
| CN | 301547686 S | 5/2011 |
| CN | 301970169 S | 6/2012 |
| CN | 102754924 A | 10/2012 |
| CN | 102754924 A | 10/2012 |
| CN | 302396126 S | 4/2013 |
| CN | 103141944 A | 6/2013 |
| CN | 203327953 U | 12/2013 |
| CN | 302799554 S | 4/2014 |
| CN | 302810246 S | 4/2014 |
| CN | 302884434 S | 8/2014 |
| CN | 302926289 S | 8/2014 |
| CN | 302950830 S | 9/2014 |
| CN | 303089422 S | 1/2015 |
| CN | 303091331 S | 1/2015 |
| CN | 303210086 S | 5/2015 |
| CN | 303103389 S | 11/2015 |
| CN | 303568163 S | 1/2016 |
| CN | 303103390 S | 2/2016 |
| DE | 4200639 A1 | 7/1992 |
| DE | 19854005 A1 | 5/2000 |
| DE | 19854005 A1 | 5/2000 |
| DE | 19854012 A1 | 5/2000 |
| DE | 19854012 A1 | 5/2000 |
| EP | 0283672 A2 | 9/1988 |
| EP | 0358114 A2 | 3/1990 |
| EP | 0503767 A1 | 9/1992 |
| EP | 0532194 A1 | 3/1993 |
| EP | 0532194 A1 | 3/1993 |
| EP | 0535695 A2 | 4/1993 |
| EP | 0535695 A2 | 4/1993 |
| EP | 0283672 B1 | 9/1993 |
| EP | 0762258 A2 | 3/1997 |
| EP | 1458388 A | 9/2004 |
| EP | 2110033 | 10/2009 |
| EP | 2110033 A1 | 10/2009 |
| EP | 2186507 A2 | 5/2010 |
| EP | 2399636 A1 | 12/2011 |
| EP | 2325093 B1 | 6/2012 |
| EP | 2573900 A1 | 3/2013 |
| EP | 2609821 A1 | 7/2013 |
| EP | 2614731 A1 | 7/2013 |
| EP | 2711006 A1 | 3/2014 |
| EP | 2641669 B1 | 5/2014 |
| EP | 2152313 B1 | 9/2014 |
| EP | 2789248 A1 | 10/2014 |
| EP | 2493342 B1 | 12/2014 |
| EP | 3024343 A2 | 1/2015 |
| EP | 2856893 A1 | 4/2015 |
| EP | 2856893 A1 | 4/2015 |
| EP | 2862454 A1 | 4/2015 |
| EP | 2862457 A1 | 4/2015 |
| EP | 2908675 A1 | 8/2015 |
| EP | 2319934 B1 | 9/2015 |
| EP | 2915443 A1 | 9/2015 |
| EP | 2944206 A1 | 11/2015 |
| EP | 2952110 A1 | 12/2015 |
| EP | 2989912 A1 | 3/2016 |
| EP | 3001918 A1 | 4/2016 |
| EP | 3007305 A1 | 4/2016 |
| EP | 3012213 A1 | 4/2016 |
| EP | 3016233 A1 | 5/2016 |
| EP | 3023016 A1 | 5/2016 |
| EP | 3023351 A1 | 5/2016 |
| EP | 3023947 A1 | 5/2016 |
| EP | 3025598 A1 | 6/2016 |
| EP | 3026779 A1 | 6/2016 |
| EP | 3031338 A1 | 6/2016 |
| EP | 3047742 A1 | 7/2016 |
| EP | 3056099 A1 | 8/2016 |
| EP | 3056099 A1 | 8/2016 |
| EP | 3061358 A1 | 8/2016 |
| EP | 3062646 A1 | 9/2016 |
| EP | 3065581 A2 | 9/2016 |
| EP | 3068244 A1 | 9/2016 |
| EP | 3075270 A1 | 10/2016 |
| EP | 3075271 A1 | 10/2016 |
| EP | 3075271 A1 | 10/2016 |
| EP | 3081102 A1 | 10/2016 |
| EP | 3081102 A1 | 10/2016 |
| EP | 3085638 A1 | 10/2016 |
| EP | 3087853 A1 | 11/2016 |
| EP | 3097803 A1 | 11/2016 |
| EP | 3103355 A1 | 12/2016 |
| EP | 3103356 A1 | 12/2016 |
| EP | 3111787 A1 | 1/2017 |
| EP | 3130238 A1 | 2/2017 |
| EP | 3132843 A1 | 2/2017 |
| EP | 3135139 A1 | 3/2017 |
| EP | 3135603 A1 | 3/2017 |
| EP | 3143882 A3 | 3/2017 |
| EP | 3143884 A3 | 4/2017 |
| EP | 3155908 A1 | 4/2017 |
| EP | 3158880 A1 | 4/2017 |
| EP | 3158881 A1 | 4/2017 |
| EP | 3195738 A2 | 7/2017 |
| EP | 3165102 A3 | 8/2017 |
| EP | 3199043 A1 | 8/2017 |
| EP | 3205220 A1 | 8/2017 |
| EP | 3205597 A1 | 8/2017 |
| EP | 3213649 A1 | 9/2017 |
| EP | 3225118 A1 | 10/2017 |
| EP | 3228198 A1 | 10/2017 |
| EP | 3228345 A1 | 10/2017 |
| ES | 2118034 A1 | 9/1998 |
| ES | 2118034 A1 | 9/1998 |
| FR | 002626416-001 | 4/2015 |
| FR | 002626416-002 | 4/2015 |
| GB | 1025630 A | 4/1966 |
| GB | 1025630 A | 4/1966 |
| GB | 1065678 A | 4/1967 |
| GB | 1065678 A | 4/1967 |
| GB | 2533174 A | 6/2016 |
| IE | S2005-0051 | 2/2005 |
| IE | S2005-0563 | 8/2005 |
| IE | S2005-0615 | 9/2005 |
| IE | S20050615 | 9/2005 |
| JP | 62-278975 | 12/1987 |
| JP | 62278975 | 12/1987 |
| JP | 64-37276 A | 2/1989 |
| JP | 02-145179 A | 6/1990 |
| JP | 03-049671 | 3/1991 |
| JP | 03-180166 | 8/1991 |
| JP | H06114105 A | 4/1994 |
| JP | 09-075058 | 3/1997 |
| JP | H09075058 A | 3/1997 |
| JP | 10-501999 A | 2/1998 |
| JP | 11178563 | 6/1999 |

(56) References Cited

FOREIGN PATENT DOCUMENTS

| | | |
|---|---|---|
| JP | 11-178563 | 7/1999 |
| JP | 2000-203639 | 7/2000 |
| JP | 2000203639 A | 7/2000 |
| JP | 2000-236865 A | 9/2000 |
| JP | 2000236865 A | 9/2000 |
| JP | 2001-165437 A | 6/2001 |
| JP | 2001161819 A | 6/2001 |
| JP | 2001165437 A | 6/2001 |
| JP | 2005-034021 A | 2/2005 |
| JP | 2006-504430 A | 2/2006 |
| JP | 2006320285 A | 11/2006 |
| JP | 2006320286 A | 11/2006 |
| JP | 2009213428 A | 9/2009 |
| JP | 2010020929 A | 1/2010 |
| JP | 2011024430 A | 2/2011 |
| JP | 2012005412 A | 1/2012 |
| JP | 2015504669 A | 2/2015 |
| JP | 201712730 A | 1/2017 |
| KR | 0193885 B1 | 6/1999 |
| KR | 101357574 B1 | 2/2014 |
| KR | 101570876 B1 | 11/2015 |
| KR | 101677435 B1 | 11/2016 |
| TW | 201436722 A | 10/2014 |
| TW | 201438608 A | 10/2014 |
| TW | 201524383 A | 7/2015 |
| WO | WO95/01137 A1 | 1/1995 |
| WO | WO97/12639 A1 | 4/1997 |
| WO | WO-9712639 A1 | 4/1997 |
| WO | WO-2000005976 A1 | 2/2000 |
| WO | WO00/28842 A1 | 5/2000 |
| WO | WO-0028842 A1 | 5/2000 |
| WO | WO03/056948 A1 | 7/2003 |
| WO | WO-03055486 A1 | 7/2003 |
| WO | WO-03056948 A1 | 7/2003 |
| WO | WO03/082031 A1 | 10/2003 |
| WO | WO-03082031 A1 | 10/2003 |
| WO | WO03/094900 A1 | 11/2003 |
| WO | WO 03/103387 A2 | 12/2003 |
| WO | WO-03101454 A1 | 12/2003 |
| WO | WO2004/064548 A1 | 8/2004 |
| WO | WO-2004064548 A1 | 8/2004 |
| WO | WO2004/080216 A1 | 9/2004 |
| WO | WO-2004080216 A1 | 9/2004 |
| WO | WO2005/020726 A1 | 3/2005 |
| WO | WO-2005020726 A1 | 3/2005 |
| WO | WO-2005060366 A2 | 7/2005 |
| WO | WO2006/015070 A1 | 2/2006 |
| WO | WO-2006021153 A1 | 3/2006 |
| WO | WO-2006022715 A1 | 3/2006 |
| WO | WO-2006082571 A1 | 8/2006 |
| WO | WO2007/026131 A1 | 3/2007 |
| WO | WO-2007039794 A2 | 4/2007 |
| WO | WO-2007042941 A2 | 4/2007 |
| WO | WO-2007066374 A1 | 6/2007 |
| WO | WO2007/078273 A1 | 7/2007 |
| WO | WO-2007078273 A1 | 7/2007 |
| WO | WO-2007095109 A2 | 8/2007 |
| WO | WO-2007117675 A2 | 10/2007 |
| WO | WO-2007/141520 A1 | 12/2007 |
| WO | WO2008/077271 A1 | 7/2008 |
| WO | WO-2008077271 A1 | 7/2008 |
| WO | WO-2008087161 A1 | 7/2008 |
| WO | WO-2008151777 A2 | 12/2008 |
| WO | WO-2009003204 A2 | 1/2009 |
| WO | WO-2010003480 A1 | 1/2010 |
| WO | WO2010/023561 A1 | 3/2010 |
| WO | WO-2010118122 A1 | 10/2010 |
| WO | WO-2010118644 A1 | 10/2010 |
| WO | WO-2010140841 A2 | 12/2010 |
| WO | WO-2010145805 A1 | 12/2010 |
| WO | WO-2011010334 A1 | 1/2011 |
| WO | WO2011/033396 A2 | 3/2011 |
| WO | WO-2011050964 A1 | 5/2011 |
| WO | WO2011/117580 A2 | 9/2011 |
| WO | WO-2011125058 A1 | 10/2011 |
| WO | WO2012/021972 A1 | 2/2012 |
| WO | WO-2012019533 A1 | 2/2012 |
| WO | WO2012/027350 A2 | 3/2012 |
| WO | WO-2012043941 A1 | 4/2012 |
| WO | WO-2012062600 A1 | 5/2012 |
| WO | WO2012/085207 A1 | 6/2012 |
| WO | WO-2012088675 A1 | 7/2012 |
| WO | WO-2012091249 A1 | 7/2012 |
| WO | WO-2012100523 A1 | 8/2012 |
| WO | WO2012/120487 A2 | 9/2012 |
| WO | WO-2012129812 A1 | 10/2012 |
| WO | WO-2012134117 A2 | 10/2012 |
| WO | WO-2012164033 A1 | 12/2012 |
| WO | WO-2012173322 A1 | 12/2012 |
| WO | WO-2012174677 A1 | 12/2012 |
| WO | WO-D079112-0010 | 12/2012 |
| WO | WO-2013012157 A1 | 1/2013 |
| WO | WO-2013020220 A1 | 2/2013 |
| WO | WO-2013030202 A1 | 3/2013 |
| WO | WO-2013034453 A1 | 3/2013 |
| WO | WO-2013040193 A2 | 3/2013 |
| WO | WO2013/044537 A1 | 4/2013 |
| WO | WO2013/050934 A1 | 4/2013 |
| WO | WO-2013044537 A1 | 4/2013 |
| WO | WO-2013076750 A1 | 5/2013 |
| WO | WO2013/083635 A1 | 6/2013 |
| WO | WO2013/089551 A1 | 6/2013 |
| WO | WO-2013083635 A1 | 6/2013 |
| WO | WO-2013089551 A1 | 6/2013 |
| WO | WO2013/098398 A2 | 7/2013 |
| WO | WO-2013110208 A1 | 8/2013 |
| WO | WO-2013110209 A1 | 8/2013 |
| WO | WO-2013110210 A1 | 8/2013 |
| WO | WO-2013113173 A1 | 8/2013 |
| WO | WO-2013113174 A1 | 8/2013 |
| WO | WO-2013113612 A1 | 8/2013 |
| WO | WO-2013116983 A1 | 8/2013 |
| WO | WO2013/142678 A1 | 9/2013 |
| WO | WO-2013131763 A1 | 9/2013 |
| WO | WO-2013142678 A1 | 9/2013 |
| WO | WO-2013150406 A2 | 10/2013 |
| WO | WO-2013156658 A1 | 10/2013 |
| WO | WO-2013165878 A1 | 11/2013 |
| WO | WO-2013171206 A1 | 11/2013 |
| WO | WO-2013174001 A1 | 11/2013 |
| WO | WO-2014020539 A1 | 2/2014 |
| WO | WO-2014020953 A1 | 2/2014 |
| WO | WO-2014023171 A1 | 2/2014 |
| WO | WO2014/040915 A1 | 3/2014 |
| WO | WO-2014032280 A1 | 3/2014 |
| WO | WO-2014040915 A1 | 3/2014 |
| WO | WO2014/047948 A1 | 4/2014 |
| WO | WO-2014047955 A1 | 4/2014 |
| WO | WO-2014067236 A1 | 5/2014 |
| WO | WO-2014071747 A1 | 5/2014 |
| WO | WO2014/093127 A2 | 6/2014 |
| WO | WO2014/101734 A1 | 7/2014 |
| WO | WO-2014101119 A1 | 7/2014 |
| WO | WO-2014101401 A1 | 7/2014 |
| WO | WO-2014101734 A1 | 7/2014 |
| WO | WO-2014106323 A1 | 7/2014 |
| WO | WO-2014110761 A1 | 7/2014 |
| WO | WO-2014113949 A1 | 7/2014 |
| WO | WO2014/118286 A2 | 8/2014 |
| WO | WO-2014117382 A1 | 8/2014 |
| WO | WO-2014121509 A1 | 8/2014 |
| WO | WO-2014125340 A1 | 8/2014 |
| WO | WO-2014127446 A1 | 8/2014 |
| WO | WO2014/139611 A1 | 9/2014 |
| WO | WO2014/140087 A1 | 9/2014 |
| WO | WO2014/150704 A2 | 9/2014 |
| WO | WO-2014134781 A1 | 9/2014 |
| WO | WO-2014144678 A2 | 9/2014 |
| WO | WO-2014146270 A1 | 9/2014 |
| WO | WO-2014147470 A2 | 9/2014 |
| WO | WO-2014150979 A2 | 9/2014 |
| WO | WO2014/159982 A1 | 10/2014 |
| WO | WO-2014161181 A1 | 10/2014 |
| WO | WO-2014166039 A1 | 10/2014 |

(56) References Cited

FOREIGN PATENT DOCUMENTS

| | | |
|---|---|---|
| WO | WO-2014167530 A1 | 10/2014 |
| WO | WO-2014169437 A1 | 10/2014 |
| WO | WO-2014169667 A1 | 10/2014 |
| WO | WO2014/187763 A1 | 11/2014 |
| WO | WO2014/187770 A2 | 11/2014 |
| WO | WO-2014185937 A1 | 11/2014 |
| WO | WO-2014186983 A1 | 11/2014 |
| WO | WO2014/205263 A1 | 12/2014 |
| WO | WO-2014194499 A1 | 12/2014 |
| WO | WO-2014195687 A1 | 12/2014 |
| WO | WO-2014198042 A1 | 12/2014 |
| WO | WO-2014201610 A1 | 12/2014 |
| WO | WO-2014201611 A1 | 12/2014 |
| WO | WO-2014201646 A1 | 12/2014 |
| WO | WO-2014201664 A1 | 12/2014 |
| WO | WO-2014201666 A1 | 12/2014 |
| WO | WO-2014201668 A1 | 12/2014 |
| WO | WO-2014205749 A1 | 12/2014 |
| WO | WO-2014205780 A1 | 12/2014 |
| WO | WO-2014205807 A1 | 12/2014 |
| WO | WO-2014205811 A1 | 12/2014 |
| WO | WO-2014206148 A1 | 12/2014 |
| WO | WO2015/006652 A1 | 1/2015 |
| WO | WO2015/009862 A2 | 1/2015 |
| WO | WO-2015000125 A1 | 1/2015 |
| WO | WO-2015000180 A1 | 1/2015 |
| WO | WO-2015003327 A1 | 1/2015 |
| WO | WO-2015003372 A1 | 1/2015 |
| WO | WO-2015003374 A1 | 1/2015 |
| WO | WO-2015006929 A1 | 1/2015 |
| WO | WO-2015010242 A1 | 1/2015 |
| WO | WO-2015010277 A1 | 1/2015 |
| WO | WO-2015010284 A1 | 1/2015 |
| WO | WO-2015010291 A1 | 1/2015 |
| WO | WO-2015010310 A1 | 1/2015 |
| WO | WO-2015010336 A1 | 1/2015 |
| WO | WO-2015010345 A1 | 1/2015 |
| WO | WO-2015010349 A1 | 1/2015 |
| WO | WO-2015013890 A1 | 2/2015 |
| WO | WO-2015013891 A1 | 2/2015 |
| WO | WO-2015013892 A1 | 2/2015 |
| WO | WO-2015013926 A1 | 2/2015 |
| WO | WO-2015013950 A1 | 2/2015 |
| WO | WO-2015013967 A1 | 2/2015 |
| WO | WO-2015015156 A1 | 2/2015 |
| WO | WO-2015017971 A1 | 2/2015 |
| WO | WO-2015018026 A1 | 2/2015 |
| WO | WO-2015018120 A1 | 2/2015 |
| WO | WO-2015021612 A1 | 2/2015 |
| WO | WO-2015021646 A1 | 2/2015 |
| WO | WO-2015021651 A1 | 2/2015 |
| WO | WO-2015021652 A1 | 2/2015 |
| WO | WO-2015021655 A1 | 2/2015 |
| WO | WO-2015021658 A1 | 2/2015 |
| WO | WO-2015024239 A1 | 2/2015 |
| WO | WO-2015024247 A1 | 2/2015 |
| WO | WO-2015026081 A1 | 2/2015 |
| WO | WO2015/028815 A1 | 3/2015 |
| WO | WO2015/040180 A2 | 3/2015 |
| WO | WO-2015027383 A1 | 3/2015 |
| WO | WO-2015027435 A1 | 3/2015 |
| WO | WO-2015027436 A1 | 3/2015 |
| WO | WO-2015027470 A1 | 3/2015 |
| WO | WO-2015028815 A1 | 3/2015 |
| WO | WO-2015032050 A1 | 3/2015 |
| WO | WO-2015032055 A1 | 3/2015 |
| WO | WO-2015032078 A1 | 3/2015 |
| WO | WO-2015032093 A1 | 3/2015 |
| WO | WO-2015035510 A1 | 3/2015 |
| WO | WO-2015035547 A1 | 3/2015 |
| WO | WO-2015035557 A1 | 3/2015 |
| WO | WO-2015035587 A1 | 3/2015 |
| WO | WO-2015035623 A1 | 3/2015 |
| WO | WO-2015035689 A1 | 3/2015 |
| WO | WO-2015037925 A1 | 3/2015 |
| WO | WO-2015039275 A1 | 3/2015 |
| WO | WO-2015039280 A1 | 3/2015 |
| WO | WO-2015039332 A1 | 3/2015 |
| WO | WO2015/058387 A1 | 4/2015 |
| WO | WO-2015042790 A1 | 4/2015 |
| WO | WO-2015042811 A1 | 4/2015 |
| WO | WO-2015042848 A1 | 4/2015 |
| WO | WO-2015042943 A1 | 4/2015 |
| WO | WO-2015051509 A1 | 4/2015 |
| WO | WO-2015051538 A1 | 4/2015 |
| WO | WO-2015054815 A1 | 4/2015 |
| WO | WO-2015054961 A1 | 4/2015 |
| WO | WO-2015055314 A1 | 4/2015 |
| WO | WO-2015058340 A1 | 4/2015 |
| WO | WO-2015058341 A1 | 4/2015 |
| WO | WO-2015058367 A1 | 4/2015 |
| WO | WO-2015058387 A1 | 4/2015 |
| WO | WO2015/063126 A1 | 5/2015 |
| WO | WO-2015062041 A1 | 5/2015 |
| WO | WO-2015066136 A1 | 5/2015 |
| WO | WO-2015066927 A1 | 5/2015 |
| WO | WO-2015070398 A1 | 5/2015 |
| WO | WO-2015070405 A1 | 5/2015 |
| WO | WO-2015071703 A1 | 5/2015 |
| WO | WO-2015073975 A1 | 5/2015 |
| WO | WO-2015074187 A1 | 5/2015 |
| WO | WO-2015074265 A1 | 5/2015 |
| WO | WO-2015074308 A1 | 5/2015 |
| WO | WO2015/082652 A1 | 6/2015 |
| WO | WO2015/084544 A1 | 6/2015 |
| WO | WO2015/089711 A1 | 6/2015 |
| WO | WO-2015077998 A1 | 6/2015 |
| WO | WO-2015077999 A1 | 6/2015 |
| WO | WO-2015078010 A1 | 6/2015 |
| WO | WO-2015079197 A1 | 6/2015 |
| WO | WO-2015089711 A1 | 6/2015 |
| WO | WO-2015091346 A2 | 6/2015 |
| WO | WO2015/101651 A1 | 7/2015 |
| WO | WO2015/109616 A1 | 7/2015 |
| WO | WO-2015013327 A3 | 7/2015 |
| WO | WO-2015106434 A1 | 7/2015 |
| WO | WO-2015106440 A1 | 7/2015 |
| WO | WO-2015107551 A2 | 7/2015 |
| WO | WO-2015107552 A1 | 7/2015 |
| WO | WO-2015109476 A1 | 7/2015 |
| WO | WO-2015109532 A1 | 7/2015 |
| WO | WO-2015109540 A1 | 7/2015 |
| WO | WO-2015109616 A1 | 7/2015 |
| WO | WO-2015109618 A1 | 7/2015 |
| WO | WO2015/124878 A1 | 8/2015 |
| WO | WO-2015117285 A1 | 8/2015 |
| WO | WO-2015120588 A1 | 8/2015 |
| WO | WO-2015120591 A1 | 8/2015 |
| WO | WO-2015120623 A1 | 8/2015 |
| WO | WO-2015123831 A1 | 8/2015 |
| WO | WO-2015127609 A1 | 9/2015 |
| WO | WO-2015128599 A1 | 9/2015 |
| WO | WO-2015137815 A1 | 9/2015 |
| WO | WO-2015140312 A1 | 9/2015 |
| WO | WO-2015140336 A1 | 9/2015 |
| WO | WO-2015140768 A2 | 9/2015 |
| WO | WO2015/148547 A1 | 10/2015 |
| WO | WO2015/149647 A1 | 10/2015 |
| WO | WO-2015143637 A1 | 10/2015 |
| WO | WO-2015143648 A1 | 10/2015 |
| WO | WO-2015143749 A1 | 10/2015 |
| WO | WO-2015143765 A1 | 10/2015 |
| WO | WO-2015144057 A1 | 10/2015 |
| WO | WO-2015149311 A1 | 10/2015 |
| WO | WO-2015149330 A1 | 10/2015 |
| WO | WO-2015149332 A1 | 10/2015 |
| WO | WO-2015149338 A1 | 10/2015 |
| WO | WO-2015149368 A1 | 10/2015 |
| WO | WO-2015149403 A1 | 10/2015 |
| WO | WO-2015149406 A1 | 10/2015 |
| WO | WO-2015150068 A1 | 10/2015 |
| WO | WO-2015154309 A1 | 10/2015 |
| WO | WO-2015154619 A1 | 10/2015 |
| WO | WO-2015157891 A1 | 10/2015 |

(56) References Cited

FOREIGN PATENT DOCUMENTS

| | | |
|---|---|---|
| WO | WO-2015157893 A1 | 10/2015 |
| WO | WO-2015157900 A1 | 10/2015 |
| WO | WO-2015157901 A1 | 10/2015 |
| WO | WO-2015157928 A1 | 10/2015 |
| WO | WO-2015158522 A1 | 10/2015 |
| WO | WO-2015158548 A1 | 10/2015 |
| WO | WO-2015161406 A1 | 10/2015 |
| WO | WO-2015161407 A1 | 10/2015 |
| WO | WO-2015161485 A1 | 10/2015 |
| WO | WO-2015161486 A1 | 10/2015 |
| WO | WO-2015161491 A1 | 10/2015 |
| WO | WO-2015161514 A1 | 10/2015 |
| WO | WO-2015161553 A1 | 10/2015 |
| WO | WO-2015161555 A1 | 10/2015 |
| WO | WO-2015161557 A1 | 10/2015 |
| WO | WO2015/168828 A1 | 11/2015 |
| WO | WO2015/169127 A1 | 11/2015 |
| WO | WO2015/175979 A1 | 11/2015 |
| WO | WO2015/179641 A1 | 11/2015 |
| WO | WO-2015068044 A3 | 11/2015 |
| WO | WO-2015165067 A1 | 11/2015 |
| WO | WO-2015165081 A1 | 11/2015 |
| WO | WO-2015165083 A1 | 11/2015 |
| WO | WO-2015165086 A1 | 11/2015 |
| WO | WO-2015165105 A1 | 11/2015 |
| WO | WO-2015165146 A1 | 11/2015 |
| WO | WO-2015168827 A1 | 11/2015 |
| WO | WO-2015168828 A1 | 11/2015 |
| WO | WO-2015168853 A1 | 11/2015 |
| WO | WO-2015168904 A1 | 11/2015 |
| WO | WO-2015168912 A1 | 11/2015 |
| WO | WO-2015172331 A1 | 11/2015 |
| WO | WO-2015172361 A1 | 11/2015 |
| WO | WO-2015172368 A1 | 11/2015 |
| WO | WO-2015172382 A1 | 11/2015 |
| WO | WO-2015172383 A1 | 11/2015 |
| WO | WO-2015172384 A1 | 11/2015 |
| WO | WO-2015172387 A1 | 11/2015 |
| WO | WO-2015172388 A1 | 11/2015 |
| WO | WO-2015172389 A1 | 11/2015 |
| WO | WO-2015172390 A1 | 11/2015 |
| WO | WO-2015172606 A1 | 11/2015 |
| WO | WO-2015174657 A1 | 11/2015 |
| WO | WO-2015174708 A1 | 11/2015 |
| WO | WO-2015175979 A1 | 11/2015 |
| WO | WO-2015176210 A1 | 11/2015 |
| WO | WO-2015176230 A1 | 11/2015 |
| WO | WO-2015176300 A1 | 11/2015 |
| WO | WO-2015176580 A1 | 11/2015 |
| WO | WO2015/193456 A1 | 12/2015 |
| WO | WO-2015180027 A1 | 12/2015 |
| WO | WO-2015180061 A1 | 12/2015 |
| WO | WO-2015180062 A1 | 12/2015 |
| WO | WO-2015180071 A1 | 12/2015 |
| WO | WO-2015180088 A1 | 12/2015 |
| WO | WO-2015180089 A1 | 12/2015 |
| WO | WO-2015180145 A1 | 12/2015 |
| WO | WO-2015184580 A1 | 12/2015 |
| WO | WO-2015184590 A1 | 12/2015 |
| WO | WO-2015184620 A1 | 12/2015 |
| WO | WO-2015184747 A1 | 12/2015 |
| WO | WO-2015188295 A1 | 12/2015 |
| WO | WO-2015188296 A1 | 12/2015 |
| WO | WO-2015189613 A1 | 12/2015 |
| WO | WO-2015190810 A1 | 12/2015 |
| WO | WO-2015192301 A1 | 12/2015 |
| WO | WO-2015192326 A1 | 12/2015 |
| WO | WO-2015192336 A1 | 12/2015 |
| WO | WO-2015192337 A1 | 12/2015 |
| WO | WO-2015192377 A1 | 12/2015 |
| WO | WO-2015193456 A1 | 12/2015 |
| WO | WO-2015196331 A1 | 12/2015 |
| WO | WO-2015196332 A1 | 12/2015 |
| WO | WO-2015196357 A1 | 12/2015 |
| WO | WO-2015196367 A1 | 12/2015 |
| WO | WO-2015196395 A1 | 12/2015 |
| WO | WO-2015196463 A1 | 12/2015 |
| WO | WO2016/012769 A1 | 1/2016 |
| WO | WO2016/014652 A1 | 1/2016 |
| WO | WO-2015148649 A3 | 1/2016 |
| WO | WO-2016000113 A1 | 1/2016 |
| WO | WO-2016000130 A1 | 1/2016 |
| WO | WO-2016000135 A1 | 1/2016 |
| WO | WO-2016000136 A1 | 1/2016 |
| WO | WO-2016000139 A1 | 1/2016 |
| WO | WO-2016000206 A1 | 1/2016 |
| WO | WO-2016000207 A1 | 1/2016 |
| WO | WO-2016000214 A1 | 1/2016 |
| WO | WO-2016000232 A1 | 1/2016 |
| WO | WO-2016000233 A1 | 1/2016 |
| WO | WO-2016000305 A1 | 1/2016 |
| WO | WO-2016008067 A1 | 1/2016 |
| WO | WO-2016008096 A1 | 1/2016 |
| WO | WO-2016008217 A1 | 1/2016 |
| WO | WO-2016009202 A1 | 1/2016 |
| WO | WO-2016011573 A1 | 1/2016 |
| WO | WO-2016012769 A1 | 1/2016 |
| WO | WO2016/020675 A1 | 2/2016 |
| WO | WO-2016015196 A1 | 2/2016 |
| WO | WO-2016015245 A1 | 2/2016 |
| WO | WO-2016015246 A1 | 2/2016 |
| WO | WO-2016015247 A1 | 2/2016 |
| WO | WO-2016015264 A1 | 2/2016 |
| WO | WO-2016015712 A1 | 2/2016 |
| WO | WO-2016019353 A1 | 2/2016 |
| WO | WO-2016019508 A1 | 2/2016 |
| WO | WO-2016019550 A1 | 2/2016 |
| WO | WO-2016019573 A1 | 2/2016 |
| WO | WO-2016020675 A1 | 2/2016 |
| WO | WO-2016023173 A1 | 2/2016 |
| WO | WO-2016023176 A1 | 2/2016 |
| WO | WO-2016023177 A1 | 2/2016 |
| WO | WO-2016023181 A1 | 2/2016 |
| WO | WO-2016023182 A1 | 2/2016 |
| WO | WO-2016023183 A1 | 2/2016 |
| WO | WO-2016023212 A1 | 2/2016 |
| WO | WO-2016023651 A1 | 2/2016 |
| WO | WO-2016023824 A1 | 2/2016 |
| WO | WO-2016023965 A1 | 2/2016 |
| WO | WO-2016026104 A1 | 2/2016 |
| WO | WO-2016026105 A1 | 2/2016 |
| WO | WO-2016026156 A1 | 2/2016 |
| WO | WO-2016026811 A1 | 2/2016 |
| WO | WO-2016028544 A1 | 2/2016 |
| WO | WO2016/030661 A1 | 3/2016 |
| WO | WO2016/040575 A1 | 3/2016 |
| WO | WO2016/041114 A1 | 3/2016 |
| WO | WO2016/041140 A1 | 3/2016 |
| WO | WO-2016029344 A1 | 3/2016 |
| WO | WO-2016029382 A1 | 3/2016 |
| WO | WO-2016029386 A1 | 3/2016 |
| WO | WO-2016029389 A1 | 3/2016 |
| WO | WO-2016029429 A1 | 3/2016 |
| WO | WO-2016029464 A1 | 3/2016 |
| WO | WO-2016029468 A1 | 3/2016 |
| WO | WO-2016029470 A1 | 3/2016 |
| WO | WO-2016029473 A1 | 3/2016 |
| WO | WO-2016029567 A1 | 3/2016 |
| WO | WO-2016030661 A1 | 3/2016 |
| WO | WO-2016033721 A1 | 3/2016 |
| WO | WO-2016033734 A1 | 3/2016 |
| WO | WO-2016033783 A1 | 3/2016 |
| WO | WO-2016033817 A1 | 3/2016 |
| WO | WO-2016034100 A1 | 3/2016 |
| WO | WO-2016038029 A1 | 3/2016 |
| WO | WO-2016040575 A1 | 3/2016 |
| WO | WO-2016041114 A1 | 3/2016 |
| WO | WO-2016041140 A1 | 3/2016 |
| WO | WO-2016041141 A1 | 3/2016 |
| WO | WO-2016041207 A1 | 3/2016 |
| WO | WO-2016041209 A1 | 3/2016 |
| WO | WO-2016045058 A1 | 3/2016 |
| WO | WO-2016046116 A1 | 3/2016 |
| WO | WO2016/050247 A1 | 4/2016 |

(56) References Cited

FOREIGN PATENT DOCUMENTS

| | | |
|---|---|---|
| WO | WO2016/054580 A1 | 4/2016 |
| WO | WO2016/058189 A1 | 4/2016 |
| WO | WO2016/062777 A1 | 4/2016 |
| WO | WO2016/063775 A1 | 4/2016 |
| WO | WO-2015192834 A3 | 4/2016 |
| WO | WO-2016049822 A1 | 4/2016 |
| WO | WO-2016049823 A1 | 4/2016 |
| WO | WO-2016049855 A1 | 4/2016 |
| WO | WO-2016049863 A1 | 4/2016 |
| WO | WO-2016050246 A1 | 4/2016 |
| WO | WO-2016050247 A1 | 4/2016 |
| WO | WO-2016054793 A1 | 4/2016 |
| WO | WO-2016055653 A1 | 4/2016 |
| WO | WO-2016058139 A1 | 4/2016 |
| WO | WO-2016058187 A1 | 4/2016 |
| WO | WO-2016058189 A1 | 4/2016 |
| WO | WO-2016059000 A1 | 4/2016 |
| WO | WO-2016060576 A1 | 4/2016 |
| WO | WO-2016061729 A1 | 4/2016 |
| WO | WO-2016061730 A1 | 4/2016 |
| WO | WO-2016061822 A1 | 4/2016 |
| WO | WO-2016061859 A1 | 4/2016 |
| WO | WO-2016062168 A1 | 4/2016 |
| WO | WO-2016062777 A1 | 4/2016 |
| WO | WO-2016063775 A1 | 4/2016 |
| WO | WO2016/065606 A1 | 5/2016 |
| WO | WO2016/071705 A1 | 5/2016 |
| WO | WO2016/071706 A1 | 5/2016 |
| WO | WO2016/074230 A1 | 5/2016 |
| WO | WO2016/076178 A1 | 5/2016 |
| WO | WO2016/079152 A1 | 5/2016 |
| WO | WO2016/079155 A1 | 5/2016 |
| WO | WO-2016065520 A1 | 5/2016 |
| WO | WO-2016065521 A1 | 5/2016 |
| WO | WO-2016065532 A1 | 5/2016 |
| WO | WO-2016065533 A1 | 5/2016 |
| WO | WO-2016065596 A1 | 5/2016 |
| WO | WO-2016065598 A1 | 5/2016 |
| WO | WO-2016065599 A1 | 5/2016 |
| WO | WO-2016065605 A1 | 5/2016 |
| WO | WO-2016065606 A1 | 5/2016 |
| WO | WO-2016065607 A1 | 5/2016 |
| WO | WO-2016070553 A1 | 5/2016 |
| WO | WO-2016071027 A1 | 5/2016 |
| WO | WO-2016071705 A1 | 5/2016 |
| WO | WO-2016071706 A1 | 5/2016 |
| WO | WO-2016074228 A1 | 5/2016 |
| WO | WO-2016074229 A1 | 5/2016 |
| WO | WO-2016074230 A1 | 5/2016 |
| WO | WO-2016074234 A1 | 5/2016 |
| WO | WO-2016074237 A1 | 5/2016 |
| WO | WO-2016076178 A1 | 5/2016 |
| WO | WO-2016079001 A1 | 5/2016 |
| WO | WO-2016079151 A1 | 5/2016 |
| WO | WO-2016079152 A1 | 5/2016 |
| WO | WO-2016079155 A1 | 5/2016 |
| WO | WO-2016079468 A1 | 5/2016 |
| WO | WO-2016079533 A1 | 5/2016 |
| WO | WO-2016079729 A1 | 5/2016 |
| WO | WO2016/082183 A1 | 6/2016 |
| WO | WO2016/084018 A1 | 6/2016 |
| WO | WO-2016058992 A3 | 6/2016 |
| WO | WO-2016059003 A3 | 6/2016 |
| WO | WO-2016082074 A1 | 6/2016 |
| WO | WO-2016082103 A1 | 6/2016 |
| WO | WO-2016082116 A1 | 6/2016 |
| WO | WO-2016082136 A1 | 6/2016 |
| WO | WO-2016082158 A1 | 6/2016 |
| WO | WO-2016082179 A1 | 6/2016 |
| WO | WO-2016082180 A1 | 6/2016 |
| WO | WO-2016082183 A1 | 6/2016 |
| WO | WO-2016082217 A1 | 6/2016 |
| WO | WO-2016082232 A1 | 6/2016 |
| WO | WO-2016082479 A1 | 6/2016 |
| WO | WO-2016086382 A1 | 6/2016 |
| WO | WO-2016090426 A1 | 6/2016 |
| WO | WO-2016090531 A1 | 6/2016 |
| WO | WO-2016090533 A1 | 6/2016 |
| WO | WO-2016090593 A1 | 6/2016 |
| WO | WO-2016090601 A1 | 6/2016 |
| WO | WO-2016090602 A1 | 6/2016 |
| WO | WO-2016090962 A1 | 6/2016 |
| WO | WO-2016092259 A1 | 6/2016 |
| WO | WO-2016095101 A1 | 6/2016 |
| WO | WO-2016095206 A1 | 6/2016 |
| WO | WO-2016095220 A1 | 6/2016 |
| WO | WO-2016095234 A1 | 6/2016 |
| WO | WO-2016095297 A1 | 6/2016 |
| WO | WO-2016096337 A1 | 6/2016 |
| WO | WO-2016096482 A1 | 6/2016 |
| WO | WO-2016096497 A1 | 6/2016 |
| WO | WO-2016096733 A1 | 6/2016 |
| WO | WO-2016096762 A1 | 6/2016 |
| WO | WO-2016099045 A1 | 6/2016 |
| WO | WO-2016099276 A1 | 6/2016 |
| WO | WO-2016101141 A1 | 6/2016 |
| WO | WO-2016101142 A1 | 6/2016 |
| WO | WO-2016101143 A1 | 6/2016 |
| WO | WO-2016101144 A1 | 6/2016 |
| WO | WO-2016101150 A1 | 6/2016 |
| WO | WO-2016101183 A1 | 6/2016 |
| WO | WO-2016101200 A1 | 6/2016 |
| WO | WO-2016101202 A1 | 6/2016 |
| WO | WO-2016101203 A1 | 6/2016 |
| WO | WO-2016101248 A1 | 6/2016 |
| WO | WO-2016103202 A1 | 6/2016 |
| WO | WO-2016105191 A1 | 6/2016 |
| WO | WO-2016036236 A3 | 7/2016 |
| WO | WO-2016106476 A1 | 7/2016 |
| WO | WO-2016106483 A1 | 7/2016 |
| WO | WO-2016106493 A1 | 7/2016 |
| WO | WO-2016106495 A1 | 7/2016 |
| WO | WO-2016106499 A1 | 7/2016 |
| WO | WO-2016106500 A1 | 7/2016 |
| WO | WO-2016106512 A1 | 7/2016 |
| WO | WO-2016108693 A1 | 7/2016 |
| WO | WO-2016108694 A1 | 7/2016 |
| WO | WO-2016109929 A1 | 7/2016 |
| WO | WO-2016109930 A1 | 7/2016 |
| WO | WO-2016109931 A1 | 7/2016 |
| WO | WO-2016109932 A1 | 7/2016 |
| WO | WO-2016109933 A1 | 7/2016 |
| WO | WO-2016109942 A1 | 7/2016 |
| WO | WO-2016109964 A1 | 7/2016 |
| WO | WO-2016109965 A1 | 7/2016 |
| WO | WO-2016110522 A1 | 7/2016 |
| WO | WO-2016112491 A1 | 7/2016 |
| WO | WO-2016112493 A1 | 7/2016 |
| WO | WO-2016112533 A1 | 7/2016 |
| WO | WO-2016112534 A1 | 7/2016 |
| WO | WO-2016112541 A1 | 7/2016 |
| WO | WO-2016112542 A1 | 7/2016 |
| WO | WO-2016112561 A1 | 7/2016 |
| WO | WO-2016112579 A1 | 7/2016 |
| WO | WO-2016115689 A1 | 7/2016 |
| WO | WO-2016115691 A1 | 7/2016 |
| WO | WO-2016115701 A1 | 7/2016 |
| WO | WO-2016115715 A1 | 7/2016 |
| WO | WO-2016116754 A1 | 7/2016 |
| WO | WO-2016116755 A1 | 7/2016 |
| WO | WO-2016118005 A1 | 7/2016 |
| WO | WO2016/127396 A1 | 8/2016 |
| WO | WO-2016119098 A1 | 8/2016 |
| WO | WO-2016119099 A1 | 8/2016 |
| WO | WO-2016119101 A1 | 8/2016 |
| WO | WO-2016119119 A1 | 8/2016 |
| WO | WO-2016119121 A1 | 8/2016 |
| WO | WO-2016119144 A1 | 8/2016 |
| WO | WO-2016119145 A1 | 8/2016 |
| WO | WO-2016119163 A1 | 8/2016 |
| WO | WO-2016119167 A1 | 8/2016 |
| WO | WO-2016119170 A1 | 8/2016 |
| WO | WO-2016119225 A1 | 8/2016 |
| WO | WO-2016119248 A1 | 8/2016 |

(56) References Cited

FOREIGN PATENT DOCUMENTS

| | | |
|---|---|---|
| WO | WO-2016119273 A1 | 8/2016 |
| WO | WO-2016119496 A1 | 8/2016 |
| WO | WO-2016122417 A1 | 8/2016 |
| WO | WO-2016123763 A1 | 8/2016 |
| WO | WO-2016123764 A1 | 8/2016 |
| WO | WO-2016123770 A1 | 8/2016 |
| WO | WO-2016123779 A1 | 8/2016 |
| WO | WO-2016123780 A1 | 8/2016 |
| WO | WO-2016123781 A1 | 8/2016 |
| WO | WO-2016124017 A1 | 8/2016 |
| WO | WO-2016124019 A1 | 8/2016 |
| WO | WO-2016124695 A1 | 8/2016 |
| WO | WO-2016124740 A1 | 8/2016 |
| WO | WO-2016124741 A1 | 8/2016 |
| WO | WO-2016127287 A1 | 8/2016 |
| WO | WO-2016127293 A1 | 8/2016 |
| WO | WO-2016127327 A1 | 8/2016 |
| WO | WO-2016127360 A1 | 8/2016 |
| WO | WO-2016127361 A1 | 8/2016 |
| WO | WO-2016127389 A1 | 8/2016 |
| WO | WO-2016127390 A1 | 8/2016 |
| WO | WO-2016127396 A1 | 8/2016 |
| WO | WO-2016127397 A1 | 8/2016 |
| WO | WO-2016127401 A1 | 8/2016 |
| WO | WO-2016127406 A1 | 8/2016 |
| WO | WO-2016127468 A1 | 8/2016 |
| WO | WO-2016127839 A1 | 8/2016 |
| WO | WO-2016128562 A1 | 8/2016 |
| WO | WO-2016131755 A1 | 8/2016 |
| WO | WO-2016132026 A1 | 8/2016 |
| WO | WO-2016134544 A1 | 9/2016 |
| WO | WO-2016135503 A1 | 9/2016 |
| WO | WO-2016138608 A1 | 9/2016 |
| WO | WO-2016138665 A1 | 9/2016 |
| WO | WO-2016138689 A1 | 9/2016 |
| WO | WO-2016141508 A1 | 9/2016 |
| WO | WO-2016141555 A1 | 9/2016 |
| WO | WO-2016141556 A1 | 9/2016 |
| WO | WO-2016141581 A1 | 9/2016 |
| WO | WO-2016141592 A1 | 9/2016 |
| WO | WO-2016141593 A1 | 9/2016 |
| WO | WO-2016145611 A1 | 9/2016 |
| WO | WO-2016145612 A1 | 9/2016 |
| WO | WO-2016145613 A1 | 9/2016 |
| WO | WO-2016145634 A1 | 9/2016 |
| WO | WO-2016145656 A1 | 9/2016 |
| WO | WO-2016145663 A1 | 9/2016 |
| WO | WO-2016149896 A1 | 9/2016 |
| WO | WO-2016149932 A1 | 9/2016 |
| WO | WO-2016149942 A1 | 9/2016 |
| WO | WO-2016150019 A1 | 9/2016 |
| WO | WO-2016150979 A1 | 9/2016 |
| WO | WO2016/156103 A1 | 10/2016 |
| WO | WO2016/165125 A1 | 10/2016 |
| WO | WO-2016154792 A1 | 10/2016 |
| WO | WO-2016154797 A1 | 10/2016 |
| WO | WO-2016154798 A1 | 10/2016 |
| WO | WO-2016154815 A1 | 10/2016 |
| WO | WO-2016154895 A1 | 10/2016 |
| WO | WO-2016154896 A1 | 10/2016 |
| WO | WO-2016154897 A1 | 10/2016 |
| WO | WO-2016154900 A1 | 10/2016 |
| WO | WO-2016154994 A1 | 10/2016 |
| WO | WO-2016155003 A1 | 10/2016 |
| WO | WO-2016155103 A1 | 10/2016 |
| WO | WO-2016155104 A1 | 10/2016 |
| WO | WO-2016155105 A1 | 10/2016 |
| WO | WO-2016155316 A1 | 10/2016 |
| WO | WO-2016156103 A1 | 10/2016 |
| WO | WO-2016156217 A1 | 10/2016 |
| WO | WO-2016156413 A1 | 10/2016 |
| WO | WO-2016161554 A1 | 10/2016 |
| WO | WO-2016161673 A1 | 10/2016 |
| WO | WO-2016162446 A1 | 10/2016 |
| WO | WO-2016162492 A1 | 10/2016 |
| WO | WO-2016165055 A1 | 10/2016 |
| WO | WO-2016165057 A1 | 10/2016 |
| WO | WO-2016165063 A1 | 10/2016 |
| WO | WO-2016165125 A1 | 10/2016 |
| WO | WO-2016166049 A1 | 10/2016 |
| WO | WO-2016166456 A1 | 10/2016 |
| WO | WO-2016166661 A1 | 10/2016 |
| WO | WO-2016166670 A1 | 10/2016 |
| WO | WO-2016168986 A1 | 10/2016 |
| WO | WO-2016169019 A1 | 10/2016 |
| WO | WO-2016169052 A1 | 10/2016 |
| WO | WO-2016169063 A1 | 10/2016 |
| WO | WO-2016169669 A1 | 10/2016 |
| WO | WO-2016169796 A1 | 10/2016 |
| WO | WO-2016169797 A1 | 10/2016 |
| WO | WO-2016172802 A1 | 11/2016 |
| WO | WO-2016172821 A1 | 11/2016 |
| WO | WO-2016172843 A1 | 11/2016 |
| WO | WO-2016172847 A1 | 11/2016 |
| WO | WO-2016172867 A1 | 11/2016 |
| WO | WO-2016172898 A1 | 11/2016 |
| WO | WO-2016172907 A1 | 11/2016 |
| WO | WO-2016172908 A1 | 11/2016 |
| WO | WO-2016172909 A1 | 11/2016 |
| WO | WO-2016172954 A1 | 11/2016 |
| WO | WO-2016174179 A1 | 11/2016 |
| WO | WO-2016176800 A1 | 11/2016 |
| WO | WO-2016177604 A1 | 11/2016 |
| WO | WO-2016179356 A1 | 11/2016 |
| WO | WO-2016179664 A1 | 11/2016 |
| WO | WO-2016179776 A1 | 11/2016 |
| WO | WO-2016179828 A1 | 11/2016 |
| WO | WO-2016183724 A1 | 11/2016 |
| WO | WO-2016184247 A1 | 11/2016 |
| WO | WO-2016184824 A1 | 11/2016 |
| WO | WO-2016171997 A3 | 12/2016 |
| WO | WO-2016187803 A1 | 12/2016 |
| WO | WO-2016187943 A1 | 12/2016 |
| WO | WO-2016188140 A1 | 12/2016 |
| WO | WO-2016188141 A1 | 12/2016 |
| WO | WO-2016188142 A1 | 12/2016 |
| WO | WO-2016188967 A1 | 12/2016 |
| WO | WO-2016189086 A1 | 12/2016 |
| WO | WO-2016191946 A1 | 12/2016 |
| WO | WO-2016193336 A1 | 12/2016 |
| WO | WO-2016193365 A1 | 12/2016 |
| WO | WO-2016193743 A1 | 12/2016 |
| WO | WO-2016197485 A1 | 12/2016 |
| WO | WO-2016197658 A1 | 12/2016 |
| WO | WO-2016198417 A1 | 12/2016 |
| WO | WO-2016198459 A1 | 12/2016 |
| WO | WO-2016198879 A1 | 12/2016 |
| WO | WO-2016199062 A1 | 12/2016 |
| WO | WO-2016199065 A1 | 12/2016 |
| WO | WO-2016199066 A1 | 12/2016 |
| WO | WO-2016200252 A1 | 12/2016 |
| WO | WO-2016200253 A1 | 12/2016 |
| WO | WO-2016200255 A1 | 12/2016 |
| WO | WO-2016200259 A1 | 12/2016 |
| WO | WO-2016200382 A1 | 12/2016 |
| WO | WO-2016201602 A1 | 12/2016 |
| WO | WO-2016201606 A1 | 12/2016 |
| WO | WO-2016201911 A1 | 12/2016 |
| WO | WO-2016202028 A1 | 12/2016 |
| WO | WO-2016202033 A1 | 12/2016 |
| WO | WO-2016202301 A1 | 12/2016 |
| WO | WO-2016202302 A1 | 12/2016 |
| WO | WO-2016202303 A1 | 12/2016 |
| WO | WO-2016202304 A1 | 12/2016 |
| WO | WO-2016207357 A1 | 12/2016 |
| WO | WO-2016208757 A1 | 12/2016 |
| WO | WO-2016208760 A1 | 12/2016 |
| WO | WO-2016193705 A3 | 1/2017 |
| WO | WO-2017000239 A1 | 1/2017 |
| WO | WO-2017001270 A1 | 1/2017 |
| WO | WO-2017001817 A1 | 1/2017 |
| WO | WO-2017001818 A1 | 1/2017 |
| WO | WO-2017001819 A1 | 1/2017 |
| WO | WO-2017001820 A1 | 1/2017 |

(56) References Cited

FOREIGN PATENT DOCUMENTS

| | | |
|---|---|---|
| WO | WO-2017005835 A1 | 1/2017 |
| WO | WO-2017007252 A1 | 1/2017 |
| WO | WO-2017008616 A1 | 1/2017 |
| WO | WO-2017009002 A1 | 1/2017 |
| WO | WO-2017011419 A1 | 1/2017 |
| WO | WO-2017012099 A1 | 1/2017 |
| WO | WO-2017012105 A1 | 1/2017 |
| WO | WO-2017012257 A1 | 1/2017 |
| WO | WO-2017012335 A1 | 1/2017 |
| WO | WO-2016172921 A8 | 2/2017 |
| WO | WO-2016178098 A3 | 2/2017 |
| WO | WO-2017015791 A1 | 2/2017 |
| WO | WO-2017015794 A1 | 2/2017 |
| WO | WO-2017015832 A1 | 2/2017 |
| WO | WO-2017015859 A1 | 2/2017 |
| WO | WO-2017016323 A1 | 2/2017 |
| WO | WO-2017017970 A1 | 2/2017 |
| WO | WO-2017020220 A1 | 2/2017 |
| WO | WO-2017020221 A1 | 2/2017 |
| WO | WO-2017020275 A1 | 2/2017 |
| WO | WO-2017020290 A1 | 2/2017 |
| WO | WO-2017023589 A1 | 2/2017 |
| WO | WO-2017024477 A1 | 2/2017 |
| WO | WO-2017024478 A1 | 2/2017 |
| WO | WO-2017024799 A1 | 2/2017 |
| WO | WO-2017024926 A1 | 2/2017 |
| WO | WO-2017025383 A1 | 2/2017 |
| WO | WO-2017028167 A1 | 2/2017 |
| WO | WO-2017028295 A1 | 2/2017 |
| WO | WO-2017029268 A1 | 2/2017 |
| WO | WO-2017029269 A1 | 2/2017 |
| WO | WO-2017029270 A1 | 2/2017 |
| WO | WO-2017021536 A3 | 3/2017 |
| WO | WO-2017031662 A1 | 3/2017 |
| WO | WO-2017031678 A1 | 3/2017 |
| WO | WO-2017031681 A1 | 3/2017 |
| WO | WO-2017033007 A1 | 3/2017 |
| WO | WO-2017033021 A1 | 3/2017 |
| WO | WO-2017033132 A1 | 3/2017 |
| WO | WO-2017035720 A1 | 3/2017 |
| WO | WO-2017036818 A1 | 3/2017 |
| WO | WO-2017036819 A1 | 3/2017 |
| WO | WO-2017036828 A1 | 3/2017 |
| WO | WO-2017036829 A1 | 3/2017 |
| WO | WO-2017036865 A1 | 3/2017 |
| WO | WO-2017036879 A1 | 3/2017 |
| WO | WO-2017041251 A1 | 3/2017 |
| WO | WO-2017042081 A1 | 3/2017 |
| WO | WO-2017045132 A1 | 3/2017 |
| WO | WO-2017045897 A1 | 3/2017 |
| WO | WO-2017045898 A1 | 3/2017 |
| WO | WO-2017045899 A1 | 3/2017 |
| WO | WO-2017046247 A1 | 3/2017 |
| WO | WO-2017046334 A1 | 3/2017 |
| WO | WO-2017046363 A1 | 3/2017 |
| WO | WO-2017046566 A1 | 3/2017 |
| WO | WO-2017049653 A1 | 3/2017 |
| WO | WO-2017049654 A1 | 3/2017 |
| WO | WO-2017051150 A1 | 3/2017 |
| WO | WO-2017051174 A1 | 3/2017 |
| WO | WO-2017051348 A1 | 3/2017 |
| WO | WO-2017051349 A1 | 3/2017 |
| WO | WO-2017046593 A3 | 4/2017 |
| WO | WO-2017054424 A1 | 4/2017 |
| WO | WO-2017054627 A1 | 4/2017 |
| WO | WO-2017054634 A1 | 4/2017 |
| WO | WO-2017055564 A1 | 4/2017 |
| WO | WO-2017055584 A1 | 4/2017 |
| WO | WO-2017055793 A1 | 4/2017 |
| WO | WO-2017055795 A1 | 4/2017 |
| WO | WO-2017055799 A1 | 4/2017 |
| WO | WO-2017055801 A1 | 4/2017 |
| WO | WO-2017055802 A1 | 4/2017 |
| WO | WO-2017055803 A1 | 4/2017 |
| WO | WO-2017055866 A1 | 4/2017 |
| WO | WO-2017056103 A1 | 4/2017 |
| WO | WO-2017057286 A1 | 4/2017 |
| WO | WO-2017059571 A1 | 4/2017 |
| WO | WO-2017060279 A1 | 4/2017 |
| WO | WO-2017063256 A1 | 4/2017 |
| WO | WO-2017063535 A1 | 4/2017 |
| WO | WO-2017064051 A1 | 4/2017 |
| WO | WO-2017064322 A1 | 4/2017 |
| WO | WO-2017064323 A1 | 4/2017 |
| WO | WO-2017064324 A1 | 4/2017 |
| WO | WO-2017064487 A1 | 4/2017 |
| WO | WO-2017066938 A1 | 4/2017 |
| WO | WO-2017066955 A1 | 4/2017 |
| WO | WO-2017067066 A1 | 4/2017 |
| WO | WO-2017067326 A1 | 4/2017 |
| WO | WO-2017068098 A1 | 4/2017 |
| WO | WO-2017068099 A1 | 4/2017 |
| WO | WO-2017068100 A1 | 4/2017 |
| WO | WO-2016096745 A9 | 5/2017 |
| WO | WO-2016173568 A3 | 5/2017 |
| WO | WO-2016198026 A3 | 5/2017 |
| WO | WO-2017051350 A3 | 5/2017 |
| WO | WO-2017070871 A1 | 5/2017 |
| WO | WO-2017071297 A1 | 5/2017 |
| WO | WO-2017071298 A1 | 5/2017 |
| WO | WO-2017072239 A1 | 5/2017 |
| WO | WO-2017072277 A1 | 5/2017 |
| WO | WO-2017072284 A1 | 5/2017 |
| WO | WO-2017075753 A1 | 5/2017 |
| WO | WO-2017075759 A1 | 5/2017 |
| WO | WO-2017075827 A1 | 5/2017 |
| WO | WO-2017075883 A1 | 5/2017 |
| WO | WO-2017075975 A1 | 5/2017 |
| WO | WO-2017076247 A1 | 5/2017 |
| WO | WO-2017076590 A1 | 5/2017 |
| WO | WO-2017081480 A1 | 5/2017 |
| WO | WO-2017082728 A1 | 5/2017 |
| WO | WO-2017084107 A1 | 5/2017 |
| WO | WO-2017084488 A1 | 5/2017 |
| WO | WO-2017084489 A1 | 5/2017 |
| WO | WO-2017084818 A1 | 5/2017 |
| WO | WO-2017084848 A1 | 5/2017 |
| WO | WO-2017084849 A1 | 5/2017 |
| WO | WO-2017084920 A2 | 5/2017 |
| WO | WO-2017085240 A1 | 5/2017 |
| WO | WO-2017085242 A1 | 5/2017 |
| WO | WO-2017081176 A3 | 6/2017 |
| WO | WO-2017088660 A1 | 6/2017 |
| WO | WO-2017089931 A1 | 6/2017 |
| WO | WO-2017091926 A1 | 6/2017 |
| WO | WO-2017092144 A1 | 6/2017 |
| WO | WO-2017093452 A1 | 6/2017 |
| WO | WO-2017093535 A1 | 6/2017 |
| WO | WO-2017096512 A1 | 6/2017 |
| WO | WO-2017096971 A1 | 6/2017 |
| WO | WO-2017096988 A1 | 6/2017 |
| WO | WO-2017097172 A1 | 6/2017 |
| WO | WO-2017097173 A1 | 6/2017 |
| WO | WO-2017097821 A1 | 6/2017 |
| WO | WO-2017101030 A1 | 6/2017 |
| WO | WO-2017101058 A1 | 6/2017 |
| WO | WO-2017101705 A1 | 6/2017 |
| WO | WO-2017102633 A1 | 6/2017 |
| WO | WO-2017102686 A1 | 6/2017 |
| WO | WO-2017102969 A1 | 6/2017 |
| WO | WO-2017107546 A1 | 6/2017 |
| WO | WO-2017108268 A1 | 6/2017 |
| WO | WO-2017108392 A1 | 6/2017 |
| WO | WO-2017108394 A1 | 6/2017 |
| WO | WO-2017108429 A1 | 6/2017 |
| WO | WO-2017109448 A2 | 6/2017 |
| WO | WO-2017109868 A1 | 6/2017 |
| WO | WO-2017110713 A1 | 6/2017 |
| WO | WO-2017036426 A3 | 7/2017 |
| WO | WO-2017113106 A1 | 7/2017 |
| WO | WO-2017113513 A1 | 7/2017 |
| WO | WO-2017113845 A1 | 7/2017 |
| WO | WO-2017114389 A1 | 7/2017 |
| WO | WO-2017117725 A1 | 7/2017 |

(56) References Cited

FOREIGN PATENT DOCUMENTS

| | | | |
|---|---|---|---|
| WO | WO-2017117742 A1 | 7/2017 |
| WO | WO-2017118135 A1 | 7/2017 |
| WO | WO-2017118138 A1 | 7/2017 |
| WO | WO-2017118347 A1 | 7/2017 |
| WO | WO-2017121156 A1 | 7/2017 |
| WO | WO-2017121253 A1 | 7/2017 |
| WO | WO-2017121296 A1 | 7/2017 |
| WO | WO-2017121546 A1 | 7/2017 |
| WO | WO-2017121979 A1 | 7/2017 |
| WO | WO-2017122196 A1 | 7/2017 |
| WO | WO-2017124419 A1 | 7/2017 |
| WO | WO-2017124662 A1 | 7/2017 |
| WO | WO-2017124957 A1 | 7/2017 |
| WO | WO-2017128038 A1 | 8/2017 |
| WO | WO-2017133056 A1 | 8/2017 |
| WO | WO-2017137138 A1 | 8/2017 |
| WO | WO-2017137554 A1 | 8/2017 |
| WO | WO-2017139963 A1 | 8/2017 |
| WO | WO-2017141017 A1 | 8/2017 |
| WO | WO-2017141018 A1 | 8/2017 |
| WO | WO-2017141358 A1 | 8/2017 |
| WO | WO-2017143494 A1 | 8/2017 |
| WO | WO-2017143495 A1 | 8/2017 |
| WO | WO-2017143515 A1 | 8/2017 |
| WO | WO-2017143865 A1 | 8/2017 |
| WO | WO-2017143953 A1 | 8/2017 |
| WO | WO-2017144400 A1 | 8/2017 |
| WO | WO-2017144861 A1 | 8/2017 |
| WO | WO-2017149288 A1 | 9/2017 |
| WO | WO-2017152481 A1 | 9/2017 |
| WO | WO-2017153051 A1 | 9/2017 |
| WO | WO-2017153270 A1 | 9/2017 |
| WO | WO-2017156694 A1 | 9/2017 |
| WO | WO-2017156695 A1 | 9/2017 |
| WO | WO-2017156696 A1 | 9/2017 |
| WO | WO-2017156733 A1 | 9/2017 |
| WO | WO-2017156743 A1 | 9/2017 |
| WO | WO-2017161715 A1 | 9/2017 |
| WO | WO-2017161725 A1 | 9/2017 |
| WO | WO-2017163044 A1 | 9/2017 |
| WO | WO-2017163045 A1 | 9/2017 |
| WO | WO-2017163046 A1 | 9/2017 |
| WO | WO-2017163047 A1 | 9/2017 |
| WO | WO-2017163050 A1 | 9/2017 |
| WO | WO-2017163051 A1 | 9/2017 |
| WO | WO-2017163052 A1 | 9/2017 |
| WO | WO-2017164474 A1 | 9/2017 |
| WO | WO-2017166263 A1 | 10/2017 |
| WO | WO-2017166334 A1 | 10/2017 |
| WO | WO-2017167169 A1 | 10/2017 |
| WO | WO-2017167513 A1 | 10/2017 |
| WO | WO-2017173669 A1 | 10/2017 |
| WO | WO-2017173947 A1 | 10/2017 |
| WO | WO-2017173951 A1 | 10/2017 |
| WO | WO-2017174754 A1 | 10/2017 |
| WO | WO-2017175166 A1 | 10/2017 |
| WO | WO-2017176111 A1 | 10/2017 |
| WO | WO-2017176113 A1 | 10/2017 |
| WO | WO-2017177897 A1 | 10/2017 |
| WO | WO-2018102696 A1 | 6/2018 |
| WO | WO-2018102699 A1 | 6/2018 |
| WO | WO-2018102701 A1 | 6/2018 |
| WO | WO-2018102703 A1 | 6/2018 |

OTHER PUBLICATIONS

Baker et al.; The pyrolysis of tobacco ingredients; J. Anal. Appl. Pyrolysis; 71 (1); pp. 223-311; Mar. 2004.
Bombick et al.; Chemcal and biological studies of a new cigarette that primarily heats tobacco; Part 3: In vitro toxicity of whole smoke; Food and Chemical Toxicology; 36(3); pp. 191-197; Mar. 1998.
Bombick et al.; Chemical and biological studies of a new cigarette that primarily heats tobacco; Part 2: In vitro toxicology of mainstream smoke condesnsate; Food and Chemical Toxicology; 36(3); pp. 183-190; Mar. 1998.
Borgerding et al.; Chemcal and biological studies of a new cigarette that primarily heats tobacco; Part 1: Chemical composition of mainstream smoke; Food and Chemical Toxicology; 36(3); pp. 169-182; Mar. 1998.
Ingebrethsen et al.; Electronic cigarette aerosol particle size distribution measurements; Inhalation Toxicology; 24(14); pp. 976-984; Dec. 2012.
Kuo et al.; Appendix D: Particle size—U.S. sieve size and tyler screen mesh equivalents; Applications of Turbulent and Multiphase Combustion; John Wiley & Sons, Inc.; pp. 541-543; May 1, 2012.
McCann et al.; Detection of carcinogens as mutagens in the *Salmonella*/microsome test: Assay of 300 chemicals: Discussion; Proc. Nat. Acad. Sci.; 73(3); pp. 950-954; Mar. 1976.
Mirriam-Webster Online Dictionary; Lighter; retrieved Jan. 4, 2013 from the internet: (http://www.merriam-webster.com/dictionary/lighter?show=0&t=1357320593); 2 pgs.; print date: Jan. 4, 2013.
Nicoli et al.; Mammalian tumor xenografts induce neovascularization in Zebrafish embryos; Cancer Research; 67(7); pp. 2927-2931; Apr. 1, 2007.
Torikai et al.; Effects of temperature, atmosphere and pH on the generation of smoke compounds duriung tobacco pyrolysis; Food and Chemical Toxicology; 42(9); pp. 1409-1417; Sep. 2004.
Ward; Green leaf threshing and redrying tobacco; Section 10B; in Tobacco Production, Chemistry and Technology; Davis and Nielsen (Eds.); Blackwell Science Ltd.; pp. 330-333; Jul. 15, 1999.
Wells; Glycerin as a constituent of cosmetics and toilet preparations; Journal of the Society of Cosmetic Chemists; 9(1); pp. 19-25; Jan. 1958.
YouTube; Firefly Vaporizor Review w/ Usage Tips by the Vape Critic; retrieved from the internet (http://www.youtube.com/watch?y=1J38N0AV7w1); 1 pg.; published Dec. 10, 2013; download/print date: Feb. 18, 2015.
Monsees et al.; U.S. Appl. No. 15/053,927 entitled "Vaporization device systems and methods," filed Feb. 25, 2016.
Bradley et al.; Electronic cigarette aerosol particle size distribution measurements; Inhal. Toxicol.; 24(14); pp. 976-984; Dec. 2012.
Bullen et al.; Effect of an electronic nicotine delivery device (e cigarette) on desire to smoke and withdrawal, user preferences and nicotine delivery: randomised cross-over trial; Tobacco Control; 19(2); pp. 98-103; Apr. 2010.
Burch et al.; Effect of pH on nicotine absorption and side effects produced by aerosolized nicotine; Journal of Aerosol Medicine: Deposition, Clearance, and Effects in the Lung; 6(1); pp. 45-52; 1993.
Capponnetto et al.; Successful smoking cessation with cigarettes in smokers with a documented history of recurring relapses: a case series; Journal of Medical Case Reports; 5(1); 6 pages; (year of pub. sufficiently earlier than effective US filing date and any foreign priority date); 2011.
Farsalinos et al.; Electronic cigarettes do not damage the heart; European Society of Cardiology; 4 pages; retrieved from the internet (http://www.escardio.org/The-ESC/Press-Office/Press-releases/Electronic-cigarettes-do-not-damage-the-heart); Aug. 25, 2012.
Food & Drug Administration; Warning letter to the Compounding Pharmacy; retrieved Oct. 10, 2014 from http://www.fda.gov/ICECI/EnfocementActions/WarningLetters/2002/ucm144843.htm; 3 pgs.; Apr. 9, 2002.
Harvest Vapor; American Blend Tobacco (product info.); retrieved from the internet (http://harvestvapor.com/); 2 pgs.; print/retrieval date: Oct. 10, 2014.
Inchem; Benzoic Acid; JECFA Evaluation Summary; retrieved Oct. 10, 2014 from http://www.inchem.org/documents/jecfa/feceval/jec_184.htm; 2 pgs..; May 28, 2005.
Inchem; Levulinic Acid; JECFA Evaluation Summary; retrieved Oct. 10, 2014 from http://www.inchem.org/documents/jecfa/feceval/jec_1266.htm; 1 pg.; Mar. 10, 2003.
Inchem; Pyruvic Acid; JECFA Evaluation Summary; retrieved Oct. 10, 2014 from http://www.inchem.org/documents/jecfa/feceval/jec_2072.htm; 1 pg.; Jan. 29, 2003.

(56) References Cited

OTHER PUBLICATIONS

Inchem; Sorbic Acid; JECFA Evaluation Summary; retrieved Oct. 10, 2014 from http://www.inchem.org/documents/jecfa/feceval/jec_2181.htm; 1 pg.; May 29, 2005.
Vansickel et al.; A clinical laboratory model for evaluating the acute effects of electronic cigarettes: Nicotine delivery profile and cardiovascular and subjective effects; Cancer Epidemiology Biomarkers Prevention; 19(8); pp. 1945-1953; (online) Jul. 20, 2010.
Zhang et al.; In vitro particle size distributions in electronic and conventional cigarette aerosols suggest comparable deposition patterns; Nicotine Tobacco Research; 15(2); pp. 501-508; Feb. 2013.
Monsees et al.; U.S. Appl. No. 15/257,748 entitled "Cartridge for use with a vaporizer device," filed Sep. 6, 2016.
Monsees et al.; U.S. Appl. No. 15/257,760 entitled "Vaporizer apparatus," filed Sep. 6, 2016.
Monsees et al.; U.S. Appl. No. 15/257,768 entitled "Vaporizer apparatus," filed Sep. 6, 2016.
Monsees et al.; U.S. Appl. No. 15/261,823 entitled "Low temperature electronic vaporization device and methods," filed Sep. 9, 2016.
Grotenhermen et al.; Developing science-based per se limits for driving under the influence of cannabis (DUIC): findings and recommendations by an expert panel; retrieved Feb. 9, 2017 from (http://www.canorml.org/healthfacts/DUICreport.2005.pdf); 49 pages; Sep. 2005.
Monsees et al.; U.S. Appl. No. 15/368,539 entitled "Low temperature electronic vaporization device and methods," filed Dec. 2, 2016.
Bowen et al.; U.S. Appl. No. 15/309,554 entitled "Systems and methods for aerosolizing a smokeable material," filed Nov. 8, 2016.
Monsees et al.; U.S. Appl. No. 15/379,898 entitled "Vaporization device systems and methods," filed Dec. 15, 2016.
Hatton et al.; U.S. Appl. No. 15/396,584 entitled "Leak-resistant vaporizer cartridges for use with cannabinoids," filed Dec. 31, 2016.
E-Cigarette Forum; pg-vg-peg (discussion/posting); retrieved from the internet: https://e-cigarette-forum.com/forum/threads/pg-vg-peg.177551; 7 pgs.; Apr. 8, 2011.
Monsees et al.; U.S. Appl. No. 15/165,954 entitled "Devices for vaporization of a substance," filed May 26, 2016.
Monsees et al.; U.S. Appl. No. 15/166,001 entitled "Electronic vaporization device," filed May 26, 2016.
Monsees et al.; U.S. Appl. No. 15/165,972 entitled "Portable devices for generating an inhalable vapor," filed May 26, 2016.
Bowen et al.; U.S. Appl. No. 15/101,303 entitled "Nicotine liquid formulations for aerosol devices and methods thereof," filed Jun. 2, 2016.
Engadget. *Juul is the e-cig that will finally stop me from smoking (I hope).* [online], published on Jun. 3, 2015. Available at: https://www.engadget.com/2015/06/03/pax-labs-juul-ecigarette/#/.
Pierce, D. *This Might Just Be the First Great E-Cig.* {online} WIRED, Published on Apr. 21, 2015. Available at: https://www.wired.com/2015/04/pax-juul-ecig/?mbid=social_twitter.
The Verge. *Startup behind the Lambo of vaporizers just launched an intelligent e-cigarette.* [online], published on Apr. 21, 2015. Available at: https://www.theverge.com/2015/4/21/8458629/pax-labs-e-cigarette-juul.
Farsalinos, Konstantinos E., et al. *Analytical Assessment of e-Cigarettes: From Contents to Chemical and Particle Exposure Profiles.* pp. 1-35. Elsevier, 2016.
Geiss, Otmar, Ivana Bianchi, and Josefa Barrero-Moreno. "Correlation of volatile carbonyl yields emitted by e-cigarettes with the temperature of the heating coil and the perceived sensorial quality of the generated vapours." *International journal of hygiene and environmental health* 219.3 (2016): 268-277.
Gillman, I. G., et al. "Effect of variable power levels on the yield of total aerosol mass and formation of aldehydes in e-cigarette aerosols." *Regulatory Toxicology and Pharmacology* 75 (2016): 58-65.
Giorgio, Agostino. "E-Cig Digital Design for the Smoke Control Optimization." *International Journal of Applied Engineering Research* 11.8 (2016): 6018-6023.

IJOY. "Who we are." *IJOY Diamond PD270 Kit*, Date Accessed Feb. 20, 2018. www.ijoycig.com/product/item-473.html.
*Kanger K1 Stabilized Wood DNA 75 BOX MOD—KangerTech.* Date Accessed Feb. 20, 2018. https://kangeronliox.com/products/kanger-k1-stabilized-wood-dna-75-box-mod.
Marshall, John R., Shahram Lotfipour, and Bharath Chakravarthy. "Growing Trend of Alternative Tobacco Use Among the Nation's Youth: A New Generation of Addicts." *Western Journal of Emergency Medicine* 17.2 (2016): 139.
Polosa, Riccardo, et al. "Effect of an electronic nicotine delivery device (e-Cigarette) on smoking reduction and cessation: a prospective 6-month pilot study." BMC public health 11.1 (2011): 786.
Poynton, Simon, et al. "A novel hybrid tobacco product that delivers a tobacco flavour note with vapour aerosol (Part 1): product operation and preliminary aerosol chemistry assessment." *Food and Chemical Toxicology* 106 (2017): 522-532.
Smok. *ProColor—SMOK® Innovation keeps changing the vaping experience!*, Date Accessed Feb. 20, 2018. www.smoktech.com/kit/procolor.
Vaporesso (Shenzhen Smoore Technology Limited). "Target Pro Vape Mod." *Vape Batteries & Mods | Target Pro Vape Mod |Vaporesso*, Date Accessed Feb. 20, 2018. www.vaporesso.com/vape-batteries-and-mods/target-pro-vape-mod.
Vaporesso (Shenzhen Smoore Technology Limited). "Tarot Pro Vape Mod." *Vape Batteries & Mods | Tarot Pro Vape Mod |Vaporeso*, Date Accessed Feb. 20, 2018. www.vaporesso.com/vape-batteries-and-mods/tarot-pro-vape-mod.
"Commission Regulation (EC) No. 1275/2008," Official Journal of the European Union, Dec. 17, 2008.
"Guideline Accompanying Commission Regulation (EC) No. 1275/2008," Official Journal of the European Union, Oct. 2009.
"Lighter." Merriam-Webster Online Dictionary. 2009. Merriam-Webster Online. Jun. 8, 2009 [http://www.merriam-webster.com/dictionary/lighter].
AMB. Manual:TranX160/Rev.10-06. published 2004-2006.
Baker et al., "The pyrolysis of tobacco ingredients," J. Anal. Appl. Pyrolysis, vol. 71, pp. 223-311 (2004).
Bombick, et al. Chemical and biological studies of a new cigarette that primarily heats tobacco. Part 2. In vitro toxicology of mainstream smoke condensate. Food and Chemical Toxicology. 1997; 36:183-190.
Bombick, et al. Chemical and biological studies of a new cigarette that primarily heats tobacco. Part 3. In vitro toxicity of whole smoke. Food and Chemical Toxicology. 1998; 36:191-197.
Borgerding, et al. Chemical and biological studies of a new cigarette that primarily heats tobacco. Part 1. Chemical composition of mainstream smoke. Food and Chemical Toxicology. 1997; 36:169-182.
Breland, Alison, et al. "Electronic cigarettes: what are they and what do they do?." Annals of the New York Academy of Sciences 1394.1 (2017): 5-30.
Brown, Christopher J., and James M. Cheng. "Electronic cigarettes: product characterisation and design considerations." Tobacco control 23.suppl 2 (2014): ii4-ii10.
Bullen, et al., "Effect of an electronic nicotine delivery device (e cigarette) on desire to smoke and withdrawal, user preferences and nicotine delivery: randomized cross-over trial," Tobacco Control, 19(2), pp. 98-103. Apr. 2010.
Burch, et al., "Effect of pH on nicotine absorption and side effects produced by areosolized nicotine," Journal of Aerosol Medicine: Deposition, Clearance, and Effects in the Lung, 6(1), pp. 45-52. 1993.
Capponnetto, et al., "Successful smoking cessation with cigarettes in smokers with a documented history of recurring relapses: a case series," Journal of Medical Case Reports; 5(1), 6 pages. 2011.
Davis & Nielsen, "Marketing, Processing and Storage: Green Leaf Threshing and Redrying Tobacco," Tobacco Production, Chemistry and Technology, (1999) Section 10B, pp. 330-333, Bill Ward, Expert Leaf Tobacco Company, Wilson, North Carolina, USA.
E-Cigarette Forum; pg-gv-peg (discussion/posting); retrieved from the Internet: https://e-cigarette-forum.com/forum/threads/pg-vg-peg.177551; 7 pgs.; Apr. 8, 2011.

(56) References Cited

OTHER PUBLICATIONS

ECF; Any interest in determining nicotine—by DVAP; (https://www.e-cigarette-forum.com/forum/threads/any-interest-in-determining-nicotine-by-dvap.35922/); blog posts dated: 2009; 8 pgs.; print/retrieval date: Jul. 31, 2014.

Electronic Vaporization Device/ Gizmodo Pax 2 Vaporizer/ Gizmodo; retrieved from http://gizmodo.com/pax-2-vaporizer-reviews-its-like-smoking-in-the-future-1718310779; posted Jul. 23, 2015, retrieved Oct. 17, 2016.

Farsalinos, et al., "Electronic cigarettes do not damage the heart," European Society of Cardiology, 4 pages, (http://www.escardio.org/The-ESC/Press-Office/Press-releases/Electronic-cigarettes-do-not-damage-the-heart). Aug. 25, 2012.

Farsalinos, Konstantinos E., et al. "Protocol proposal for, and evaluation of, consistency in nicotine delivery from the liquid to the aerosol of electronic cigarettes atomizers: regulatory implications." Addiction 111.6 (2016): 1069-1076.

Fc Vaporizer Review Forum; Pax Vaporizer by Ploom; retrieved from : http://fuckcombustion.com/threads/pax-vaporizer-by-ploom.6223/; pp. 2 & 11 (2 pgs.); retrieval date: Nov. 16, 2015.

Flouris, et al., "Acute impact of active and passive electronic cigarette smoking on serum cotinine and lung function," Inhal. Toxicol., 25(2), pp. 91-101. Feb. 2013.

Food & Drug Administration; Warning letter to the Compounding Pharmacy, retrieved Oct. 10, 2014 from http://www.fda.gov/ICECI/EnforcementActions/WarningLetters/2002/ucm144843.htm, 3 pages. Apr. 9, 2002.

Goniewicz, et al., "Nicotine levels in electronic cigarettes," Nicotine Tobacco Research, 15(1), pp. 158-166, Jan. 2013.

Gregory, Andrew, "E-cigarettes to go on prescription under move to class them as medicines," Mirror, Jun. 12, 2013. http://www.mirror.co.uk/news/uk-news/e-cigarettes-go-prescription-under-move-1949018.

Grotenhermen, et al., Developing science-based per se limits for driving under the influence of cannabis (DUIC): findings and recommendations by an expert panel; retreived Feb. 9, 2017 from (http://www.canorml.org/healthfacts/DUICreport.2005.pdf); Sep. 2005.

Harvest Vapor, American Blend Tobacco (product info), retrieved from the internet (http://harvestvapor.com/), 2 pages. Oct. 10, 2014.

Hurt, et al., "Treating tobacco dependence in a medical setting," CA: A Cancer Journal for Clinicians, 59(5), pp. 314-326. Sep. 2009.

Inchem; Benzoic Acid; JECFA Evaluation Summary; retrieved Oct. 10, 2014 from http://www.inchem.org/documents/jecfa/feceval/jec_184.htm, 2 pages. May 28, 2005.

Inchem; Levulinic Acid; JECFA Evaluation Summary; retrieved Oct. 10, 2014 from http://www.inchem.org/documents/jecfa/feceval/jec_1266.htm, 2 pages. Mar. 10, 2003.

Inchem; Pyruvic Acid; JECFA Evaluation Summary; retrieved Oct. 10, 2014 from http://www.inchem.org/documents/jecfa/feceval/jec_2072.htm, 2 pages. Jan. 29, 2003.

Inchem; Sorbic Acid; JECFA Evaluation Summary; retrieved Oct. 10, 2014 from http://www.inchem.org/documents/jecfa/feceval/jec_2181.htm, 2 pages.. May 29, 2005.

Ingebrethsen et al., "Electronic Cigarette aerosol particle size distribution measurements", Inhalation Toxicology, 2012; 24 (14): 976-984.

Kuo et al. Applications of Turbulent and Multiphase Combustion, Appendix D: Particle Size—U.S. Sieve Size and Tyler Screen Mesh Equivalents, 2012, p. 541-543.

McCann et al., "Detection of carcinogens as mutagens in the Salmonella/microsome test: Assay of 300 chemicals: discussion." Proct. Nat. Acad. Sci, USA, Mar. 1976, vol. 73 (3), 950-954.

Mylaps, "Rechargeable Transponder Battery Status and Charging Instructions," Sep. 9, 2010.

Nicoli et al., Mammalian tumor xenografts induce neovascularization in Zebrafish embryos. Cancer Research, 67:2927-2931 (2007).

PAX Labs, Inc.; JUUL product information ©2016; retrieved from https://www.juulvapor.com/shop-juul/; 6 pgs.; retrieved Mar. 9, 2016.

Perfetti, "Structural study of nicotine salts," Beitrage Zur Tabakforschung International, Contributions to Tobacco Research, 12(2), pp. 43-54. Jun. 1983.

Poynton, Simon, et al. "A novel hybrid tobacco product that delivers a tobacco flavour note with vapour aerosol (part 1): Product operation and preliminary aerosol chemistry assessment." Food and Chemical Toxicology (2017).

Seeman, et al., "The form of nicotine in tobacco. Thermal transfer of nicotine and nicotine acid salts to nicotine in the gas phase," J Aric Food Chem, 47(12), pp. 5133-5145. Dec. 1999.

SRNT Subcommittee on Biochemical Verification, "Biochemical verification of tobacco use and cessation," Nicotine & Tobacco Research 4, pp. 149-159, 2002.

Tarantola, Andrew. "The Pax 2 vaporizer makes its predecessor look half-Baked." Engadget, Jul. 14, 2016, www.engadget.com/2015/04/20/pax-2-vaporizer-review/. Accessed Sep. 5, 2017.

Torikai et al., "Effects of temperature, atmosphere and pH on the generation of smoke compounds during tobacco pyrolysis," Food and Chemical Toxicology 42 (2004) 1409-1417.

Vansickel, et al. "A clinical laboratory model for evaluating the acute effects of electronic cigarettes: Nicotine delivery profile and cardiovascular and subjective effects," Cancer Epidemiology Biomarkers Prevention, 19(9), pp. 1945-1953. Jul. 20, 2010.

Vansickel, et al., "Electronic cigarettes: effective nicotine delivery after acute administration," Nicotine & Tobacco Research, 15(1), pp. 267-270. Jan. 2013.

VapeWorld; Original PAX Vaporizers for Portable and Home Use; retrieved from: https://www.vapeworld.com/pax-vaporizer-by-ploom?gclid=CPCi1PKojskCFU06gQodPr; 9 pgs.; retrieved Nov. 13, 2015.

Wells. "Glycerin as a Constituent of Cosmetics and Toilet Preparations." Journal of the Society of Cosmetic Chemists, 1958; 9(1): 19-25.

Williams, Monique, and Prue Talbot. "Variability among electronic cigarettes in the pressure drop, airflow rate, and aerosol production." Nicotine & Tobacco Research 13.12 (2011).

Youtube, "Pax 2 Unboxing," retreived from www.youtube.com/watch?v=Vjccs8co3YY, posted Apr. 20, 2015.

YouTube; Firefly Vaporizor Review w/ Usage Tips by the Vape Critic; retrieved from the internet (http://www.youtube.com/watch?v=1J38N0AV7wl); published Dec. 10, 2013; download/print date: Feb. 18, 2015.

Youtube; Pax by Ploom Vaporizer Review; posted Aug. 14, 2013, retrieved Sep. 8, 2016, https://www.youtube.com/watch?v=Jm06zW3-cxQ.

Zhang, et al., "In vitro partical size distributions in electronic and conventional cigarette aerosols suggest comparable deposition patterns," Nicotine Tobacci Research, 15(2), pp. 501-508. Feb. 2013.

* cited by examiner

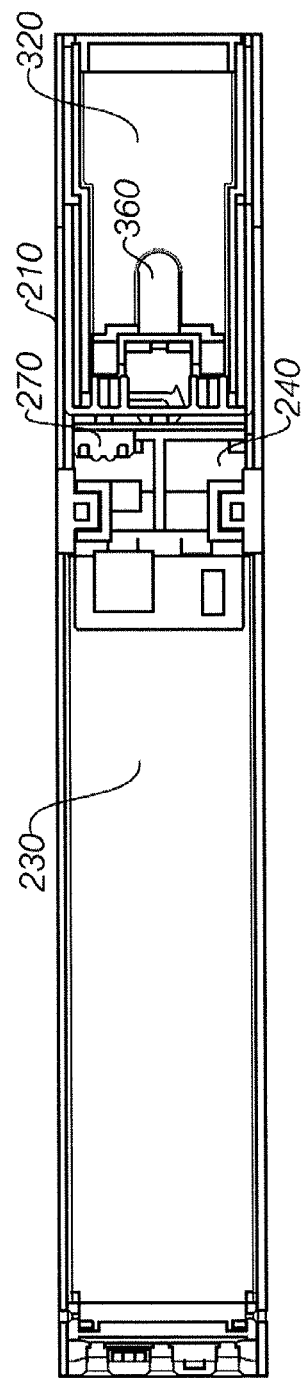
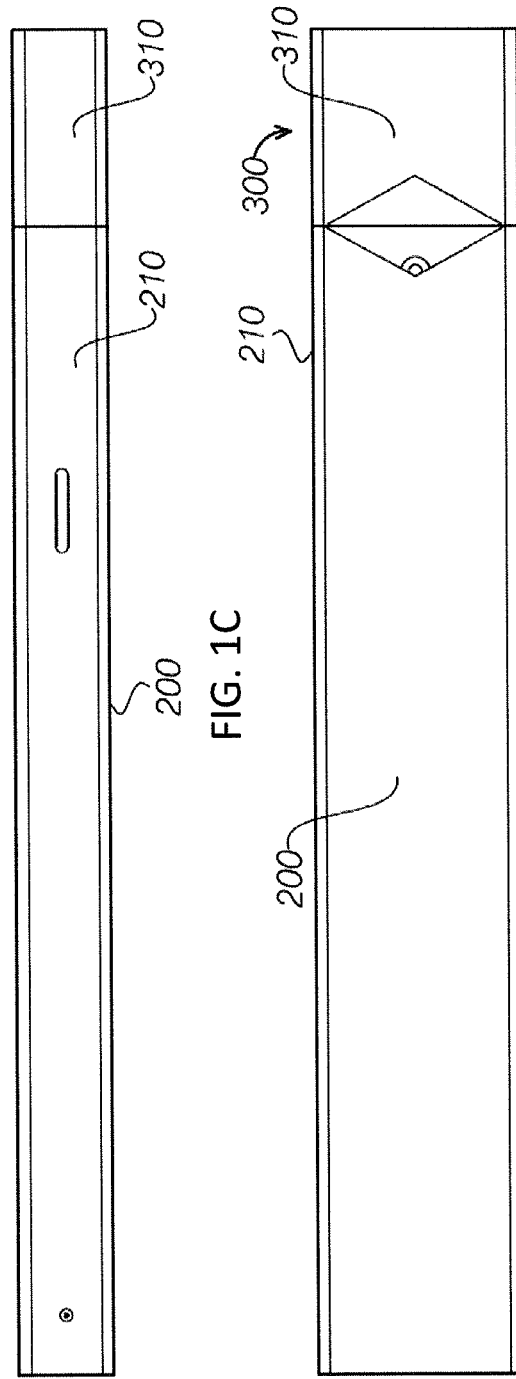
FIG. 1B
FIG. 1C
FIG. 1D

| MEASURED TPM (mg) | PREDICTED TPM (mg) | % ERROR |
| --- | --- | --- |
| 37.0 | 34.99 | -5.4% |
| 34.5 | 34.39 | -0.3% |
| 33.0 | 38.42 | 16.4% |
| 33.6 | 35.96 | 7.0% |
| 35.2 | 39.45 | 12.1% |
| 36.3 | 39.39 | 8.5% |
| 36.5 | 39.39 | 7.9% |
| 45.5 | 47.85 | 5.2% |
| 38.4 | 36.14 | -5.9% |
| 43.7 | 42.06 | -3.8% |
| 34.4 | 33.79 | -1.8% |
| 43.2 | 40.85 | -5.4% |
| 38.2 | 37.66 | -1.4% |
| 40.8 | 39.64 | -2.8% |
| 40.5 | 42.05 | 3.8% |
| 45.2 | 43.75 | -3.2% |
| 46.8 | 44.75 | -4.4% |
| 41.5 | 35.22 | -15.1% |
| 48.8 | 43.51 | -10.8% |
| 49.6 | 45.66 | -7.9% |
| 51.3 | 50.08 | -2.4% |
| 32.8 | 36.70 | 11.9% |
| 43.8 | 47.58 | 8.6% |
| 37.0 | 40.72 | 10.1% |
| 39.8 | 42.17 | 6.0% |
| 40.9 | 43.12 | 5.4% |
| 44.7 | 44.30 | -0.9% |
| 42.5 | 42.57 | 0.2% |
| 56.5 | 55.78 | -1.3% |
| 47.2 | 46.22 | -2.1% |
| 35.9 | 35.47 | -1.2% |

FIG. 3

| | |
|---|---|
| TARGET (mg) | 40.00 |
| MEAN (mg) | 42.13 |
| STANDARD DEVIATION | 2.51 |
| CV | 5.96% |
| MAX ERROR FROM TARGET | 16.50% |
| MAX ERROR FROM MEAN | 10.62% |

| MEASURED TPM (mg) | % ERROR FROM TARGET | % ERROR FROM MEAN |
|---|---|---|
| 38.6 | -3.50% | -8.37% |
| 38.5 | -3.75% | -8.61% |
| 40.2 | 0.50% | -4.58% |
| 41.8 | 4.50% | -0.78% |
| 45.5 | 13.75% | 8.00% |
| 44.1 | 10.25% | 4.68% |
| 45.8 | 14.50% | 8.72% |
| 44.2 | 10.50% | 4.92% |
| 41.6 | 4.00% | -1.25% |
| 38.2 | -4.50% | -9.32% |
| 46.5 | 16.25% | 10.38% |
| 42.8 | 7.00% | 1.60% |
| 40.5 | 1.25% | -3.86% |
| 43.5 | 8.75% | 3.26% |
| 40.5 | 1.25% | -3.86% |
| 42.6 | 6.50% | 1.12% |
| 40.4 | 1.00% | -4.10% |
| 43.9 | 9.75% | 4.21% |
| 38.6 | -3.50% | -8.37% |
| 42.8 | 7.00% | 1.60% |
| 41.0 | 2.50% | -2.68% |
| 46.6 | 16.50% | 10.62% |
| 43.4 | 8.50% | 3.02% |
| 40.3 | 0.75% | -4.34% |
| 41.3 | 3.25% | -1.97% |

| DURATION (seconds) | TPM (mg) |
|---|---|
| 0.1 | 0.07 |
| 0.3 | 0.12 |
| 0.5 | 0.20 |
| 0.7 | 0.28 |
| 1.0 | 0.33 |
| 1.5 | 0.70 |
| 2.0 | 0.95 |
| 2.5 | 1.51 |
| 3.0 | 2.10 |
| ... | ... |

CALIBRATED DOSE CONTROL

CROSS REFERENCE TO RELATED APPLICATIONS

This application claims priority to U.S. Provisional Application No. 62/088,464 filed Dec. 5, 2014, titled "CALIBRATED DOSE CONTROL AND HEAT BLOCK RESERVOIR FOR E-VAPORIZER DEVICE," and U.S. Provisional Application No. 62/199,828, filed Jul. 31, 2015, titled "CALIBRATED DOSE CONTROL," each of which is herein incorporated by reference in its entirety.

This patent application may also be related to U.S. patent application Ser. No. 14/581,666, filed Dec. 23, 2014 and titled "VAPORIZATION DEVICE SYSTEMS AND METHODS," Publication No. US-2015-0208729-A1 which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, systems and methods described herein may be useful for determining a dosage of a vapor and/or an amount of active ingredient in the vapor to a user inhaling the vapor.

BACKGROUND

Vaporizing devices, including electronic vaporizer devices or e-vaporizer devices, allow the delivery of vapor containing one or more active ingredient by inhalation of the vapor. Electronic vaporizer devices are gaining increasing popularity both for prescriptive medical use, in delivering medicaments, and for consumption of tobacco and other plant-based smokeable materials. Electronic vaporizer devices in particular may be portable, self-contained and convenient for use. Unfortunately, such devices, even when adapted for medical use, may vary in the amount of vapor and/or active ingredient provided.

To date, attempts to determine the dosage of vapor and/or an active ingredient in the vapor have been unsatisfactory. Systems that pre-determine dosage by restricting the amount of material to be delivered in a session assume, often incorrectly, that all of the material will be inhaled, and may not be adjustable for partial dosages. Such systems may also meter the amount of material, and require accurate measurement of the mass and/or volume of material being delivered for vaporization, or measure the difference between a starting mass/volume and post-delivery mass or volume. These measurements may be difficult, requiring a high level of accuracy and expense, and may result in inaccurate results.

What is needed is a method and apparatus (e.g., system and/or device) for delivering vapor and accurately, e.g., within a reasonable margin of accuracy/error, the delivered dosage. In particular, it would be helpful to provide methods and apparatuses for determining delivered doses of vapor and/or ingredients within the vapor by monitoring the electrical activity, and in some cases the temperature (which may be estimated electrically or measured directly) of the apparatus. Further, it would be helpful to provide such methods and apparatuses to deliver predetermined doses and/or to alert a use or caregiver when a threshold dosage has been reached or exceeded. Further, it may also be helpful to provide an electronic record of doses delivered.

SUMMARY OF THE DISCLOSURE

Disclosed herein are methods and apparatuses, including devices and systems that may estimate, measure and/or predict the amount of vapor and/or material (including active ingredients) in the vapor that can be delivered to a user. In particular, described herein are electronic vaporizers and methods of using them that determined a dose/amount of vapor and/or a material in the vapor based primarily or exclusively on the electrical properties, e.g., power or energy applied to the vaporizing element (e.g., coil) and, in some variations, the temperature of the material as it is vaporized. In some variations the temperature of the material as it is being vaporized may be estimated/approximated based on the electrical properties, e.g., the temperature coefficient of resistance or TCR, of the vaporizing element.

In general, the methods and apparatuses described herein may accurately determine the dosage delivered to within about 20% of an actual dosage delivered (e.g., within about 19%, within about 18%, within about 17%, within about 16%, within about 15%, within about 14%, within about 13%, within about 12%, within about 11%, within about 10%, etc.).

Also described herein are method and apparatuses for calibrating. Calibration may be performed automatically or manually, and may be performed at the factory. In some variations, calibration may be performed by the user. Calibration may include the input of values, including constant values. Calibration may be performed when the material being vaporized, including either or both the carrier and/or the active ingredient, are changed.

Although many of the examples described herein are directed to determining dosage of nicotine or other tobacco-related materials, it should be understood that these methods and apparatuses may be used for delivery and dosage determination of any vaporizable material, including therapeutic drugs. Examples of active ingredients that may be used as described herein are provided below, and may include botanicals, nutraceuticals, pharmaceuticals, and the like, including combinations of these. The methods and apparatuses described herein may provide relatively pure material directly to the lungs, which may speed the action in the body, including both the time of onset and the off-time.

In some embodiments, disclosed herein are methods and devices that allow a user to control the amount of vapor generated from a vaporizable material. This allows for customization of the vaping experience for a variety of vaporizable materials, and an overall improved user experience. The methods of this disclosure can be implemented using any electronic vaporizer device or vaporizing device configured as specified herein.

For example, the present disclosure provides a method of dose control and calibration of electronic vaporizer devices comprising measuring the amount of material vaporized from a vaporizable material from an electronic vaporizer device or vaporizing device relative to power, time and temperature. These methods and apparatuses may include a vaporized dose (e.g. mass) prediction system comprising setting-up a relationship of total particulate matter (TPM) or active ingredient vaporization or release as a function of temperature (which may be determined by electrical resistivity or otherwise measured by a temperature-proportionate property), time (which may be associated with detection of puffing/inhalation by the user) and power consumption of the vaporizing element(s). In some embodiments, the present disclosure provides a method of metered dose control and calibration of electronic vaporizer devices comprising measuring the amount of material vaporized from a vaporizable material from an electronic vaporizer device or vaporizing device relative to power and temperature; particularly, a method comprising a vaporized dose prediction system comprising setting-up a relationship of total particulate matter (TPM) or active ingredient vaporization or release as a function of temperature and power consumption.

Thus, described herein are methods of determining a dose of a vaporizable material delivered to a user of a vaporizing device over a time period. The time period typically comprises a plurality of sequential time intervals. In any of these methods and apparatuses the vaporizing device may include a heater controller, a heater, a source of the vaporizable material and a vaporized dose predictor unit. For example, a method may include: calculating, for each of the sequential time intervals, a partial dose, wherein the partial dose is calculated from a power delivered by the heater controller to the heater to vaporize the vaporizable material during a partial dose time interval, a temperature of the vaporizable material being vaporized during the partial dose time interval, and a temperature of the vaporizable material being vaporized before the partial dose time interval; and summing the calculated partial doses in the vaporized dose predictor unit to determine a total dose of vapor delivered during the time period.

Any of the calculation or summing steps may be performed in the device (e.g., locally, e.g., within a controller which may include or be part of the vaporized dose predictor unit that is within the same housing as other portions of the device such as the heater control), and/or they may be performed remotely, e.g., in a processor that receives, such as wirelessly, the power, temperature(s) and/or partial dose information. The vaporized dose predictor unit (which may be referred to herein as a vaporized dose predictor or vaporized dose predictor circuitry, or vaporized dose predictor control logic) may be located remotely from other portions of the device, including in a remote server (e.g., cloud-based server, smartphone or wearable apparatus, etc.) and may receive the information wirelessly.

In general, any of these methods may also include determining an amount of active ingredient delivered to the user based on the total dose of vapor delivered. This may be performed using the concentration of active material within the source of vaporizable material, for example (e.g., giving the amount of active ingredient/unit mass or unit volume or the vaporizable material in the source of vaporizable material).

Any of these methods may also include determining a change in temperature ($\Delta T$) of the vaporizable material being vaporized for each of the sequential time intervals relative the temperature of the vaporizable material being vaporized.

Any appropriate time interval (dose time interval), which may be sequential (e.g., sequential time intervals) may be used, and may be based on or reflective of the sampling rate of the apparatus for determining the dose. For example, the time interval may be between about 200 msec and about 10 msec.

The calculation of dose may also include calculating, for each of the sequential time intervals, a partial dose that is further based upon a latent heat and a specific heat of the material. For example, as described in greater detail herein, constants may be empirically or theoretically (e.g., from the latent heat and/or specific heat of the material being vaporized) and may be initially provided to the devices described herein, or may be periodically updated (e.g., in a calibration step) the any of these devices.

In general, the calculations of partial dose (vapor mass) being delivered by the device may be based on the mass/energy balance in the material being vaporized by balancing the energy put into the material by the heater (e.g., joule heating coil), including the change in energy due to evaporation, the change in heat as it is absorbed by the material to be vaporized, and the energy lost from the system via heat transfer. As described by the inventors herein, this may be expressed with surprising accuracy in terms of the energy (power) applied to the heater and the temperature just before and during/after vaporization of the vaporizable material. Variations in the structure of the vaporizer (heater shape, material, size, etc.) and the material being vaporized may be accounted for as constants and ignored (e.g., providing a unit-less or self-referencing value). For example, the steps of calculating, for each of the sequential time intervals, a partial dose may include subtracting from a first constant times the power delivered by the heater controller to the heater to vaporize the vaporizable material during the partial dose time interval, a second constant times the temperature of the vaporizable material being vaporized during the partial dose time interval and a third constant times the temperature of the vaporizable material being vaporized before the partial dose time interval. Alternatively, the steps of calculating, for each of the sequential time intervals, a partial dose may include subtracting from a first constant times the power delivered by the heater controller to the heater to vaporize the vaporizable material during the partial dose time interval, a different second constant times the difference between the temperature of the vaporizable material being vaporized during the partial dose time interval and the temperature of the vaporizable material being vaporized before the partial dose time interval, and a different third constant times the temperature of the vaporizable material being vaporized before the partial dose time interval.

In general, calculating a partial dose may use the temperature of the vaporizable material being vaporized during the partial dose time interval and the temperature of the vaporizable material being vaporized before the partial dose time interval comprises using an electrical property of the heater that is proportional to the temperature of the heater as the temperature of the vaporizable material being vaporized during the partial dose time interval. Thus, the temperature referred to in any of the calculation steps described herein (e.g., the temperature of the vaporizable material being vaporized during the partial dose time interval and the temperature of the vaporizable material being vaporized before the partial dose time interval) may refer to any value that is proportional to the actual temperature (e.g., using a temperature coefficient of resistance value to determine a value proportionally related to temperature, without requiring the conversion (using constants determined from the system to convert to ° C. or ° F.).

In general the methods and apparatuses described herein may implement the resulting dose information (or partial, running or summed dose information), e.g., to report and/or control operation of the apparatus or transmit to a secondary (e.g., remote) apparatus. For example, any of these methods may also include alerting the user when the total dose of vapor delivered during the time period meets or exceeds a preset threshold. Any of these methods may also include disabling the device when the total dose of vapor delivered during the time period meets or exceeds a preset threshold. Any of these methods (or devices configured to implement them) may further include calculating and displaying a cumulative total dose of vapor delivered over a session period that includes the time period. Thus, the total running dose over multiple puffs (each puff may be considered a time period, or the time period may an entire session in which the apparatus is turned on for vaporizing the material, or multiple on periods until reset by the user).

In general, any of these methods may include detecting a user's puff on the vaporizer device, wherein the time period corresponds to a duration of the detected user's puff.

Any appropriate material to be vaporized (vaporizable material) may be used. In general, the vaporizable material may be a liquid. The vaporizable material may comprise any active ingredient(s). For example, the vaporizable material may comprise a tobacco-based material. The vaporizable material may comprise a botanical. The vaporizable material may comprise a nicotine compound. The vaporizable material may comprise a cannabinoid. The vaporizable material may comprise one or more of: cetirizine, ibuprofen, naproxen, omeprazole, doxylamine, diphenhydramine, melatonin, or meclizine. The vaporizable material may comprise one or more of: albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and formoterol, or mometasone and formoterol. The vaporizable material may comprise one or more of: a polyphonel, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a senna glycoside, cinnamaldehyde, or Vitamin D. The vaporizable material may comprise a nicotine salt, glycerin, and propylene glycol.

As mentioned, the vaporized dose predictor unit may be part of a controller. In some variations, both the vaporized dose predictor and the heater controller are part of the same controller. In some variations the vaporized dose predictor and the heater controller are separate.

Another example of the methods of determining a dose of a vaporizable material delivered to a user of a vaporizing device over a time period as described herein (e.g., wherein the time period comprises a plurality of sequential time intervals, and wherein the vaporizing device includes a heater controller, a heater, a source of the vaporizable material and a vaporized dose predictor unit) may include: transmitting a power delivered by the heater controller to the heater at each of the plurality of sequential time intervals from the power controller to the vaporized dose predictor unit; calculating, for each of the sequential time intervals, a partial dose, wherein the partial dose is calculated from the power delivered by the heater controller to the heater to vaporize the vaporizable material during each of the plurality of sequential time intervals, a temperature of the vaporizable material being vaporized during each of the plurality of sequential time intervals, and a temperature of the vaporizable material being vaporized before each of the plurality of sequential time intervals; and summing the calculated partial doses in the vaporized dose predictor unit to determine a total dose of vapor delivered during the time period.

Any of these methods may also include transmitting the temperature of the vaporizable materials being vaporized during each of the plurality of sequential time intervals from the power controller to the vaporized dose predictor unit.

Another example of a method of determining a dose of a vaporizable material delivered to a user of a vaporizing device over a time period (e.g., wherein the time period comprises a plurality of sequential time intervals, and wherein the vaporizing device includes a heater controller, a heater, a source of the vaporizable material including an active ingredient, and a vaporized dose predictor unit) may include: calculating, for each of the sequential time intervals, a partial dose, wherein the partial dose is calculated from a power delivered by the heater controller to the heater to vaporize the vaporizable material during a partial dose time interval, a temperature of the vaporizable material being vaporized during the partial dose time interval, and a temperature of the vaporizable material being vaporized immediately before the partial dose time interval; summing the calculated partial doses in the vaporized dose predictor unit to determine a total dose of vapor delivered during the time period; and determining an amount of active ingredient delivered to the user based on the total dose of vapor delivered.

A method of determining an amount of vapor delivered to a user of a vaporizing device may include: measuring an amount of power delivered from a power source of the vaporizer device over a first period of time; measuring a temperature of a material being vaporized in the vaporizer device over the first period of time; and determining an amount of vapor delivered to the user during the first period of time based upon the measured amount of power and a change in the measured temperature during the first period of time.

Any of these methods may also include detecting an amount of active ingredient delivered to the user based upon the determined amount of vapor. The measuring step may be performed at any appropriate frequency, such as a frequency of between 5 Hz and 50 Hz within the first period of time. The measuring steps may be performed at a frequency of between 10 Hz and 30 Hz within the first period of time.

As mentioned above, determining the amount of vapor delivered to the user during the first period of time may be further based upon a latent heat and a specific heat of the material.

In any of these methods, determining the amount of vapor delivered to the user during the first period of time comprises calculating based upon the formula:

$$\Delta m_{vap,cumulative} = \sum_{i=1}^{i=n} a[Pi - b(T_i - T_{i-1}) - cT_i]$$

where $\Delta m_{vap,cumulative}$ cumulative is the total amount of vapor delivered to the user, a is a constant, b is a constant, c is a constant, P is the measured power, and $T_i$ is the measured temperature from the first period of time, and $T_{i-1}$ is a measured temperature from an immediately preceding time period.

Any of these methods may also include alerting the user when the determined amount of vapor delivered to the user meets or exceeds a preset vapor threshold, and/or disabling the device when the determined amount of vapor meets or exceeds a preset vapor threshold.

Any of these methods may also include detecting a user's puff on the vaporizer device, wherein the measuring steps are performed only during the detected puff.

As mentioned above, in any of the methods described herein, appropriate material to be vaporized (vaporizable material) may be used. In general, the vaporizable material may be a liquid. The vaporizable material may comprise any active ingredient(s). For example, the vaporizable material may comprise a tobacco-based material. The vaporizable material may comprise a botanical. The vaporizable material may comprise a nicotine compound. The vaporizable material may comprise a cannabinoid. The vaporizable material may comprise one or more of: cetirizine, ibuprofen, naproxen, omeprazole, doxylamine, diphenhydramine, melatonin, or meclizine. The vaporizable material may comprise one or more of: albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and formoterol, or mometasone and formoterol. The vaporizable material may comprise one or more of: a polyphonel, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a senna glycoside, cinnamaldehyde, or Vitamin D. The vaporizable material may comprise a nicotine salt, glycerin, and propylene glycol.

Also described herein are vaporization apparatuses, such as devices and systems, configured to determine a dose of the vapor being delivered. For example, a vaporizer device may include: a heater controller; a heater coupled to the heater controller so that the heater controller applies power to the heater; a source of vaporizable material; and a vaporized dose predictor unit receiving input from the heater controller, wherein the vaporized dose predictor is configured to determine a dose of vapor delivered to a user during a time period based upon: an amount of power delivered by the heater controller to the heater to vaporize the vaporizable material during each of a plurality of partial dose time intervals within the time period, a temperature of the vaporizable material being vaporized during each partial dose time interval, and a temperature of the vaporizable material being vaporized before each partial dose time interval.

Any of these devices may also include an output configured to present the amount of vapor delivered by the user during the time period.

Any appropriate output may be used, including a video display, LED, speaker, wireless transmitter, etc. Any of the apparatuses described herein may include a temperature sensor configured to sense a temperature of the vaporizable material being vaporized during each partial dose time interval. As described herein, the temperature sensor may be a separate and/or dedicated (e.g., thermistor) or it may determine the temperature (e.g., of the heater and/or the material being heated) based on the relative resistance of the heater itself.

As mentioned, the vaporized dose predictor unit may include a controller. For example, the vaporized dose predictor unit may be integral with the heater controller. The vaporized dose predictor may be configured to determine the amount of vapor delivered as dose of vapor delivered. The vaporized dose predictor may be configured to determine an amount of active ingredient delivered to the user based on the dose of vapor delivered.

In any of the apparatuses described herein, the partial dose time intervals may each be between about 200 msec and about 10 msec.

The vaporized dose predictor unit may be configured to calculate, for each of the partial dose time intervals, a partial dose by subtracting from a first constant times the power delivered by the heater controller to the heater to vaporize the vaporizable material during the partial dose time interval, a second constant times the temperature of the vaporizable material being vaporized during the partial dose time interval and a third constant times the temperature of the vaporizable material being vaporized before the partial dose time interval.

In general, the vaporized dose predictor unit may be configured to determine the amount of vaporizable material delivered to the user.

As described herein, the vaporized dose predictor unit is configured to use an electrical property of the heater that is proportional to the temperature of the heater as the temperature of the vaporizable material being vaporized during the partial dose time interval.

Any of these apparatuses may include an alarm configured to alert the user when the total dose of vapor delivered during the time period meets or exceeds a preset threshold. Any of these apparatuses may include dose control logic configured to disable the device when the total dose of vapor delivered during the time period meets or exceeds a preset threshold.

Any of these apparatuses may also include a puff detector configured to detect a user puffing on the device. In some variations, the vaporized dose predictor unit may be configured to set the time period as a duration of a detected user's puff (e.g., between 0.5-15 sec, between 0.5-20 sec, between 0.5 to 10 seconds, etc.).

The source of vaporizable material may be a liquid or a solid or a gel. The vaporizable material is preferably a liquid.

Other methods and apparatus variations are also described. For example, described herein are methods for quantifying and controlling an amount of a vapor and/or one or more material(s) within the vapor that is delivered to a user from a reservoir of vaporizable material in an electronic vaporizer device. The electronic vaporizer device may include a puff sensor, a power source (e.g., battery, capacitor, etc.), a heating element controller, and a heating element. A separate temperature sensor may also be included, or it may be part of the heating element controller, which may estimate temperature of the heating element (e.g., resistive coil, etc.) based on a change in resistance due to temperature (e.g., TCR), and may therefore include a reference resistor. One or more additional temperature sensors may also be included. These apparatuses may also include a vaporized dose predictor unit, which may be separate from (and may receive inputs from) the temperature controller or it may be integrated with it. In some variations the apparatus also includes an alert unit and/or a controlling logic for controlling operation of the apparatus based on the determined/estimated dosage (e.g., turning off, triggering an alert, etc.).

For example, a method of operating the device may include: (optionally) a puff sensor detecting a user's puff, the heating element controller measuring an amount of power delivered from the power source during the user's puff (e.g., at multiple discrete time intervals during the puff); the temperature sensor measuring a temperature or a temperature profile of the material being vaporized (e.g., at or near the heating element) during the user's puff; the vaporized dose predictor calculating the amount of the vapor delivered to the user from the vaporizable material based upon the amount of the power and the temperature during the user's puff, or based upon the amount of the power and the temperature profile during the user's puff; and a) engaging the alert unit to alert the user when the amount of the vapor delivered meets or exceeds a preset vapor amount threshold for the user's puff, or when a cumulative amount of the vapor delivered from a plurality of puffs meets or exceeds a preset vapor amount threshold, or b) implementing the controlling logic to disable or modify an output of one or more features of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b). In certain embodiments, the method comprises storing a plurality of measurements of temperature, temperature profiles, amount of power delivered, or a combination thereof, in a memory unit. In certain embodiments, the method comprises adjusting the preset vapor amount threshold from one puff to the next, based on the amount of the vapor delivered to the user by the user's prior puff. In certain embodiments, the electronic vaporizer device comprises a timer, and the method may comprise engaging the timer to measure a puff duration. In certain embodiments, the method comprises storing a plurality of measurements of temperature, temperature profiles, amount of power delivered, puff duration or a combination thereof in a memory unit. In certain embodiments, the method comprises normalizing the amount of the vapor delivered to the user to the puff duration. In certain embodiments, the method comprises attaching a separate pod to the device, the separate pod configured to hold a vaporizable material. In certain embodiments, the method comprises calculating the amount of the vapor delivered to a user from the vaporizable material in milligrams of total particulate matter. In certain embodiments, the method comprises calculating the amount of the vapor delivered to a user from the vaporizable material in milligrams of an active ingredient. In certain embodiments, the method comprises adjusting the preset vapor amount threshold. In certain embodiments, the electronic vaporizer device comprises a heating reservoir distinct from the heating element, and the method comprises preheating a vaporizable material to a preset temperature. In certain embodiments, the vaporizable material is a liquid, viscous liquid, wax or loose-leaf material. In certain embodiments, the vaporizable material is a tobacco-based material. In certain embodiments, the vaporizable material is a botanical. In certain embodiments, the vaporizable material is a medicinal compound. In certain embodiments, the vaporizable material is nicotine. In certain embodiments, the vaporizable material is a cannabinoid. In certain embodiments, the vaporizable material is *Cannabis*. In certain embodiments, the method comprises adjusting a type of the vaporizable material. In certain embodiments, the method comprises adjusting the type of the vaporizable material to a liquid, viscous liquid, wax or loose-leaf material. In certain embodiments, the method comprises adjusting the type of the vaporizable material to a tobacco-based material. In certain embodiments, the method comprises adjusting the type of the vaporizable material to a botanical. In certain embodiments, the method comprises adjusting the type of the vaporizable material to a medicinal compound. In certain embodiments, the method comprises adjusting the type of the vaporizable material to nicotine. In certain embodiments, the method comprises adjusting the type of the vaporizable material to a cannabinoid. In certain embodiments, the method comprises adjusting the type of the vaporizable material to *Cannabis*. Adjusting the vaporizable material may include adjusting the apparatus or method to account for the change in constants and/or calibrating the apparatus to account for changes in the constants that may be used to give a calibrated (e.g., mass or mass/time) output, as described in greater detail herein.

In certain embodiments, the alert unit comprises a piezoelectric speaker, and the method comprises alerting the user by activating the piezoelectric speaker to produce an audible sound when the amount of the vapor delivered to the user meets or exceeds the preset vapor amount threshold. In certain embodiments, the alert unit comprises a light emitting diode, and the method comprises alerting the user by illuminating the light emitting diode when the amount of the vapor delivered to the user meets or exceeds the preset vapor amount threshold. In certain embodiments, the alert unit comprises a vibration motor, and the method comprises alerting the user by activating the vibration motor when the amount of the vapor delivered to the user meets or exceeds the preset vapor amount threshold. In certain embodiments, the controlling logic comprises a software module. In certain embodiments, the controlling logic comprises a hardware element. In certain embodiments, the electronic vaporizer device comprises a display unit, wherein the method comprises providing feedback to the user via the display. In certain embodiments, the electronic vaporizer device is a single-use electronic vaporizer device. In certain embodiments, the electronic vaporizer device is provided to an analytical smoking machine.

In a certain embodiment provided herein, is an electronic vaporizer device configured to quantify and control an amount of a vapor delivered to a user from a vaporizable material in the electronic vaporizer device, wherein the electronic vaporizer device comprises: a puff sensor configured to detect a user's puff; a heating element controller configured to measure an amount of power delivered from a power source during the user's puff; a temperature sensor configured to measure a temperature or a temperature profile generated by a heating element during the user's puff; a vaporized dose predictor unit configured to calculate the amount of the vapor delivered to the user from the vaporizable material based upon the amount of the power and the temperature during the user's puff or based upon the amount of the power and the temperature profile during the user's puff; and one or more of a) an alert unit configured to alert the user when the amount of vapor delivered meets or exceeds a preset vapor amount threshold for the user's puff, or when a cumulative amount of the vapor delivered from a plurality of puffs meets or exceeds a preset vapor amount threshold, and b) a controlling logic configured to automatically disable one or more feature of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b). In certain embodiments, the electronic vaporizer device comprises a memory unit, configured to store a plurality of measurements of temperature, temperature profile, power delivered, or a combination thereof. In certain embodiments, the electronic vaporizer device comprises a timer configured to determine a puff duration. In certain embodiments, the electronic vaporizer device comprises a memory unit, configured to store a plurality of measurements of temperature, temperature profile, power delivered, puff duration or a combination thereof. In certain embodiments, the electronic vaporizer device is configured to normalize the amount of the vapor delivered to the user to the puff duration. In certain embodiments, the electronic vaporizer device comprises a separate pod attached to the device, the separate pod configured to hold a vaporizable material. In certain embodiments, the electronic vaporizer device is configured to calculate the amount of the vapor delivered to the user from a vaporizable material in milligrams of total particulate matter. In certain embodiments, the electronic vaporizer device is configured to calculate the amount of the vapor delivered to the user from a vaporizable material in milligrams of total particulate matter. In certain embodiments, the electronic vaporizer device is configured to allow adjustment of the preset vapor amount threshold. In certain embodiments, the electronic vaporizer device comprises a heating reservoir distinct from the heating element. In certain embodiments, the electronic vaporizer device comprises a vaporizable material that is a liquid, viscous liquid, wax or loose-leaf material. In certain embodiments, the electronic vaporizer device comprises a vaporizable material that is a tobacco-based material. In certain embodiments, the electronic vaporizer device comprises a vaporizable material that is a botanical. In certain embodiments, the electronic vaporizer device comprises a vaporizable material that is a medicinal compound. In certain embodiments, the electronic vaporizer device comprises a vaporizable material that is nicotine. In certain embodiments, the electronic vaporizer device comprises a vaporizable material that is a cannabinoid. In certain embodiments, the electronic vaporizer device comprises a vaporizable material that is *Cannabis*. In certain embodiments, the electronic vaporizer device is configured to allow adjustment of a type of the vaporizable material. In certain embodiments, the type of the vaporizable material is adjustable to a liquid, viscous liquid, wax or loose-leaf material. In certain embodiments, the type of the vaporizable material is adjustable to a tobacco-based material. In certain embodiments, the type of the vaporizable material is adjustable to a botanical. In certain embodiments, the type of the vaporizable material is adjustable to a medicinal compound. In certain embodiments, the type of the vaporizable material is adjustable to nicotine. In certain embodiments, the type of the vaporizable material is adjustable to a cannabinoid. In certain embodiments, the type of the vaporizable material is adjustable to *Cannabis*. In certain embodiments, the alert unit comprises a piezoelectric speaker. In certain embodiments, the alert unit comprises a light emitting diode. In certain embodiments, the alert unit comprises a vibration motor. In certain embodiments, the controlling logic comprises a software module. In certain embodiments, the controlling logic comprises a hardware element. In certain embodiments, the electronic vaporizer device comprises a display unit, configured to provide feedback to the user. In certain embodiments, the electronic vaporizer device is a single-use electronic vaporizer device. In certain embodiments, the electronic vaporizer device is a vaporizing device.

In a certain embodiment provided herein, is a method, the method comprising an electronic vaporizer device configured to quantify and control an amount of a vapor delivered to a user from a vaporizable material in the electronic vaporizer device, wherein the electronic vaporizer device comprises: a puff sensor configured to detect a user's puff; a heating element controller configured to measure an amount of power delivered from a power source during the user's puff; a temperature sensor configured to measure a temperature or a temperature profile generated by a heating element during the user's puff; a vaporized dose predictor unit configured to calculate the amount of the vapor delivered to the user from the vaporizable material based upon the amount of the power and the temperature during the user's puff or based upon the amount of the power and the temperature profile during the user's puff; and one or more of a) an alert unit configured to alert the user when the amount of vapor delivered meets or exceeds a preset vapor amount threshold for the user's puff, or when a cumulative amount of the vapor delivered from a plurality of puffs meets or exceeds a preset vapor amount threshold, and b) a controlling logic configured to automatically disable one or more feature of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b). In certain embodiments, the electronic vaporizer device comprises a memory unit, configured to store a plurality of measurements of temperature, temperature profile, power delivered, or a combination thereof. In certain embodiments, the electronic vaporizer device comprises a timer configured to determine a puff duration. In certain embodiments, the electronic vaporizer device comprises a memory unit, configured to store a plurality of measurements of temperature, temperature profile, power delivered, puff duration or a combination thereof. In certain embodiments, the electronic vaporizer device is configured to normalize the amount of the vapor delivered to the user to the puff duration. In certain embodiments, the electronic vaporizer device comprises a separate pod attached to the device, the separate pod configured to hold a vaporizable material. In certain embodiments, the electronic vaporizer device is configured to calculate the amount of the vapor delivered to the user from a vaporizable material in milligrams of total particulate matter. In certain embodiments, the electronic vaporizer device is configured to calculate the amount of the vapor delivered to the user from a vaporizable material in milligrams of total particulate matter. In certain embodiments, the electronic vaporizer device is configured to allow adjustment of the preset vapor amount threshold. In certain embodiments, the electronic vaporizer device comprises a heating reservoir distinct from the heating element. In certain embodiments, the electronic vaporizer device comprises a vaporizable material that is a liquid, viscous liquid, wax or loose-leaf material. In certain embodiments, the electronic vaporizer device comprises a vaporizable material that is a tobacco-based material. In certain embodiments, the electronic vaporizer device comprises a vaporizable material that is a botanical. In certain embodiments, the electronic vaporizer device comprises a vaporizable material that is a medicinal compound. In certain embodiments, the electronic vaporizer device comprises a vaporizable material that is nicotine. In certain embodiments, the electronic vaporizer device comprises a vaporizable material that is a cannabinoid. In certain embodiments, the electronic vaporizer device comprises a vaporizable material that is *Cannabis*. In certain embodiments, the electronic vaporizer device is configured to allow adjustment of a type of the vaporizable material. In certain embodiments, the type of the vaporizable material is adjustable to a liquid, viscous liquid, wax or loose-leaf material. In certain embodiments, the type of the vaporizable material is adjustable to a tobacco-based material. In certain embodiments, the type of the vaporizable material is adjustable to a botanical. In certain embodiments, the type of the vaporizable material is adjustable to a medicinal compound. In certain embodiments, the type of the vaporizable material is adjustable to nicotine. In certain embodiments, the type of the vaporizable material is adjustable to a cannabinoid. In certain embodiments, the type of the vaporizable material is adjustable to *Cannabis*. In certain embodiments, the alert unit comprises a piezoelectric speaker. In certain embodiments, the alert unit comprises a light emitting diode. In certain embodiments, the alert unit comprises a vibration motor. In certain embodiments, the controlling logic comprises a software module. In certain embodiments, the controlling logic comprises a hardware element. In certain embodiments, the electronic vaporizer device comprises a display unit, configured to provide feedback to the user. In certain embodiments, the electronic vaporizer device is a single-use electronic vaporizer device. In certain embodiments, the electronic vaporizer device is a vaporizing device.

BRIEF DESCRIPTION OF THE DRAWINGS

The novel features of the invention are set forth with particularity in the description. Like numbers refer to like elements throughout the description of the figures. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 1B-1D shows one example of a vaporizing apparatus as described herein, in cross-sectional, side and top views, respectively.

FIG. 3 is a table showing a comparison between actual measured dosage (total particulate matter, or TPM, vaporized) and the dosage predicted as described herein based on discrete estimates at multiple time intervals during a puff (inhalation) using the power applied to the vaporization element (heater) and the temperature of the vaporization element or the temperature of the material being vaporized at the start and finish of each of the multiple time intervals.

FIG. 4 is another table comparing measured and estimated doses (in TPM) during a trail in humans using one variation of the methods described herein.

FIG. 7 schematically illustrates one example of a heater (atomizer) and vaporizable material reservoir for forming a vapor as described herein. In this example the heater includes a wick connected to the reservoir and a heating element in contact with the wick; the wick and heating element extend in an airflow path for drawing out the vapor formed. In this example, the walls of the reservoir are heated.

DETAILED DESCRIPTION

Figure 1A:
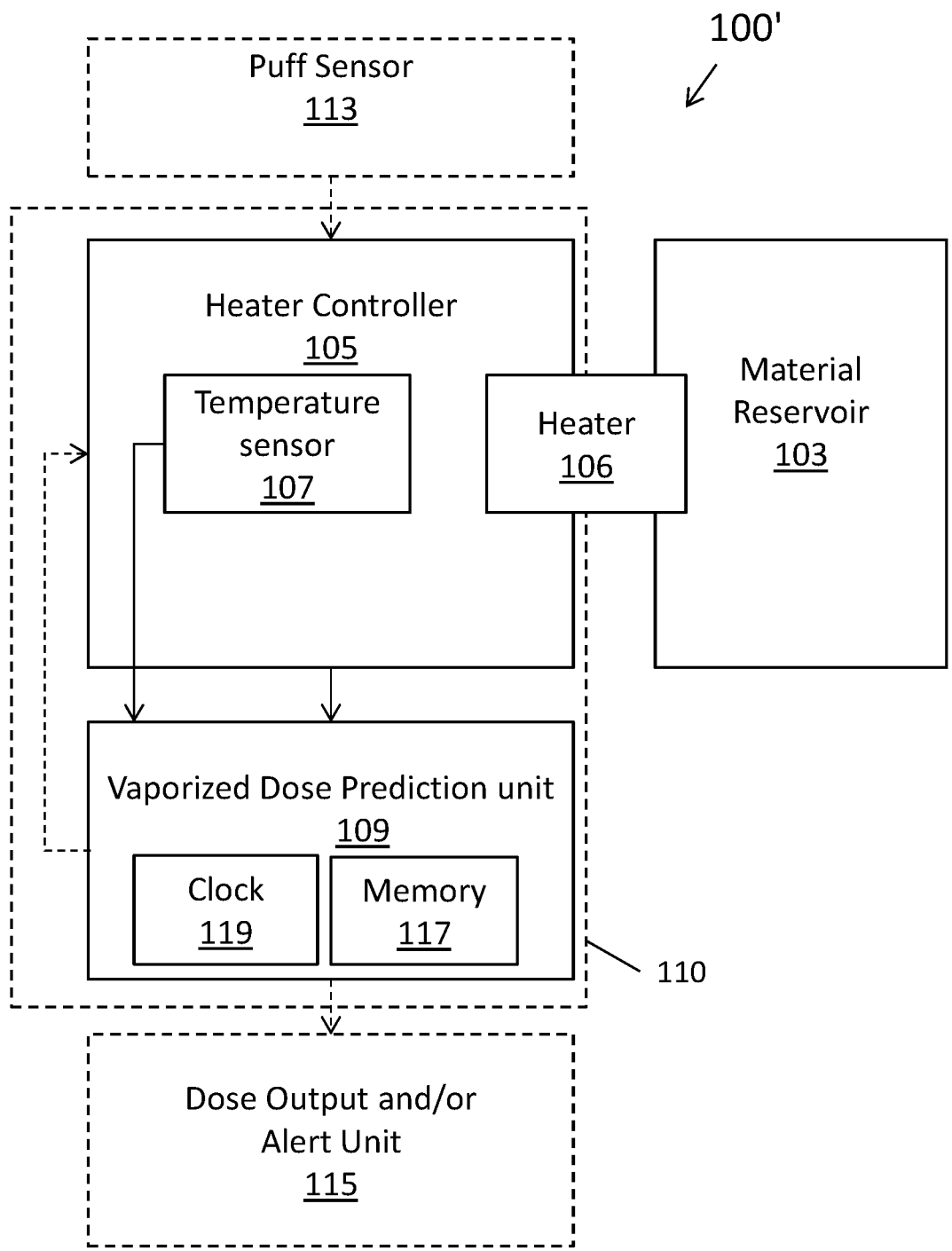
FIG. 1A is a schematic of a vaporizing apparatus including a vaporized dose estimation/prediction unit.

The present disclosure provides a method for quantifying and controlling an amount of a vapor delivered to a user from a vaporizable material in an electronic vaporizer device comprising measuring the vaporizable material intake evaporated, aerosolized or vaporized from a vaporizable material in a vaporizing device or electronic vaporizer device relative to power consumed during vaporization and temperature produced during vaporization. Also provided in this disclosure are calibration methods that may include establishing a relationship of total particulate matter (TPM) vaporized from a vaporizable material as a function of temperature generated and power consumed. Calibration may be performed one time (e.g., at a factory) or it may be performed by the user. Alternatively or additionally, the user may be requested or required to perform a calibration step that include inputting an identifier of the material be vaporized (e.g., selecting or inputting the material and/or concentration, or a reference identified, such as a lot number or the like that can be linked to the material being vaporized). For example, a user may scan (e.g., using a QR code, bar code, or equivalent) the vaporizable material or packing and/or inserts affiliated with the vaporizable material. In some variations the apparatus includes a look-up table corresponding to a variety of vaporizable materials that may include values for calibrating the apparatus, including the constants referred to herein that may be used to calibrate the mass of the vapor and/or one or more components (e.g., active agents/active ingredients) in the vaporizable material.

The term "vape" or "vaping", as used herein, refers to the action of or the experience of using a vaporization device, such as an electronic vaporizer device for the delivery of vapor to a user.

The term "puff" refers to the process of removing vapor from a vaporization device or e-vaporizer device using a suction mechanism. In certain embodiments, the suction mechanism is a user. In certain embodiments, the suction mechanism is an analytical smoking machine. Commonly used synonyms for puff are drag, draw, hit, suck, pull, inhale, or smoke for example.

As used herein a dose may refer to the amount or quantity of the vapor and/or material (e.g., active ingredient(s), etc.) taken at a particular time. The dose may be quantified as a mass, or a mass/time, depending on the context. The dose may be dose/puff.

The term "puff duration" as used herein, refers to a length of time during which a vaporization device or electronic vaporizer device is coupled to a suction mechanism. In certain embodiments, the suction mechanism is a user. In certain embodiments, the suction mechanism is an analytical smoking machine. In certain embodiments, suction is provided through a mouthpiece.

The term "puff volume" as used herein, refers to a volume leaving a vaporizer device (e.g. standard reference vaporizer device, test vaporizer device, electronic vaporizer device, or vaporization device.). The volume can comprise one or more gas, solid, and/or liquid species. The puff volume can comprise an amount in ml (or cc) of air or aerosol drawn through a device, for example, either an analytical smoke machine or an electronic vaporizer device.

The term "puff frequency" as used herein refers to a number of puffs in a certain time period. In certain embodiments, the puff frequency is calculated using a mean number of puffs per a unit of time that is milliseconds, seconds, minutes or hours. In certain embodiments, the puff frequency is calculated using 1, 2, 3, 4, 5, 6, 7, 8, 9, or 10 consecutive puffs. In certain embodiments, the puff frequency is calculated using 10, 20, 30, 40, 50, 60, 70, 80, 90, or 100 consecutive puffs. In certain embodiments, the puff frequency is 1 puff every 1 second. In certain embodiments, the puff frequency is 1 puff about every 2 seconds. In certain embodiments, the puff frequency is 1 puff about every 3 seconds. In certain embodiments, the puff frequency is 1 puff about every 4 seconds. In certain embodiments, the puff frequency is 1 puff about every 5 seconds. In certain embodiments, the puff frequency is 1 puff about every 6 seconds. In certain embodiments, the puff frequency is 1 puff about every 7 seconds. In certain embodiments, the puff frequency is 1 puff about every 8 seconds. In certain embodiments, the puff frequency is 1 puff about every 9 seconds. In certain embodiments, the puff frequency is 1 puff every 10 seconds. In certain embodiments, the puff frequency is 1 puff about every 15 seconds. In certain embodiments, the puff frequency is 1 puff about every 20 seconds. In certain embodiments, the puff frequency is 1 puff about every 25 seconds. In certain embodiments, the puff frequency is 1 puff about every 30 seconds. In certain embodiments, the puff frequency is 1 puff about every 35 seconds. In certain embodiments, the puff frequency is 1 puff about every 40 seconds. In certain embodiments, the puff frequency is 1 puff about every 45 seconds. In certain embodiments, the puff frequency is 1 puff about every 50 seconds. In certain embodiments, the puff frequency is 1 puff about every 55 seconds. In certain embodiments, the puff frequency is 1 puff about every 60 seconds.

The term "total particulate matter (TPM)", as used herein, refers to an amount of matter removed from an organic material by evaporation, vaporization or aerosolization by puffing on vaporizer or electronic vaporizer device; and as used herein, can be synonymous to the phrase "mass vaporized", or "mass aerosolized", or "$m_{vap}$" or "evaporated mass."

The term "analytical smoking machine", as used herein refers to a tool that can puff on a cigarette or vaporizer device with a specified and controlled puff volume and duration.

The term "vaporizable material", as used herein, refers to a formulation of material, including in particular an organic material or botanical that is placed in a vaporization device, electronic vaporizer device, or pod (or a proprietary container) that houses the formulation. The vaporizable material can be a liquid, oil, or wax. In certain embodiments, the vaporizable material is a loose leaf substance. In certain embodiments, the vaporizable material can contain medicinal properties that ameliorate symptoms of a medical condition. In certain embodiments, the vaporizable material can contain a recreational drug.

As used herein, the term "vapor" refers to the output of a vaporizer device, including a chemical compound or mixture of chemical compounds in the gas phase or as an aerosol.

The term "memory unit," as used herein, refers to a non-transitory computer readable medium, software or algorithm for data storage. In certain embodiments, a memory unit is a solid state device. In certain embodiments, a memory unit is internal to the device. In certain embodiments, a memory unit stores data in random access memory (RAM). In certain embodiments, a memory unit is a hard disk, tape drive, or other external device. In certain embodiments, a memory unit refers to a device configured as a permanent holding place for digital data, until purposely erased. A memory unit also refers to devices configured as non-volatile memory chips such as flash, Read-Only memory (ROM) and/or Electrically Erasable Programmable Read-Only Memory (EEPROM).

The term "adjusting," as used herein, may refer to choosing a pod, choosing an operating parameter, choosing a type of a vaporizable material, choosing a dosage in an amount of TPM, an amount of an active ingredient, or a percentage, ratio or fraction of TPM or an active ingredient, and/or may refer to calibrating the apparatus.

The term "nicotine" as used herein refers to nicotine, nicotine salts of organic acid, and common nicotine derivatives such as; norcotinine, nornicotine, nicotine N-oxide, cotinine N-oxide, 3-hydroxycotinine and 5-hydroxycotinine.

The term "cannabinoid" refers to plant based or synthetic chemical compounds capable of acting on cannabinoid receptors and inducing a biological effect. Cannabinoids include acids, salts, and bioactive stereo isomers.

The term "*Cannabis*" refers to plants of the genus *Cannabis* and loose-leaf products or extracts thereof.

In general, described herein are methods for quantifying and, in some variations, controlling an amount of a vapor delivered to a user from a vaporizable material in an electronic vaporizer device. In some variations, the electronic vaporizer device comprises (optionally): a puff sensor, a power source, a heating element controller, a heating element, a temperature sensor, a vaporized dose predictor unit, an alert unit and/or a controlling logic. A method for quantifying and/or controlling may include: (optionally) a puff sensor detecting a user's puff, the heating element controller measuring an amount of power delivered from the power source during the user's puff; the temperature sensor measuring a temperature or a temperature profile generated by the heating element during the user's puff; the vaporized dose predictor unit calculating the amount of the vapor delivered to the user from the vaporizable material based upon the amount of the power and the temperature during the user's puff, or based upon the amount of the power and the temperature profile during the user's puff and a) engaging the alert unit to alert the user when the amount of the vapor delivered meets or exceeds a preset vapor amount threshold for the user's puff, or when a cumulative amount of the vapor delivered from a plurality of puffs meets or exceeds a preset vapor amount threshold, or b) implementing the controlling logic to disable or modify an output of one or more features of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b).

As will be apparent when described in greater detail below, the puff sensor is not necessary; the apparatus and methods described herein will simply return a zero value for the dose delivered when the user is not puffing, since the vaporizer will not form the vapor in the absence of puffing. In addition, the methods described may be considered generally discrete, in that the estimation of vapor dose is performed at discrete intervals forming partial doses that may later be added up to form the overall dose delivered. This configuration may, in part, allow these methods and apparatuses to function with surprising accuracy despite highly variable puffing durations and profiles.

Also provided herein are electronic vaporizers configured to quantify and/or control an amount of a vapor delivered to a user from a vaporizable material in the electronic vaporizer device, wherein the electronic vaporizer device may comprise any of: (optionally) a puff sensor configured to detect a user's puff; a heater controller (also referred to as a heating element controller) configured to determine an amount of power delivered from a power source during the user's puff; a temperature sensor (which may be a direct sensor such as a thermistor, or it may be a temperature sensing unit that determines the temperature, e.g., of the heater, based on electrical properties of the heater) configured to determine a temperature or a temperature profile generated by a heating element during the user's puff; a vaporized dose predictor (also referred to as a vaporized dose predictor unit or circuitry) that calculates the amount of the vapor delivered to the user from the vaporizable material based upon the power applied to the heater and the temperature of the heater (which may be an estimate of the temperature of the vaporizable material as it is vaporized) during a user's puff, or based upon the amount of the power and the temperature profile during the user's puff; and one or more of: a) an alert unit configured to alert the user when the amount of vapor delivered meets or exceeds a preset vapor amount threshold for the user's puff, or when a cumulative amount of the vapor delivered from a plurality of puffs meets or exceeds a preset vapor amount threshold, and b) a disabling unit configured to automatically disable one or more feature of the electronic vaporizer device when the amount of the vapor delivered meets or exceeds a preset vapor amount threshold for the user's puff, or when a cumulative amount of the vapor delivered from a plurality of puffs meets or exceeds a preset vapor amount threshold, or c) both a) and b).

FIG. 1A is a schematic illustration of one example of an electronic vaporization device 100' including a vaporized dose predictor unit 109. In general any of the vaporizer apparatuses described herein may include a heater controller 105, a heater 106, a source of vaporizable material 103, a power source (e.g., battery, not shown), and a vaporized dose predictor unit 109. The vaporized dose predictor unit 109 may include a clock 119 and/or a memory (memory unit) 117, or these elements may be part of an overall circuitry including a processor 110 which communicates with the vaporized dose prediction unit.

The heater may be any appropriate heater, including resistive heaters such as a resistive coil. The heater is typically coupled to the heater controller so that the heater controller applies power (e.g., from the power source) to the heater. The heater controller may include regulatory control logic to regulate the temperature of the heater by adjusting the applied power. The heater controller may include a dedicated or general-purpose processor, circuitry, or the like and is generally connected to the power source and may receive input from the power source to regulate the applied power to the heater. The controller forming or including the heater controller may also include additional controllers/processors and executing logic 110, such as the vaporized dose predictor unit, alert/alarm logic, and/or temperature detector/sensor 107, or these components may be separate.

Any a source of vaporizable material may be used, including a reservoir (e.g., well, pod, cartridge, or the like), which includes the material to be vaporized. The material to be vaporized may include a carrier and one or more active ingredients, as discussed in greater detail herein.

In general, the vaporized dose predictor unit is configured to divide up a time period (e.g., during a single puff) into a plurality of sequential time intervals, which may be referred to as partial dose intervals, and determine the partial dose (or mass) of vapor produced during each partial dose interval. The vaporized dose predictor unit may then sum these up to determine the actual dose produced and presumably delivered to the user. Thus, the device, including the vaporized dose predictor unit may include a timer or clock 117 and can generate intervals of any appropriate duration within a time period (e.g., between 10 msec and 200 msec). Thus, the vaporized dose predictor unit may sample at a frequency related to the duration of the time intervals (e.g., between 5 Hz and 100 Hz, etc., between 5 Hz and 120 Hz, between 5 Hz and 140 Hz, between 5 Hz and 150 Hz, between 5 Hz and 180 Hz, between 5 Hz and 200 Hz, between 5 Hz and 300 Hz, etc.). The vaporized dose predictor unit generally bases the calculation of each partial dose on input from the heater controller, which may include the power applied before or at the start of each partial dose interval. The vaporized dose predictor unit also receives an input proportional to the temperature at the start and at the end of each partial dose interval (e.g., the temperature or a value proportional to the temperature at the end of the immediately previous partial dose interval). In variations in which the temperature is an average value for each dose interval, the vaporized dose predictor unit may receive the temperature (or a proportional value) for a dose interval and the temperature (or a proportional value) of the dose interval immediately preceding it. The vaporized dose predictor unit may then use this applied power and temperature information to calculate the dose (e.g., mass) of vapor during that interval, as will be described in greater detail below. These interval values (dose interval values) may be summed over the entire time period to determine the overall dose of vapor generated; the vaporized dose predictor unit may also then convert this dose of vapor to a dose of an active ingredient in the vapor, by, e.g., converting based on the concentration of active ingredient in the vaporizable material. U.S. patent application Ser. No. 14/581,666, filed Dec. 23, 2014 and titled "Vaporization Device Systems and Methods," previously incorporated by reference in its entirety, also describes vaporizers including methods and apparatuses for temperature measurement and control similar to that described above.

As mentioned above, in some variations the temperatures for the vaporizable material being vaporized by the device are determined from the heater, without requiring an additional sensor. For example, the relative change in resistance of the heater (e.g., the temperature coefficient of resistivity) may be used, along with a reference resistor, to approximate the temperature of the heater. Although a conversation factor may be used to convert the ratio of heater resistivity and reference resistivity to an actual temperature value, in some variations the system, and particularly the vaporized dose predictor unit, may use the proportional value directly, without multiplying by a conversion factor. These values are therefore "proportional" to the temperature. For example, any of these apparatuses may include logic for determining the temperature of the heater based on the TCR. The resistance of the heater (e.g., a resistive heater) may be measured ($R_{heater}$) during operation of the apparatus as well as the resistance of a eater, reference ($R_{reference}$) resistor separate from the heater. The ratio of the heater resistance to the reference resistance ($R_{heater}/R_{reference}$) is linearly proportional with the temperature (above room temp) of the heater, and may be directly converted to a calibrated temperature. For example, a change in temperature of the heater relative to room temperature may be calculated using an expression such as $(R_{heater}/R_{reference}-1)*(1/TCR)$, where TCR is the temperature coefficient of resistivity for the heater. In one example, TCR for a particular device heater is 0.00014. In determining the partial doses and doses described herein, the temperature value used (e.g., the temperature of the vaporizable material during a dose interval, $T_i$, described in more detail below) may refer to the unitless resistive ratio (e.g., $R_{heater}/R_{reference}$) or it may refer to the normalized/corrected temperature (e.g., in ° C.).

Thus, the vaporized dose predictor unit may be configured to determine a dose of vapor delivered to a user during a time period based upon: an amount of power delivered by the heater controller to the heater to vaporize the vaporizable material during each of a plurality of partial dose time intervals within the time period, a temperature of the vaporizable material being vaporized during each partial dose time interval, and a temperature of the vaporizable material being vaporized before each partial dose time interval. As just mentioned, the temperature of the vaporizable material being vaporized may refer to an input that is proportional to the temperature.

Other optional features shown in FIG. 1A may include a puff sensor 113 and/or dose output 115. The puff sensor typically detects the application of a puff by the user, and may include a pressure sensor, flow sensor, or contact sensor (e.g., lip contact sensor). A dose output may include any appropriate output, including a visual output (e.g., LED, monitor, etc.), audio output (buzzer, tone, etc.), tactile output (vibrator, etc.), or the like. The dose output may act as an alarm or alert to the user, e.g., when a dose threshold has been reached.

FIGS. 1B-1D show an exemplary compact electronic vaporizer device assembly 100, such as an electronic cigarette, medical inhaler, or other inhalation device, for generating an inhalable aerosol. The compact electronic device 100 can include a device body 200 with a cartridge receptacle 210 for receiving a cartridge 300 or a "pod" that can be removably inserted into the device body 200. A mouthpiece 310 allows the user to puff on the device to inhale material aerosolized by the device.

The device body 200 can include a power source 230, such as a rechargeable battery, a printed circuit board (PCB) 240 containing a microcontroller with the operating logic and software instructions for the device, and a puff sensor 270 for sensing when the user is drawing vapor from the device.

The cartridge 300 can include a heater 360 and a material storage compartment 320 configured to store the material to be vaporized. The heater 360 may be powered by the power source 230. In this example, the heater 360 may be used as a temperature sensor as described above and herein, e.g., using the temperature coefficient of resistance (TCR) and a reference resistance. Alternatively or additionally, a separate temperature sensor (e.g., thermistor, etc.) that is in thermal contact with the heater and/or vaporizable material may be used. The temperature sensor may, in general, be configured to measure a temperature of a vaporizable material within the heater 360. The temperature of the heater may be controlled by the microcontroller of the PCB 240.

The device 100 (or any other vaporizable device) can include on-board processing configured to determine an amount of material vaporized and delivered to the user.

Figure 1E:
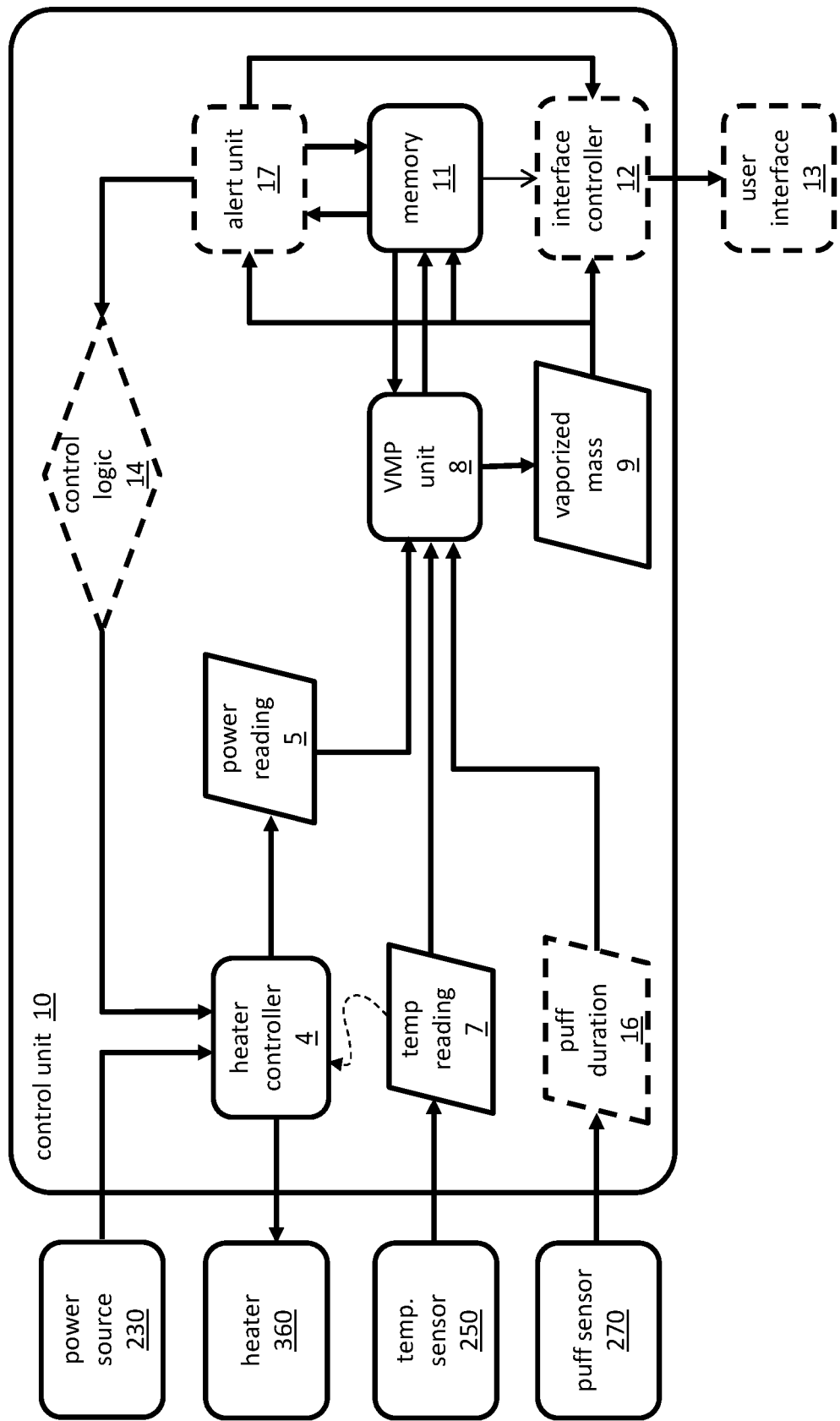
FIG. 1E is an example of an exemplary apparatus able to determine the amount of material vaporized by the device.

FIG. 1E shows a flowchart that represents another exemplary vaporizer apparatus capable of determining the amount of material vaporized within the apparatus (device 100). As shown, the power source 230, heater 360, temperature sensor 250, and puff sensor 270 are communicatively coupled to a control unit 10 (which can be part of one or more printed circuit board(s) 240 shown in FIGS. 1B-1D).

The control unit 10 can include a heating element controller 4, vaporized mass predictor (VMP or VMP unit, which may be a type of vaporized dose estimation/prediction unit) 8, and a memory unit 11. In some embodiments, a user interface 13 on the device can provide the user with information related to the device, such as the amount of vapor inhaled. An interface controller 12 within the control unit can be configured to control the user interface 13. In a certain embodiment, the device additionally comprises an alert unit 17.

To determine an amount of vapor received by the user, the control unit 10 can relay a temperature reading 7 and a power reading 5 during a puff duration 16 (which can be determined by the puff sensor 270) to the VMP unit 8, which can calculate a predicted vaporized mass 9. In certain embodiments, the VMP unit 8 relays the predicted vaporized mass 9 to the memory unit 11. In certain embodiments, the VMP unit 8 relays the predicted vaporized mass to the user interface controller 12. In a certain embodiment, the processor comprises a controlling logic 14 that relays instructions to the heating element controller 4. In a certain embodiment, the method comprises activating an alert unit.

Calculation of Vaporizable Material Vaporized—Exemplary Method

In a certain embodiment, the amount of vapor generated from a vaporizable material within a vaporizing device, such as device 100, can be calculated from the power supplied to a vaporizable material by a power source, and the temperature generated during vaporization. In some embodiments, the amount of vapor generated from a vaporized material can be calculated as a function of energy consumed and temperature generated during vaporization. That is, the power consumed by the power source (such as power source 240), as set by the heater controller (though in some variations it could be measured from the heater or power source) and the temperature of the vaporized material (such as within the chamber 32), as measured by a temperature sensor (such as temperature sensor 250) can be used to determine the amount of vapor generated and/or inhaled.

In some embodiments, the total mass vaporized can be predicted or determined based upon equation 1:

$$\Delta m_{vap,cumulative} = \sum_{i=1}^{i=n} a[P_i - b(T_i - T_{i-1}) - cT_i] \quad \text{(equation 1)}$$

where $\Delta m_{vap,cumulative}$ is the total mass vaporized during sampling intervals i=1 to i=n, each interval being of a fixed time increment; $P_i$ is power supplied during interval i; a, b, and c are constants; $T_i$ is temperature reading for interval i; $T_{i-1}$ is temperature reading for interval immediately before the current interval (i−1 immediately prior to interval i). Note that in some variations, the temperature may be temperature relative to room (or starting) temperature and may be expressed as $T_i'$ (e.g., $T_i'$, $T_{i-1}'$, etc.)

An alternative expression of this relationship may be described as:

$$\Delta m_{vap,cumulative} = \sum_{i=1}^{i=n} [aP_i - dT_i - eT_{i-1}] \quad \text{(equation 2)}$$

In this example, different coefficient may be used (e.g., d, e); this expression may be more simply implemented using a microcontroller than equation 1, as it has fewer arithmetic functions required, though it is mathematically equivalent.

The coefficients a, b, and c may reflect physical constants whose values can be determined experimentally and can vary depending on the vaporizable material used. For example, the constants a, b, and c can depend upon the latent heat and the specific heat of the material being vaporized. The constants can further depend upon the overall mass of the system that needs to be heated (such as the liquid material and the heater, e.g., a wick and coil). In one exemplary embodiment described below, a is equal to 0.025, b is equal to 367, and c is equal to 30. In another embodiment, a can be equal to 0.18, b can be equal to 2000, and c can be equal to 50. These constants may be determined empirically or based on theoretical values knowing the dimensions and material properties of the vaporizable material and heater.

For example, in some embodiments, the coefficients a, b, and c can be determined by collecting an amount of data and running a mathematical algorithm. For example, an analytical inhalation or smoking machine can be used to test the vaporizing device under one or more conditions. Total particulate matter (TPM) can be collected from the vaporizing device using the analytical inhalation or smoking machine. In some cases, the TPM can be collected on a filter pad. The filter pad can be weighed before and after TPM is collected on the filter such that the weight of the TPM on the filter can be determined. In some embodiments, the empirical determination of (a, b and c) is accomplished by measuring power and temperature over a series of puffs and measuring the cumulative mass lost by the device for those puffs gravimetrically. The mass lost by the device is taken as being equal to total delivered mass of TPM (mg). Best values for a, b, and c are then determined by fitting the above equation to the experimental mass delivery, power and temperature data. Adjustments in the constants (e.g., a, b, c or a, d, e) can be made to accommodate the variance in the type of the device and of the formulation.

One example of a method for determining the values of the constants associated with the relationship between the mass of vapor emitted, power applied to vaporize the material during a particular time interval (e.g., portion of a puff) and the temperature of the material before and after vaporization during that period is described below. In this example, the device may be first weighed. Then, a series of puffs may be taken while logging the power (e.g., at a sampling frequency such as 20 Hz, e.g. between 5 Hz and 100 Hz, 5 Hz and 200 Hz, etc.) and the temperature through the duration of the trial. The device may then be weighed again. This may be repeated many times (e.g., more than 5, 10, 15, 20, 25, 30, 35, 40, 45, 50, 60, 70, 80, 90, 100, 120, 150, 200, etc., or between 5 and 1000, between 10 and 500, between 10 and 200, etc.) to achieve a sufficiently sized data set. In one example, the process is repeated 29 times. The m_vap may then be calculated for each sample by subtracting the final mass from the initial mass. Alternatively, the mass of the vapor may be directly measured, e.g., by applying the vapor onto a filter pad and use the change in mass of the pad to get m_vap; this may be less accurate because some of the vapor might go through the pad or deposit on other surfaces. For simple gravimetric analysis, measuring the device may be preferred.

After collecting all the data, the m_vap estimates, as well as a set of values for temp and power over the duration for each sample may then be used to solve for the constants. For example, in equation (1), the constants a, b, and c may be determined from this data. Alternative expression of the equation (e.g., see equation 2, described below) may be used. For example, the values of a, b, and c may be determined such that $SUM[t=1 \text{ to } t=n](aP-b(T_i-T_{i-1})-cT_i)$ may be solved to find the best fit to the m_vap that was measured for each sample. As mentioned, this may be performed for any expression of the vapor mass, applied power and temperatures measured. In some variations this may be performed using a gradient descent algorithm, to fit the data to the appropriate equation. A gradient descent algorithm may be beneficial because is computationally cheap to find the optimal values of the constants (e.g., a, b, and c) such that error is minimized. However, any appropriate curve-fitting algorithm or method may be used. In this first example, three different constants are fit to a rather large dataset.

In some embodiments, the time interval i (e.g., the partial dose time interval) can be between 20 ms and 200 ms (e.g., less than 200 msec, 180 msec, 150 msec, 120 msec, 100 msec, 90 msec, 80 msec, 70 msec, 60 msec, 50 msec, 40 msec, 30 msec, 20 msec, 10 msec, etc.). The temperature and power measurements can be taken at a frequency of between 5 and 50 Hz, such as between 10 and 30 Hz, such as at approximately 20 Hz.

In general, the power to may refer to power delivered to heat the vaporizable material (e.g., in some variations, the power applied by the heater controller to the heater) to vaporize the vaporizable material during a partial dose time interval. The power applied may be read directly from the heater controller (e.g., a watts, joules, joules/sec$^2$, volts*volts, volts*volts/resistance, etc.) and/or may be sensed, e.g., using any appropriate power sensor (voltmeter, hall effect sensor, inductive sensor, direct measurement sensor, voltage response measurement sensor, etc.). The power may be detected either immediately before or during the time interval (e.g., partial dose interval), representing the power applied to vaporize the material during that interval. For example, the power used to determine a partial dose may be transmitted from the heater controller simultaneous with applying the power to the heater; in some variations the power ($P_i$) is the power applied during the interval immediately before the interval i (e.g., i–1) because this power is then absorbed by the vaporizable material during the dose interval being measured. Alternative, when the power ($P_i$) may be the power sensed directly or indirectly during the relevant dose interval (i).

Similarly, the temperature measured may be the temperature of the vaporizable material being vaporized during the partial dose time interval ($T_i$). This may be sensed directly or indirectly during, at the start and/or at the end of the dose interval. For intervals that are sufficiently brief, this distinction may be irrelevant. The temperature of the vaporizable material being vaporized before the partial dose time interval may refer to the dose from the immediately prior time interval (e.g., $T_{i-1}$), which may also be the temperature at the start, end or during the prior time interval. Alternatively, in some variations the temperature of the of the vaporizable material being vaporized before the partial dose time interval may refer to the temperature of the material to be vaporized immediately before the Pi is applied (e.g., at the start or just before the start, of the application of power); the temperature of the vaporizable material being vaporized during the partial dose time interval may refer to the temperature of the material at the end of the interval application of power.

The temperature and power applied to the material to be vaporized typically refers to the temperature and power applied to the portion of the material (e.g., the material on the wick in some variations) that will end up reforming into a vapor through the application of the energy, e.g., near the surface, rather than the bulk of the material to be vaporized.

In some embodiments, the temperature and power readings can be gathered only when a user's puff is detected, such as through puff sensor 270. Detection of the user's puff can thus activated the microcontroller to begin calculating the amount of vapor drawn, while detection of the end of the user's puff can cause the microcontroller to stop calculating the amount of vapor drawn. Thus, in some embodiments, equation 1 can be integrated over the duration of a puff. In other embodiments, the measurements can be taken continuously and integrated over the duration of time that the device is on. In yet another embodiment, the integration time period can be pre-set or user selected.

In some embodiments, the TPM can be adjusted to determine the total amount of a particular compound inhaled, such as the total amount of an active ingredient, such as nicotine. For example, the TPM can be multiplied by the percentage of active ingredient in the vaporizable material, as described further below.

Figure 10:
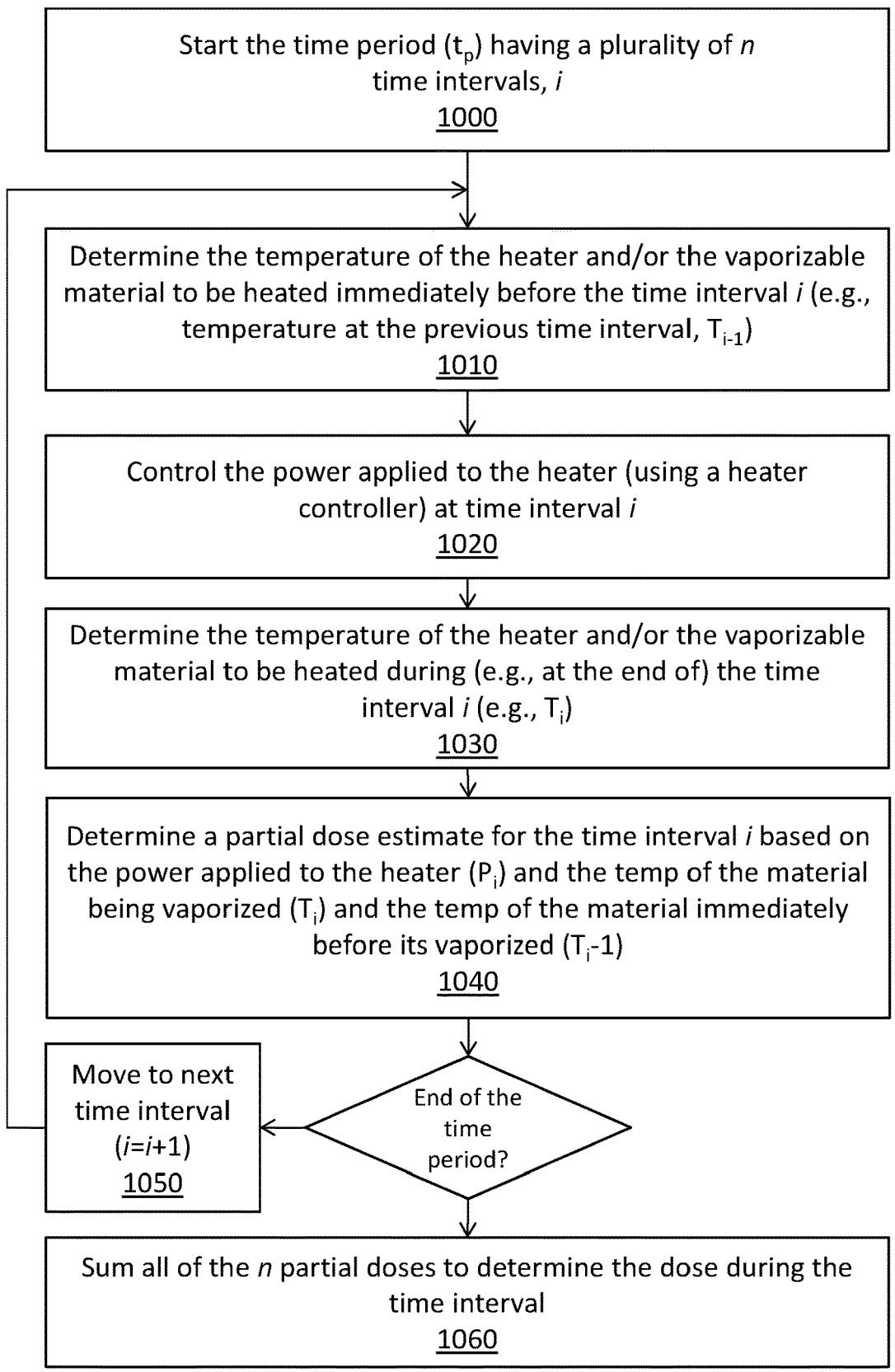
FIG. 10 schematically illustrates one method of determining a dose of vapor over a time interval as described herein.

FIG. 10 illustrates this first method of determining a vapor dose over a time interval as just described. For example, in FIG. 10 the time period for determining the dose ($t_p$) may be initially set or started 1000. The start of the time period may be triggered by the user, physician or other party (e.g., manually) or it may automatically start, e.g., when a user begins puffing on the vaporizer (e.g., using a puff sensor). The duration of the time period may also be predetermined (e.g., fixed, e.g., at 2 sec, 3 sec, 4 sec, 5 sec, 6 sec, 7 sec, 8 sec, 9 sec, 10 sec, 11 sec, 12 sec, 13 sec, 14 sec, 15 sec, 16 sec, 17 sec, 18 sec, 19 sec, 20 sec, 25 sec, 30 sec, 35 sec, 40 sec, 45 sec, 50 sec, 55 sec, 60 sec, 1.5 min, 2 min, 3 min, 4 min, 5 min, 10 min, 12 min, 15 min, 20 min, 30 min, 1 hr, 2 hr, 3 hr, 4 hr, 5 hr, 6 hr, 7 hr, 8 hr, 9 hr, 10 hr, 11 hr, 12 hr, etc.) or it may be variable, including set by the use or it may be determined by sensing the end of a puff. In some variations, the time period is set as the start of a session so that the total dose is determined for the entire session, which may include multiple puffs. In some variations, each puff is considered a time period (e.g., using a puff sensor); the dose may be determined per puff, or it may be aggregated over all of the puffs in a session (where a session may be defined as within a particular time window, e.g., 5 minutes, 10 minutes, 20 minutes, 30 minutes, 1 hour, 2 hours, etc.).

The time period typically includes a number of time intervals i (also referred to herein as partial dose time intervals), which divide the time up in to discrete sample periods for which a partial dose may be calculated. The number of time intervals (n) may be predetermined, when the time period is fixed, or it may be open (e.g., continuously incremented). The duration of the time intervals may be fixed or variable, though they are typically fixed. The duration may be, for example, between about 200 msec and about 10 msec. The time intervals may be immediately adjacent to each other (e.g., in real time), or they may be separated by an off period. The time intervals may generally be considered sequential.

For each time interval, a partial dose of vaporizable material (e.g., vapor, including any active ingredients) may be calculated. This may be controlled and/or performed by a vaporized dose predictor (e.g., VMP unit) portion of the apparatus (or in communication with the apparatus), as described above. During each time increment, i, the apparatus may store the temperature of the heater and/or the vaporizable material near the heater, from the previous time interval, $T_{i-1}$ 1010. This temperature value ($T_{i-1}$) may reflect the temperature of the material to be vaporized during this time interval and may therefore be the temperature at the very start (or just before the very start) of the time interval. During each time interval the apparatus controls the power applied to the heater for that interval (i) 1020. Note that when power is not being applied to heat heater, the power value may be zero; if the heater is still at a different temperature than the previous time increment (i−1), then there may still be vapor produced, if not then little vapor may be produced. The power controller (heater controller) may transmit the power that is causing to be delivered to the heater to the vaporized dose predictor.

The apparatus may also transmit the temperature of the heater and/or the vaporizable material to be vaporized (e.g., the material near the heater) during the time interval ($T_i$) to the vaporized dose predictor 1030.

The system may then determine (e.g., using the vaporized dose predictor) a partial dose estimate for the current time interval, i, using the power applied to the heater and the temperature immediately prior to the interval ($T_{i-1}$) and the temperature during the interval ($T_i$) 1040. For example, either equations 1 or 2, discussed above, may be implemented by the vaporized dose predictor. The partial dose estimate may be stored (e.g., separately as a discrete datum, or added to a cumulative dose for the time period, or both), along with any of the information ($P_i$, $T_i$, etc.). The vaporized dose predictor may include one or more memories (e.g., memory registers) for storing these values (note that the $T_i$ in the current interval may become the $T_{i-1}$ during the next interval.

At the end of each time interval, the apparatus may check to see if the end of the time period has been reached, either because of a predetermined number of intervals (n) has been reached (i=n) or because of some other triggering event (e.g., the end of a puff, end of a session, etc.), or both. If not, then the system may move onto the next interval, incrementing the interval (i=i+1) 1050. Once the end has been reached, in some variations (e.g., where a cumulative register has not been kept), all of the partial doses may be added 1060. Note that in any of these variations, this step of adding all of the partial doses may be done in an ongoing manner, e.g., accumulating them (summing them) as each new interval is passed. Thus, the step of summing the calculated partial doses in the vaporized dose predictor unit to determine a total dose of vapor delivered during the time period may be done either at the end of the time period or it may be done during the duration of the time period, as the partial doses are determined.

Examples

Figure 2:
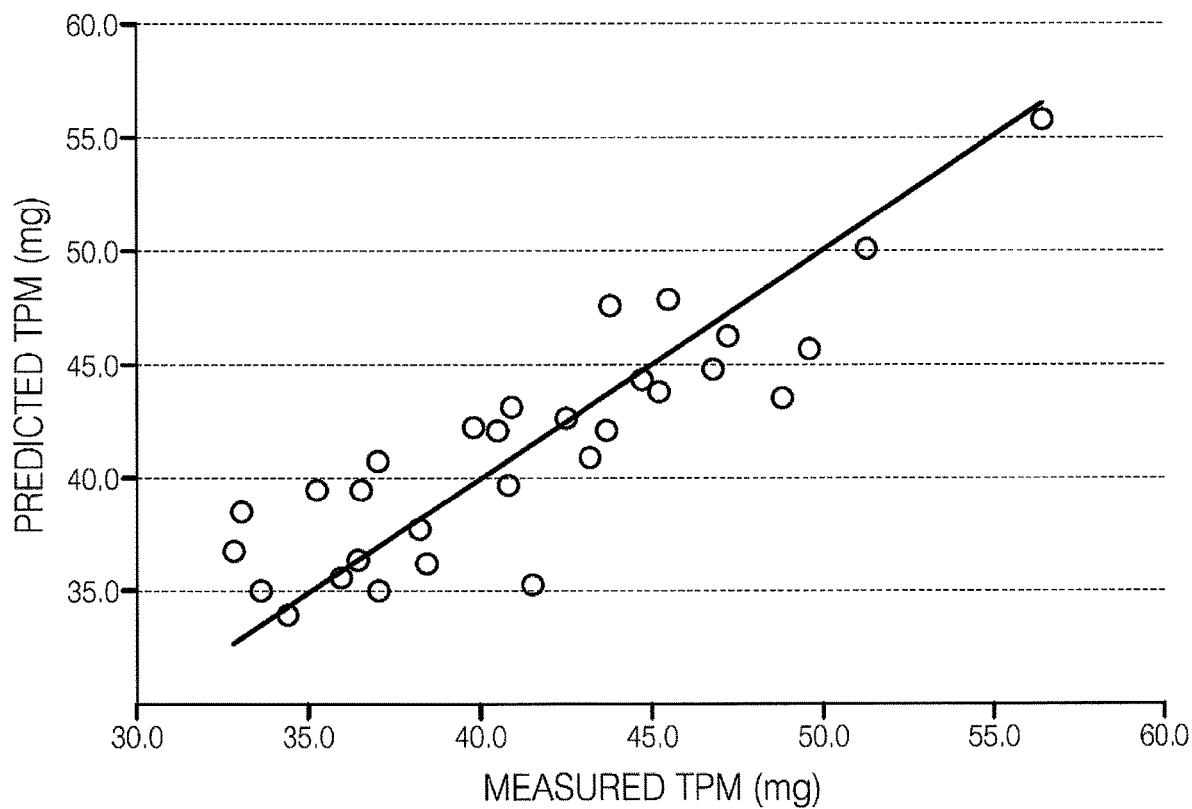
FIG. 2 illustrates the accuracy of the methods and apparatuses for estimating/predicting vapor dosage as described herein, showing a comparison of the dose estimated as described herein (solid line) compared to actual measured dose delivered (circles).

FIGS. 2 and 3 show a relationship of predicted TPM using equation 1 and actual readings of TPM, using an inhalation or smoking machine. The graph of FIG. 2 shows the relationship of predicted TPM (solid line) and measured TPM (dots) for the machine trials. In this trial, the R-squared is 0.78.

To gather the data for FIGS. 2 and 3, an inhalation or smoking machine was set up using an e-vaporizer device loaded with a separate detachable pod holding a vaporizable material. Two devices were arranged in series. Measurement for temperature and power were collected. Ten puffs were taken with the inhalation or smoking machine (at 55 cc/3 sec). The mass loss (or TPM loss) was measured every ten puffs. 31 sample readings were collected using two prototype electronic vaporizer device devices and four prototype pods. The data collected for power and temperature were analyzed. A comparison of the power and temperature data were compared to actual measured mass loss data to correlate the evaporation rate to energy consumption and temperature. It was found that with an $R^2$=0.78, twenty-nine (29) samples fell within ±15% and the remaining two (2) samples fell within ±17%. FIG. 2 shows a graphical relationship of the total particulate mass (TPM), predicted and the measured values. FIG. 3 shows the full data set of predicted values against the actual readings.

In the example shown in FIG. 2, by performing the vaporized mass prediction formula according to equation 1 as described herein, the tabular and graphical relationship of predicted TPM (mg) to actual TPM (mg) can be established. The vaporized mass prediction formula can be utilized to create a program that can be utilized by the VMP unit. The values can be transmitted to the calibrating device through a wireless or wired data transfer, and more preferably can be embedded directly into the vaporizing device itself. The results of the smoking experiment shown in FIG. 2 can provide information to and permit the user, or other individual, to control the amount of vaporizable material correlated to the TPM level.

The results in FIGS. 2 and 3 demonstrate that equation 1 can advantageously improve over inconsistencies that can arrive when function-fitting and/or assuming that the puffing duration and/or power to mass removal can be correlated.

A smoking test by human subjects was also conducted using electronic vaporizer devices configured with separate detachable pods holding vaporizable material. The criteria for the human subjects included a voluntary participation of users, who already smoked or vaped, either regularly or habitually, a diversity in smoking patterns or random puffing habits. Participants were asked to puff normally, and a wide variety of puffing behaviors were observed from subject to subject and even between puffs from the same subject. Thus, participants' puffing attributes were variable and included puffing from 1 to 5 mg per puff; e.g., for some subject's puffs were consistently approximately 3 mg, while others were 2 mg in one puff and 4 mg in the next. The table of FIG. 4 shows the measured TPM for human trials. The first column shows % error from target (which was 40 mg). The second column shows error from mean, which can be a metric for further adjustment of the vaporized mass prediction formula. The formulations of vaporizable materials in the proprietary pods can contain 40 mg of total liquid, which can correspond to 2 mg of nicotine (5% nicotine by mass). The test shows that calibration of the device can accurately portion a dose that can be of a specific metered dose. Here, the smoking test was run with eleven human subjects. The twenty-three sample readings (or results) fall within ±15% of the 40 mg target. The other two samples are within ±17%. The mean of the samples taken is 42.1 mg. Coefficient of variance is 5.96%. All samples fall within ±11% of the mean.

Figure 5:
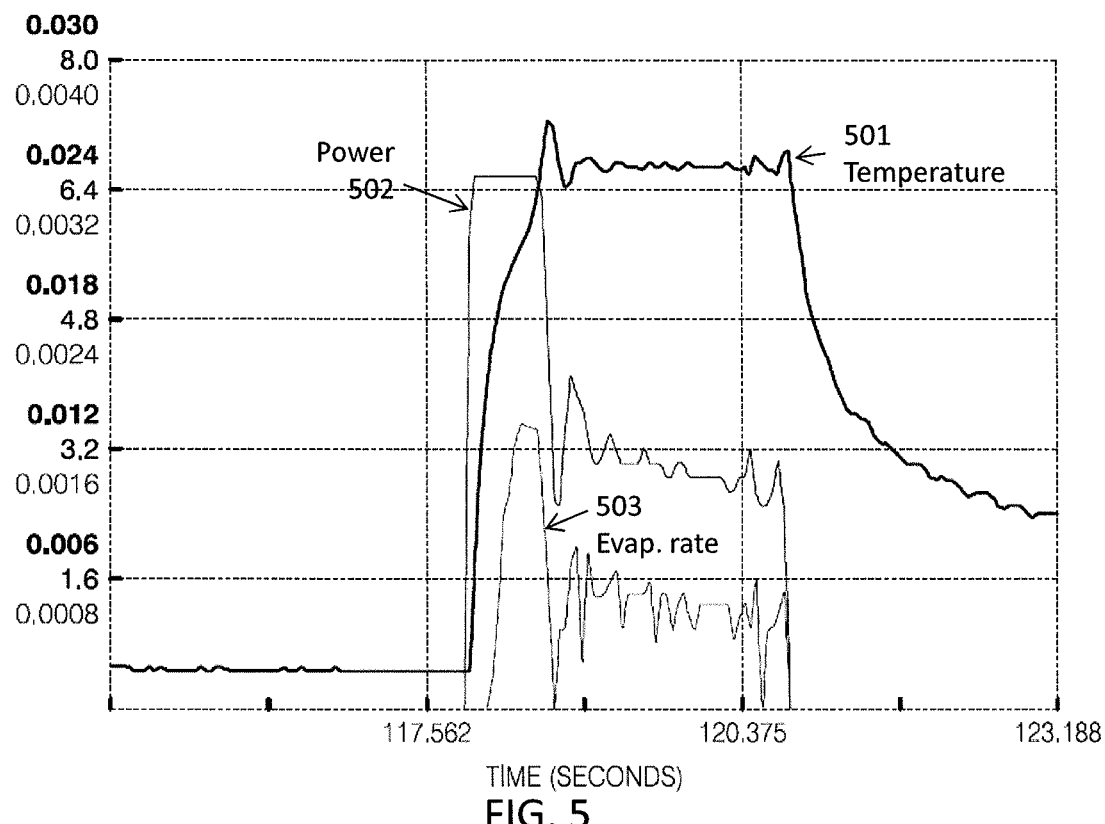
FIGS. 5 and 6 graphically illustrate the relationship between applied power at a vaporizer heater, temperature of the heater, and an estimated evaporation rate (dose) at a 35 cc and 70 cc control "puff", respectively.
Figure 6:
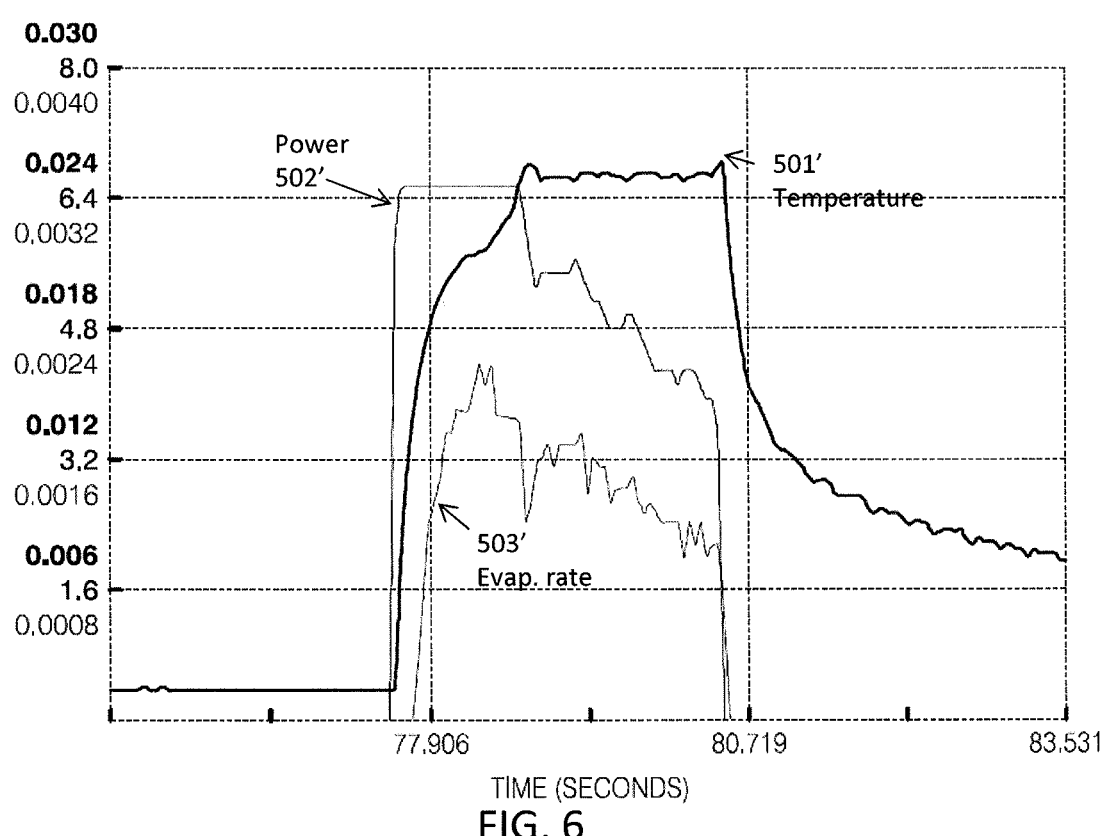

In some embodiments, merely measuring a puff duration can result in inaccurate quantitation of a vaporized mass. FIG. 5 and FIG. 6 show graphs that correlate TPM, as a function of power, time and temperature. In performing the vaporized mass prediction method as described herein, where upon a relationship of TPM (mg) as a function of power, time and temperature can be established.

In an aspect, in FIG. 5 and FIG. 6, the present disclosure illustrates the real-time graph program capturing mass vaporized (mg) as a function of power, time and temperature. In FIG. 5 and FIG. 6, the thickest line 501, 501' (labeled temperature) is given by the resistance ratio that ($R_{heater}/R_{reference}$) that is proportional to the temperature of the heater (show subtracted from 1); this may multiplied by 1/TCR to convert to units (e.g., ° C.), for example. Thus, in calculating the dose, the temperature ($T_i$ and $T_{i-1}$) determined for each interval is the measured resistance of the coil and baseline is a baseline resistance (established separate from the heater, presumably at room temperature). The temperature rise is linear with temperature rise above room temperature by a factor of 1/TCR, where TCR is the temperature coefficient of resistance. In both FIG. 5 and FIG. 6, the line of medium thickness 502, 502' (labeled power) is power delivered to the coil (e.g., in watts). Further, in both FIG. 5 and FIG. 6, the thinnest line 503, 503' (labeled evaporation rate) is evaporation (vaporization) rate, in this example in mg/msec. This may be derived by implementing a formula such as expressed in equation 1 or equation 2, previously discussed. The values in this example may be divided by 50 ms/sample (the interval time) to arrive at mg/msec instead of mg/sample. This curve can be integrated over the time course of the puff to give the total dose delivered from a puff. In FIG. 5 and FIG. 6, the axes on the left are scaled differently for the power, temperature and evaporation rates. FIG. 5 and FIG. 6 illustrate examples of puffs taken at two different predetermined puff profiles. In FIG. 5, a 35 cc puff was pulled over about 3 seconds. In FIG. 6, a 70 cc puff over about 3 seconds, where the flow rate in FIG. 6 is twice that in FIG. 5. Illustratively, comparing FIG. 6 to FIG. 5, there is a higher mass removal (mass vaporized) for the faster puff of FIG. 6. Different puffs vaporize differing amounts of material. The present disclosure presents that the system is responsive to varying puff profiles, which do not typically have a uniform flow rate during the puff, and the duration may vary. This behavior can be further supported by the human study that is discussed above, where consistent results were obtained, even with variances in puffing attributes representative of individual or unique human puffs.

Calculation of Vaporizable Material Vaporized—Second Exemplary Method

In some embodiments, a vaporizing device, such as device 100, can be calibrated based on a previous measurement performed using a same or similar device such that an amount of vaporized material can be determined based upon the performance of the same or similar device. For example, the device can be calibrated through a function fit method to determine a relationship between total particulate matter (TPM) release content (mg) and one or more vaporization parameters of aerosolizing materials from the device by a function fit method.

In some cases, the method for calibration of the device to obtain active material content from the relationship of total particulate matter (TPM) release content (mg) to vaporization parameters of aerosolizing materials can comprise setting up an analytical inhalation or smoking machine to its functioning operating parameters and testing the device under one or more conditions. In some cases, conditions that can be varied can comprise puff volume and/or flow rate. The conditions (e.g., vaporization parameters) can include one or more variable chosen from the group consisting of puff duration (sec), puff volume (ml), flow rate (ml/sec), power (watts), voltage (volts). In some cases, exemplary ranges include, but are not limited to 1 mL-100 mL volume; 0.2 s-10 s duration; 2-100 mL/s; 2.5-4.2V, respectively.

Total particulate matter (TPM) can be collected from the electronic vaporizer device. In some cases, the TPM can be collected on a filter pad. The filter pad can be weighed before and after TPM is collected on the filter such that the weight of the TPM on the filter can be determined. In some cases, the weight of the filter can be tared. The weight of the material in the device to be vaporized can be recorded prior to vaporization. In some cases, the weight of the vaporizable material in the device can be measured and recorded prior to operating the device. The weight of the vaporizable material in the device can be measured and recorded after one or more puffs on the device. A difference in weight of the vaporizable material between the initial weight and the weight after one or more puffs can be compared to a weight of TPM collected on the filter. In some cases, the difference in weight of the vaporizable material between the initial weight and the weight after one or more puffs and the weight of TPM collected on the filter can be substantially the same. The TPM collected on the filter can comprise material vaporized from the vaporizable material in the device during the one or more puffs.

In some cases, an analytical inhalation or smoking device can be a machine configured to simulate inhalation of a vaporized material from a vaporizing device by a human. While the machine smoking device vaporizes the formulation in the one or more devices, TPM from the device can be collected onto one or more filter pads. Each device can have TPM released from the electronic vaporizer device collected on a different filter pad. For each filter pad the amount of TPM released by a device can be determined. The amount of TPM released by an individual device relative to the initial weight of vaporizable material can be calculated. In some cases, this procedure can be repeated with variable inhalation conditions, for example, with progressively increasing and/or decreasing puff duration (sec) of the machine inhalation or smoking device. In some cases, the procedure can be repeated with varying puff volume (ml) of the machine smoking device. The puff volume can vary in the range of 1 mL-100 mL, more preferably, 20-80 mL, most preferably 30-60 mL. In some cases, the procedure can be repeated with varying flow rate of the machine smoking device. Flow rate of the machine inhalation or smoking device can vary in a range of 2-100 mL/s, more preferably, 5-50 mL/s, most preferably 10-30 mL/s. In some cases, the procedure can be repeated with varying power of the machine inhalation or smoking device. Power (watts) of the smoking device can vary in the range of 2 watts to 20 watts, more preferably 3 watts to 8 watts. In some cases, the procedure can be repeated with varying voltage of the machine inhalation or smoking device. Voltage of the device can vary in a range of 2.5-4.2V, more preferably 3.0-4.2V.

Figures 9A, 9B:
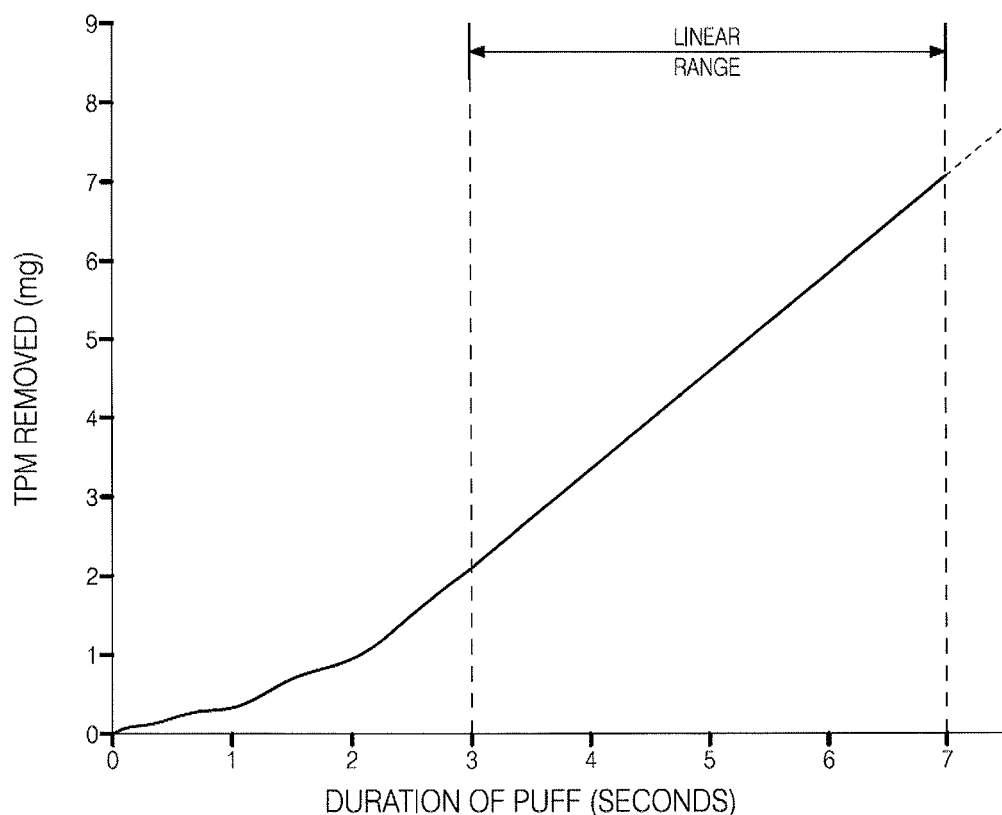
FIG. 9A is a table illustrating one variation of a look-up table that can be used to estimate the amount of vapor inhaled by a user based upon calibration data.
FIG. 9B graphically illustrates data such as that shown in FIG. 9A, which may be used to estimate the amount of vapor inhaled by a user.

The puff volumes to the corresponding TPM release content (mg) can be tabulated. A relationship between puff volume and corresponding TPM release content (mg) can be displayed graphically and/or in a table and can be used to predict, determine, or estimate the amount of vapor consumed by the user when using a device. For example, FIGS. 9A and 9B show an exemplary look-up table and graph that can be used to determine or estimate the amount of vapor inhaled by a user based upon calibration data previously gathered from an inhalation or smoking machine. The values can be transmitted to the device, such as the microcontroller within the PCB 240 of device 100, through a wireless or wired data transfer. The results of the calibration experiment shown in FIGS. 9A and 9B can provide information to and permit the user, or other individual, to understand or control the amount of active material correlated to the TPM level.

Vaporized Mass Predictor Unit

A vaporizer device, such as devices 10, 100, 100', may include a vaporized mass predictor (e.g., VMP unit), such as within the control unit 10, 110. The VMP 109 may execute the logic described herein to determine the dose delivered according to any of the methods described herein. In certain embodiments, the VMP is communicatively coupled to one or more of: a puff sensor (optional), a heater (e.g., heating element) controller, an alert unit and/or controlling logic. In certain embodiments, a VMP unit is communicatively coupled to a puff sensor, timer, heater controller and either the alert unit or controlling logic. In certain embodiments, the VMP includes software (e.g., a software module or control logic) that runs on the processor. The VMP unit may integrate power readings from the heater controller, temperature readings from the temperature sensor; and in some cases puff duration or puff frequency readings from the puff sensor and timer. The VMP unit will then calculate how much vapor has been vaporized from a vaporizable material.

In some embodiments, the VPM unit of each device can be calibrated separately. In some embodiments, a VPM calibration can be set based upon a known vaporization material. In some embodiments, the device can include a user interface that allows the user to input the material being vaporized, which in turn sets the constants a, b, c for equation 1 and/or the function fit curve or look-up table.

In some embodiments, the VMP (or another component of the control unit) can calculate the active material content based upon the TPM. The TPM to active material content can be correlated based on the composition of the organic materials loaded into the electronic vaporizer device. For example, for an organic material, that contains a percentage of 20-25% active material, would correlate to a TPM, mg, containing said percentage of active material. In some cases, it may be reasonable to assume total conversion (aerosolization) of the active material. For example, for organic material selected from *cannabis* extract, where the organic material is a *cannabis* extract containing 25% cannabidiol (CBD), then the TPM, mg, correlated to said 25% CBD, means the TPM, mg has the percentage of said active compound, preferably assuming total conversion (aerosolization) of the active material.

In certain embodiments, the VMP unit is adjustable by the user, and allows the user to preset an amount of vaporizable material to be vaporized before the user is alerted, or elements of the vaporizer device are disabled, or the controlling logic is implemented. In certain embodiments, the VMP unit will then engage an alert unit that alerts a user when a preset amount of a vaporizable material is vaporized. In certain embodiments, the VMP unit will then disable the vaporizer device when a preset amount of a vaporizable material is vaporized. In certain embodiments, the VMP is user adjustable, so that the vaporizer device will vaporize a target amount of material in a single puff.

In certain embodiments, the VMP is user adjustable, so that the vaporizer device will vaporize a target amount of material in a plurality of puffs. In certain embodiments, the VMP is user adjustable, so that the vaporizer device will vaporize a target amount of material in a single puff. In some variations, the VMP is user adjustable so that the device can be disable for a period of time after the target amount of material has been vaporized. The VMP may be user adjustable so that the device can engage an alert after a target amount of material has been vaporized. In certain embodiments, the VMP engages an alert when the amount of vaporizable material in the vaporizer device falls below a preset threshold. In certain embodiments, the VMP unit is communicatively coupled to a memory unit and stores a plurality of any of the following measurements: power, temperature, puff duration readings, or any combination thereof. In certain embodiments, the VMP unit will calculate a cumulative amount of vaporizable material that is vaporized. If for example a user does not fully vaporize the preset limit in one puff the VMP unit will keep track of the amount of vaporizable material vaporized over a plurality of puffs. In certain embodiments, the VMP unit is a software module. In certain embodiments, the VMP unit is a microprocessor. In certain embodiments, the VMP unit will generate a puff profile that tracks power, temperature, pressure or a combination thereof over time.

In certain embodiments, the accuracy of the measured TPM vaporized from a VMP unit is at least ±25% of a predicted value. In certain embodiments, the accuracy of the measured TPM vaporized from a VMP unit is at least ±20% of a predicted value. In certain embodiments, the accuracy of the measured TPM vaporized from a VMP unit is at least ±15% of a predicted value. In certain embodiments, the accuracy of the measured TPM vaporized from a VMP unit is at least ±10% of a predicted value. In certain embodiments, the accuracy of the measured TPM vaporized from a VMP unit is at least ±5% of a predicted value. In certain embodiments, the VMP unit is a software component associated with the processor.

In certain embodiments, the preset amount of vaporized material allowed before the VMP unit engages an alert is adjustable. In certain embodiments, the preset amount of vaporized material allowed before the VMP unit engages the controlling logic is adjustable. Adjustment allows a user to be alerted when a certain amount of vaporizable material has been vaporized, and inhaled by the user, this allows for an improved user experience by precise control in dosage of a vaporizable material (e.g., nicotine, cannabinoid). In certain embodiments, a user can preset an amount of vaporizable material vaporized in mg of TPM. In certain embodiments, the preset amount of vaporizable material vaporized in mg of TPM is between about 1 mg and about 1000 mg. In certain embodiments, the preset amount of vaporizable material vaporized in mg of TPM is between about 1 mg and about 100 mg. In certain embodiments, the preset amount of vaporizable material vaporized in mg of TPM is between about 10 mg and about 100 mg. In certain embodiments, the preset amount of vaporizable material vaporized in mg of TPM is between about 10 mg and about 1000 mg. In certain embodiments, the preset amount of vaporizable material vaporized in mg of TPM is between about 1 mg and about 50 mg. In certain embodiments, the preset amount of vaporizable material vaporized in mg of TPM is between about 1 mg and about 25 mg. In certain embodiments, the preset amount of vaporizable material vaporized in mg of TPM is less than about 1 mg. In certain embodiments, the preset amount of vaporizable material vaporized in mg of TPM is about 1 mg. In certain embodiments, the preset amount of vaporizable material vaporized in mg of TPM is about 2 mg. In certain embodiments, the preset amount of vaporizable material vaporized in mg of TPM is about 3 mg. In certain embodiments, the preset amount of vaporizable material vaporized in mg of TPM is about 4 mg. In certain embodiments, the preset amount of vaporizable material vaporized in mg of TPM is about 5 mg. In certain embodiments, the preset amount of vaporizable material vaporized in mg of TPM is about 6 mg. In certain embodiments, the preset amount of vaporizable material vaporized in mg of TPM is about 7 mg. In certain embodiments, the preset amount of vaporizable material vaporized in mg of TPM is about 8 mg. In certain embodiments, the preset amount of vaporizable material vaporized in mg of TPM is about 9 mg. In certain embodiments, the preset amount of vaporizable material vaporized in mg of TPM is about 10 mg. In certain embodiments, the preset amount of vaporizable material vaporized in mg of TPM is about 20 mg. In certain embodiments, the preset amount of vaporizable material vaporized in mg of TPM is about 30 mg. In certain embodiments, the preset amount of vaporizable material vaporized in mg of TPM is about 40 mg. In certain embodiments, the preset amount of vaporizable material vaporized in mg of TPM is about 50 mg. In certain embodiments, the preset amount of vaporizable material vaporized in mg of TPM is about 60 mg. In certain embodiments, the preset amount of vaporizable material vaporized in mg of TPM is about 70 mg. In certain embodiments, the preset amount of vaporizable material vaporized in mg of TPM is about 80 mg. In certain embodiments, the preset amount of vaporizable material vaporized in mg of TPM is about 90 mg. In certain embodiments, the preset amount of vaporizable material vaporized in mg of TPM is about 100 mg.

In certain embodiments, a user can preset an amount of vaporizable material vaporized in mg of an active ingredient (e.g., nicotine, cannabinoid, THC). In certain embodiments, the preset amount of vaporizable material vaporized in mg of an active ingredient is between about 1 mg and about 1000 mg. In certain embodiments, the preset amount of vaporizable material vaporized in mg of an active ingredient is between about 1 mg and about 100 mg. In certain embodiments, the preset amount of vaporizable material vaporized in mg of an active ingredient is about 0.05 mg. In certain embodiments, the preset amount of vaporizable material vaporized in mg of an active ingredient is about 0.1 mg. In certain embodiments, the preset amount of vaporizable material vaporized in mg of an active ingredient is about 0.2 mg. In certain embodiments, the preset amount of vaporizable material vaporized in mg of an active ingredient is about 0.3 mg. In certain embodiments, the preset amount of vaporizable material vaporized in mg of an active ingredient is about 0.4 mg. In certain embodiments, the preset amount of vaporizable material vaporized in mg of an active ingredient is about 0.5 mg. In certain embodiments, the preset amount of vaporizable material vaporized in mg of an active ingredient is about 0.6 mg. In certain embodiments, the amount of vaporizable material vaporized in mg of an active ingredient is about 0.7 mg. In certain embodiments, the preset amount of vaporizable material vaporized in mg of an active ingredient is about 0.8 mg. In certain embodiments, the preset amount of vaporizable material vaporized in mg of an active ingredient is about 0.9 mg. In certain embodiments, the preset amount of vaporizable material vaporized in mg of an active ingredient is about 1 mg. In certain embodiments, the preset amount of vaporizable material vaporized in mg of an active ingredient is about 2 mg. In certain embodiments, the preset amount of vaporizable material vaporized in mg of an active ingredient is about 3 mg. In certain embodiments, the preset amount of vaporizable material vaporized in mg of an active ingredient is about 4 mg. In certain embodiments, the preset amount of vaporizable material vaporized in mg of an active ingredient is about 5 mg. In certain embodiments, the preset amount of vaporizable material vaporized in mg of an active ingredient is about 6 mg. In certain embodiments, the preset amount of vaporizable material vaporized in mg of an active ingredient is about 7 mg. In certain embodiments, the preset amount of vaporizable material vaporized in mg of an active ingredient is about 8 mg. In certain embodiments, the preset amount of vaporizable material vaporized in mg of an active ingredient is about 9 mg. In certain embodiments, the preset amount of vaporizable material vaporized in mg of an active ingredient is about 10 mg. In certain embodiments, the preset amount of vaporizable material vaporized in mg of an active ingredient is about 10 mg. In certain embodiments, the preset amount of vaporizable material vaporized in mg of an active ingredient is about 20 mg. In certain embodiments, the preset amount of vaporizable material vaporized in mg of an active ingredient is about 30 mg. In certain embodiments, the preset amount of vaporizable material vaporized in mg of an active ingredient is about 40 mg. In certain embodiments, the preset amount of vaporizable material vaporized in mg of an active ingredient is about 50 mg. In certain embodiments, the preset amount of vaporizable material vaporized in mg of an active ingredient is about 60 mg. In certain embodiments, the preset amount of vaporizable material vaporized in mg of an active ingredient is about 70 mg. In certain embodiments, the preset amount of vaporizable material vaporized in mg of an active ingredient is about 80 mg. In certain embodiments, the preset amount of vaporizable material vaporized in mg of an active ingredient is about 90 mg. In certain embodiments, the preset amount of vaporizable material vaporized in mg of an active ingredient is about 100 mg.

In a certain embodiment, the VMP unit is user adjustable using a button. In a certain embodiment, the VMP unit is user adjustable using a dial. In a certain embodiment, the VMP unit is user adjustable using a capacitive interface. In a certain embodiment, the VMP unit is user adjustable using a wireless connection. In a certain embodiment, the VMP unit is user adjustable using voice communication.

In a certain embodiment, the type of vaporizable material is adjustable. In a certain embodiment the type of vaporizable material that is adjustable is nicotine. In a certain embodiment, the type of vaporizable material that is adjustable is a *Cannabis*. In a certain embodiment, the type of vaporizable material that is adjustable is a cannabinoid. In a certain embodiment, the type of vaporizable material that is adjustable is a medicinal compound. In a certain embodiment, the type of vaporizable material that is adjustable is a botanical. In a certain embodiment, the type of vaporizable material that is adjustable is a nutraceutical. In some embodiments, the type of material that is adjustable is formulation specific (e.g., a percent compound dissolved in a specific solvent).

In a certain embodiment, the VMP unit integrates readings from the puff sensor, temperature sensor, heating element controller and timer to create profiles of the readings. A power profile is the change in power delivery over time. A temperature profile is the change in temperature over time. In a certain embodiment, the profile is measured from the initiation of the puff, as measured by the puff sensor to the cessation of the puff, as measured by the puff sensor. In a certain embodiment, the VMP unit stores a plurality of profiles in a memory unit.

In real time, the VMP unit can take a device's data and use it to calculate cumulative TPM in mg. For example, when the TPM reaches 40 mg, the human subject can be prompted to stop puffing, or the heating element can be adjusted or turned off. The constants can be modified to account for different pods and different liquids.

In certain embodiments, the electronic vaporizer device utilizing the method of determining the amount of vapor delivered to the user described herein, such as device 100, comprises an alert unit. In certain embodiments, the alert unit alerts a user when a preset amount of vaporizable material is vaporized. In certain embodiments, the alert unit notifies the user when the vaporizer device is low on vaporizable material. In certain embodiments, the alert unit alerts the user when the amount of vaporizable material in the vaporizer device falls below 10%. In certain embodiments, the alert unit alerts the user when the amount of vaporizable material in the vaporizer device falls below 5%. In certain embodiments, the alert unit is a light emitting diode (LED). In certain embodiments, the alert unit is an organic light emitting diode (OLED). In certain embodiments, the LED or OLED is communicatively coupled to the VMP unit. In certain embodiments, the LED or OLED illuminates when the amount of vapor delivered to a user meets or exceeds a preset amount. In certain embodiments, the LED or OLED flashes when the amount of vapor delivered to a user meets or exceeds a preset amount. In certain embodiments, the LED or OLED emits light in different color spectrums. In certain embodiments, the LED or OLED emits red light. In certain embodiments, the LED or OLED emits orange light. In certain embodiments, the LED or OLED emits yellow light. In certain embodiments, the LED or OLED emits green light. In certain embodiments, the LED or OLED emits blue light. In certain embodiments, the LED or OLED emits purple light. In certain embodiments, the LED or OLED emits more than one color light, the more than one color can be any combination of the above mentioned colors. In certain embodiments, the LED or OLED emits flashing light in any of the aforementioned colors.

In certain embodiments, the electronic vaporizer device utilizing the method comprises an alert unit. In certain embodiments, the alert unit is a piezoelectric speaker. In certain embodiments, the piezoelectric speaker is communicatively coupled to the VMP unit. In certain embodiments, the piezoelectric speaker emits sound when the amount of vapor delivered to a user meets or exceeds a preset amount. In certain embodiments, the sound is a chime, bell, tone, multitoned sound, song or the like.

In certain embodiments, the electronic vaporizer device utilizing the method comprises an alert unit. In certain embodiments, the alert unit is a vibration motor, which provides tactile feedback to the user. In certain embodiments, the vibration motor is communicatively coupled to the VMP unit. In certain embodiments, the vibration motor activates when the amount of vapor delivered to a user meets or exceeds a preset amount.

In certain embodiments, the electronic vaporizer device utilizing the method comprises more than one alert unit. In certain embodiments, the more than one alert unit is an LED or OLED, a piezoelectric speaker, vibration motor or any combination thereof.

The alert unit (or simply the alert) may be configured as a dose output, as shown schematically in FIG. 1. The dose output may be a visual output (e.g., LCD/LED, etc.) and/or a wireless output to a display device (e.g., a smartphone or other wearable device running an application that communicates with the vaporization device, typically wirelessly). The application and therefore the hardware (e.g., wearable device, remote server, etc.) running the application may store, analyze, transmit, display and/or aggregate the dose information (and/or the raw timing, temperature and power, etc., data).

In certain embodiments, the electronic vaporizer device utilizing the method of determining the amount of vapor delivered to the user described herein, such as device 100, includes a controlling logic or a disabling unit. In certain embodiments, the controlling logic is a software module. In certain embodiments, the controlling logic is a firmware module. In certain embodiments, the controlling logic is a hardware element. In certain embodiments, the controlling logic will prompt the VMP unit to relay instructions to the heating element controller to allow a user to vaporize a target amount of TPM in a single puff. In certain embodiments, the controlling logic will prompt the VMP unit to relay instructions to the heating element controller to allow a user to vaporize a target amount of TPM in a plurality of puffs. In certain embodiments, the controlling logic is communicatively coupled to VMP unit. In certain embodiments, the controlling logic inactivates the heating element. In certain embodiments, the controlling logic modifies the amount of power delivered to the heating element. In certain embodiments, the controlling logic turns the electronic vaporizer device off. In certain embodiments, the user can override the controlling logic to restore proper operation of the vaporizer device.

In any of the apparatuses described herein, the electronic vaporizer device utilizing the method of determining the amount of vapor produced (and therefore delivered to a user), such as devices 10, 100. 100', may include a memory. In certain embodiments, the memory (e.g., memory unit) is hardware that is communicatively coupled to the VMP. In certain embodiments, the memory is internal to the electronic vaporizer device. In certain embodiments, the memory is external to the electronic vaporizer device. In certain embodiments, the memory is configured to store a plurality of any of temperature, power, pressure, time, puff duration, puff frequency measurements and combinations thereof. In certain embodiments, the memory unit is a solid state memory. In certain embodiments, the memory unit is a hard disk.

In any of the electronic vaporizer device described herein, such as devices 10, 100. 100', the apparatus may include a processor. In certain embodiments, the processor may include software, firmware and/or hardware that executes the controlling logic of the device. In certain embodiments, the processor is communicatively coupled to the VMP unit. In certain embodiments, the VMP unit and the processor are the same element. In certain embodiments, the processor is communicatively coupled to the user interface. In certain embodiments, the processor is communicatively coupled to the memory unit.

As described above, the electronic vaporizer devices described herein may include a power source, such as power source 230. In certain embodiments, the power source is removable. In certain embodiments, the power source is a battery. In certain embodiments, the power source is a rechargeable battery. In certain embodiments, the rechargeable battery is a lithium ion battery. In certain embodiments, the rechargeable battery is compatible with a USB charging cable. In certain embodiments, the electronic vaporizer device with a rechargeable battery is compatible with a micro USB charging cable. In certain embodiments, the rechargeable battery is compatible with a charging cradle. A charging cradle is any physical device capable of supporting the electronic vaporizer device while charging; the cradle can either be integral to the electronic vaporizer device, or separate from the electronic vaporizer device. In certain embodiments, the charging cradle has charging contacts, configured to mate to contacts on the electronic vaporizer device. In certain embodiments, the charging cradle charges the electronic vaporizer device using induction technology. In certain embodiments, the charging cradle is an induction charging mat.

The power source may be configured to deliver power to the heating element, and may be regulated by the heater controller. The heater controller may therefore receive charge/power level input from the power source and may adjust its output accordingly. In certain embodiments, the power source is configured to deliver an adjustable amount of power. In certain embodiments, the amount of power is adjustable by the user. In certain embodiments, the amount of power is adjusted by the VMP unit. As mentioned, the power source may be communicatively coupled to the heater controller. In certain embodiments, the power source is configured to deliver an adjustable amount of power and is controlled by the VMP unit. In certain embodiments, the power source delivers between 1 and 100 watts of power. In certain embodiments, the power source delivers between 1 and 50 watts of power. In certain embodiments, the power source delivers between 1 and 20 watts of power. In certain embodiments, the power source delivers between 1 and 10 watts of power. In certain embodiments, the power source delivers between 1 and 8 watts of power. In certain embodiments, the power source delivers between 2 and 10 watts of power. In certain embodiments, the power source delivers between 10 and 100 watts of power. In certain embodiments, the power source delivers between 10 and 50 watts of power. In certain embodiments, the power source delivers between 10 and 20 watts of power. In certain embodiments, the power source delivers about 4 watts of power. In certain embodiments, the power source delivers about 4.5 watts of power. In certain embodiments, the power source delivers about 5 watts of power. In certain embodiments, the power source delivers about 5.5 watts of power. In certain embodiments, the power source delivers about 6 watts of power. In certain embodiments, the power source delivers about 6.5 watts of power. In certain embodiments, the power source delivers about 7 watts of power. In certain embodiments, the power source delivers about 7.5 watts of power. In certain embodiments, the power source delivers about 8 watts of power. In certain embodiments, the power source delivers about 8.5 watts of power. In certain embodiments, the power source delivers about 9 watts of power. In certain embodiments, the power source delivers about 10 watts of power. In certain embodiments, the power source delivers about 20 watts of power. In certain embodiments, the power source delivers about 30 watts of power. In certain embodiments, the power source delivers about 40 watts of power. In certain embodiments, the power source delivers about 10 watts of power. In certain embodiments, the power source delivers about 50 watts of power. In certain embodiments, the power source delivers about 60 watts of power. In certain embodiments, the power source delivers about 70 watts of power. In certain embodiments, the power source delivers about 80 watts of power. In certain embodiments, the power source delivers about 90 watts of power. In certain embodiments, the power source delivers about 100 watts of power. The power applied may alternatively or additionally (and equivalently) be expressed in joules. For example, in certain embodiments, the power source delivers between 1 and 1000 joules to the heater. In certain embodiments, the power source delivers between 1 and 500 joules to the heater. In certain embodiments, the power source delivers between 1 and 100 joules to the heater. In certain embodiments, the power source delivers between 1 and 50 joules to the heater. In certain embodiments, the power source delivers between 1 and 25 joules to the heater. In certain embodiments, the power source delivers between 5 and 25 joules to the heater. In certain embodiments, the power source delivers between 1 and 20 joules to the heater. In certain embodiments, the power source delivers between 5 and 20 joules to the heater. In certain embodiments, the power source delivers between 10 and 500 joules to the heater. In certain embodiments, the power source delivers between 10 and 100 joules to the heater. In certain embodiments, the power source delivers between 10 and 50 joules to the heater. In certain embodiments, the power source delivers between 10 and 20 joules to the heater.

As described above, any of the vaporizer apparatuses described herein may include a heater (heating element). In certain embodiments, the heater is a resistive heating element. In certain embodiments, the heating element forms a coil. In certain embodiments, the coil is wrapped around a wick. In certain embodiments, the wick is in contact with a vaporizable material. In certain embodiments, the wick projects into the vaporizable material.

In certain embodiments, the heating element heats the vaporizable material to between 40 and 1000 degrees Celsius. In certain embodiments, the heating element heats the vaporizable material to between 100 and 900 degrees Celsius. In certain embodiments, the heating element heats the vaporizable material to between 100 and 800 degrees Celsius. In certain embodiments, the heating element heats the vaporizable material to between 100 and 700 degrees Celsius. In certain embodiments, the heating element heats the vaporizable material to between 100 and 600 degrees Celsius. In certain embodiments, the heating element heats the vaporizable material to between 100 and 500 degrees Celsius. In certain embodiments, the heating element heats the vaporizable material to between 100 and 400 degrees Celsius. In certain embodiments, the heating element heats the vaporizable material to between 100 and 300 degrees Celsius. In certain embodiments, the heating element heats the vaporizable material to between 180 and 250 degrees Celsius. In certain embodiments, the heating element heats the vaporizable material to between 100 degrees Celsius and 200 degrees Celsius. In certain embodiments, the heating element heats the vaporizable material to between 125 degrees Celsius and 175 degrees Celsius. In certain embodiments, the heating element heats the vaporizable material to about 150 degrees Celsius. In certain embodiments, the heating element heats the vaporizable material to between 200 and 300 degrees Celsius. In certain embodiments, the heating element heats the vaporizable material to between 225 and 275 degrees Celsius. In certain embodiments, the heating element heats the vaporizable material to about 250 degrees Celsius. In certain embodiments, the heating element heats the vaporizable material to between 300 and 400 degrees Celsius. In certain embodiments, the heating element heats the vaporizable material to between 325 and 375 degrees Celsius. In certain embodiments, the heating element heats the vaporizable material to about 350 degrees Celsius. In certain embodiments, the heating element heats the vaporizable material to between 400 and 500 degrees Celsius. In certain embodiments, the heating element heats the vaporizable material to between 500 and 600 degrees Celsius. In certain embodiments, the heating element heats the vaporizable material to between 600 and 700 degrees Celsius. In certain embodiments, the heating element heats the vaporizable material to between 700 and 800 degrees Celsius. In certain embodiments, the heating element heats the vaporizable material to between 800 and 900 degrees Celsius. In certain embodiments, the heating element heats the vaporizable material to between 900 and 1000 degrees Celsius. In certain embodiments, when the vaporizable material is *Cannabis* or a cannabinoid, the heating element heats the vaporizable material to between 300 and 400 degrees Celsius. In certain embodiments, when the vaporizable material is *Cannabis* or a cannabinoid, the heating element heats the vaporizable material to between 325 and 375 degrees Celsius. In certain embodiments, when the vaporizable material is *Cannabis* or a cannabinoid, the heating element heats the vaporizable material to about 350 degrees Celsius. In certain embodiments, when the vaporizable material is nicotine or a nicotine derivative, the heating element heats the vaporizable material to between 200 and 300 degrees Celsius. In certain embodiments, when the vaporizable material is nicotine or a nicotine derivative, the heating element heats the vaporizable material to between 225 and 275 degrees Celsius. In certain embodiments, when the vaporizable material is nicotine or a nicotine derivative, the heating element heats the vaporizable material to about 250 degrees Celsius.

In one embodiment, the heating element is housed within a vaporization chamber surrounded by vaporization chamber walls. The vaporization chamber is also referred to as the atomizer. In some embodiments, the vaporization chamber walls can be constructed of any material capable of withstanding repeated heating to the operating temperature of the vaporizer device. In some embodiments, the vaporization chamber walls can be constructed of any material capable of withstanding repeated heating to 300 degrees Celsius. The vaporization chamber possesses an air inlet, to allow the entrance of air to the atomizer, and an air outlet, to allow vapor to escape to the user. Vaporizable material is introduced to the atomizer by a wick, which is in fluid communication with a vaporizable material. The vaporizable material can be stored in a tank integral to the electronic vaporizer device or in a removable tank (pod), configured to be detached from the vaporizer device after it is depleted. In an alternative embodiment, the heater element is in an oven configuration, wherein the heating element surrounds a chamber with stainless steel walls, and heats a vaporizable material, placed within the chamber, by conduction. In an oven configuration, the inside of the oven can be exposed to the outside by removal of an oven lid, which allows loading of a vaporizable material. The oven can further contain an outlet that allows vapor to escape to the user.

In any of the vaporizer devices described herein, the apparatus may include a heater controller (e.g., a heating element controller). In certain embodiments, the heater controller operates the heating element. In certain embodiments, the heater controller switches the heater on and off, and/or switches the heater on and off in a rapid "pulsed" fashion. In certain embodiments, the heater controller is configured to detect and/or control the power delivered from the power source. In certain embodiments, the heater controller is configured to detect and/or control the voltage delivered from the power source. In certain embodiments, the heater controller is configured to detect and/or control the current delivered from the power source. In certain embodiments, the heater controller is configured to detect and/or control the power, voltage and/or current delivered, or any combination thereof from the power source. In certain embodiments, the heater controller is connected in series with the power source and the heater. In certain embodiments, the heater controller is connected to the power source in parallel with the heater. In certain embodiments, the heater controller is configured to detect and/or control the power delivered from the power source in Watts. In certain embodiments, the heater controller is configured to detect and/or control the voltage delivered from the power source in Volts. In certain embodiments, the heater controller is configured to detect and/or control the current delivered from the power source in Amps. In certain embodiments, the heater controller is communicatively coupled to the VMP unit.

In certain embodiments, the heater controller is configured to regulate the operation of the heater. In certain embodiments, the heater controller is configured to regulate the temperature of the heater. In certain embodiments, the heater controller is configured to regulate the voltage delivered to the heater by the power source. In certain embodiments, the heater controller is configured to regulate the current delivered to the heating element by the power source. In certain embodiments, the heater controller is configured to regulate the wattage delivered to the heater by the power source. In certain embodiments, the heater controller is configured to regulate the temperature of the heater by regulating power delivered from the power source. In certain elements, the heating element controller is communicatively coupled to the processor. In certain embodiments, the heater controller is configured to receive instructions from the processor.

As discussed above, and described in U.S. patent application Ser. No. 14/581,666, the heater controller may use control logic (e.g., a PID loop) including one or more inputs such as the temperature, e.g., determined using the coefficient of resistance or TCR of the heater. Thus, in determining the dose (e.g., partial doses of a puff), the apparatus may advantageously use just electrical values (resistance and power values) from the controller, once calibrated with the appropriate constants (which may be analytically or theoretically determined as mentioned above, or may be assumed/ignored).

Cartridge

As described above, in some embodiments, the electronic vaporizer device utilizing the method of determining the amount of vapor delivered to the user described herein, such as device 100, includes a separate detachable pod configured to hold a vaporizable material. In certain embodiments, the pod is any receptacle or tank configured to hold a vaporizable material. In certain embodiments, the pod is removable. In certain embodiments, the pod is replaceable. In certain embodiments, the pod and the electronic vaporizer device form a single unit after the pod is attached to the electronic vaporizer device. In certain embodiments, the pod further comprises a mouthpiece. In certain embodiments, the electronic vaporizer device utilizing the method does not comprise a separate pod configured to hold a vaporizable material, and vaporizable material is stored in the electronic vaporizer device. In certain embodiments, the separate pod contains a vaporization chamber. In certain embodiments, the pod holds between 0.1 and 10 ml of a liquid, viscous liquid or wax. In certain embodiments, the pod holds between 1 and 10 ml of a liquid, viscous liquid or wax. In certain embodiments, the pod holds between 0.1 and 2 ml of a liquid, viscous liquid or wax. In certain embodiments, the pod holds between 0.5 and 1.5 ml of a liquid, viscous liquid or wax.

In some embodiments, the cartridge can be filled with non-hydroscopic solvents and/or be substantially airtight so as to avoid absorption of water in the cartridge, thereby ensuring a predictable and accurate dose calculation.

Temperature Sensor

As described above, any of the vaporizer apparatuses described herein, such as devices 10, 100, 100' in FIGS. 1A-1C, can include one or more temperature sensors, such as temperature sensor 250. In certain embodiments, the temperature sensor is configured to measure the temperature of the heating element. The temperature sensor may include software and hardware for measuring the resistance that may be integral with (or separate from) any of the controller and/or processors described herein. In certain embodiments, the temperature sensor is configured to measure the temperature of a vaporization chamber housing the heating element. In certain embodiments, the temperature sensor is configured to measure the temperature of an oven chamber heated by the heating element. In certain embodiments, the temperature sensor measures heat in degrees Celsius. In certain embodiments, the temperature sensor measures heat in degrees Fahrenheit. In certain embodiments, the temperature sensor measures heat in degrees Kelvin. In certain embodiments, the temperature sensor is a thermocouple. In certain embodiments, the temperature sensor is a thermistor. In certain embodiments, the temperature sensor is an infrared temperature sensor. In certain embodiments, the temperature sensor is a relative resistance gradient measurement system. In certain embodiments, the temperature sensor is the heater coil used to heat the vaporizable material.

In certain embodiments, the temperature sensor measures a temperature to an accuracy of ±0.1 degrees Celsius. In certain embodiments, the temperature sensor measures a temperature to an accuracy of ±0.2 degrees Celsius. In certain embodiments, the temperature sensor measures a temperature to an accuracy of ±0.3 degrees Celsius. In certain embodiments, the temperature sensor measures a temperature to an accuracy of ±0.4 degrees Celsius. In certain embodiments, the temperature sensor measures a temperature to an accuracy of 0.5 degrees Celsius. It should be noted that the accuracy of the measured temperature may be as poor as +/−25° C. (e.g., less than 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., etc.). In certain embodiments, the temperature sensor measures temperature indirectly by measuring the resistance of the heating element. In certain embodiments, resistance is measured in Ohms. In certain, embodiments, the temperature sensor is capable of measuring a temperature profile, which is a change in temperature over time.

Puff Sensor

As described above, the vaporizer apparatuses described herein may optionally include a puff sensor. In certain embodiments, the puff sensor measures the initiation of the users puff. In certain embodiments, the puff sensor measures the cessation of the users puff. In certain embodiments, the puff sensor measures the duration of the users puff. In certain embodiments, the puff sensor measures the velocity and amount of air traveling through the electronic vaporizer device. In certain embodiments, the puff sensor is a button that is pressed upon initiation of a user's puff. In certain embodiments, the puff sensor is a pressure sensor. In certain embodiments, the pressure sensor is a Venturi meter. In certain embodiments, the pressure sensor is an orifice plate. In certain embodiments, the pressure sensor is a Dall tube. In certain embodiments, the pressure sensor is a pitot-static tube. In certain embodiments, the pressure sensor is a multi-hole pressure probe. In certain embodiments, the pressure sensor is a cone meter. In certain embodiments, the puff sensor comprises a button that is pressed by the user to initiate a puff. In certain embodiments, the puff sensor is a flow meter. In certain embodiments, the flow meter is a turbine flow meter. In certain embodiments, the puff sensor is communicatively coupled to the VMP unit. In certain embodiments, the puff sensor is configured to measure a puff initiated by the user. In certain embodiments, the puff sensor is configured to measure a puff initiated by an analytical smoking machine.

Timer

In certain embodiments, the electronic vaporizer device utilizing the method of determining the amount of vapor delivered to the user described herein, such as device 100, includes a timer. In a certain embodiment, the timer is communicatively coupled to the temperature sensor. In certain embodiments, the timer is communicatively coupled to the puff sensor. In certain embodiments, the timer measures a puff duration. In certain embodiments, the timer measures a puff frequency. In certain embodiments, the timer is communicatively coupled to the VMP unit. In certain embodiments, the timer is communicatively coupled to both the puff sensor and the VMP unit. In some instances, a puff duration can range from about 0.1 seconds to about 10 seconds. In some instances, a puff duration can range from about 1 second to about 5 seconds. In some instances, a puff duration can range from about 1 second to about 4 seconds. In some instances, a puff duration can range from about 1 second to about 3 seconds. In some instances, a puff duration can range from about 1 second to about 2 seconds. In certain embodiments, the accuracy of a measurement of the puff duration is within about ±0.05 seconds. In certain embodiments, the accuracy of a measurement of the puff duration is within about ±0.1 seconds. In certain embodiments, the accuracy of a measurement of the puff duration is within about +0.2 seconds. In certain embodiments, the accuracy of a measurement of the puff duration is within about ±0.3 seconds. In certain embodiments, the accuracy of a measurement of the puff duration is within about ±0.4 seconds. In certain embodiments, the accuracy of a measurement of the puff duration is within about +0.5 seconds.

Figure 7:
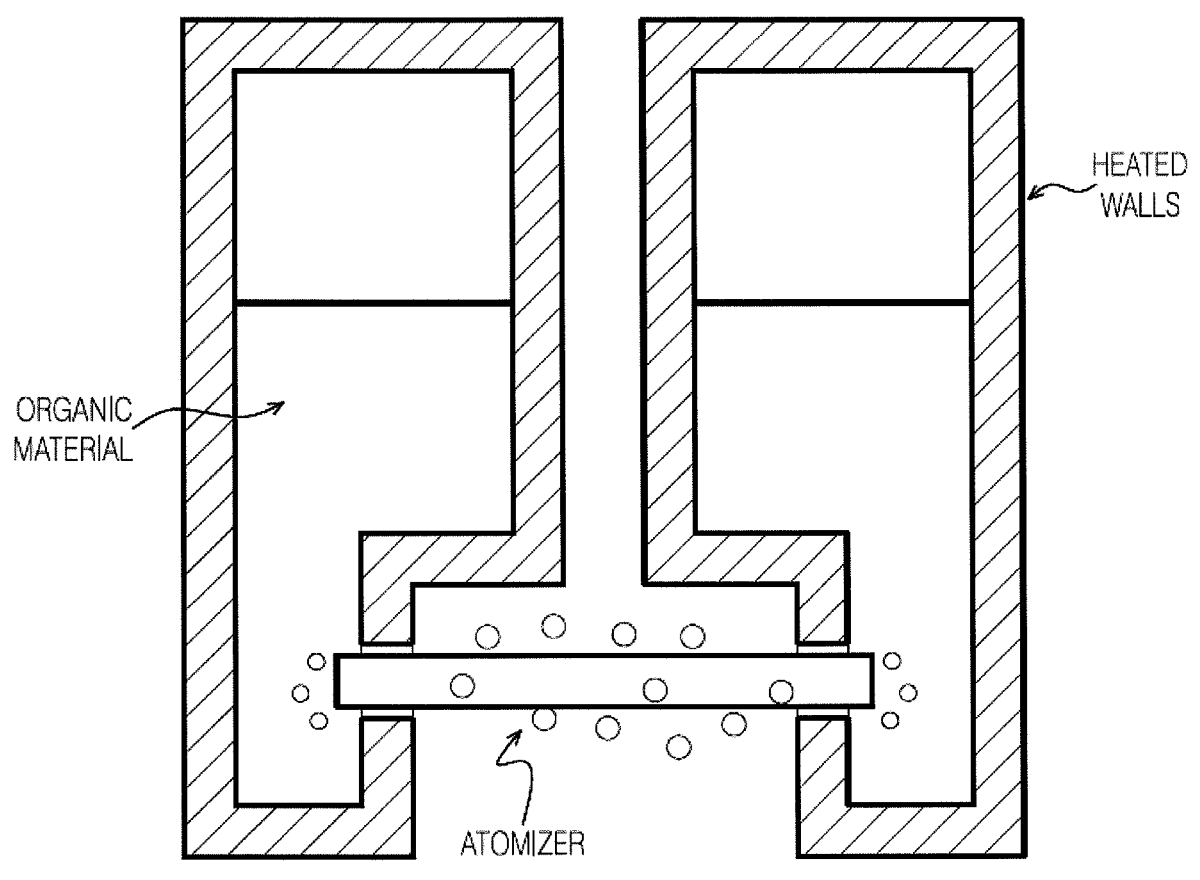

In some variations, the heated reservoir may be heated. Referring to FIG. 7, in certain embodiments, the electronic vaporizer device utilizing the method of determining the amount of vapor delivered to the user described herein, such as device 100, includes a heat block reservoir (or heat reservoir or heat block).

Figure 8:
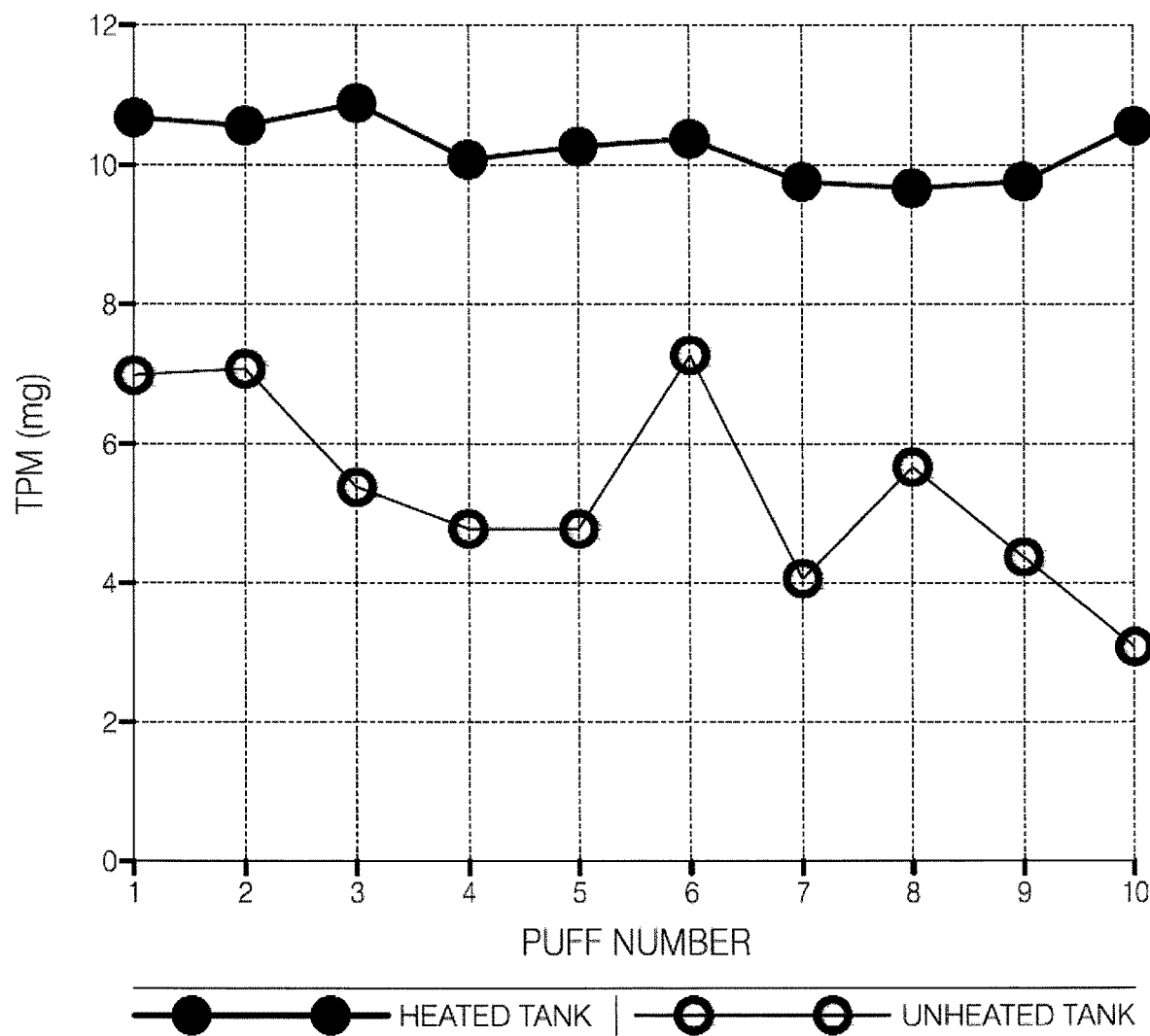
FIG. 8 is a graph illustrating the number of puffs relative to the TPM release content (mg) of a non-heated reservoir of an electronic vaporizer device compared with the number of puffs relative to the TPM release content (mg) of a heat reservoir of an electronic vaporizer device having a heated reservoir ("tank").

Heating the reservoir may allow for a more controlled initial state, which may enhance the predictability of the dose estimation. This is illustrated in FIG. 8. In some variations, and particularly those illustrated above, heating the reservoir may be unnecessary as sufficiently accurate dose (vapor) estimations may be determined. FIGS. 9A and 9B conceptual relate to a model which may benefit from using a heated reservoir. Alternatively, just the portion of the vaporizable material feeding into the vaporizing region (e.g., wick) may be heated.

Smoking vaporizable organic formulations that may be thick (non-flowing) or non-liquid with electronic vaporizer devices can pose a challenge. However, there remains an unmet need of vaporizing organic formulations that are otherwise thick (non-flowing) liquids or non-liquids, that include, but are not limited to, for example, *Cannabis* extracts. In certain embodiments, the heat reservoir is distinct form the heating element. In certain embodiments, the heat reservoir is fluidly coupled to the heater element. In certain embodiments, the heat reservoir is constructed of stainless steel. In certain embodiments, the heat reservoir is constructed of high temperature plastic. In certain embodiments, the heat reservoir preheats a viscous, semi-solid or solid composition, before vaporization with the heating element. In certain embodiments, the heat reservoir preheats a vaporizable material to between 40 degrees Celsius and 100 degrees Celsius. In certain embodiments, the heat reservoir preheats a vaporizable material to between 40 degrees Celsius and 80 degrees Celsius. In certain embodiments, the heat reservoir preheats a vaporizable material to between 40 degrees Celsius and 60 degrees Celsius. In certain embodiments, the heat reservoir preheats a vaporizable material to about 50 degrees Celsius. In certain embodiments, the heat reservoir preheats a vaporizable material to between 50 degrees Celsius and 100 degrees Celsius. In certain embodiments, the heat reservoir preheats a vaporizable material to between 60 degrees Celsius and 100 degrees Celsius. In certain embodiments, the heat reservoir preheats a vaporizable material to between 70 degrees Celsius and 100 degrees Celsius. In certain embodiments, the heat reservoir preheats a vaporizable material to between 80 degrees Celsius and 100 degrees Celsius. In certain embodiments, the heat reservoir preheats a vaporizable material to between 90 degrees Celsius and 100 degrees Celsius. In certain embodiments, the heat block is configured to warm material that exhibits a viscosity between 50 and 1000 Centipoise. In certain embodiments, the heat block is configured to warm material that exhibits a viscosity between 1,000 and 5,000 Centipoise. In certain embodiments, the heat block is configured to warm material that exhibits a viscosity between 5,000 and 50,000 Centipoise. In certain embodiments, the heat block is configured to warm material that exhibits a viscosity above 5,000 Centipoise (or above 10,000 Centipoise, above 20,000 Centipoise, above 30,000 Centipoise, above 40,000 Centipoise, etc.).

An analytical vaporizer device smoking machine was employed in this example, which is similar to machines known in the art. An electronic vaporizer device including a heat block reservoir for thick (non-flowing) liquids or non-liquids, was compared to an electronic vaporizer device without a heat reservoir. The heat reservoir preheats the thick (non-flowing) liquids or non-liquids. When the thick (non-flowing) liquids or non-liquids are preheated prior to vaporization the effect of uneven heating is reduced during vaporization. FIG. 8 shows graphical data depicting the number of puffs relative to the TPM release content (mg) of a non-heated reservoir of an electronic vaporizer device compared with the number of puffs relative to the TPM release content (mg) of a heat reservoir of an electronic vaporizer device, where the latter's reservoir was pre-heated to a temperature of 40-60° C. Where the reservoir was pre-heated to a temperature of 40-60° C., a more or less consistent amount of TPM (mg) was generated from a viscous or thick non-flowing organic formulation; while the electronic vaporizer device without a heat block reservoir, vaporized inconsistent amounts of TPM (mg). An inconsistency of the TPM produced by the unheated reservoir can be a result of uneven heating of the vaporizable material.

Vaporizable Material

As described above, the vaporizer apparatuses described herein may be used with (and may include or be configured specifically for) any appropriate vaporizable material. In certain embodiments, the vaporizable material is an organic material. In certain embodiments, vaporizable material is a liquid, viscous liquid, wax or loose-leaf material. In certain embodiments, the vaporizable material is a tobacco-based material. In certain embodiments, the vaporizable material is a *Cannabis* based material. In certain embodiments, the vaporizable material is a botanical. In certain embodiments, the vaporizable material is nicotine, a nicotine derivative or a nicotine salt. In certain embodiments, the vaporizable material is a nutraceutical. In certain embodiments, the vaporizable material contains a cannabinoid. In certain embodiments, the vaporizable material is a medicinal compound.

In certain embodiments, the vaporizable material exhibits a viscosity between 1 and 50 Centipoise. In certain embodiments, the vaporizable material exhibits a viscosity between 50 and 1,000 Centipoise. In certain embodiments, the vaporizable material exhibits a viscosity between 1,000 and 5,000 Centipoise. In certain embodiments, the vaporizable material exhibits a viscosity between 5,000 and 10,000 Centipoise. In certain embodiments, the vaporizable material exhibits a viscosity above 10,000 Centipoise.

In certain embodiments, the vaporizable material contains nicotine. In certain embodiments, the vaporizable material contains a nicotine derivative. In certain embodiments, the nicotine derivative is an acid salt of nicotine. In certain embodiments, the acid salt of nicotine comprises an organic acid. In certain embodiments, the acid salt of nicotine does not comprise an inorganic acid. In certain embodiments, the nicotine derivative is cotinine, In certain embodiments, the nicotine derivative is norcotinine. In certain embodiments, the nicotine derivative is nornicotine. In certain embodiments, the nicotine derivative is nicotine N-oxide. In certain embodiments, the nicotine derivative is cotinine N-oxide. In certain embodiments, the nicotine derivative is 3-hydroxycotinine. In certain embodiments, the nicotine derivative is 5-hydroxycotinine.

In certain embodiments, the vaporizable material is a formulation of nicotine, nicotine derivatives, or a nicotine salt. In some formulations the concentration of nicotine or derivatives thereof in the formulation is about 1% (w/w) to about 25% (w/w). In some formulations the concentration of nicotine or derivatives thereof; in the formulation is about 1% (w/w) to about 20% (w/w). In some formulations the concentration of nicotine in the formulation is about 1% (w/w) to about 18% (w/w). In some embodiments, the concentration of nicotine in the formulation is about 1% (w/w) to about 15% (w/w). In some embodiments, the concentration of nicotine in the formulation is about 1% (w/w) to about 10% (w/w). In some embodiments, the concentration of nicotine in the formulation is about 1% (w/w) to about 8% (w/w). In some embodiments, the concentration of nicotine in the formulation is about 2% (w/w) to about 10% (w/w). In some formulations the concentration of nicotine in the formulation is about 4% (w/w) to about 12% (w/w). In some formulations the concentration of nicotine in the formulation is about 4% (w/w). In some embodiments, the concentration of nicotine in the formulation is about 2% (w/w).

Nicotine salt formulations are formed by the addition of a suitable acid to nicotine or a derivative thereof, including organic or inorganic acids. In some formulations provided herein, suitable organic acids are carboxylic acids. Examples of organic carboxylic acids disclosed herein are monocarboxylic acids, dicarboxylic acids (organic acid containing two carboxylic acid groups), carboxylic acids containing an aromatic group such as benzoic acids, hydroxycarboxylic acids, heterocyclic carboxylic acids, terpenoid acids, sugar acids; such as the pectic acids, amino acids, cycloaliphatic acids, aliphatic carboxylic acids, keto carboxylic acids, and the like. In some formulations provided herein, the organic acids used herein are monocarboxylic acids. In some formulations provided herein the organic carboxylic acid is benzoic, levulinic, acetic, lactic, citric, sorbic, lauric, salicylic, pyruvic or a combination thereof. In some formulations provided herein the organic carboxylic acid is not levulinic. Nicotine salts are formed from the addition of a suitable acid to nicotine. In some formulations provided herein, the stoichiometric ratios of the nicotine to acid (nicotine:acid) are 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In some formulations provided herein, the stoichiometric ratios of the nicotine to acid are 1:1, 1:2, 1:3, or 1:4 (nicotine:acid).

In certain embodiments, the pH of the nicotine formulation is acidic. In certain embodiments, the pH of the nicotine formulation is <7.0. In certain embodiments, the pH of the nicotine formulation is <6.0. In certain embodiments, the pH of the nicotine formulation is <5.0. In certain embodiments, the pH of the nicotine formulation is <4.0. In certain embodiments, the pH of the nicotine formulation is >3.0. In certain embodiments, the pH of the nicotine formulation is >4.0. In certain embodiments, the pH of the nicotine formulation is >5.0. In certain embodiments, the pH of the nicotine formulation is >6.0.

In certain embodiments, the vaporizable material contains organic material from a *Cannabis* genus plant. In certain embodiments, the vaporizable material contains an extract from a *Cannabis* genus plant. In certain embodiments, the vaporizable material contains a cannabinoid. In certain embodiments, the cannabinoid is tetrahydrocannabinol (THC). In certain embodiments, the cannabinoid is carmabigerolic acid (CBGA). In certain embodiments, the cannabinoid is cannabigerol (CBG). In certain embodiments, the cannabinoid is tetrahydrocannabinolic acid (THCA). In certain embodiments, the cannabinoid is cannabichromene (CBC). In certain embodiments, the cannabinoid is cannabicyclol (CBL). In certain embodiments, the cannabinoid is cannabivarin (CBV). In certain embodiments, the cannabinoid is cannabichromevarin (CBCV). In certain embodiments, the cannabinoid is cannabigerovarin (CBGV). In certain embodiments, the cannabinoid is cannabigerol Monomethyl Ether (CBGM). In certain embodiments, the cannabinoid is delta-8-tetrahydrocannabinol (D8THC). In certain embodiments, the cannabinoid is delta-9-tetrahydrocannabinol (D9THC). In certain embodiments, the cannabinoid is tetrahydrocannabivarin (THCV). In certain embodiments, the cannabinoid is cannabinolic acid (CBNA). In certain embodiments, the cannabinoid is Cannabinol (CBN). In certain embodiments, the cannabinoid is cannabidiolic acid (CBDA). In certain embodiments, the cannabinoid is Cannabidivaric acid (CBDVA). In certain embodiments, the cannabinoid is cannabidiol (CBD). In certain embodiments, the cannabinoid is cannabichromenic acid (CBCA). In certain embodiments, the cannabinoid is Cannabichromene (CBC). In certain embodiments, the cannabinoid is cannabicyclolic acid (CBLA). In certain embodiments, the cannabinoid is an stereo isomer of any of the above mentioned cannabinoids. In certain embodiments, the cannabinoid is a salt of any of the above mentioned cannabinoids.

In certain embodiments, the vaporizable material is a cannabinoid formulation. In certain embodiments, the concentration of cannabinoid in the cannabinoid formulation is from 1-99% cannabinoid. In certain embodiments, the concentration of cannabinoid in the cannabinoid formulation is from 5-95% cannabinoid. In certain embodiments, the concentration of cannabinoid in the cannabinoid formulation is from 10-90% cannabinoid. In certain embodiments, the concentration of cannabinoid in the cannabinoid formulation exceeds about 99% cannabinoid. In certain embodiments, the concentration of cannabinoid in the cannabinoid formulation exceeds about 98% cannabinoid. In certain embodiments, the concentration of cannabinoid in the cannabinoid formulation exceeds about 97% cannabinoid. In certain embodiments, the concentration of cannabinoid in the cannabinoid formulation exceeds about 96% cannabinoid. In certain embodiments, the concentration of cannabinoid in the cannabinoid formulation exceeds about 95% cannabinoid. In certain embodiments, the concentration of cannabinoid in the cannabinoid formulation exceeds about 94% cannabinoid. In certain embodiments, the concentration of cannabinoid in the cannabinoid formulation exceeds about 93% cannabinoid. In certain embodiments, the concentration of cannabinoid in the cannabinoid formulation exceeds about 92% cannabinoid. In certain embodiments, the concentration of cannabinoid in the cannabinoid formulation exceeds about 91% cannabinoid. In certain embodiments, the concentration of cannabinoid in the cannabinoid formulation exceeds about 90% cannabinoid. In certain embodiments, the concentration of cannabinoid in the cannabinoid formulation exceeds about 80% cannabinoid. In certain embodiments, the concentration of cannabinoid in the cannabinoid formulation exceeds about 70% cannabinoid. In certain embodiments, the concentration of cannabinoid in the cannabinoid formulation exceeds about 60% cannabinoid. In certain embodiments, the concentration of in the cannabinoid formulation exceeds about 50% cannabinoid. In certain embodiments, the concentration of in the cannabinoid formulation exceeds about 40% cannabinoid. In certain embodiments, the concentration of cannabinoid in the cannabinoid formulation exceeds about 30% cannabinoid. In certain embodiments, the concentration of cannabinoid in the cannabinoid formulation exceeds about 20% cannabinoid. In certain embodiments, the concentration of cannabinoid in the cannabinoid formulation exceeds about 10% cannabinoid. In certain embodiments, the concentration of cannabinoid in the cannabinoid formulation is from about 1% to about 10% cannabinoid. In certain embodiments, the concentration of cannabinoid in the cannabinoid formulation is from about 10% to about 20% cannabinoid. In certain embodiments, the concentration of cannabinoid in the cannabinoid formulation is from about 20% to about 30% cannabinoid. In certain embodiments, the concentration of cannabinoid in the cannabinoid formulation is from about 30% to about 40% cannabinoid. In certain embodiments, the concentration of cannabinoid in the cannabinoid formulation is from about 40% to about 50% cannabinoid. In certain embodiments, the concentration of cannabinoid in the cannabinoid formulation is from about 50% to about 60% cannabinoid. In certain embodiments, the concentration of cannabinoid in the cannabinoid formulation is from about 60% to about 70% cannabinoid. In certain embodiments, the concentration of cannabinoid in the cannabinoid formulation is from about 70% to about 80% cannabinoid. In certain embodiments, the concentration of cannabinoid in the cannabinoid formulation is from about 80% to about 90% cannabinoid. In certain embodiments, the concentration of cannabinoid in the cannabinoid formulation is from about 90% to about 100% cannabinoid.

In certain embodiments, the pH of the cannabinoid formulation is acidic. In certain embodiments, the pH of the cannabinoid formulation is <7.0. In certain embodiments, the pH of the cannabinoid formulation is <6.0 In certain embodiments, the pH of the cannabinoid formulation is <5.0. In certain embodiments, the pH of the cannabinoid formulation is <4.0. In certain embodiments, the pH of the cannabinoid formulation is >3.0. In certain embodiments, the pH of the cannabinoid formulation is >4.0. In certain embodiments, the pH of the cannabinoid formulation is >5.0. In certain embodiments, the pH of the cannabinoid formulation is >6.0. In certain embodiments, the pH of the cannabinoid formulation is basic. In certain embodiments, the pH of the cannabinoid formulation is <10.0. In certain embodiments, the pH of the cannabinoid formulation is <9.0 In certain embodiments, the pH of the cannabinoid formulation is <8.0. In certain embodiments, the pH of the cannabinoid formulation is >7.0. In certain embodiments, the pH of the cannabinoid formulation is >8.0. In certain embodiments, the pH of the cannabinoid formulation is >9.0. In certain embodiments, the pH of the cannabinoid formulation is >10.0.

In certain embodiments, the vaporizable material is a *Cannabis* formulation. In certain embodiments, the concentration of the *Cannabis* formulation is from 1-99% *Cannabis*. In certain embodiments, the concentration of the *Cannabis* formulation is from 5-95% *Cannabis*. In certain embodiments, the concentration of the *Cannabis* formulation is from 10-90% *Cannabis*. In certain embodiments, the *Cannabis* formulation exceeds about 99% *Cannabis*. In certain embodiments, the *Cannabis* formulation exceeds about 98% *Cannabis*. In certain embodiments, the *Cannabis* formulation exceeds about 97% *Cannabis*. In certain embodiments, the *Cannabis* formulation exceeds about 96% *Cannabis*. In certain embodiments, the *Cannabis* formulation exceeds about 95% *Cannabis*. In certain embodiments, the *Cannabis* formulation exceeds about 94% *Cannabis*. In certain embodiments, the *Cannabis* formulation exceeds about 93% *Cannabis*. In certain embodiments, the *Cannabis* formulation exceeds about 92% *Cannabis*. In certain embodiments, the *Cannabis* formulation exceeds about 91% *Cannabis*. In certain embodiments, the *Cannabis* formulation exceeds about 90% *Cannabis*. In certain embodiments, the *Cannabis* formulation exceeds about 80% *Cannabis*. In certain embodiments, the *Cannabis* formulation exceeds about 70% *Cannabis*. In certain embodiments, the *Cannabis* formulation exceeds about 60% *Cannabis*. In certain embodiments, the *Cannabis* formulation exceeds about 50% *Cannabis*. In certain embodiments, the *Cannabis* formulation exceeds about 40% *Cannabis*. In certain embodiments, the *Cannabis* formulation exceeds about 30% *Cannabis*. In certain embodiments, the *Cannabis* formulation exceeds about 20% *Cannabis*. In certain embodiments, the *Cannabis* formulation exceeds about 10% *Cannabis*.

In certain embodiments, the pH of the *Cannabis* formulation is acidic. In certain embodiments, the pH of the *Cannabis* formulation is <7.0. In certain embodiments, the pH of the *Cannabis* formulation is <6.0 In certain embodiments, the pH of the *Cannabis* formulation is <5.0. In certain embodiments, the pH of the *Cannabis* formulation is <4.0. In certain embodiments, the pH of the *Cannabis* formulation is >3.0. In certain embodiments, the pH of the *Cannabis* formulation is >4.0. In certain embodiments, the pH of the *Cannabis* formulation is >5.0. In certain embodiments, the pH of the *Cannabis* formulation is >6.0. In certain embodiments, the pH of the *Cannabis* formulation is basic. In certain embodiments, the pH of the *Cannabis* formulation is <10.0. In certain embodiments, the pH of the *Cannabis* formulation is <9.0 In certain embodiments, the pH of the *Cannabis* formulation is <8.0. In certain embodiments, the pH of the *Cannabis* formulation is >7.0. In certain embodiments, the pH of the *Cannabis* formulation is >8.0. In certain embodiments, the pH of the *Cannabis* formulation is >9.0. In certain embodiments, the pH of the *Cannabis* formulation is >10.0.

In certain embodiments, the vaporizable material contains a medicinal compound as an active ingredient. The medicinal compounds that are active ingredients for vaporization with the electronic vaporizer device utilizing the method herein, include drugs that can be heated without combustion to vaporization for inhalation delivery at a temperature range of, e.g., about 100° C. (e.g., for water-based carriers, e.g., about 100° C., 105° C., 110° C., 120° C., 130° C., 140° C., 150° C., 160° C., 170° C., etc.; for ethanol-based formulations, e.g., about 50° C., about 60° C., about 70° C., about 80° C., etc.) to about (e.g., below) the temperature at which the active ingredient thermally decomposes (e.g., less than about 150° C., 160° C., 170° C., 180° C., 190° C., 200° C., 210° C., 220° C., 230° C., 240° C., 250° C., 260° C., 270° C., 280° C., 290° C., 300° C., etc.). In certain embodiments, the drugs can be neat or are solubilized in a pharmaceutically acceptable solvent. In certain embodiments, the drugs can include over the counter (OTC) substances as aides for various ailments; wherein said drugs can include known respiratory aides for asthma or chronic obstructive pulmonary disease (COPD). The vaporizable materials that are active ingredients for vaporization with the device(s) herein described, can include drugs that can be heated to vaporization for inhalation delivery, without combustion; wherein said drugs can include over the counter (OTC) substances from the group comprising upper respiratory aides (like cetirizine), analgesics and internal medication aides (like ibuprofen, naproxen), heartburn aides (like omeprazole), sleeping aides (like doxylamine, diphenhydramine, melatonin), or motion sickness aides (like meclizine). In certain embodiments, the vaporizable material can contain respiratory aides for asthma or chronic obstructive pulmonary disease (COPD) such as short acting beta-agonist (like albuterol, levalbuterol, pirbuterol), long acting beta-agonist (like salmeterol, formoterol), anti-cholinergics (like atropine sulfate, ipratropium bromide), leukotriene modifiers (like montelukast, zafirlukast), cartico-steriods (like fluticasone, budesonide, mometasone), theophylline (like theophylline), or combination corticosteroid and beta agonist, long lasting (fluticasone and salmeterol, budesonide and formoterol, mometasone and formoterol). In certain embodiments, the vaporizable material can contain botanicals and/or nutraceuticals such as tea (polyphenols, flavonoids, green tea catechins+/−caffeine); horehound (phenol flavonoid glycosides, labdane diterpenoids, yohimbe, cranberry/grape (proanthocyanidins), black cohosh (terpene glycoside fraction (actine/cimifugoside), flax seed (omega fatty acids), echinacea (echinacoside), valerian (alkaloids, gabapentin, isovaleric acid, terpenes), senna (senna glycosides), cinnamon (cinnamaldehyde, phenols, terpenes), vitamin D, saw palmetto (fatty acids), or caffeine. In certain embodiments, the vaporizable material is soluble to at least fifty percent by weight in any suitable carrier solvent such as glycols (such as propylene glycol and vegetable glycerin), ethylene glycol, dipropylene glycol, trimethylene glycol, ethanol, and combinations thereof. In certain embodiments, the medicinal compound is terpinolene. In certain embodiments, the medicinal compound is Linalool. In certain embodiments, the medicinal compound is phytol, In certain embodiments, the medicinal compound is beta myrcene. In certain embodiments, the medicinal compound is citronellol. In certain embodiments, the medicinal compound is caryophyllene oxide. In certain embodiments, the medicinal compound is alpha pinene. In certain embodiments, the medicinal compound is limonene. In certain embodiments, the medicinal compound is beta caryophyllene. In certain embodiments, the medicinal compound is humulene. In certain embodiments, the vaporizable material is an essential oil.

User Interface

In certain embodiments, the vaporizer apparatuses described herein may include a user interface. In certain embodiments, the user interface is a display. In certain embodiments, the display is an LCD. In certain embodiments, the display is an LED. In certain embodiments, the display is an OLED. In certain embodiments, the display provides a user interface. In certain embodiments, the display is touch sensitive. In certain embodiments, the display communicates puff frequency, puff duration, amount of TPM vaporized, amount of active ingredient vaporized, or any combination thereof. In certain embodiments, the display allows the user to select the type of vaporizable material. In certain embodiments, the display allows the user to select the amount of vaporizable material vaporized before the alert unit alerts the user or the vaporizer device is disabled, or both. In certain embodiments, the electronic vaporizer device utilizing the method comprises a user interface controller. In certain embodiments, the user interface controller is communicatively coupled to the display. In certain embodiments, the user interface controller is a software module that controls information communicated via the display.

In some embodiments, the user interface can be configured to allow a user to change and/or monitor the settings and state of the electronic vaporizer device. For example, in one embodiment, user control means can be used to limit the usage of the device, relative to any of calculated TPM, puff duration, puff volume, voltage or heat temperature, singly or in combination.

Further, the vaporizer device described herein can include at least one of a switch, a keypad, a display, an input/output port, and a wireless transceiver. In one embodiment, the input/output port and the wireless transceiver can be employed to create a communications link between the control unit of the electronic vaporizer device and an external computer, such as a cell phone or personal computer.

The foregoing disclosure and description of the invention are illustrative and explanatory thereof and various adaptations may be made without departing from the spirit of the invention.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of determining a dose of a vaporizable material when using a vaporizing device over a time period, wherein the time period comprises a plurality of sequential time intervals, and wherein the vaporizing device includes a heater controller, a heater, a source of the vaporizable material including an active ingredient, and a dose predictor, the method comprising:
applying power, from the heater controller to the heater, to vaporize the vaporizable material during the time period;
transmitting a power reading of the power applied from the heater controller to the heater at each of the plurality of sequential time intervals, from the heater controller to the dose predictor;
calculating, for each of the plurality of sequential time intervals and at the dose predictor, a partial dose, wherein the partial dose is calculated based on subtracting a second term from a first term, wherein the first term comprises the power reading of the power applied from the heater controller to the heater to vaporize the vaporizable material during a partial dose time interval, and wherein the second term comprises a temperature of the vaporizable material during the partial dose time interval or a temperature of the vaporizable material before the partial dose time interval;
summing the calculated partial doses, at the dose predictor, to determine a total dose delivered during the time period;
determining an amount of active ingredient delivered to the user based on the total dose of vapor delivered; and
providing feedback, based on the total dose, to modify the operation of the vaporizer device.

2. A method of determining a dose of a vaporizable material when using a vaporizing device over a time period, wherein the time period comprises a plurality of sequential time intervals, and wherein the vaporizing device includes a heater controller, a heater, a source of the vaporizable material, and a dose predictor, the method comprising:
applying power, from the heater controller to the heater, to vaporize the vaporizable material during the time period;
transmitting a power reading of the power applied from the heater controller to the heater at each of the plurality of sequential time intervals, from the heater controller to the dose predictor;
calculating, for each of the plurality of sequential time intervals and at the dose predictor, a partial dose, wherein the partial dose is calculated based on subtracting a second term and a third term from a first term, wherein the first term comprises the power reading of the power applied from the heater controller to the heater to vaporize the vaporizable material during a partial dose time interval, wherein the second term comprises a temperature of the vaporizable material during the partial dose time interval, and wherein the third term comprises a temperature of the vaporizable material before the partial dose time interval;
summing the calculated partial doses, at the dose predictor, to determine a total dose delivered during the time period; and
providing feedback, based on the total dose, to modify the operation of the vaporizer device.

3. The method of claim 2, further comprising determining an amount of active ingredient delivered to a user based on the total dose delivered.

4. The method of claim 2, wherein calculating further comprises determining a change in temperature ($\Delta T$) of the vaporizable material being vaporized for each of the sequential time intervals relative the temperature of the vaporizable material being vaporized.

5. The method of claim 2, wherein the sequential time intervals are between about 200 msec and about 10 msec.

6. The method of claim 2, wherein calculating, for each of the sequential time intervals, the partial dose is further based upon a latent heat and a specific heat of the material.

7. The method of claim 2, wherein subtracting the second term and the third term from the first term comprises subtracting, from a first constant times the power reading of the power applied from the heater controller during the partial dose time interval, a second constant times the temperature of the vaporizable material during the partial dose time interval and a third constant times the temperature of the vaporizable material before the partial dose time interval.

8. The method of claim 2, wherein the temperature of the vaporizable material during the partial dose time interval and the third term comprises the temperature of the vaporizable material being vaporized before the partial dose time interval are determined based on an electrical property of the heater that is proportional to the temperature of the heater.

9. The method of claim 2, wherein providing the feedback comprises alerting a user when the total dose delivered during the time period meets or exceeds a preset threshold.

10. The method of claim 2, wherein providing the feedback comprises disabling the device when the total dose delivered during the time period meets or exceeds a preset threshold.

11. The method of claim 2, further comprising calculating and displaying a cumulative total dose delivered over a session period that includes the time period.

12. The method of claim 2, further comprising detecting a user's puff on the vaporizer device, wherein the time period corresponds to a duration of the detected user's puff.

13. The method of claim 2, wherein the vaporizable material comprises a liquid.

14. The method of claim 2, wherein the vaporizable material comprises a tobacco-based material.

15. The method of claim 2, wherein the vaporizable material comprises a botanical.

16. The method of claim 2, wherein the vaporizable material comprises a nicotine compound.

17. The method of claim 2, wherein the vaporizable material comprises a cannabinoid.

18. The method of claim 2, wherein the vaporizable material comprises at least one of: cetirizine, ibuprofen, naproxen, omeprazole, doxylamine, diphenhydramine, melatonin, or meclizine.

19. The method of claim 2, wherein the vaporizable material comprises at least one of: albuterol, levalbuterol, pirbuterol, salmeterol, formoterol, atropine sulfate, ipratropium bromide, fluticasone, budesonide, mometasone, montelukast, zafirlukast, theophylline, fluticasone and salmeterol, budesonide and formoterol, and mometasone and formoterol.

20. The method of claim 2, wherein the vaporizable material comprises at least one of: a polyphonel, a green tea catechin, caffeine, a phenol, a glycoside, a labdane diterpenoid, yohimbine, a proanthocyanidin, terpene glycoside, an omega fatty acid, echinacoside, an alkaloid, isovaleric acid, a terpene, gamma-aminobutyric acid, a senna glycoside, cinnamaldehyde, and Vitamin D.

21. The method of claim 2, wherein the vaporizable material comprises a nicotine salt, glycerin, and propylene glycol.

22. The method of claim 2, wherein the dose predictor is part of a controller comprising the heater controller.

23. The method of claim 2, wherein summing the calculated partial doses comprises aggregating the calculated partial doses as each partial dose is calculated.

24. A method of determining a dose of a vaporizable material when using a vaporizing device over a time period, wherein the time period comprises a plurality of sequential time intervals, and wherein the vaporizing device includes a heater controller, a heater, a source of the vaporizable material, and a dose predictor, the method comprising:
   applying power, from the heater controller to the heater, to vaporize the vaporizable material during the time period;
   transmitting a power reading of the power applied from the heater controller to the heater at each of the plurality of sequential time intervals, from the heater controller to the dose predictor;
   calculating, for each of the plurality of sequential time intervals and at the dose predictor, a partial dose, wherein the partial dose is calculated based on subtracting a second term and a third term from a first term, wherein the first term comprises the power reading of the power applied from the heater controller to the heater to vaporize the vaporizable material during each of the plurality of sequential time intervals, wherein the second term comprises a temperature of the vaporizable material during each of the plurality of sequential time intervals, and wherein the third term comprises a temperature of the vaporizable material before each of the plurality of sequential time intervals;
   summing the calculated partial doses, at the dose predictor, to determine a total dose delivered during the time period; and
   providing feedback, based on the total dose, to modify the operation of the vaporizer device.

25. The method of claim 24, further comprising:
   transmitting the temperature of the vaporizable material during each of the plurality of sequential time intervals, from the heater controller to the dose predictor.

* * * * *

UNITED STATES PATENT AND TRADEMARK OFFICE
CERTIFICATE OF CORRECTION

PATENT NO. : 10,512,282 B2
APPLICATION NO. : 14/960259
DATED : December 24, 2019
INVENTOR(S) : Adam Bowen et al.

It is certified that error appears in the above-identified patent and that said Letters Patent is hereby corrected as shown below:

In the Claims

In Column 50, Line 25, in Claim 8, after "and" delete "the third term comprises"

In Column 50, Line 26, in Claim 8, after "material" delete "being vaporized"

In Column 50, Line 64, in Claim 20, delete "polyphonel" and insert --polyphenol--

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*